(12) United States Patent
Vetter et al.

(10) Patent No.: US 11,884,703 B2
(45) Date of Patent: *Jan. 30, 2024

(54) METHODS OF PROCESSING A FLUID INCLUDING A RECOMBINANT THERAPEUTIC PROTEIN AND USE THEREOF

(71) Applicant: Genzyme Corporation, Cambridge, MA (US)

(72) Inventors: Tarl Vetter, Bridgewater, NJ (US); Michael Coolbaugh, Bridgewater, NJ (US); Veena Warikoo, Westford, MA (US); Konstantin Konstantinov, Waban, MA (US)

(73) Assignee: Genzyme Corporation, Cambridge, MA (US)

( * ) Notice: Subject to any disclaimer, the term of this patent is extended or adjusted under 35 U.S.C. 154(b) by 442 days.

This patent is subject to a terminal disclaimer.

(21) Appl. No.: 17/180,272

(22) Filed: Feb. 19, 2021

(65) Prior Publication Data

US 2021/0171572 A1 Jun. 10, 2021

Related U.S. Application Data

(62) Division of application No. 15/677,888, filed on Aug. 15, 2017, now Pat. No. 10,968,252.

(Continued)

(51) Int. Cl.
*C07K 1/34* (2006.01)
*B01D 61/14* (2006.01)
(Continued)

(52) U.S. Cl.
CPC ............ *C07K 1/34* (2013.01); *B01D 15/1864* (2013.01); *B01D 61/145* (2013.01);
(Continued)

(58) Field of Classification Search
CPC ............ B01D 15/1864; B01D 2315/16; B01D 61/145; B01D 61/146; C07K 1/34; C07K 16/00; C07K 2317/21; C07K 2317/31
See application file for complete search history.

(56) References Cited

U.S. PATENT DOCUMENTS 6,139,746 A 10/2000 Kopf
6,296,770 B1 10/2001 Wilcox et al.
(Continued)

FOREIGN PATENT DOCUMENTS

CN 102911268 2/2013
CN 104884467 9/2015
(Continued)

OTHER PUBLICATIONS

Office Action in Japanese Patent Application No. 2019-508971, dated Jan. 25, 2022, 13 pages (with English translation).
(Continued)

*Primary Examiner* — Dirk R Bass
(74) *Attorney, Agent, or Firm* — Fish & Richardson P.C.

(57) ABSTRACT

Provided herein are methods of processing a fluid that include the use of one or both of a circuit system including a tangential flow filtration (TFF) unit and a circuit system including a tangential flow virus filtration (TFVF) unit. Also provided are integrated and continuous processes for manufacturing a therapeutic protein drug substance that include a step of processing a fluid including the recombinant therapeutic protein using any of the methods provided herein.

20 Claims, 13 Drawing Sheets

Related U.S. Application Data

(60) Provisional application No. 62/375,689, filed on Aug. 16, 2016.

(51) Int. Cl.
    *C07K 16/00* (2006.01)
    *B01D 15/18* (2006.01)

(52) U.S. Cl.
    CPC ............ *B01D 61/146* (2022.08); *C07K 16/00* (2013.01); *B01D 2315/06* (2013.01); *C07K 2317/21* (2013.01); *C07K 2317/31* (2013.01)

(56) References Cited

U.S. PATENT DOCUMENTS

| | | |
|---|---|---|
| 6,365,395 B1 | 4/2002 | Antoniou |
| 6,375,847 B1 | 4/2002 | Hartmann |
| 6,586,172 B1 | 7/2003 | Gunn et al. |
| 7,384,549 B2 | 6/2008 | De Los Reyes |
| 7,695,675 B2 | 4/2010 | Kaiser et al. |
| 7,988,859 B2 | 8/2011 | Shinkazh |
| 8,528,225 B2 | 9/2013 | Weisselberg |
| 2003/0229212 A1 | 12/2003 | Fahrner et al. |
| 2006/0051347 A1 | 3/2006 | Winter |
| 2008/0017576 A1 | 1/2008 | Belfort et al. |
| 2008/0207487 A1 | 8/2008 | DeFrees et al. |
| 2010/0237013 A1 | 9/2010 | Burke et al. |
| 2012/0164066 A1 | 6/2012 | Greene et al. |
| 2014/0255994 A1 | 9/2014 | Konstantinov et al. |
| 2015/0274773 A1 | 10/2015 | Becker et al. |
| 2018/0051054 A1 | 2/2018 | Vetter et al. |

FOREIGN PATENT DOCUMENTS

| | | |
|---|---|---|
| CN | 105377874 | 3/2016 |
| EP | 1203774 | 5/2002 |
| JP | 2003-012693 | 1/2003 |
| JP | 2008-512473 | 4/2008 |
| JP | 2015-533378 | 11/2015 |
| JP | 2016-510981 | 4/2016 |
| KR | 10-2007-0109975 | 11/2007 |
| WO | WO 2006/031560 | 3/2006 |
| WO | WO 2014/067898 | 5/2014 |
| WO | WO 2014/137903 | 9/2014 |

OTHER PUBLICATIONS

Office Action in Korean Patent Application No. 10-2019-7007518, dated Mar. 29, 2022, 8 pages (with English translation).

Office Action in Mexican Patent Application No. MX/a/2019/001859, dated Jan. 27, 2022, 13 pages (with English summary).

Office Action in Chinese Patent Application No. 201780063527.0, dated Feb. 4, 2023, 12 pages (with English translation).

Japanese Office Action in Patent Application No. 2019-508971, dated Jun. 1, 2021, 13 pages (with English translation).

Russian Office Action in Patent Application No. 2019107142, dated May 4, 2021, 19 pages (with English translation).

"Cross Flow Filtration Method Handbook," dated Jan. 1, 2014, retrieved from the Internet: URL: https://www.gelifesciences.com/gehcls_images/GELS/Related%20Content/Files/1392028292867/litdoc29085076_20140313045908.pdf [retrieved on Jun. 26, 2015].

Acrivos et al., "Enhanced sedimentation in settling tanks with inclined walls," Journal of Fluid Mechanics, 1979, 92(3):435-457.

Aniceto et al., "Simulated Moving Bed Strategies and Designs: From Established Systems to the Latest Developments," Separation & Purification Reviews, 2015, 44(1):41-73.

Anspach et al., "Expanded-bed chromatography in primary protein purification," Journal of Chromatography A, 1999, 865(1-2):129-144.

Aumann et al., "A Continuous Multicolumn Countercurrent Solvent Gradient Purification (MCSGP) Process," Biotechnology and Bioengineering, 2007, 98(5):1043-1055.

Aumann et al., "A semicontinuous 3-column countercurrent solvent gradient purification (MCSGP) process," Biotechnology and Bioengineering, Feb. 2008, 99(3):728-733.

Avgerinos et al., "Spin Filter Perfusion System for High Density Cell Culture: Production of Recombinant Urinary Type Plasminogen Activator in CHO Cells," Nature Biotechnology, Jan. 1990, 8(1):54-58.

Azevedo et al., "Chromatography-free recovery of biopharmaceuticals through aqueous two-phase processing," Trends in Biotechnology, Apr. 2009, 27( 4):240-247.

Azevedo et al., "Partitioning of human antibodies in polyethylene glycol-sodium citrate aqueous two-phase systems," Separation and Purification Technology, Feb. 2009, 65(1):14-21.

Bae et al., "Evaluation of Viral Inactivation Efficacy of a Continuous Flow Ultraviolet-C Reactor (UVivatec)," Korean Journal of Microbiology and Biotechnology, Dec. 2009, 37(4):377-382.

Basu et al., "Protein crystals for the delivery of biopharmaceuticals," Expert Opinion on Biological Therapy, 2004, 4(3):301-317.

Bell et al., "The Formation of Protein Precipitates and Their Centrifugal Recovery," Downstream Processing, 1983, pp. 1-72.

Besselink et al., "Are axial and radial flow chromatography different?," Journal of Chromatography A, Jan. 2013, 1271(1): 105-114.

Bierau et al., "A comparison of intensive cell culture bioreactors operating with Hybridomas modified for inhibited apoptotic response," Journal of Biotechnology, Jul. 1998, 62 (3):195-207.

Bloomingburg et al., "Separation of protein mixtures by continuous annular chromatography with step elution," The Chemical Engineering Journal and the Biochemical Engineering Journal, Aug. 1994, 55(1-2):B19-B274.

Boycott et al., "Sedimentation of Blood Corpuscles," Nature, Jan. 1920, 104:532.

Brennan et al., "A perfusion system for antibody production by shear-sensitive hybridoma cells in a stirred reactor," Biotechnology Techniques, Sep. 1987, 1(3):169-174.

Brodsky et al., "Caprylic acid precipitation method for impurity reduction: An alternative to conventional chromatography for monoclonal antibody purification," Biotechnology and Bioengineering, Apr. 2012, 109(10):2589-2598.

Buchacher et al., "Purification of intravenous immunoglobulin G from human plasma—aspects of yield and virus safety," Biotechnology Journal, Feb. 2006, 1(2):148-163.

Cabanne et al., "Evaluation of radial chromatography versus axial chromatography, practical approach," Journal of Chromatography B, Jan. 2007, 845(2):191-199.

Caillet-Fauquet et al., "Continuous-flow UVC irradiation: a new, effective, protein activity-preserving system for inactivating bacteria and viruses, including erythrovirus B19," Journal of Virological Methods, Jun. 2004, 118(2):131-139.

Castilho et al., "An integrated process for mammalian cell perfusion cultivation and product purification using a dynamic filter," Biotechnol. Prog., Jul. 2002, 18(4):776-781.

Castilho et al., "Animal cell separation," Animal Cell Technology: From Biopharmaceuticals to Gene Therapy, 2008, pp. 273-294.

Chang, "Continuous fractionation of human plasma proteins by precipitation from the suspension of the recycling stream," Biotechnology and Bioengineering, May 1988, 31(8):841-846.

Chase, "Purification of proteins by adsorption chromatography in expanded beds," Trends in Biotechnology, Aug. 1994, 12(8):296-303.

Chhatre et al., "A decision-support model for evaluating changes in biopharmaceutical manufacturing processes," Bioprocess and Biosystems Engineering, Nov. 2006, 30(1): 1-11.

Chotteau et al., "Perfusion Processes," Animal Cell Culture, Nov. 2014, pp. 407-443.

Clincke et al., "Very high density of CHO cells in perfusion by ATF or TFF in WAVE bioreactor™. Part I. Effect of the cell density on the process," Biotechnology Progress, Feb. 2013, 29(3):754-767.

Crowley et al., "Using sound waves for cGMP manufacturing of a fusion protein with mammalian cells," BioProcess International, 2004, 2(3):46-50.

(56) References Cited

OTHER PUBLICATIONS

Dalm et al., "Effect of feed and bleed rate on hybridoma cells in an acoustic perfusion bioreactor: Part I. Cell density, viability, and cell-cycle distribution," Biotechnology and Bioengineering, Sep. 2004, 88(5):547-557.
Dalwadi et al., "Comparison of Diafiltration and Tangential Flow Filtration for Purification of Nanoparticle Suspensions," Pharmaceutical Research, 22(12):2152-2162, Dec. 1, 2005.
De la Broise et al., "Long-term perfusion culture of hybridoma: A "grow or die" cell cycle system," Biotechnology and Bioengineering, Oct. 1991, 38(7):781-787.
De Meyer et al., "Evaluation of spin freezing versus conventional freezing as part of a continuous pharmaceutical freeze-drying concept for unit doses," International Journal of Pharmaceutics, Dec. 2015, 496(1):75-85.
Deo et al., "Practical Considerations in Operation and Scale-up of Spin-Filter Based Bioreactors for Monoclonal Antibody Production," Biotechnology Progress, 1996, 12(1):57-64.
Doblhoff-Dier et al., "A Novel Ultrasonic Resonance Field Device for the Retention of Animal Cells," Biotechnology Progress, 1994, 10(4):428-432.
Dutta et al., "Performance optimization of continuous countercurrent tangential chromatography for antibody capture," Biotechnology Progress, Feb. 2016, 32(2):430-439.
Dutta et al., "Purification of monoclonal antibodies from clarified cell culture fluid using Protein A capture continuous countercurrent tangential chromatography," Journal of Biotechnology, Nov. 2015, 213:54-64.
Eggersgluess et al., "Multi-Stage Aqueous Two-Phase Extraction for the Purification of Monoclonal Antibodies," Chemical Engineering & Technology, Feb. 2014, 37(4):675-682.
Elsayed et al., "Application of hydrocyclones for continuous cultivation of SP-2/0 cells in perfusion bioreactors: Effect of hydrocyclone operating pressure," BMC Proceedings, Nov. 2011, 5(Supp. 8):p. 65.
Elsayed et al., "The Potential of Hydrocyclone Application for Mammalian Cell Separation in Perfusion Cultivation Bioreactors," International Journal of Biotechnology for Wellness Industries, Dec. 2013, 2(4):153-163.
Elsayed et al., "Use of Hydrocyclones for Mammalian Cell Retention: Separation Efficiency and Cell Viability (Part 1)," Engineering in Life Sciences, Sep. 2006, 6(4):347-354.
Emery et al., "Oxygenation of intensive cell-culture system," Applied Microbiology and Biotechnology, Nov. 1995, 43(6):1028-1033.
Espitia-Saloma et al., "An integrated practical implementation of continuous aqueous two-phase systems for the recovery of human IgG: From the microdevice to a multistage bench-scale mixer-settler device," Biotechnology Journal, Feb. 2016, 11(5):708-716.
Espitia-Saloma et al., "Continuous aqueous two-phase systems devices for the recovery of biological products," Food and Bioproducts Processing, Apr. 2014, 92(2):101-112.
European Communication in Patent Application No. 17762255.2, dated Apr. 5, 2019, 2 pages.
European Communication in Patent Application No. 17762255.2, dated Jun. 22, 2020, 4 pages.
Farid, "Process economics of industrial monoclonal antibody manufacture," Journal of Chromatography B, Mar. 2007, 848(1):8-18.
Feuser et al., "Interaction of mammalian cell culture broth with adsorbents in expanded bed adsorption of monoclonal antibodies," Process Biochemistry, Feb. 1999, 34(2): 159-165.
Fox et al., "Continuous chromatography apparatus : I. Construction," Journal of Chromatography A, 1969, 43:48-54.
Fox, "Continuous chromatography apparatus: II. Operation," Journal of Chromatography A, 1969, 43:55-60.
Furuta et al., "Continuous crystallization using a sonicated tubular system for controlling particle size in an API manufacturing process," Chemical Engineering and Processing: Process Intensification, Apr. 2016, 102:210-218.
Gagnon et al., "Technology trends in antibody purification," Journal of Chromatography A, Jan. 2012, 1221:57-70.

Gaida et al., "Selective Retention of Viable Cells in Ultrasonic Resonance Field Devices," Biotechnology Progress, 1996, 12(1):73-76.
Gebauer et al., "Engineered protein scaffolds as next-generation antibody therapeutics," Current Opinion in Chemical Biology, Jul. 2009, 13(3):245-255.
Giddings, "Theory of Minimum Time Operation in Gas Chromatography," Analytical Chemistry, Mar. 1962, 34(3):314-319.
Giovannini et al., "Isolation of a recombinant antibody from cell culture supernatant: Continuous annular versus batch and expanded-bed chromatography," Biotechnology and Bioengeering, Jun. 2001, 73(6):522-529.
Godawat et al., "Periodic counter-current chromatography—design and operational considerations for integrated and continuous purification of proteins," Biotechnology Journal, Oct. 2012, 7(12): 1496-1508.
Gomes et al., "Purification of plasmid DNA with aqueous two phase systems of PEG 600 and sodium citrate/ammonium sulfate," Separation and Purification Technology, Feb. 2009, 65(1):22-30.
Gorenflo et al., "Optimization of an Acoustic Cell Filter with a Novel Air-Backflush System," Biotechnology Progress, Feb. 2003, 19(1):30-36.
Gorenflo et al., "Scale-up and optimization of an acoustic filter for 200 L/day perfusion of a CHO cell culture," Biotechnology and Bioengineering, Sep. 2002, 80(4):438-444.
Gottschlich et al., "Purification of monoclonal antibodies by simulated moving-bed chromatography," Journal of Chromatography A, Mar. 1997, 765(2):201-206.
Greenfield et al., "Experience in scale-up of homogeneous perfusion culture for hybridomas," Bioprocess Engineering, Jun. 1991, 6(5):213-219.
Gu et al., "A theoretical study of multicomponent radial flow chromatography," Chemical Engineering Science, 1991, 46(5): 1279-1288.
Hamamoto et al., "Perfusion culture of hybridoma cells using a centrifuge to separate cells from culture mixture," Journal of Fermentation and Bioengineering, 1989, 67(3):190-194.
Hammerschmidt et al., "Continuous polyethylene glycol precipitation of recombinant antibodies: Sequential precipitation and resolubilization," Process Biochemistry, Feb. 2016, 51(2):325-332.
Hammerschmidt et al., "Continuous precipitation of IgG from CHO cell culture supernatant in a tubular reactor," Biotechnology Journal, Aug. 2015, 10(8):1196-1205.
Hammerschmidt et al., "Economics of recombinant antibody production processes at various scales: Industry-standard compared to continuous precipitation," Biotechnology Journal, Apr. 2014, 9(6):766-775.
Haraguchi et al., "Phase equilibrium and insulin partitioning in aqueous two-phase systems containing block copolymers and potassium phosphate," Fluid Phase Equilibria, Jan. 2004, 215(1): 1-15.
Hart et al., "Large Scale, In Situ Isolation of Periplasmic IGF-I from *E. coli*," Nature Biotechnology, Nov. 1994, 12(11):1113-1117.
Hecht et al., "Efficiency improvement of an antibody production process by increasing the inoculum density," Biotechnology Progress, Feb. 2014, 30(3):607-615.
Hekmat, "Large-scale crystallization of proteins for purification and formulation," Bioprocess Biosystems Engineering, Feb. 2015, 38(7):1209-1231.
Himmelfarb et al., "Spin Filter Culture: The Propagation of Mammalian Cells in Suspension," Science, May 1969, 164(3879):555-557.
Huang et al., "Mathematical models of radial chromatography," The Chemical Engineering Journal, Jul. 1988, 38(3):179-186.
Hülscher et al., "Selective recycle of viable animal cells by coupling of airlift reactor and cell settler," Biotechnology and Bioengineering, Feb. 1992, 39(4):442-446.
Imamoglu, "Simulated Moving Bed Chromatography (SMB) for Application in Bioseparation," Modern Advances in Chromatography, May 2002, pp. 211-231.
Indian Office Action in Patent Application No. 201917009564, dated Jan. 4, 2021, 9 pages.
Israel Office Action in Patent No. 264828, dated Feb. 9, 2020, 4 pages (with English translation).

(56) References Cited

OTHER PUBLICATIONS

Ito et al., "Centrifugal precipitation chromatography," Journal of Chromatography B, Jan. 2010, 878(2):154-164.
Jen et al., "Review: Hydrogels for cell immobilization," Biotechnology and Bioengineering, May 1996, 50(4):357-364.
Jockwer et al., "The use of hydroclones for mammalian cell retention in perfusion bioreactors," Animal Cell Technology: From Target to Market, 2001, pp. 301-306.
Johnson et al., "Use of the Centritech Lab Centrifuge for Perfusion Culture of Hybridoma Cells in Protein-Free Medium," Biotechnology Progress, 1996, 12(6):855-864.
Jungbauer et al., "Continuous downstream processing of biopharmaceuticals," Trends in Biotechnology, Aug. 2013,31(8):479-492.
Kang et al., "Development of a novel and efficient cell culture flocculation process using a stimulus responsive polymer to streamline antibody purification processes," Biotechnology and Bioengineering, Jun. 2013, 110(11):2928-2937.
Karst et al., "Characterization and comparison of ATF and TFF in stirred bioreactors for continuous mammalian cell culture processes," Biochemical Engineering Journal, Jun. 2016, 110:17-26.
Kawahara et al., "High-density culture of FM-3A cells using a bioreactor with an external tangential-flow filtration device," Cytotechnology, Jan. 1994, 14(1):61-66.
Kebler et al., "Step gradients in 3-zone simulated moving bed chromatography: Application to the purification of antibodies and bone morphogenetic protein-2," Journal of Chromatography A, Dec. 2007, 1176(1):69-78.
Kelly et al., "Understanding and modeling alternating tangential flow filtration for perfusion cell culture," Biotechnology Progress, Nov. 2014, 30(6):1291-1300.
Kilburn et al., "Enhanced sedimentation of mammalian cells following acoustic aggregation," Biotechnology and Bioengineering, Aug. 1989, 34(4):559-562.
Kim et al., "Application of a Cell-Once-Through Perfusion Strategy for Production of Recombinant Antibody from rCHO Cells in a Centritech Lab II Centrifuge System," Biotechnology Progress, 2007, 23(5):1186-1197.
Kim et al., "Improved cosmetic activity by optimizing the Lithospermum erythrorhizon extraction process," Cytotechnology, Jan. 2015, 67:51-65.
Kim et al., "Limited Use of Centritech Lab II Centrifuge in Perfusion Culture of rCHO Cells for the Production of Recombinant Antibody," Biotechnology Progress, Jan. 2008, 24(1):166-174.
Kinna et al., "IMAC capture of recombinant protein from unclarified mammalian cell feed streams," Biotechnology and Bioengineering, Jan. 2016, 113(1):130-140.
Kitano et al., "Production of human monoclonal antibodies by heterohybridomas," Applied Microbiology and Biotechnology, Jul. 1986, 24(4):282-286.
Klutz et al., "Continuous viral inactivation at low pH value in antibody manufacturing," Chemical Engineering and Processing: Process Intensification, Apr. 2015, 102:88-101.
Klutz et al., "Developing the biofacility of the future based on continuous processing and single-use technology," Journal of Biotechnology, Nov. 2015, 213:120-130.
Klutz et al., "Narrow residence time distribution in tubular reactor concept for Reynolds number range of 10-100," Chemical Engineering Research and Design, Mar. 2015, 95:22-33.
Kohara et al., "Enhanced Settling of Mammalian Cells in Tanks with Inclined Plates/ Simulation by Fluid Mechanical Model and Experiment," Journal of Chemical Engineering of Japan, Jun. 1995, 28(6):703-707.
Krober et al., "Continuous purification of influenza virus using simulated moving bed chromatography," Journal of Chromatography A, Sep. 2013, 1307:99-110.
Kula et al., "Protein Purification, Aqueous Liquid Extraction," Encyclopedia of Bioprocess Technology: Fermentation, Biocatalysis, and Bioseparation, Oct. 2002, 29 pages.
Kumar et al., "Type-specific separation of animal cells in aqueous two-phase systems using antibody conjugates with temperature-sensitive polymers," Biotechnology and Bioengineering, Oct. 2001, 75(5):570-580.
Kurnik et al.,"Buffer exchange using size exclusion chromatography, countercurrent dialysis, and tangential flow filtration: Models, development, and industrial application," Biotechnology and Bioengineering, Jan. 1995, 45(2):149-157.
Kyung et al., "High density culture of mammalian cells with dynamic perfusion based on on-line oxygen uptake rate measurements," Cytotechnology, Jan. 1994, 14(3):183-190.
Lawton et al., "Continuous Crystallization of Pharmaceuticals Using a Continuous Oscillatory Baffled Crystallizer," Organic Process Research Development, Oct. 2009, 13(6): 1357-1363.
Lay et al., "Continuous Radial Flow Chromatography of Proteins," Food and Bioproducts Processing, Mar. 2006, 84(1):78-83.
Li et al., "Design of a UV-C irradiation process for the inactivation of viruses in protein solutions," Biologicals, Jun. 2005, 33(2):101-110.
Li et al., "Multistage Continuous Mixed-Suspension, Mixed-Product Removal (MSMPR) Crystallization with Solids Recycle," Organic Process Research & Development, Dec. 2015, 20(2):510-516.
Lin et al., "Evaluation and characterization of axial distribution in expanded bed. I. Bead size, bead density and local bed voidage," Journal of Chromatography A, Aug. 2013, 1304:78-84.
Liu et al., "Recovery and Purification Process Development for Monoclonal Antibody Production," MAbs, Sep. 2010, 5:480-499.
Lorenz et al., "The effect of low intensity ultraviolet-C light on monoclonal antibodies," Biotechnology Progress, Apr. 2009, 25(2):476-482.
Low et al., "Future of antibody purification," Journal of Chromatography B, Mar. 2007, 848(1):48-63.
Lydersen et al., "Acid precipitation of mammalian cell fermentation broth," Annals of the New York Academy of Sciences, Nov. 1994, 745(1):222-231.
Mahajan et al., "Improving affinity chromatography resin efficiency using semi-continuous chromatography," Journal of Chromatography A, Mar. 2012, 1227: 154-162.
Martin et al., "Novel small scale TFF cell retention device for perfusion cell culture systems," BMC Proceedings, 2015, 9(Suppl 9): P25, 2 pages.
Martin, "Summarizing Paper," Discussions of the Faraday Society, Oct. 1949, 7:332-336.
Mascia et al., "End-to-End Continuous Manufacturing of Pharmaceuticals: Integrated Synthesis, Purification, and Final Dosage Formation," Angewandte Chemie International Edition, Oct. 2013, 52(47): 12359-12363.
Mashayekhi et al., "Concentration of mammalian genomic DNA using two-phase aqueous micellar systems," Biotechnology and Bioengineering, Apr. 2009, 102(6):1613-1623.
McNerney et al., "PDADMAC Flocculation of Chinese Hamster Ovary Cells: Enabling a Centrifuge-Less Harvest Process for Monoclonal Antibodies," MAbs, Mar. 2015, 2:413-427.
Mercille et al., "Filtration-based perfusion of hybridoma cultures in protein-free medium: Reduction of membrane fouling by medium supplementation with DNase I," Biotechnology and Bioengineering, Apr. 1994, 43(9):833-846.
Mercille et al., "Understanding factors that limit the productivity of suspension-based perfusion cultures operated at high medium renewal rates," Biotechnology and Bioengineering, Mar. 2000, 67(4):435-450.
Meuwly et al., "Packed-bed bioreactors for mammalian cell culture: Bioprocess and biomedical applications," Biotechnology Advances, Jan. 2007, 25(1):45-56.
Mexican Office Action in Patent Application No. MX/a/2019/001859, dated Feb. 25, 2021, 9 pages (with English translation).
Muendges et al., "Multistage aqueous two-phase extraction of a monoclonal antibody from cell supernatant," Biotechnology Progress, Apr. 2015, 31(4):925-936.
Muller-Spath et al., "Chromatographic separation of three monoclonal antibody variants using multicolumn countercurrent solvent

(56) References Cited

OTHER PUBLICATIONS gradient purification (MCSGP)," Biotechnology and Bioengineering, Feb. 2008, 100(6):1166-1177.
Mun et al., "Optimal Design of a Size-Exclusion Tandem Simulated Moving Bed for Insulin Purification," Industrial & Engineering Chemistry Research, Apr. 2003, 42 (9):1977-1993.
Napadensky et al., "Continuous Countercurrent Tangential Chromatography for Monoclonal Antibody Purification," Separation Science and Technology, Feb. 2013, 48(9): 1289-1297.
Neugebauer et al., "Continuous Crystallization of Proteins in a Tubular Plug-Flow Crystallizer," Crystal Growth & Design, Feb. 2015, 15(3): 1089-1095.
Nicholas et al., "Continuous chromatography apparatus: III. Application", Journal of Chromatography A, 1969, 43:61-65.
Non Final Office Action in U.S. Appl. No. 15/677,888, dated Nov. 12, 2019, 16 pages.
Owen et al., "Direct purification of lysozyme using continuous counter-current expanded bed adsorption," Journal of Chromatography A, Jan. 1997, 757 (1):41-49.
Owen et al., "Modeling of the continuous counter-current expanded bed adsorber for the purification of proteins," Chemical Engineering Science, Sep. 1999, 54(17):3765-3781.
Ozyurt et al., "Recovery of antithrombin III from milk by expanded bed chromatography," Journal of Chromatography A, Jan. 2002, 944(1):203-210.
Padawer et al., "Case Study: An accelerated 8-day monoclonal antibody production process based on high seeding densities," Biotechnology Progress, Apr. 2013, 29(3):829-832.
Pattasseril et al., "Downstream Technology Landscape for Large-Scale Therapeutic Cell Processing," BioProcess International, Mar. 2013, 11(3):38-47.
PCT International Preliminary Report on Patentability in International Appln. No. PCT/US2017/046930, dated Feb. 19, 2019, 7 pages.
PCT International Search Report and Written Opinion in International Appln. No. PCT/US2017/046930, dated Oct. 27, 2017, 11 pages.
Peters et al., "Implementation of a crystallization step into the purification process of a recombinant protein," Protein Expression and Purification, Jan. 2005, 39(1):43-53.
Pinto et al., "Separation of CHO cells using hydrocyclones," Cytotechnology, Nov. 2007, 56(1):57-67.
Piret et al., "Immobilized mammalian cell cultivation in hollow fiber bioreactors," Biotechnology Advances, 1990, 8(4):763-784.
Poechlauer et al., "Continuous Processing in the Manufacture of Active Pharmaceutical Ingredients and Finished Dosage Forms: An Industry Perspective," Organic Process Research & Development, Sep. 2012, 16(10):1586-1590.
Pohlscheidt et al., "Optimizing capacity utilization by large scale 3000 L perfusion in seed train bioreactors," Biotechnology Progress, Jan. 2013, 29(1):222-229.
Power et al., "Design and optimization of a multistage continuous cooling mixed suspension, mixed product removal crystallizer," Chemical Engineering Science, Sep. 2015, 133:125-139.
Pui et al., "Batch and Semicontinuous Aggregation and Sedimentation of Hybridoma Cells by Acoustic Resonance Fields," Biotechnology Progress, Mar. 1995, 11(2):146-152.
Rajendran et al., "Simulated moving bed chromatography for the separation of enantiomers," Journal of Chromatography A, Jan. 2009, 1216 (4):709-738.
Reuveny et al., "Comparison of cell propagation methods for their effect on monoclonal antibody yield in fermenters," Journal of Immunological Methods, Jan. 1986, 86(1):61-69.
Rey et al., "Glimpses into the Realm of Freeze-Drying: Classical Issues and New Ventures," Freeze Drying/Lyophilization of Pharmaceutical and Biological Products, 2010, pp. 1-28.
Riske et al., "The use of chitosan as a flocculant in mammalian cell culture dramatically improves clarification throughput without adversely impacting monoclonal antibody recovery," Journal of Biotechnology, Mar. 2007, 128(4):813-823.

Rosa et al., "Application of aqueous two-phase systems to antibody purification: A multi-stage approach," Journal of Biotechnology, Feb. 2009, 139(4):306-313.
Rosa et al., "Aqueous two-phase systems: A viable platform in the manufacturing of biopharmaceuticals," Journal of Chromatography A, Apr. 2010, 1217(16):2296-2305.
Rosa et al., "Continuous aqueous two-phase extraction of human antibodies using a packed column," Journal of Chromatography B, Jan. 2012, 880:148-156.
Rosa et al., "Continuous purification of antibodies from cell culture supernatant with aqueous two-phase systems: From concept to process," Biotechnology Journal, Mar. 2013, 8(3):352-362.
Roth et al., "Using an external vortex flow filtration device for perfusion cell culture," Pharmaceutical Technology, Oct. 1997, 21(10):116-122.
Roush et al., "Advances in Primary Recovery: Centrifugation and Membrane Technology," Biotechnology Progress, 2008, 24(3):488-495.
Ruiz-Ruiz et al., "Aqueous two-phase affinity partitioning systems: Current applications and trends," Journal of Chromatography A, Jun. 2012, 1244:1-13.
Russian Office Action in Patent Application No. 2019107142, dated Dec. 17, 2020, 18 pages (with English translation).
Schmidt et al., "Crystallization for the Downstream Processing of Proteins," Engineering in Life Sciences, Jun. 2005, 5(3):273-276.
Schwartz et al., "Introduction to Tangential Flow Filtration for Laboratory and Process Development Applications," dated Jan. 1, 2002, pp. 1-12, retrieved from the Internet: URL: http://separations.co.za/fileadmin/themes/default/pdf/2.%20PRODUCT%20LINES/R.%20PALL/ii.%20BIOPHARMACEUTICALS/Content%20Element%204/Minimate%20System.pdf [retrieved on Oct. 20, 2017].
Seamans et al., "Kinetics of growth and antibody production by a hybridoma cell line in a perfusion culture," Journal of Fermentation and Bioengineering, 1990, 70(4):241-245.
Searles et al., "Viable Cell Recycle with an Inclined Settler in the Perfusion Culture of Suspended Recombinant Chinese Hamster Ovary Cells," Biotechnology Progress, Mar. 1994, 10(2):198-206.
Shen et al., "CFD-aided cell settler design optimization and scale-up: Effect of geometric design and operational variables on separation performance," Biotechnology Progress, Apr. 2011, 27(5):1282-1296.
Shintani et al., "Comparison of culture methods for human-human hybridomas secreting anti-HBsAg human monoclonal antibodies," Cytotechnology, Jul. 1991, 6(3):197-208.
Shirgaonkar et al., "Acoustic cell filter: a proven cell retention technology for perfusion of animal cell cultures", Biotechnology Advances, Jul. 2004, 22(6):433-444.
Singapore Written Opinion in Patent Application No. 11201901220X, dated Oct. 15, 2020, 8 pages.
Singh et al., "Clarification technologies for monoclonal antibody manufacturing processes: Current state and future perspectives," Biotechnology and Bioengineering, Aug. 2015, 113(4):698-716.
Smith et al., "Hydrophobic interaction ligand selection and scale-up of an expanded bed separation of an intracellular enzyme from *Saccharomyces cerevisiae*," Journal of Chromatography A, Aug. 2002, 968 (1):121-128.
Sommer et al., "Combined polyethylene glycol and CaCl2 precipitation for the capture and purification of recombinant antibodies," Process Biochemistry, Nov. 2014, 49(11):2001-2009.
Su et al., "Pharmaceutical crystallisation processes from batch to continuous operation using MSMPR stages: Modelling, design, and control," Chemical Engineering Processing: Process Intensification, Mar. 2015, 89:41-53.
Sun et al., "Chromatography of human prothrombin from Nitschmann fraction III on DEAE Sepharose Fast Flow using axial and radial flow column," Biomedical Chromatography, Nov. 2000, 14(7):478-482.
Takahashi et al., "Continuous Separations of Amino Acids by Using an Annular Chromatograph with Rotating Inlet and Outlet," Separation Science and Technology, 1991, 26(1):1-13.

(56) References Cited

OTHER PUBLICATIONS

Takamatsu et al., "Large-scale perfusion culture process for suspended mammalian cells that uses a centrifuge with multiple settling zones," Applied Microbiology and Biotechnology, May 1996, 45(4):454-457.
Takazawa et al., "High cell density perfusion culture of mouse-human hybridomas," Applied Microbiology and Biotechnology, Dec. 1989, 32(3):280-284.
Tao et al., "Development and implementation of a perfusion-based high cell density cell banking process," Biotechnology Progress, Mar. 2011, 27(3):824-829.
Tharakan et al., "Ligand efficiency in axial and radial flow immunoaffinity chromatography of factor IX," Journal of Chromatography A, May 1995, 702(1):191-196.
Thommes, "Fluidized Bed Absorption as a Primary Recovery Step in Protein Purification," New Enzymes for Organic Synthesis, 1997, pp. 185-230.
Tokashiki et al., "High density culture of hybridoma cells using a perfusion culture vessel with an external centrifuge," Cytotechnology, May 1990, 3(3):239-244.
Tolbert et al., "Large-scale rotating filter perfusion system for high-density growth of mammalian suspension cultures," In Vitro, Oct. 1981, 17(10):885-890.
Tscheliessnig et al., "Ethanol precipitation for purification of recombinant antibodies," Journal of Biotechnology, Oct. 2014, 188:17-28.
Tyo et al., "Dense cultures of animal cells at the industrial scale," Enzyme and Microbial Technology, Sep. 1987, 9(9):514-520.
USPTO Final Office Action in U.S. Appl. No. 15/677,888, dated Feb. 28, 2020, 11 pages.
USPTO Final Office Action in U.S. Appl. No. 15/677,888, dated Aug. 12, 2020, 11 pages.
Vallez-Chetreaunu et al., "An on-line method for the reduction of fouling of spin-filters for animal cell perfusion cultures," Journal of Biotechnology, Jun. 2007, 130(3):265-273.
Vazquez-Villegas et al., "Continuous enzyme aqueous two-phase extraction using a novel tubular mixer-settler in multi-step counter-current arrangement," Separation and Purification Technology, Feb. 2015, 141:263-268.
Velez et al., "Use of Tangential Flow Filtration in Perfusion Propagation of Hybridoma Cells for Production of Monoclonal Antibodies," Biotechnology and Bioengineering, 1989, 33(7):938-940.
Vogel et al., "A new large-scale manufacturing platform for complex biopharmaceuticals," Biotechnology and Bioengineering, Jun. 2012, 109 (12):3049-3058.
Vogel et al., "Continuous annular chromatography: General characterization and application for the isolation of recombinant protein drugs," Biotechnology and Bioengineering, Sep. 2002, 80(5):559-568.
Wang et al., "A simple apparatus for measuring cell settling velocity," Biotechnology Progress, Mar. 2010, 26(5):1361-1366.
Wang et al., "Virus inactivation and protein recovery in a novel ultraviolet-C reactor," Vox Sanguinis, 2004, 86(4):230-238.
Warikoo et al., "A new use for existing technology—continuous precipitation for purification of recombination proteins," Biotechnology Journal, Mar. 2015, 10(8): 1101-1102.
Warikoo et al., "Integrated continuous production of recombinant therapeutic proteins," Biotechnology and Bioengineering, Jun. 2012, 109(12):3018-3029.
Watt, "Automatically Controlled Continuous Recovery of Plasma Protein Fractions for Clinical Use: A Preliminary Report," Vox Sanguinis, Jan. 1970, 18(1):42-61.
Weaver et al., "Uridine phosphorylase purified from total crude extracts of *E. coli* using Q Sepharose and radial-flow chromatography," BioPharm, 1990, 3(7):25-28.
Wong et al., "Development of Continuous Crystallization Processes Using a Single-Stage Mixed-Suspension, Mixed-Product Removal Crystallizer with Recycle," Crystal Growth & Design, Oct. 2012, 12(11):5701-5707.
Wright et al., "A Novel Seed-Train Process: Using High-Density Cell Banking, a Disposable Bioreactor, and Perfusion Technologies," Bioprocess International, Mar. 2015, 10 pages.
Xie et al., "Preparative chromatographic separation: Simulated moving bed and modified chromatography methods," Biotechnology and Bioprocess Engineering, Dec. 2001, 6(6):363-375.
Xu et al., "High-density mammalian cell cultures in stirred-tank bioreactor without external pH control," Journal of Biotechnology, Aug. 2016, 231:149-159.
Yabannavar et al., "Mammalian cell retention in a spinfilter perfusion bioreactor," Biotechnology and Bioengineering, Oct. 1992, 40(8):925-933.
Yang et al., "Perfusion seed cultures improve biopharmaceutical fed-batch production capacity and product quality," Biotechnology Progress, Feb. 2014, 30(3):616-625.
Zhao et al., "Adsorbents for Expanded Bed Adsorption: Preparation and Functionalization," Chinese Journal of Chemical Engineering, 2009, 17(4):678-687.
Office Action in Brazilian Application No. BR112019003013-1, dated Sep. 20, 2022, 5 pages (with English translation).
Mexican Office Action in Patent Application No. MX/A/2019/001859, dated Aug. 6, 2021, 9 pages (with English translation).
European Search Report in Patent Application No. 21193609.1, dated Dec. 21, 2021, 9 pages.
Office Action in Mexican Patent Application No. MX/a/2019/001859, dated Jul. 25, 2022, 11 pages (with English summary).
Office Action in Japanese Patent Application No. 2022-082749, dated Jun. 13, 2023, 12 pages (with English translation).
Office Action in Chinese Patent Appln. No. 201780063527.0, dated Jul. 5, 2022, 19 pages (with English translation).
Grein et al., "Virus Separation Using Membranes," Animal Cell Biotechnology: Methods and Protocols, Methods in Molecular Biology, 2014, 1104: 459-491.
Taiwanese Office Action in Patent Application No. 106127646, dated Sep. 6, 2021, 3 pages (English translation only).

METHODS OF PROCESSING A FLUID INCLUDING A RECOMBINANT THERAPEUTIC PROTEIN AND USE THEREOF

CROSS-REFERENCE TO RELATED APPLICATIONS

This application is a divisional of U.S. patent application Ser. No. 15/677,888, filed Aug. 15, 2017, which claims priority to U.S. Provisional Patent Application Ser. No. 62/375,689, filed Aug. 16, 2016; the entire contents of which are herein incorporated by reference.

TECHNICAL FIELD

This invention relates to methods of biotechnology and the biomanufacturing of recombinant proteins.

BACKGROUND

Mammalian cells containing a nucleic acid that encodes a recombinant protein are often used to produce therapeutically or commercially important proteins. In the current environment of diverse product pipelines, biotechnology companies are increasingly driven to develop innovative solutions for highly flexible and cost-effective manufacturing of therapeutic protein drug substances.

SUMMARY

The present invention is based, at least in part, on the discovery that circuit systems including a tangential flow filtration (TFF) unit or a tangential flow virus filtration (TFVF) unit can be used to continuously perform the unit operation of ultrafiltration/diafiltration and virus filtration, respectively. In view of this discovery, provided herein are methods of processing a fluid that include the use of one or both of a circuit system including a tangential flow filtration (TFF) unit and a circuit system including a tangential flow virus filtration (TFVF) unit. Also provided are integrated and continuous processes for manufacturing a therapeutic protein drug substance that include a step of processing a fluid including the recombinant therapeutic protein using any of the methods provided herein.

Provided herein are methods of processing a fluid including a recombinant therapeutic protein that include: (a) providing a circuit system including (i) a tangential flow filtration (TFF) unit having first and second inlets, and (ii) a conduit in fluid communication between the first and second inlets, including at least one port for flowing fluid into or out of, or both, of the system, where the system is configured such that fluid can be flowed through the conduit and the TFF unit, and filtrate not including the recombinant therapeutic protein can be collected from the TFF unit; (b) continuously flowing a fluid including a recombinant therapeutic protein into the circuit system through one of the at least one port, and discarding filtrate not including the recombinant therapeutic protein for a first period of time; (c) continuously flowing a diafiltration medium into the circuit system through one of the at least one port, and discarding filtrate not including the recombinant therapeutic protein for a second period of time; and (d) collecting a fluid including the recombinant therapeutic protein that is present in the circuit system after the first and second time periods through one of the at least one port. In some embodiments of these methods, step (b) includes continuously flowing the fluid into the circuit system at a rate of about 0.1 mL/minute to about 100 L/minute (e.g., about 0.5 mL/minute to about 200 mL/minute). In some embodiments of these methods, the first period of time is about 0.1 minute to about 12 hours (e.g., about 10 minutes to about 4 hours). In some embodiments of these methods, the flowing of the fluid into the circuit system in step (b) occurs unidirectionally. In some embodiments of these methods, step (c) includes continuously flowing the diafiltration medium into the circuit system at a rate of about 0.1 mL/minute to about 100 L/minute (e.g., about 0.5 mL/minute to about 200 mL/minute). In some embodiments of these methods, the second period of time is about 5 minutes to about 12 hours (e.g., about 10 minutes to about 4 hours). In some embodiments of these methods, the flowing of the diafiltration medium into the circuit system in step (c) occurs unidirectionally. In some embodiments of these methods, the conduit has an inner diameter of about 5 mm to about 5 cm (e.g., about 10 mm to about 3 cm). In some embodiments of these methods, the TFF unit comprises one or more tangential filter(s) having a surface area of about 0.1 $cm^2$ to about 50 $cm^2$ (e.g., about 0.5 $cm^2$ to about 20 $cm^2$). In some embodiments of these methods, the circuit system further includes a pump (e.g., a peristaltic pump) disposed in the conduit.

Some embodiments of these methods further include: (e) providing a second circuit system including (i) a tangential flow virus filtration (TFVF) unit having first and second inlets, and (ii) a conduit in fluid communication between the first and second inlets of the TFVF unit, including at least one port for flowing fluid into or out of, or both, of the second system, where the second system is configured such that fluid can be flowed through the conduit and the TFVF unit, and filtrate including the recombinant therapeutic protein can be collected from the TFVF unit; and (f) flowing the collected fluid of step (d) into the second system using a connecting conduit in fluid communication between a port in the system and a port in the second system, and collecting filtrate including the recombinant therapeutic protein from the TFVF unit for a third period of time. In some embodiments of these methods, step (f) includes flowing the fluid into the second system at a rate of about 0.1 mL/minute to about 100 L/minute (e.g., about 0.5 mL/minute to about 200 mL/minute). In some embodiments of these methods, the third period of time is about 0.1 minute to about 12 hours (e.g., about 10 minutes to about 2 hours). In some embodiments of these methods, the flowing of the fluid into the second system in step (f) occurs unidirectionally. In some embodiments of these methods, the conduit in fluid communication between the first and second inlets of the TFVF unit has an inner diameter of about 5 mm to about 5 cm (e.g., about 10 mm to about 3 cm). In some embodiments of these methods, the TFVF unit includes one or more tangential virus filter(s) having a surface area of about 0.1 $cm^2$ to about 100 $m^2$ (e.g., about 0.5 $cm^2$ to about 200 $cm^2$). In some embodiments of these methods, the connecting conduit has an inner diameter of about 5 mm to about 10 cm (e.g., about 10 mm to about 5 cm). In some embodiments of these methods, the second system further includes a pump (e.g., a peristaltic pump) disposed in the conduit in fluid communication between the first and second inlets of the TFVF unit.

Also provided are methods for processing a fluid including a recombinant therapeutic protein that include: (a) providing a circuit system including (i) a tangential flow virus filtration (TFVF) unit having first and second inlets, and (ii) a conduit in fluid communication between the first and second inlets of the TFVF unit, including at least one port for flowing fluid into or out of, or both, of the system, where the system is configured such that fluid can be flowed through the conduit and the TFVF unit, and filtrate including the recombinant therapeutic protein can be collected from the TFVF unit; (b) continuously flowing a fluid including a recombinant therapeutic protein into the circuit system through one of the at least one port, and collecting filtrate including the recombinant therapeutic protein from the TFVF unit for a period of time. In some embodiments of these methods, step (b) includes continuously flowing the fluid into the system at a rate of about 0.1 mL/minute to about 100 L/minute (e.g., about 0.5 mL/minute to about 200 mL/minute). In some embodiments of these methods, the period of time is about 5 minutes to about 12 hours (e.g., about 10 minutes to about 3 hours). In some embodiments of these methods, the flowing of the fluid into the system in step (b) occurs unidirectionally. In some embodiments of these methods, the conduit has an inner diameter of about 5 mm to about 5 cm (e.g., about 10 mm to about 3 cm). In some embodiments of these methods, the TFVF unit includes one or more tangential virus filter(s) having a surface area of about 0.1 $cm^2$ to about 100 $m^2$ (e.g., about 0.5 $cm^2$ to about 200 $cm^2$). In some embodiments of these methods, the system further includes a pump (e.g., a peristaltic pump) disposed in the conduit.

Also provided are integrated and continuous processes for manufacturing a therapeutic protein drug substance that include: (a) providing a liquid culture medium including a recombinant therapeutic protein that is substantially free of cells, where the liquid culture medium is fed into a first multi-column chromatography system (MCCS1); (b) capturing said recombinant therapeutic protein in the liquid culture medium using the MCCS1, where the eluate of the MCCS1 including the recombinant therapeutic protein is continuously fed into a second multi-column chromatography system (MCCS2); (c) purifying and polishing the recombinant therapeutic protein using the MCCS2, wherein the eluate from the MCCS2 is a fluid including the recombinant therapeutic protein; (d) processing the fluid including the recombinant therapeutic protein using a method of any methods described herein; where the process is integrated and runs continuously from said liquid culture medium to the collected fluid or filtrate including the recombinant therapeutic protein, where the collected fluid or filtrate is the therapeutic protein drug substance. In some embodiments of these processes, the MCCS1 performs at least two different unit operations. In some embodiments of these processes, the MCCS1 performs the unit operations of capturing the recombinant therapeutic protein and inactivating viruses. In some embodiments of these processes, the use of the MCCS1 or the MCCS2, or both, involves column switching. In some embodiments of these processes, the MCCS1 and/or MCCS2 utilizes at least two chromatography columns. In some embodiments of these processes, the MCCS1 and/or MCCS2 utilizes at least two chromatographic membranes. In some embodiments of these processes, the MCCS1 and/or MCCS2 utilizes at least one chromatography column and at least one chromatographic membrane. In some embodiments of these processes, the MCCS1 is a first periodic counter current chromatography system (PCCS1). In some embodiments of these processes, the PCCS1 includes a four-column PCCS. In some embodiments of these processes, three of the four columns in the four-column PCCS perform the unit operation of capturing the recombinant therapeutic protein from the liquid culture medium. In some embodiments of these processes, the capturing is performed using affinity chromatography, cation exchange chromatography, anion exchange chromatography, or molecular sieve chromatography. In some embodiments of these processes, the affinity chromatography is performed with a capture mechanism selected from the group of: protein A-binding capture mechanism, substrate-binding capture mechanism, antibody- or antibody fragment-binding capture mechanism, aptamer-binding capture mechanism, and cofactor-binding capture mechanism. In some embodiments of these processes, the affinity chromatography is performed with a protein A-binding capture mechanism, and the recombinant therapeutic protein is an antibody or an antibody fragment. In some embodiments of these processes, the eluate containing the recombinant therapeutic protein from three of the four columns in the four-column PCCS is fed into the fourth column of the four-column PCCS. In some embodiments of these processes, the fourth column of the four-column PCCS performs the unit operation of inactivating viruses by holding the eluate containing recombinant therapeutic protein at a low pH for viral inactivation. In some embodiments of these processes, the fourth column of the four-column PCCS holds the eluate containing the recombinant protein at a low pH for viral inactivation for a period of about 10 minutes to about 1.5 hours.

In some embodiments of these processes, the MCCS2 is a second periodic counter current chromatography system (PCCS2). Some embodiments of these processes further include adjusting the pH of the eluate from the fourth column of the four-column PCCS using an in-line buffer adjustment reservoir before the eluate from the fourth column of the four-column PCCS is fed into the PCCS2. In some embodiments of these processes, the PCCS2 includes three chromatography columns and a chromatographic membrane. In some embodiments of these processes, the three chromatographic columns in the PCCS2 perform the unit operation of purifying the recombinant therapeutic protein from the eluate of the PCCS1 through cation or anion exchange chromatography. In some embodiments of these processes, the eluate from the three chromatography columns in the PCCS2 is fed into the chromatographic membrane in the PCCS2. In some embodiments of these processes, the chromatographic membrane in the PCCS2 performs the unit operation of polishing the recombinant therapeutic protein present in the eluate from the three chromatographic columns in the PCCS2 through cation or anion exchange chromatography. In some embodiments of these processes, the chromatographic membrane in the PCCS2 performs the unit operation of polishing through cation exchange chromatography. In some embodiments of these processes, the flow through and wash of the chromatographic membrane includes the recombinant therapeutic protein. Some embodiments of these processes further include adjusting the ionic concentration of the eluate from the three columns in the PCCS2 using in-line buffer adjustment before the eluate from the three columns in the PCCS2 is fed into the chromatographic membrane in the PCCS2. Some embodiments of these processes further include the use of a break tank between the PCCS1 and the PCCS2. Some embodiments of these processes further include filtering the eluate from the PCCS1 before it is fed into the PCCS2. Some embodiments of these processes further include formulating the therapeutic protein drug substance into a pharmaceutical composition. In some embodiments of any of methods or processes described herein, the recombinant therapeutic protein is an antibody or antibody fragment, an enzyme, an engineered protein, or an immunogenic protein or protein fragment.

As used herein, the word "a" before a noun represents one or more of the particular noun. For example, the phrase "a mammalian cell" represents "one or more mammalian cells."

The terms "tangential flow filtration unit" or "TFF unit" are art-known and mean a device that includes at least one housing (such as a cylinder) and at least one cross-flow (tangential) filter positioned in the housing such that a large portion of the filter's surface is positioned parallel to the flow of a fluid (e.g., a cell culture) through the unit. TFF units are well-known in the art and are commercially available. The housing can include a first inlet/outlet and a second inlet/outlet positioned, e.g., to allow fluid to pass through the first inlet/outlet, cross the at least one cross-flow filter, and through the second inlet/outlet. In some examples, a circuit system can include multiple TFF units, e.g., connected in series and/or in parallel. For example, a circuit system that includes two or more TFF units can include fluid conduits fluidly connecting neighboring pairs of TFF units in the system. In other examples, a circuit system can include two or more sets of two or more TFF units fluidly connected by fluid conduits. Any of the TFF units described herein or known in the art are capable of receiving fluid in a first flow direction and a second flow direction.

The terms "tangential flow virus filtration unit" or "TFVF unit" are art-known and mean a device that includes at least one housing (such as a cylinder) and at least one cross-flow (tangential) virus filter positioned in the housing such that a large portion of the virus filter's surface is positioned parallel to the flow of a fluid (e.g., a cell culture) through the unit. The housing can include a first inlet/outlet and a second inlet/outlet positioned, e.g., to allow fluid to pass through the first inlet/outlet, cross the at least one cross-flow virus filter, and through the second inlet/outlet. In some examples, a circuit system can include multiple TFVF units, e.g., connected in series and/or in parallel. For example, a circuit system that includes two or more TFVF units can include fluid conduits fluidly connecting neighboring pairs of TFVF units in the system. In other examples, a circuit system can include two or more sets of two or more TFVF units fluidly connected by fluid conduits. Any of the TFVF units described herein or known in the art are capable of receiving fluid in a first flow direction and a second flow direction.

The term "cross-flow filter" or "tangential filter" is art known and means a filter that designed such that it can be positioned in a TFF or a TFVF unit such that a large portion of the filter's surface is parallel to the flow (e.g., first and second flow direction) of a fluid (e.g., a fluid including a recombinant therapeutic protein). For example, a cross-flow filter can have any shape that allows for tangential flow filtration, e.g., a tubular or rectangular shape. Particularly useful cross-flow filters are designed to result in a low amount of fluid turbulence or sheer stress in the fluid (e.g., cell culture) when the fluid is flowed (e.g., unidirectionally flowed to bidirectionally flowed) across the surface of the cross-flow filter. Cross-flow filters are commercially available, e.g., from Sartorius, MembraPure, Millipore, and Pall Corporation.

The term "low turbulence pump" or "LTP" is art-known and means a device that can move a fluid (e.g., a fluid including a recombinant therapeutic protein) within a system or circuit in a single direction (e.g., a first or second flow direction) or reversibly flowing a fluid (e.g., a fluid including a recombinant therapeutic protein) in two directions (a first and second flow direction) within the system without inducing a substantial amount of sheer stress or fluid turbulence in the fluid (e.g., a fluid including a recombinant therapeutic protein). When a LTP is used to flow a fluid (e.g., a fluid including a recombinant therapeutic protein) in alternating first and second flow directions, the second flow direction is approximately opposite to that of the first flow direction. An example of a LTP is a peristaltic pump. Other examples of LTPs are known in the art.

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. Additional examples of mammalian cells are known in the art.

The term "substantially free" means a composition (e.g., a liquid culture medium) that is at least or about 90% free (e.g., at least or about 95%, 96%, 97%, 98%, or at least or about 99% free, or about 100% free) of a specified substance (e.g., a mammalian cell).

The term "0.5× volume" means about 50% of the volume. The term "0.6× volume" means about 60% of the volume. Likewise, 0.7×, 0.8×, 0.9×, and 1.0× means about 70%, 80%, 90%, or 100% of the volume, respectively.

The term "culturing" or "cell culturing" means the maintenance or proliferation of a mammalian cell under a controlled set of physical conditions.

The term "culture of mammalian cells" means a liquid culture medium containing a plurality of mammalian cells that is maintained or proliferated under a controlled set of physical conditions.

The term "liquid culture medium" means a fluid that contains sufficient nutrients to allow a cell (e.g., a mammalian cell) to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Another example of liquid culture medium is minimal medium (e.g., a medium containing only inorganic salts, a carbon source, and water). Non-limiting examples of liquid culture medium are described herein. Additional examples of liquid culture medium are known in the art and are commercially available. A liquid culture medium can contain any density of mammalian cells. For example, as used herein, a volume of liquid culture medium removed from a bioreactor can be substantially free of mammalian cells.

The term "animal-derived component free liquid culture medium" means a liquid culture medium that does not contain any components (e.g., proteins or serum) derived from a mammal.

The term "serum-free liquid culture medium" means a liquid culture medium that does not contain a mammalian serum.

The term "serum-containing liquid culture medium" means a liquid culture medium that contains a mammalian serum.

The term "chemically-defined liquid culture medium" is a term of art and means a liquid culture medium in which all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

The term "agitation" means stirring or otherwise moving a portion of liquid culture medium in a bioreactor. This is performed in order to, e.g., increase the dissolved $O_2$ concentration in the liquid culture medium in a bioreactor. Agitation can be performed using any art known method, e.g., an instrument or propeller. Exemplary devices and methods that can be used to perform agitation of a portion of the liquid culture medium in a bioreactor are known in the art.

The term "therapeutic protein drug substance" means a recombinant protein (e.g., an immunoglobulin, protein fragment, engineered protein, or enzyme) that has been sufficiently purified or isolated from contaminating proteins, lipids, and nucleic acids (e.g., contaminating proteins, lipids, and nucleic acids present in a liquid culture medium or from a host cell (e.g., from a mammalian, yeast, or bacterial host cell)) and biological contaminants (e.g., viral and bacterial contaminants), and can be formulated into a pharmaceutical agent without any further substantial purification and/or decontamination step.

The term "integrated process" means a process which is performed using structural elements that function cooperatively to achieve a specific result (e.g., the generation of a therapeutic protein drug substance from a liquid culture medium).

The term "continuous process" means a process which continuously feeds fluid through at least a part of the system. For example, in any of the exemplary continuous biological manufacturing systems described herein, a liquid culture medium containing a recombinant therapeutic protein is continuously fed into the system while it is in operation and a therapeutic protein drug substance is fed out of the system. In another example, a continuous process is a process which continuously feeds a liquid culture medium containing a recombinant therapeutic protein from a bioreactor through a first MCCS. Another example of a continuous process is a process which continuously feeds a liquid culture medium containing a recombinant therapeutic protein from a bioreactor through a first and second MCCS. Additional examples include a process which continuously feeds a liquid culture medium containing a recombinant therapeutic protein through a first MCCS, a process that continuously feeds a liquid culture medium containing a recombinant therapeutic protein through a first and second MCCS, or a process that continuously feeds a fluid containing a recombinant therapeutic protein through a second MCCS.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')2 fragment, or an scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) containing a total of two or more interconnected or switching chromatography columns and/or chromatographic membranes. Additional examples of multi-column chromatography systems are described herein and are known in the art.

The term "capturing" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight), concentrate, and stabilize a recombinant therapeutic protein from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a recombinant therapeutic protein (e.g., through the use of affinity chromatography). Non-limiting methods for capturing a recombinant therapeutic protein from a liquid culture medium or diluted liquid culture medium are described herein and others are known in the art. A recombinant therapeutic protein can be captured from a liquid culture medium using at least one chromatography column and/or chromatographic membrane (e.g., any of the chromatography columns and/or chromatographic membranes described herein).

The term "purifying" means a step performed to isolate a recombinant therapeutic protein from one or more other impurities (e.g., bulk impurities) or components present in a fluid containing a recombinant therapeutic protein (e.g., liquid culture medium proteins or one or more other components (e.g., DNA, RNA, other proteins, endotoxins, viruses, etc.) present in or secreted from a mammalian cell). For example, purifying can be performed during or after an initial capturing step. Purification can be performed using a resin, membrane, or any other solid support that binds either a recombinant therapeutic protein or contaminants (e.g., through the use of affinity chromatography, hydrophobic interaction chromatography, anion or cation exchange chromatography, or molecular sieve chromatography). A recombinant therapeutic protein can be purified from a fluid containing the recombinant therapeutic protein using at least one chromatography column and/or chromatographic membrane (e.g., any of the chromatography columns or chromatographic membranes described herein).

The term "polishing" is a term of art and means a step performed to remove remaining trace or small amounts of contaminants or impurities from a fluid containing a recombinant therapeutic protein that is close to a final desired purity. For example, polishing can be performed by passing a fluid containing the recombinant therapeutic protein through a chromatographic column(s) or membrane absorber(s) that selectively binds to either the target recombinant therapeutic protein or small amounts of contaminants or impurities present in a fluid containing a recombinant therapeutic protein. In such an example, the eluate/filtrate of the chromatographic column(s) or membrane absorber(s) contains the recombinant therapeutic protein.

The term "eluate/filtrate" is a term of art and means a fluid that is emitted from a chromatography column or chromatographic membrane that contains a detectable amount of a recombinant therapeutic protein.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein.

The term "perfusion bioreactor" means a bioreactor containing a plurality of cells (e.g., mammalian cells) in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch bioreactor" is a term of art and means a bioreactor containing a plurality of cells (e.g., mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

The term "clarified liquid culture medium" means a liquid culture medium obtained from a bacterial or yeast cell culture that is substantially free (e.g., at least 80%, 85%, 90%, 92%, 94%, 96%, 98%, or 99% free) of bacteria or yeast cells.

The term "unit operation" is a term of art and means a functional step that can be performed in a process of manufacturing a therapeutic protein drug substance from a liquid culture medium. For example, a unit of operation can be filtering (e.g., removal of contaminant bacteria, yeast viruses, or mycobacteria, and/or particular matter from a fluid containing a recombinant therapeutic protein), capturing, epitope tag removal, purifying, holding or storing, polishing, viral inactivating, adjusting the ionic concentration and/or pH of a fluid containing the recombinant therapeutic protein, and removing unwanted salts.

"Specific productivity rate" or "SPR" is a term of art and as used herein refers to the mass or enzymatic activity of a recombinant therapeutic protein produced per mammalian cell per day. The SPR for a recombinant therapeutic antibody is usually measured as mass/cell/day. The SPR for a recombinant therapeutic enzyme is usually measured as units/cell/day or (units/mass)/cell/day.

"Volume productivity rate" or "VPR" is a term of art and as used herein refers to the mass or enzymatic activity of recombinant therapeutic protein produced per volume of culture (e.g., per L of bioreactor, vessel, or tube volume) per day. The VPR for a recombinant therapeutic antibody is usually measured as mass/L/day. The VPR for a recombinant therapeutic enzyme is usually measured as units/L/day or mass/L/day.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
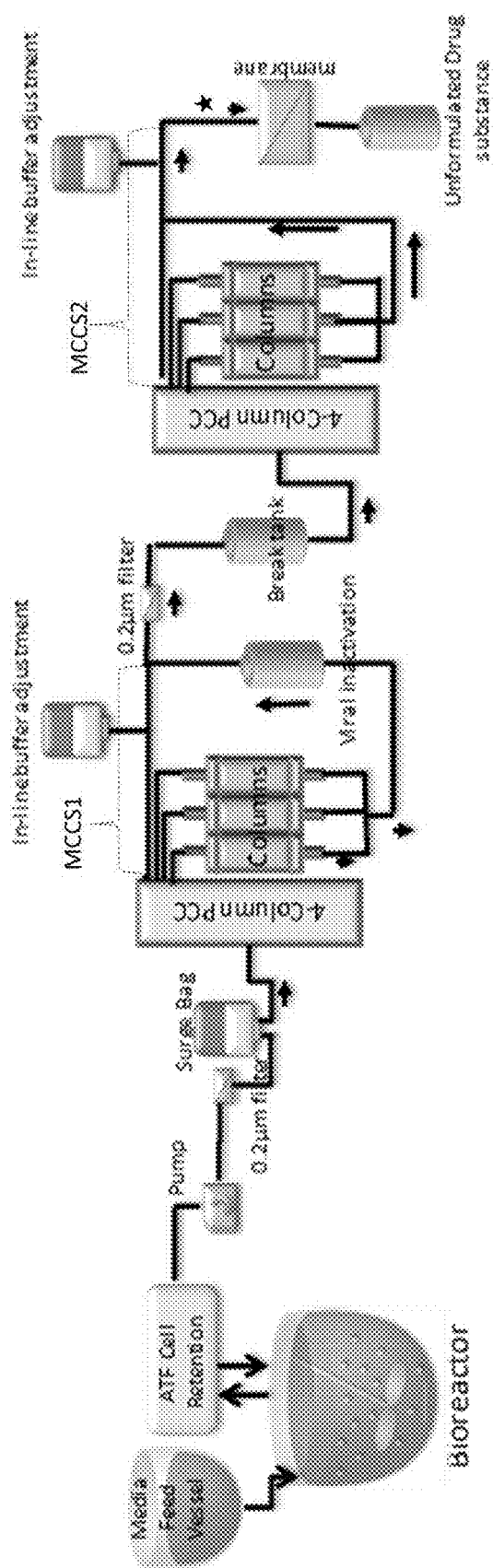
FIG. 1 is a schematic showing a two-PCCS manufacturing system connected with a perfusion culture bioreactor that results in the continuous manufacture of a therapeutic protein drug substance. The asterisk indicates an exemplary position where one or both of a circuit system including a tangential flow filtration (TFF) unit (e.g., any of the circuit systems including a TFF unit described herein) and a circuit system including a tangential flow virus filtration (TFVF) unit (e.g., any of the circuit systems including a TFVF unit described herein) can be positioned in this exemplary manufacturing system.

Provided herein are methods of processing a fluid including a recombinant therapeutic protein that include (a) providing a circuit system including (i) a tangential flow filtration (TFF) unit having first and second inlets, and (ii) a conduit in fluid communication between the first and second inlets, including at least one port for flowing fluid into or out of, or both, of the system, where the system is configured such that fluid can be flowed through the conduit and the TFF unit, and filtrate not including the recombinant therapeutic protein can be collected from the TFF unit; (b) continuously flowing a fluid including a recombinant therapeutic protein into the circuit system through one of the at least one port, and discarding filtrate not including the recombinant therapeutic protein for a first period of time; (c) continuously flowing a diafiltration medium into the circuit system through one of the at least one port, and discarding filtrate not including the recombinant therapeutic protein for a second period of time; and (d) collecting a fluid including the recombinant therapeutic protein that is present in the circuit system after the first and second time periods through one of the at least one port. Also provided are methods of processing a fluid including a recombinant therapeutic protein that include: (a) providing a circuit system including (i) a tangential flow virus filtration (TFVF) unit having first and second inlets, and (ii) a conduit in fluid communication between the first and second inlets of the TFVF unit, including at least one port for flowing fluid into or out of, or both, of the system, where the system is configured such that fluid can be flowed through the conduit and the TFVF unit, and filtrate including the recombinant therapeutic protein can be collected from the TFVF unit; and (b) continuously flowing a fluid including a recombinant therapeutic protein into the circuit system through one of the at least one port, and collecting filtrate comprising the recombinant therapeutic protein from the TFVF unit for a period of time. As can be appreciated by those skilled in the art, some embodiments of these methods can further include recirculating any fluid including the recombinant therapeutic protein in the conduit of the circuit system including a TFVF unit that did not pass through the one or more tangential virus filters in the TFVF unit (e.g., acts as a buffer when a new volume of a fluid including the recombinant therapeutic protein is flowed into the conduit of the circuit system including a TFVF unit).

Also provided are integrated and continuous processes for manufacturing a therapeutic protein drug substance that include: (a) providing a liquid culture medium including a recombinant therapeutic protein that is substantially free of cells, wherein the liquid culture medium is fed into a first multi-column chromatography system (MCCS1); (b) capturing the recombinant therapeutic protein in the liquid culture medium using the MCCS1, where the eluate of the MCCS1 containing the recombinant therapeutic protein is continuously fed into a second multi-column chromatography system (MCCS2); (c) purifying and polishing the recombinant therapeutic protein using the MCCS2, where the eluate from the MCCS2 is a fluid including the recombinant therapeutic protein; (d) processing the fluid including the recombinant therapeutic protein using a method of any of the methods described herein, where the process is integrated and runs continuously from said liquid culture medium to the collected fluid or filtrate comprising the recombinant therapeutic protein, wherein the collected fluid or filtrate is the therapeutic protein drug substance.

Methods of Processing a Fluid Including a Recombinant Therapeutic Protein that Include the Use of a Circuit System Including a TFF Unit Provided herein are methods of processing a fluid including a recombinant therapeutic protein that include: providing a circuit system including: (a) a tangential flow filtration (TFF) unit having first and second inlets, and (ii) a conduit in fluid communication between the first and second inlets, including at least one port for flowing fluid into or out of, or both, of the system; (b) continuously flowing a fluid including a recombinant therapeutic protein into the circuit system through one of the at least one port, and discarding filtrate not including the recombinant therapeutic protein for a first period of time; (c) continuously flowing a diafiltration medium into the circuit system through one of the at least one port, and discarding filtrate not including the recombinant therapeutic protein for a second period of time; and (d) collecting a fluid including the recombinant therapeutic protein that is present in the circuit system after the first and second time points through one of the at least one port. As can be appreciated by those skilled in the art, some embodiments of these methods include recirculating any fluid including the recombinant therapeutic protein in the conduit of the circuit system including a TFF unit that did not pass through the one or more tangential filters in the TFF unit (e.g., acts as a buffer when a new volume of a fluid including the recombinant therapeutic protein and/or a diafiltration medium is flowed into the conduit of the circuit system including a TFF unit).

In some embodiments, the TFF unit includes one, two, three, four, five, six, seven, eight, nine, ten, eleven, or twelve tangential filters. In some examples of these methods, the TFF unit can include one or more tangential filter(s) having a surface area of about 0.05 $cm^2$ to about 50 $cm^2$, about 48 $cm^2$, about 46 $cm^2$, about 44 $cm^2$, about 42 $cm^2$, about 40 $cm^2$, about 38 $cm^2$, about 36 $cm^2$, about 34 $cm^2$, about 32 $cm^2$, about 30 $cm^2$, about 28 $cm^2$, about 26 $cm^2$, about 24 $cm^2$, about 22 $cm^2$, about 20 $cm^2$, about 18 $cm^2$, about 16 $cm^2$, about 14 $cm^2$, about 12 $cm^2$, about 10 $cm^2$, about 9.5 $cm^2$, about 9.0 $cm^2$, about 8.5 $cm^2$, about 8.0 $cm^2$, about 7.5 $cm^2$, about 7.0 $cm^2$, about 6.5 $cm^2$, about 6.0 $cm^2$, about 5.5 $cm^2$, about 5.0 $cm^2$, about 4.5 $cm^2$, about 4.0 $cm^2$, about 3.5 $cm^2$, about 3.0 $cm^2$, about 2.5 $cm^2$, about 2.0 $cm^2$, about 1.5 $cm^2$, about 1.0 $cm^2$, about 0.5 $cm^2$, or about 0.1 $cm^2$; about 0.1 $cm^2$ to about 50 $cm^2$, about 48 $cm^2$, about 46 $cm^2$, about 44 $cm^2$, about 42 $cm^2$, about 40 $cm^2$, about 38 $cm^2$, about 36 $cm^2$, about 34 $cm^2$, about 32 $cm^2$, about 30 $cm^2$, about 28 $cm^2$, about 26 $cm^2$, about 24 $cm^2$, about 22 $cm^2$, about 20 $cm^2$, about 18 $cm^2$, about 16 $cm^2$, about 14 $cm^2$, about 12 $cm^2$, about 10 $cm^2$, about 9.5 $cm^2$, about 9.0 $cm^2$, about 8.5 $cm^2$, about 8.0 $cm^2$, about 7.5 $cm^2$, about 7.0 $cm^2$, about 6.5 $cm^2$, about 6.0 $cm^2$, about 5.5 $cm^2$, about 5.0 $cm^2$, about 4.5 $cm^2$, about 4.0 $cm^2$, about 3.5 $cm^2$, about 3.0 $cm^2$, about 2.5 $cm^2$, about 2.0 $cm^2$, about 1.5 $cm^2$, about 1.0 $cm^2$, or about 0.5 $cm^2$; about 0.5 $cm^2$ to about 50 $cm^2$, about 48 $cm^2$, about 46 $cm^2$, about 44 $cm^2$, about 42 $cm^2$, about 40 $cm^2$, about 38 $cm^2$, about 36 $cm^2$, about 34 $cm^2$, about 32 $cm^2$, about 30 $cm^2$, about 28 $cm^2$, about 26 $cm^2$, about 24 $cm^2$, about 22 $cm^2$, about 20 $cm^2$, about 18 $cm^2$, about 16 $cm^2$, about 14 $cm^2$, about 12 $cm^2$, about 10 $cm^2$, about 9.5 $cm^2$, about 9.0 $cm^2$, about 8.5 $cm^2$, about 8.0 $cm^2$, about 7.5 $cm^2$, about 7.0 $cm^2$, about 6.5 $cm^2$, about 6.0 $cm^2$, about 5.5 $cm^2$, about 5.0 $cm^2$, about 4.5 $cm^2$, about 4.0 $cm^2$, about 3.5 $cm^2$, about 3.0 $cm^2$, about 2.5 $cm^2$, about 2.0 $cm^2$, about 1.5 $cm^2$, or about 1.0 $cm^2$; about 1.0 $cm^2$ to about 50 $cm^2$, about 48 $cm^2$, about 46 $cm^2$, about 44 $cm^2$, about 42 $cm^2$, about 40 $cm^2$, about 38 $cm^2$, about 36 $cm^2$, about 34 $cm^2$, about 32 $cm^2$, about 30 $cm^2$, about 28 $cm^2$, about 26 $cm^2$, about 24 $cm^2$, about 22 $cm^2$, about 20 $cm^2$, about 18 $cm^2$, about 16 $cm^2$, about 14 $cm^2$, about 12 $cm^2$, about 10 $cm^2$, about 9.5 $cm^2$, about 9.0 $cm^2$, about 8.5 $cm^2$, about 8.0 $cm^2$, about 7.5 $cm^2$, about 7.0 $cm^2$, about 6.5 $cm^2$, about 6.0 $cm^2$, about 5.5 $cm^2$, about 5.0 $cm^2$, about 4.5 $cm^2$, about 4.0 $cm^2$, about 3.5 $cm^2$, about 3.0 cm², about 2.5 cm², about 2.0 cm², about 1.5 cm²; about 1.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², about 3.5 cm², about 3.0 cm², about 2.5 cm², or about 2.0 cm²; about 2.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², about 3.5 cm², about 3.0 cm², or about 2.5 cm²; about 2.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², about 3.5 cm², or about 3.0 cm²; about 3.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², or about 3.5 cm²; about 3.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², or about 4.0 cm²; about 4.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², or about 4.5 cm²; about 4.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², or about 5.0 cm²; about 5.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², or about 5.5 cm²; about 5.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², or about 6.0 cm²; about 6.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², or about 6.5 cm²; about 6.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², or about 7.0 cm²; about 7.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², or about 7.5 cm²; about 7.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², or about 8.0 cm²; about 8.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², or about 8.5 cm²; about 8.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², or about 9.0 cm²; about 9.0 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², or about 9.5 cm²; about 9.5 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², or about 10 cm²; about 10 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², or about 12 cm²; about 12 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², or about 14 cm²; about 14 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², or about 16 cm²; about 16 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², or about 18 cm²; about 18 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², or about 20 cm²; about 20 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², or about 22 cm²; about 22 cm² to about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², or about 24 cm²; about 24 cm² to about 50 cm², about 48 cm², about 46 cm², about 44 cm², about 42 cm², about 40 cm², about 38 cm², about 36 cm², about 34 cm², about 32 cm², about 30 cm², about 28 cm², or about 26 cm²; about 26 cm² to about 50 cm², about 48 cm², about 46 cm², about 44 cm², about 42 cm², about 40 cm², about 38 cm², about 36 cm², about 34 cm², about 32 cm², about 30 cm², or about 28 cm²; about 28 cm² to about 50 cm², about 48 cm², about 46 cm², about 44 cm², about 42 cm², about 40 cm², about 38 cm², about 36 cm², about 34 cm², about 32 cm², or about 30 cm²; about 30 cm² to about 50 cm², about 48 cm², about 46 cm², about 44 cm², about 42 cm², about 40 cm², about 38 cm², about 36 cm², about 34 cm², or about 32 cm²; about 32 cm² to about 50 cm², about 48 cm², about 46 cm², about 44 cm², about 42 cm², about 40 cm², about 38 cm², about 36 cm², or about 34 cm²; about 34 cm² to about 50 cm², about 48 cm², about 46 cm², about 44 cm², about 42 cm², about 40 cm², about 38 cm², or about 36 cm²; about 36 cm² to about 50 cm², about 48 cm², about 46 cm², about 44 cm², about 42 cm², about 40 cm², or about 38 cm²; about 38 cm² to about 50 cm², about 48 cm², about 46 cm², about 44 cm², about 42 cm², or about 40 cm²; about 40 cm² to about 50 cm², about 48 cm², about 46 cm², about 44 cm², or about 42 cm²; about 42 cm² to about 50 cm², about 48 cm², about 46 cm², or about 44 cm²; about 44 cm² to about 50 cm², about 48 cm², or about 46 cm²; about 46 cm² to about 50 cm² or about 48 cm²; or about 48 cm² to about 50 cm².

In some embodiments, the one or more tangential filters in the TFF unit can have a molecular weight cut-off of about 1 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, about 150 kDa, about 100 kDa, about 80 kDa, about 60 kDa, about 40 kDa, about 20 kDa, about 10 kDa, or about 5 kDa; about 5 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, about 150 kDa, about 100 kDa, about 80 kDa, about 60 kDa, about 40 kDa, about 20 kDa, or about 10 kDa; about 10 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, about 150 kDa, about 100 kDa, about 80 kDa, about 60 kDa, about 40 kDa, or about 20 kDa; about 20 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, about 150 kDa, about 100 kDa, about 80 kDa, about 60 kDa, or about 40 kDa; about 40 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, about 150 kDa, about 100 kDa, about 80 kDa, or about 60 kDa; about 60 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, about 150 kDa, about 100 kDa, or about 80 kDa; about 80 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, about 150 kDa, or about 100 kDa; about 100 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, about 200 kDa, or about 150 kDa; about 150 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, about 250 kDa, or about 200 kDa; about 200 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, about 300 kDa, or about 250 kDa; about 250 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, about 350 kDa, or about 300 kDa; about 300 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, about 400 kDa, or about 350 kDa; about 350 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, about 450 kDa, or about 400 kDa; about 400 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, about 500 kDa, or about 450 kDa; about 450 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, about 550 kDa, or about 500 kDa; about 500 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, about 600 kDa, or about 550 kDa; about 550 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, about 650 kDa, or about 600 kDa; about 600 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, about 700 kDa, or about 650 kDa; about 650 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, about 750 kDa, or about 700 kDa; about 700 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, about 800 kDa, or about 750 kDa; about 750 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, about 850 kDa, or about 800 kDa; about 800 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, about 900 kDa, or about 850 kDa; about 850 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, about 950 kDa, or about 900 kDa; about 900 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, about 1,000 kDa, or about 950 kDa; about 950 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, about 1,400 kDa, about 1,200 kDa, or about 1,000 kDa; about 1,000 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, or about 1,400 kDa; about 1,200 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, about 1,600 kDa, or about 1,400 kDa; about 1,400 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, about 1,800 kDa, or about 1,600 kDa; about 1,600 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, about 2,000 kDa, or about 1,800 kDa; about 1,800 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, about 4,000 kDa, or about 2,000 kDa; about 2,000 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, about 6,000 kDa, or about 4,000 kDa; about 4,000 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, about 8,000 kDa, or about 6,000 kDa; about 6,000 kDa to about 25,000 kDa, about 24,000 kDa, about 22,000 kDa, about 20,000 kDa, about 18,000 kDa, about 16,000 kDa, about 14,000 kDa, about 12,000 kDa, about 10,000 kDa, or about 8,000 kDa; about 8,000 kDa to about 25,000 kDa, about 24,000 kDa, about 22,000 kDa, about 20,000 kDa, about 18,000 kDa, about 16,000 kDa, about 14,000 kDa, about 12,000 kDa, or about 10,000 kDa; about 10,000 kDa to about 25,000 kDa, about 24,000 kDa, about 22,000 kDa, about 20,000 kDa, about 18,000 kDa, about 16,000 kDa, about 14,000 kDa, or about 12,000 kDa; about 12,000 kDa to about 25,000 kDa, about 24,000 kDa, about 22,000 kDa, about 20,000 kDa, about 18,000 kDa, about 16,000 kDa, or about 14,000 kDa; about 14,000 kDa to about 25,000 kDa, about 24,000 kDa, about 22,000 kDa, about 20,000 kDa, about 18,000 kDa, or about 16,000 kDa; about 16,000 kDa to about 25,000 kDa, about 24,000 kDa, about 22,000 kDa, about 20,000 kDa, or about 18,000 kDa; about 18,000 kDa to about 25,000 kDa, about 24,000 kDa, about 22,000 kDa, or about 20,000 kDa; about 20,000 kDa to about 25,000 kDa, about 24,000 kDa, or about 22,000 kDa; about 22,000 kDa to about 25,000 kDa or about 24,000 kDa; or about 23,000 kDa to about 25,000 kDa. In some embodiments, the TFF unit includes one or more tangential filters made of, e.g., cellulose (e.g., regenerated cellulose) or polyethersulfone. Non-limiting examples of one or more tangential filters that can be used in the TFF unit are commercially available from Millipore (e.g., Ultracel® and Biomax®). Additional commercial sources of one or more tangential filters that can be used in the TFF unit are known in the art.

The conduit can be simple tubing, e.g., biocompatible tubing. Non-limiting examples of useful tubing include silicone rubber, polyurethane, polydioxanone (PDO), polyhydroxyalkanoate, polyhydroxybutyrate, poly(glycerol sebacate), polyglycolide, polylactide, polycaprolactone, or polyanhydride, or copolymers or derivatives including these and/or other polymers. Alternatively or in addition, any of the conduits described herein can include polyvinyl chloride. A conduit can be, e.g., weldable transfer tubing.

In some embodiments, the internal diameter of the conduit can be about 5 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, about 12 mm, about 10 mm, about 8 mm, or about 6 mm; about 6 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, about 12 mm, about 10 mm, or about 8 mm; about 8 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, about 12 mm, or about 10 mm; about 10 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, or about 12 mm; about 12 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, or about 14 mm; about 14 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, or about 16 mm; about 16 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, or about 18 mm; about 18 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, or about 20 mm; about 20 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, or about 22 mm; about 22 mm to about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, or about 24 mm; about 24 mm to about 50 mm, about 48 mm, about 46 mm, about 44 mm, about 42 mm, about 40 mm, about 38 mm, about 36 mm, about 34 mm, about 32 mm, about 30 mm, about 28 mm, or about 26 mm; about 26 mm to about 50 mm, about 48 mm, about 46 mm, about 44 mm, about 42 mm, about 40 mm, about 38 mm, about 36 mm, about 34 mm, about 32 mm, about 30 mm, or about 28 mm; about 28 mm to about 50 mm, about 48 mm, about 46 mm, about 44 mm, about 42 mm, about 40 mm, about 38 mm, about 36 mm, about 34 mm, about 32 mm, or about 30 mm; about 30 mm to about 50 mm, about 48 mm, about 46 mm, about 44 mm, about 42 mm, about 40 mm, about 38 mm, about 36 mm, about 34 mm, or about 32 mm; about 32 mm to about 50 mm, about 48 mm, about 46 mm, about 44 mm, about 42 mm, about 40 mm, about 38 mm, about 36 mm, or about 34 mm; about 34 mm to about 50 mm, about 48 mm, about 46 mm, about 44 mm, about 42 mm, about 40 mm, about 38 mm, or about 36 mm; about 36 mm to about 50 mm, about 48 mm, about 46 mm, about 44 mm, about 42 mm, about 40 mm, to about 38 mm; about 38 mm to about 50 mm, about 48 mm, about 46 mm, about 44 mm, about 42 mm, or about 40 mm; about 40 mm to about 50 mm, about 48 mm, about 46 mm, about 44 mm, or about 42 mm; about 42 mm to about 50 mm, about 48 mm, about 46 mm, or about 44 mm; about 44 mm to about 50 mm, about 48 mm, or about 46 mm; about 46 mm to about 50 mm or about 48 mm; or about 48 mm to about 50 mm.

In some embodiments, the conduit has a total length of about 1.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, about 8.0 cm, about 6.0 cm, about 4.0 cm, or about 2.0 cm; about 2.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, about 8.0 cm, about 6.0 cm, or about 4.0 cm; about 4.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, about 8.0 cm, or about 6.0 cm; about 6.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, or about 8.0 cm; about 8.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, or about 10 cm; about 10 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, or about 12 cm; about 12 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, or about 14 cm; about 14 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, or about 16 cm; about 16 cm to about 75 cm, about 70 cm, about 65 cm, about 60 cm, about 55 cm, about 50 cm, about 45 cm, about 40 cm, about 35 cm, about 30 cm, about 25 cm, about 20 cm, or about 18 cm; about 18 cm to about 75 cm, about 70 cm, about 65 cm, about 60 cm, about 55 cm, about 50 cm, about 45 cm, about 40 cm, about 35 cm, about 30 cm, about 25 cm, or about 20 cm; about 20 cm to about 75 cm, about 70 cm, about 65 cm, about 60 cm, about 55 cm, about 50 cm, about 45 cm, about 40 cm, about 35 cm, about 30 cm, or about 25 cm; about 25 cm to about 75 cm, about 70 cm, about 65 cm, about 60 cm, about 55 cm, about 50 cm, about 45 cm, about 40 cm, about 35 cm, or about 30 cm; about 30 cm to about 75 cm, about 70 cm, about 65 cm, about 60 cm, about 55 cm, about 50 cm, about 45 cm, about 40 cm, or about 35 cm; about 35 cm to about 75 cm, about 70 cm, about 65 cm, about 60 cm, about 55 cm, about 50 cm, about 45 cm, or about 40 cm; about 40 cm to about 75 cm, about 70 cm, about 65 cm, about 60 cm, about 55 cm, about 50 cm, or about 45 cm; about 45 cm to about 75 cm, about 70 cm, about 65 cm, about 60 cm, about 55 cm, or about 50 cm; about 50 cm to about 75 cm, about 70 cm, about 65 cm, about 60 cm, or about 55 cm; about 55 cm to about 75 cm, about 70 cm, about 65 cm, or about 60 cm; about 60 cm to about 75 cm, about 70 cm, or about 65 cm; about 65 cm to about 75 cm or about 70 cm; or about 70 cm to about 75 cm.

Additional examples of conduits and properties of conduits that can be used in the circuit system are well-known by those in the art.

In some examples, the circuit system includes one, two, three, four, or five ports. In some examples, the at least one port can be a valve. In other examples, the at least one port can be an injection port or can have a ribbed threading. The at least one port can be any type of port commonly known in the art.

In some examples, the circuit system can further include a pump (e.g., a low-turbulence pump, e.g., a peristaltic pump) disposed in the conduit.

In some examples, step (b) includes continuously flowing (e.g., unidirectionally or bidirectionally flowing) the fluid including the recombinant therapeutic protein into the circuit system at a rate of between about 0.05 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, about 1.0 mL/minute, about 0.5 mL/minute, or about 0.1 mL/minute; about 0.1 mL/minute to about 100 L/minute, about 90

L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, about 1.0 mL/minute, or about 0.5 mL/minute; about 0.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, or about 1.0 mL/minute; about 1.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, or about 1.5 mL/minute; about 1.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, or about 2.0 mL/minute; about 2.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, or about 2.5 mL/minute; about 2.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, or about 3.0 mL/minute; about 3.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, or about 3.5 mL/minute; about 3.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, or about 4.0 mL/minute; about 4.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, or about 4.5 mL/minute; about 4.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, or about 5.0 mL/minute; about 5.0 mL/minute to about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, or about 5.5 mL/minute; about 5.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, or about 6.0 mL/minute; about 6.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, or about 6.5 mL/minute; about 6.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, or about 7.0 mL/minute; about 7.0 mL/minute to about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, or about 7.5 mL/minute; about 7.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, or about 8.0 mL/minute; about 8.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, or about 8.5 mL/minute; about 8.5 mL/minute to about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, or about 9.0 mL/minute; about 9.0 mL/minute to about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, or about 9.5 mL/minute; about 9.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, or about 10 mL/minute; about 10 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, or about 14 mL/minute; about 14 mL/minute to about 25 mL/minute, about 24 mL/minute, about 22 mL/minute, about 20 mL/minute, about 18 mL/minute, or about 16 mL/minute; about 16 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, or about 18 mL/minute; about 18 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, or about 20 mL/minute; about 20 mL/minute to about 100 L/minute, about 90

L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, or about 22 mL/minute; about 22 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute or about 24 mL/minute; about 23 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, or about 25 mL/minute; about 25 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, or about 50 mL/minute; about 50 mL to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, or about 100 mL/minute; about 100 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, or about 150 mL/minute; about 150 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, or about 200 mL/minute; about 200 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, or about 250 mL/minute; about 250 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, or about 300 mL/minute; about 300 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, or about 350 mL/minute; about 350 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, or about 400 mL/minute; about 400 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, or about 450 mL/minute; about 450 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, or about 500 mL/minute; about 500 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, or about 550 mL/minute; about 550 mL to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, or about 600 mL/minute; about 600 mL to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, or about 650 mL/minute; about 650 mL to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, or about 700 mL/minute; about 700 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, or about 750 mL/minute; about 750 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, or about 800 mL/minute; about 800 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, or about 850 mL/minute; about 850 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, or about 900 mL/minute; about 900 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, or about 950 mL/minute; about 950 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, or about 1 L/minute; about 1 L/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, or about 5 L/minute; about 5 L/minute to about 100 L/minute, about 90 L/minute, about 80 L/minute, about 70 L/minute, about 60 L/minute, about 50 L/minute, about 40 L/minute, about 30 L/minute, about 20 L/minute, or about 10 L/minute; about 10 L/minute to about 100 L/minute, about 90 L/minute, about 80 L/minute, about 70 L/minute, about 60 L/minute, about 50 L/minute, about 40 L/minute, about 30 L/minute, or about 20 L/minute; about 20 L/minute to about 100 L/minute, about 90 L/minute, about 80 L/minute, about 70 L/minute, about 60 L/minute, about 50 L/minute, about 40 L/minute, or about 30 L/minute; about 30 L/minute to about 100 L/minute, about 90 L/minute, about 80 L/minute, about 70 L/minute, about 60 L/minute, about 50 L/minute, or about 40 L/minute; about 40 L/minute to about 100 L/minute, about 90 L/minute, about 80 L/minute, about 70 L/minute, about 60 L/minute, or about 50 L/minute; about 50 L/minute to about 100 L/minute, about 90 L/minute, about 80 L/minute, about 70 L/minute, or about 60 L/minute; about 60 L/minute to about 100 L/minute, about 90 L/minute, about 80 L/minute, or about 70 L/minute; about 70 L/minute to about 100 L/minute, about 90 L/minute, or about 80 L/minute; about 80 L/minute to about 100 L/minute, or about 90 L/minute; or about 90 L/minute to about 100 L/minute.

In some examples, step (b) includes continuously flowing (e.g., unidirectionally or bidirectionally flowing) a fluid including about 0.01 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, about 3.0 mg/mL, about 2.5 mg/mL, about 2.0 mg/mL, about 1.5 mg/mL, about 1.0 mg/mL, about 0.5 mg/mL, about 0.1 mg/mL, or about 0.05 mg/mL; about 0.05 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, about 3.0 mg/mL, about 2.5 mg/mL, about 2.0 mg/mL, about 1.5 mg/mL, about 1.0 mg/mL, about 0.5 mg/mL, or about 0.1 mg/mL; about 0.1 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, about 3.0 mg/mL, about 2.5 mg/mL, about 2.0 mg/mL, about 1.5 mg/mL, about 1.0 mg/mL, or about 0.5 mg/mL; about 0.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, about 3.0 mg/mL, about 2.5 mg/mL, about 2.0 mg/mL, about 1.5 mg/mL, or about 1.0 mg/mL; about 1.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, about 3.0 mg/mL, about 2.5 mg/mL, about 2.0 mg/mL, or about 1.5 mg/mL; about 1.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, about 3.0 mg/mL, about 2.5 mg/mL, or about 2.0 mg/mL; about 2.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, about 3.0 mg/mL, or about 2.5 mg/mL; about 2.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, about 3.5 mg/mL, or about 3.0 mg/mL; about 3.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, about 4.0 mg/mL, or about 3.5 mg/mL; about 3.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, about 5.0 mg/mL, about 4.5 mg/mL, or about 4.0 mg/mL; about 4.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, or about 4.5 mg/mL; about 4.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, about 5.5 mg/mL, or about 5.0 mg/mL; about 5.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, about 6.0 mg/mL, or about 5.5 mg/mL; about 5.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, about 6.5 mg/mL, or about 6.0 mg/mL; about 6.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, about 7.0 mg/mL, or about 6.5 mg/mL; about 6.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, about 7.5 mg/mL, or about 7.0 mg/mL; about 7.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, about 8.0 mg/mL, or about 7.5 mg/mL; about 7.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, about 8.5 mg/mL, or about 8.0 mg/mL; about 8.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, about 9.0 mg/mL, or about 8.5 mg/mL; about 8.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, 9.5 mg/mL, or about 9.0 mg/mL; about 9.0 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, or 9.5 mg/mL; about 9.5 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, or about 10 mg/mL; about 10 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, or about 12 mg/mL; about 12 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, or about 14 mg/mL; about 14 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, or about 16 mg/mL; about 16 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, or about 18 mg/mL; about 18 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, or about 20 mg/mL; about 20 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, or about 22 mg/mL; about 22 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, or about 24 mg/mL; about 24 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, or about 26 mg/mL; about 26 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, or about 28 mg/mL; about 28 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, or about 30 mg/mL; about 30 mg/mL to about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, or about 32 mg/mL; about 32 mg/mL to about 50 mg/mL, about 48 mg/mL, about 46 mg/mL, about 44 mg/mL, about 42 mg/mL, about 40 mg/mL, about 38 mg/mL, about 36 mg/mL, or about 34 mg/mL; about 34 mg/mL to about 50 mg/mL, about 48 mg/mL, about 46 mg/mL, about 44 mg/mL, about 42 mg/mL, about 40 mg/mL, about 38 mg/mL, or about 36 mg/mL; about 36 mg/mL to about 50 mg/mL, about 48 mg/mL, about 46 mg/mL, about 44 mg/mL, about 42 mg/mL, about 40 mg/mL, or about 38 mg/mL; about 38 mg/mL to about 50 mg/mL, about 48 mg/mL, about 46 mg/mL, about 44 mg/mL, about 42 mg/mL, or about 40 mg/mL; about 40 mg/mL to about 50 mg/mL, about 48 mg/mL, about 46 mg/mL, about 44 mg/mL, or about 42 mg/mL; about 42 mg/mL to about 50 mg/mL, about 48 mg/mL, about 46 mg/mL, or about 44 mg/mL; about 44 mg/mL to about 50 mg/mL, about 48 mg/mL, or about 46 mg/mL; about 46 mg/mL to about 50 mg/mL or about 48 mg/mL; or about 48 mg/mL to about 50 mg/mL, recombinant therapeutic protein into the circuit system In some embodiments, the first period of time can be about 0.1 minute to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, about 5 minutes, about 2 minutes, or about 1 minute; about 1 minute to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, about 5 minutes, or about 2 minutes; about 2 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, or about 5 minutes; about 5 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, or about 10 minutes; about 10 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, or about 15 minutes; about 15 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, or about 20 minutes; about 20 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, or about 25 minutes; about 25 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, or about 30 minutes; about 30 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, or about 35 minutes; about 35 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, or about 40 minutes; about 40 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, or about 45 minutes; about 45 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, or about 50 minutes; about 50 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, or about 55 minutes; about 55 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, or about 1.0 hour; about 1.0 hour to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, or about 1.5 hours; about 1.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, or about 2.0 hours; about 2.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, or about 2.5 hours; about 2.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, or about 3.5 hours; about 3.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, or about 3.5 hours; about 3.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, or about 4.0 hours; about 4.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, or about 4.5 hours; about 4.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, or about 5.0 hours; about 5.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, or about 5.5 hours; about 5.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, or about 6.0 hours; about 6.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, or about 6.5 hours; about 6.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, or about 7 hours; about 7 hours to about 12 hours, about 11.5 hours, about 11 hours, about 10.5 hours, about 10 hours, about 9.5 hours, about 9.0 hours, about 8.5 hours, about 8.0 hours, or about 7.5 hours; about 7.5 hours to about 12 hours, about 11.5 hours, about 11 hours, about 10.5 hours, about 10 hours, about 9.5 hours, about 9.0 hours, about 8.5 hours, or about 8.0 hours; about 8.0 hours to about 12 hours, about 11.5 hours, about 11 hours, about 10.5 hours, about 10 hours, about 9.5 hours, about 9.0 hours, or about 8.5 hours; about 8.5 hours to about 12 hours, about 11.5 hours, about 11 hours, about 10.5 hours, about 10 hours, about 9.5 hours, or about 9.0 hours; about 9.0 hours to about 12 hours, about 11.5 hours, about 11 hours, about 10.5 hours, about 10 hours, or about 9.5 hours; about 9.5 hours to about 12 hours, about 11.5 hours, about 11 hours, about 10.5 hours, or about 10 hours; about 10 hours to about 12 hours, about 11.5 hours, about 11 hours, or about 10.5 hours; about 10.5 hours to about 12 hours, about 11.5 hours, or about 11 hours; about 11 hours to about 12 hours, or about 11.5 hours.

In some examples, step (c) includes continuously flowing (e.g., unidirectionally or bidirectionally flowing) a diafiltration medium into the circuit system at a rate of between about 0.05 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, about 1.0 mL/minute, about 0.5 mL/minute, or about 0.1 mL/minute; about 0.1 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, about 1.0 mL/minute, or about 0.5 mL/minute; about 0.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, or about 1.0 mL/minute; about 1.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, or about 1.5 mL/minute; about 1.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, or about 2.0 mL/minute; about 2.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, or about 2.5 mL/minute; about 2.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, or about 3.0 mL/minute; about 3.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, or about 3.5 mL/minute; about 3.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, or about 4.0 mL/minute; about 4.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, or about 4.5 mL/minute; about 4.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, or about 5.0 mL/minute; about 5.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, or about 5.5 mL/minute; about 5.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, or about 6.0 mL/minute; about 6.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, or about 6.5 mL/minute; about 6.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, or about 7.0 mL/minute; about 7.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, or about 7.5 mL/minute; about 7.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, or about 8.0 mL/minute; about 8.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, or about 8.5 mL/minute; about 8.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, or about 9.0 mL/minute; about 9.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, or about 9.5 mL/minute; about 9.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, or about 12 mL/minute; about 12 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, or about 14 mL/minute; about 14 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, or about 16 mL/minute; about 16 mL/minute to about 100 L/minute, about 90 L/minute, about 80 L/minute, about 70 L/minute, about 60 L/minute, about 50 L/minute, about 40 L/minute, about 30

L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, or about 18 mL/minute; about 18 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, or about 20 mL/minute; about 20 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, or about 22 mL/minute; about 22 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, or about 24 mL/minute; about 23 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, or about 25 mL/minute; about 25 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, or about 50 mL/minute; about 50 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, or about 100 mL/minute; about 100 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, or about 150 mL/minute; about 150 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, or about 200 mL/minute; about 200 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, or about 250 mL/minute; about 250 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, or about 300 mL/minute; about 300 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, or about 350 mL/minute; about 350 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, or about 400 mL/minute; about 400 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, or about 450 mL/minute; about 450 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, or about 500 mL/minute; about 500 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, or about 550 mL/minute; about 550 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, or about 600 mL/minute; about 600 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, or about 650 mL/minute; about 650 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, or about 750 mL/minute; about 750 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, or about 800 mL/minute; about 800 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, or about 850 mL/minute; about 850 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, or about 900 mL/minute; about 900 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, or about 950 mL/minute; about 950 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, or about 1 L/minute; about 1 L/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, or about 5 L/minute; about 5 L/minute to about 100 L/minute, about 90 L/minute, about 80 L/minute, about 70 L/minute, about 60 L/minute, about 50 L/minute, about 40 L/minute, about 30 L/minute, about 20 L/minute, or about 10 L/minute; about 10 L/minute to about 100 L/minute, about 90 L/minute, about 80 L/minute, about 70 L/minute, about 60 L/minute, about 50 L/minute, about 40 L/minute, about 30 L/minute, or about 20 L/minute; about 20 L/minute to about 100 L/minute, about 90 L/minute, about 80 L/minute, about 70 L/minute, about 60 L/minute, about 50 L/minute, about 40 L/minute, or about 30 L/minute; about 30 L/minute to about 100 L/minute, about 90 L/minute, about 80 L/minute, about 70 L/minute, about 60 L/minute, about 50 L/minute, or about 40 L/minute; about 40 L/minute to about 100 L/minute, about 90 L/minute, about 80 L/minute, about 70 L/minute, about 60 L/minute, or about 50 L/minute; about 50 L/minute to about 100 L/minute, about 90 L/minute, about 80 L/minute, about 70 L/minute, or about 60 L/minute; about 60 L/minute to about 100 L/minute, about 90 L/minute, about 80 L/minute, or about 70 L/minute; about 70 L/minute to about 100 L/minute, about 90 L/minute, or about 80 L/minute; about 80 L/minute to about 100 L/minute or about 90 L/minute; or about 90 L/minute to about 100 L/minute.

A diafiltration medium can be, e.g., a physiologically acceptable buffer (e.g., phosphate buffered saline or a buffer used to formulate the recombinant therapeutic protein, e.g., a buffer comprising one or more of glycine, phosphate, acetate, citrate, a bulking agent (e.g., a non-reducing carbohydrate, e.g., sucrose), a surfactant (e.g., polysorbate 80, Triton X-100, and Tween).

In some examples of these methods, the second period of time can be about 0.1 minute to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, about 5 minutes, about 2 minutes, or about 1 minute; about 1 minute to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, about 5 minutes, or about 2 minutes; about 2 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, or about 5 minutes; about 5 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, or about 10 minutes; about 10 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, or about 15 minutes; about 15 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, or about 20 minutes; about 20 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, or about 25 minutes; about 25 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, or about 30 minutes; about 30 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, or about 35 minutes; 35 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, or about 40 minutes; about 40 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, or about 45 minutes; about 45 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, or about 50 minutes; about 50 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, or about 55 minutes; about 55 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, or about 1.0 hour; about 1.0 hour to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, or about 1.5 hours; about 1.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, or about 2.0 hours; about 2.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, or about 2.5 hours; about 2.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, or about 3.0 hours; about 3.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, or about 3.5 hours; about 3.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, or about 4.0 hours; about 4.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, or about 4.5 hours; about 4.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, or about 5.0 hours; about 5.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, or about 5.5 hours; about 5.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, or about 6.0 hours; about 6.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, or about 6.5 hours; about 6.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, or about 7 hours; about 7 hours to about 12 hours, about 11.5 hours, about 11 hours, about 10.5 hours, about 10 hours, about 9.5 hours, about 9.0 hours, about 8.5 hours, about 8.0 hours, or about 7.5 hours; about 7.5 hours to about 12 hours, about 11.5 hours, about 11 hours, about 10.5 hours, about 10 hours, about 9.5 hours, about 9.0 hours, about 8.5 hours, or about 8.0 hours; about 8.0 hours to about 12 hours, about 11.5 hours, about 11 hours, about 10.5 hours, about 10 hours, about 9.5 hours, about 9.0 hours, or about 8.5 hours; about 8.5 hours to about 12 hours, about 11.5 hours, about 11 hours, about 10.5 hours, about 10 hours, about 9.5 hours, or about 9.0 hours; about 9.0 hours to about 12 hours, about 11.5 hours, about 11 hours, about 10.5 hours, about 10 hours, or about 9.5 hours; about 9.5 hours to about 12 hours, about 11.5 hours, about 11 hours, about 10.5 hours, or about 10 hours; about 10 hours to about 12 hours, about 11.5 hours, about 11 hours, or about 10.5 hours; about 10.5 hours to about 12 hours, about 11.5 hours, or about 11 hours; about 11 hours to about 12 hours, or about 11.5 hours.

In some embodiments, the fluid including the recombinant therapeutic protein that is collected in step (d) includes a concentration of recombinant therapeutic protein of about 0.1 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, about 2.0 mg/mL, about 1.5 mg/mL, about 1.0 mg/mL, or about 0.5 mg/mL; about 0.5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, about 2.0 mg/mL, about 1.5 mg/mL, or about 1.0 mg/mL; about 1.0 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, about 2.0 mg/mL, or about 1.5 mg/mL; about 1.5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, or about 2.0 mg/mL; about 2.0 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, or about 2.5 mg/mL; about 2.5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, or about 3 mg/mL; about 3 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, or about 4 mg/mL; about 4 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, or about 5 mg/mL; about 5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, or about 6 mg/mL; about 6 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, or about 7 mg/mL; about 7 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, or about 8 mg/mL; about 8 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, or about 9 mg/mL; about 9 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, or about 10 mg/mL; about 10 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, or about 12 mg/mL; about 12 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, or about 14 mg/mL; about 14 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, or about 16 mg/mL; about 16 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, or about 18 mg/mL; about 18 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, or about 20 mg/mL; about 20 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, or about 22 mg/mL; about 22 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, or about 24 mg/mL; about 24 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, or about 26 mg/mL; about 26 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, or about 28 mg/mL; about 28 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, or about 30 mg/mL; about 30 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, or about 32 mg/mL; about 32 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, or about 34 mg/mL; about 34 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, or about 36 mg/mL; about 36 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, or about 38 mg/mL; about 38 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, or about 40 mg/mL; about 40 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, or about 44 mg/mL; about 44 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, or about 46 mg/mL; about 46 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, or about 48 mg/mL; about 48 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, or about 50 mg/mL; about 50 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, or about 52 mg/mL; about 52 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, or about 54 mg/mL; about 54 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, or about 56 mg/mL; about 56 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, or about 58 mg/mL; about 58 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, or about 60 mg/mL; about 60 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, or about 62 mg/mL; about 62 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, or about 64 mg/mL; about 64 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, or about 66 mg/mL; about 66 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, or about 68 mg/mL; about 68 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, or about 70 mg/mL; about 70 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, or about 72 mg/mL; about 72 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, or about 74 mg/mL; about 74 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, or about 76 mg/mL; about 76 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, or about 78 mg/mL; about 78 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, or about 80 mg/mL; about 80 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, or about 82 mg/mL; about 82 mg/mL to about 100 mg/mL, about 98 mg/mL, 96 mg/mL, about 94 mg/mL, about 92 mg/mL, about 90 mg/mL, about 88 mg/mL, about 86 mg/mL, or about 84 mg/mL; about 84 mg/mL to about 100 mg/mL, about 98 mg/mL, 96 mg/mL, about 94 mg/mL, about 92 mg/mL, about 90 mg/mL, about 88 mg/mL, or about 86 mg/mL; about 86 mg/mL to about 100 mg/mL, about 98 mg/mL, 96 mg/mL, about 94 mg/mL, about 92 mg/mL, about 90 mg/mL, or about 88 mg/mL; about 88 mg/mL to about 100 mg/mL, about 98 mg/mL, 96 mg/mL, about 94 mg/mL, about 92 mg/mL, or about 90 mg/mL; about 90 mg/mL to about 100 mg/mL, about 98 mg/mL, 96 mg/mL, about 94 mg/mL, or about 92 mg/mL; about 92 mg/mL to about 100 mg/mL, about 98 mg/mL, 96 mg/mL, or about 94 mg/mL; about 94 mg/mL to about 100 mg/mL, about 98 mg/mL, or 96 mg/mL; about 96 mg/mL to about 100 mg/mL or about 98 mg/mL; or about 98 mg/mL to about 100 mg/mL.

In some embodiments, these fold-diafiltration achieved after the first and second time periods is about 1-fold to about 20-fold, about 19-fold, about 18-fold, about 17-fold, about 16-fold, about 15-fold, about 14-fold, about 13-fold, about 12-fold, about 11-fold, about 10-fold, about 9-fold, about 8-fold, about 7-fold, about 6-fold, about 5-fold, about 4-fold, about 3-fold, or about 2-fold; about 2-fold to about 20-fold, about 19-fold, about 18-fold, about 17-fold, about 16-fold, about 15-fold, about 14-fold, about 13-fold, about 12-fold, about 11-fold, about 10-fold, about 9-fold, about 8-fold, about 7-fold, about 6-fold, about 5-fold, about 4-fold, or about 3-fold; about 3-fold to about 20-fold, about 19-fold, about 18-fold, about 17-fold, about 16-fold, about 15-fold, about 14-fold, about 13-fold, about 12-fold, about 11-fold, about 10-fold, about 9-fold, about 8-fold, about 7-fold, about 6-fold, about 5-fold, or about 4-fold; about 4-fold to about 20-fold, about 19-fold, about 18-fold, about 17-fold, about 16-fold, about 15-fold, about 14-fold, about 13-fold, about 12-fold, about 11-fold, about 10-fold, about 9-fold, about 8-fold, about 7-fold, about 6-fold, or about 5-fold; about 5-fold to about 20-fold, about 19-fold, about 18-fold, about 17-fold, about 16-fold, about 15-fold, about 14-fold, about 13-fold, about 12-fold, about 11-fold, about 10-fold, about 9-fold, about 8-fold, about 7-fold, or about 6-fold; about 6-fold to about 20-fold, about 19-fold, about 18-fold, about 17-fold, about 16-fold, about 15-fold, about 14-fold, about 13-fold, about 12-fold, about 11-fold, about 10-fold, about 9-fold, about 8-fold, or about 7-fold; about 7-fold to about 20-fold, about 19-fold, about 18-fold, about 17-fold, about 16-fold, about 15-fold, about 14-fold, about 13-fold, about 12-fold, about 11-fold, about 10-fold, about 9-fold, or about 8-fold; about 8-fold to about 20-fold, about 19-fold, about 18-fold, about 17-fold, about 16-fold, about 15-fold, about 14-fold, about 13-fold, about 12-fold, about 11-fold, about 10-fold, or about 9-fold; about 9-fold to about 20-fold, about 19-fold, about 18-fold, about 17-fold, about 16-fold, about 15-fold, about 14-fold, about 13-fold, about 12-fold, about 11-fold, or about 10-fold; about 10-fold to about 20-fold, about 19-fold, about 18-fold, about 17-fold, about 16-fold, about 15-fold, about 14-fold, about 13-fold, about 12-fold, or about 11-fold; about 11-fold to about 20-fold, about 19-fold, about 18-fold, about 17-fold, about 16-fold, about 15-fold, about 14-fold, about 13-fold, or about 12-fold; about 12-fold to about 20-fold, about 19-fold, about 18-fold, about 17-fold, about 16-fold, about 15-fold, about 14-fold, or about 13-fold; about 13-fold to about 20-fold, about 19-fold, about 18-fold, about 17-fold, about 16-fold, about 15-fold, or about 14-fold; about 14-fold to about 20-fold, about 19-fold, about 18-fold, about 17-fold, about 16-fold, or about 15-fold; about 15-fold to about 20-fold, about 19-fold, about 18-fold, about 17-fold, or about 16-fold; about 16-fold to about 20-fold, about 19-fold, about 18-fold, or about 17-fold; about 17-fold to about 20-fold, about 19-fold, or about 18-fold; about 18-fold to about 20-fold or about 19-fold; or about 19-fold to about 20-fold.

In some embodiments, the circuit system does not include a holding tank.

In other embodiments of this method, during the first period of time, a fluid including the recombinant therapeutic protein and the diafiltration medium are continuously flowed together into the circuit system, and then during the second period of time, only the diafiltration medium is continuously flowed into the circuit system.

The fluid can be collected in step (d) using a syringe, gravity, or a pump (e.g., a peristaltic pump disposed in the conduit). Additional means for collecting the fluid including the recombinant therapeutic protein in step (d) are known in the art.

Some examples of these methods further include: (e) providing a second circuit system including (i) a tangential flow virus filtration (TFVF) unit having first and second inlets, and (ii) a conduit in fluid communication between the first and second inlets of the TFVF unit, including at least one port for flowing fluid into or out of, or both, of the second system, where the second system is configured such that fluid can be flowed through the conduit and the TFVF unit, and filtrate including the recombinant therapeutic protein can be collected from the TFVF unit; and (f) flowing the collected fluid of step (d) into the second system using a connecting conduit in fluid communication between a port in the system and a port in the second system, and collecting filtrate including the recombinant therapeutic protein from the TFVF unit for a third period of time. As can be appreciated by those skilled in the art, some embodiments of these methods can further include recirculating any fluid including the recombinant therapeutic protein in the conduit of the second circuit system (including a TFVF unit) that did not pass through the one or more tangential virus filters in the TFVF unit (e.g., acts as a buffer when a new volume of a fluid including the recombinant therapeutic protein is flowed into the conduit of the circuit system including a TFVF unit).

In some embodiments, the TFVF unit includes one, two, three, four, five, six, seven, eight, nine, ten, eleven, or twelve tangential virus filters. In some examples of these methods, the TFVF unit can include one or more tangential virus filter(s) having a surface area of about 0.05 cm$^2$ to about 100 m$^2$, about 90 m$^2$, about 80 m$^2$, about 70 m$^2$, about 60 m$^2$, about 50 m$^2$, about 45 m$^2$, about 40 m$^2$, about 35 m$^2$, about 30 m$^2$, about 25 m$^2$, about 20 m$^2$, about 15 m$^2$, about 10 m$^2$, about 5 m$^2$, about 1 m$^2$, about 800 cm$^2$, about 600 cm$^2$, about 400 cm$^2$, about 200 cm$^2$, about 150 cm$^2$, about 100 cm$^2$, about 50 cm$^2$, about 48 cm$^2$, about 46 cm$^2$, about 44 cm$^2$, about 42 cm$^2$, about 40 cm$^2$, about 38 cm$^2$, about 36 cm$^2$, about 34 cm$^2$, about 32 cm$^2$, about 30 cm$^2$, about 28 cm$^2$, about 26 cm$^2$, about 24 cm$^2$, about 22 cm$^2$, about 20 cm$^2$, about 18 cm$^2$, about 16 cm$^2$, about 14 cm$^2$, about 12 cm$^2$, about 10 cm$^2$, about 9.5 cm$^2$, about 9.0 cm$^2$, about 8.5 cm$^2$, about 8.0 cm$^2$, about 7.5 cm$^2$, about 7.0 cm$^2$, about 6.5 cm$^2$, about 6.0 cm$^2$, about 5.5 cm$^2$, about 5.0 cm$^2$, about 4.5 cm$^2$, about 4.0 cm$^2$, about 3.5 cm$^2$, about 3.0 cm$^2$, about 2.5 cm$^2$, about 2.0 cm$^2$, about 1.5 cm$^2$, about 1.0 cm$^2$, about 0.5 cm$^2$, or about 0.1 cm$^2$; about 0.1 cm$^2$ to about 100 m$^2$, about 90 m$^2$, about 80 m$^2$, about 70 m$^2$, about 60 m$^2$, about 50 m$^2$, about 45 m$^2$, about 40 m$^2$, about 35 m$^2$, about 30 m$^2$, about 25 m$^2$, about 20 m$^2$, about 15 m$^2$, about 10 m$^2$, about 5 m$^2$, about 1 m$^2$, about 800 cm$^2$, about 600 cm$^2$, about 400 cm$^2$, about 200 cm$^2$, about 150 cm$^2$, about 100 cm$^2$, about 50 cm$^2$, about 48 cm$^2$, about 46 cm$^2$, about 44 cm$^2$, about 42 cm$^2$, about 40 cm$^2$, about 38 cm$^2$, about 36 cm$^2$, about 34 cm$^2$, about 32 cm$^2$, about 30 cm$^2$, about 28 cm$^2$, about 26 cm$^2$, about 24 cm$^2$, about 22 cm$^2$, about 20 cm$^2$, about 18 cm$^2$, about 16 cm$^2$, about 14 cm$^2$, about 12 cm$^2$, about 10 cm$^2$, about 9.5 cm$^2$, about 9.0 cm$^2$, about 8.5 cm$^2$, about 8.0 cm$^2$, about 7.5 cm$^2$, about 7.0 cm$^2$, about 6.5 cm$^2$, about 6.0 cm$^2$, about 5.5 cm$^2$, about 5.0 cm$^2$, about 4.5 cm$^2$, about 4.0 cm$^2$, about 3.5 cm$^2$, about 3.0 cm$^2$, about 2.5 cm$^2$, about 2.0 cm$^2$, about 1.5 cm$^2$, about 1.0 cm$^2$, or about 0.5 cm$^2$; about 0.5 cm$^2$ to about 100 m$^2$, about 90 m$^2$, about 80 m$^2$, about 70 m$^2$, about 60 m$^2$, about 50 m$^2$, about 45 m$^2$, about 40 m$^2$, about 35 m$^2$, about 30 m$^2$, about 25 m$^2$, about 20 m$^2$, about 15 m$^2$, about 10 m$^2$, about 5 m$^2$, about 1 m$^2$, about 800 cm$^2$, about 600 cm$^2$, about 400 cm$^2$, about 200 cm$^2$, about 150 cm$^2$, about 100 cm$^2$, about 50 cm$^2$, about 48 cm$^2$, about 46 cm$^2$, about 44 cm$^2$, about 42 cm$^2$, about 40 cm$^2$, about 38 cm$^2$, about 36 cm$^2$, about 34 cm$^2$, about 32 cm$^2$, about 30 cm$^2$, about 28 cm$^2$, about 26 cm$^2$, about 24 cm$^2$, about 22 cm$^2$, about 20 cm$^2$, about 18 cm$^2$, about 16 cm$^2$, about 14 cm$^2$, about 12 cm$^2$, about 10 cm$^2$, about 9.5 cm$^2$, about 9.0 cm$^2$, about 8.5 cm$^2$, about 8.0 cm$^2$, about 7.5 cm$^2$, about 7.0 cm$^2$, about 6.5 cm$^2$, about 6.0 cm$^2$, about 5.5 cm$^2$, about 5.0 cm$^2$, about 4.5 cm$^2$, about 4.0 cm$^2$, about 3.5 cm$^2$, about 3.0 cm$^2$, about 2.5 cm$^2$, about 2.0 cm$^2$, about 1.5 cm$^2$, or about 1.0 cm$^2$; about 1.0 cm$^2$ to about 100 m$^2$, about 90 m$^2$, about 80 m$^2$, about 70 m$^2$, about 60 m$^2$, about 50 m$^2$, about 45 m$^2$, about 40 m$^2$, about 35 m$^2$, about 30 m$^2$, about 25 m$^2$, about 20 m$^2$, about 15 m$^2$, about 10 m$^2$, about 5 m$^2$, about 1 m$^2$, about 800 cm$^2$, about 600 cm$^2$, about 400 cm$^2$, about 200 cm$^2$, about 150 cm$^2$, about 100 cm$^2$, about 50 cm$^2$, about 48 cm$^2$, about 46 cm$^2$, about 44 cm$^2$, about 42 cm$^2$, about 40 cm$^2$, about 38 cm$^2$, about 36 cm$^2$, about 34 cm$^2$, about 32 cm$^2$, about 30 cm$^2$, about 28 cm$^2$, about 26 cm$^2$, about 24 cm$^2$, about 22 cm$^2$, about 20 cm$^2$, about 18 cm$^2$, about 16 cm$^2$, about 14 cm$^2$, about 12 cm$^2$, about 10 cm$^2$, about 9.5 cm$^2$, about 9.0 cm$^2$, about 8.5 cm$^2$, about 8.0 cm$^2$, about 7.5 cm$^2$, about 7.0 cm$^2$, about 6.5 cm$^2$, about 6.0 cm$^2$, about 5.5 cm$^2$, about 5.0 cm$^2$, about 4.5 cm$^2$, about 4.0 cm$^2$, about 3.5 cm$^2$, about 3.0 cm$^2$, about 2.5 cm$^2$, about 2.0 cm$^2$, or about 1.5 cm$^2$; about 1.5 cm$^2$ to about 100 m$^2$, about 90 m$^2$, about 80 m$^2$, about 70 m$^2$, about 60 m$^2$, about 50 m$^2$, about 45 m$^2$, about 40 m$^2$, about 35 m$^2$, about 30 m$^2$, about 25 m$^2$, about 20 m$^2$, about 15 m$^2$, about 10 m$^2$, about 5 m$^2$, about 1 m$^2$, about 800 cm$^2$, about 600 cm$^2$, about 400 cm$^2$, about 200 cm$^2$, about 150 cm$^2$, about 100 cm$^2$, about 50 cm$^2$, about 48 cm$^2$, about 46 cm$^2$, about 44 cm$^2$, about 42 cm$^2$, about 40 cm$^2$, about 38 cm$^2$, about 36 cm$^2$, about 34 cm$^2$, about 32 cm$^2$, about 30 cm$^2$, about 28 cm$^2$, about 26 cm$^2$, about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², about 3.5 cm², about 3.0 cm², about 2.5 cm², or about 2.0 cm²; about 2.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², about 3.5 cm², about 3.0 cm², or about 2.5 cm²; about 2.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², about 3.5 cm², or about 3.0 cm²; about 3.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², about 4.0 cm², or about 3.5 cm²; about 3.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², about 4.5 cm², or about 4.0 cm²; about 4.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², about 5.0 cm², or about 4.5 cm²; about 4.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², about 5.5 cm², or about 5.0 cm²; about 5.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², about 6.0 cm², or about 5.5 cm²; about 5.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², or about 6.0 cm²; about 6.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², about 7.0 cm², about 6.5 cm², or about 6.5 cm²; about 6.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², about 7.5 cm², or about 7.0 cm²; about 7.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², about 8.0 cm², or about 7.5 cm²; about 7.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², about 8.5 cm², or about 8.0 cm²; about 8.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², about 9.0 cm², or about 8.5 cm²; about 8.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², about 9.5 cm², or about 9.0 cm²; about 9.0 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², about 10 cm², or about 9.5 cm²; about 9.5 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², about 12 cm², or about 10 cm²; about 10 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², about 14 cm², or about 12 cm²; about 12 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², about 16 cm², or about 14 cm²; about 14 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², about 18 cm², or about 16 cm²; about 16 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², about 20 cm², or about 18 cm²; about 18 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², about 22 cm², or about 20 cm²; about 20 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², about 24 cm², or about 22 cm²; about 22 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², about 26 cm², or about 24 cm²; about 24 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², about 28 cm², or about 26 cm²; about 26 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², about 30 cm², or about 28 cm²; about 28 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², about 32 cm², or about 30 cm²; about 30 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², about 34 cm², or about 32 cm²; about 32 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², about 36 cm², or about 34 cm²; about 34 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², about 38 cm², or about 36 cm²; about 36 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², about 40 cm², or about 38 cm²; about 38 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², about 42 cm², or about 40 cm²; about 40 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², about 44 cm², or about 42 cm²; about 42 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², about 46 cm², or about 44 cm²; about 44 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm², about 48 cm², or about 46 cm²; about 46 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², about 50 cm² or about 48 cm²; about 48 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², about 100 cm², or about 50 cm²; about 50 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², about 150 cm², or about 100 cm²; about 100 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², about 200 cm², or about 150 cm²; about 150 cm² to about 100 m², about 90 m², about 80 m², about 70 m², about 60 m², about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², about 400 cm², or about 200 cm²; about 200 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², about 600 cm², or about 400 cm²; about 400 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm², or about 600 cm²; about 600 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², about 1 m², about 800 cm²; about 800 cm² to about 100 m², about 90 m², about 80 m², about 70 m², about 60 m², about 50 m², about 45 m², about 40 m², about 35 m², about 30 m², about 25 m², about 20 m², about 15 m², about 10 m², about 5 m², or about 1 m²; about 1 m² to about 50 m², about 45 m², about 40 m², about 35 m², about 30 m², about 25 m², about 20 m², about 15 m², about 10 m², or about 5 m²; about 5 m² to about 100 m², about 90 m², about 80 m², about 70 m², about 60 m², about 50 m², about 45 m², about 40 m², about 35 m², about 30 m², about 25 m², about 20 m², about 15 m², or about 10 m²; about 10 m² to about 100 m², about 90 m², about 80 m², about 70 m², about 60 m², about 50 m², about 45 m², about 40 m², about 35 m², about 30 m², about 25 m², about 20 m², or about 15 m²; about 15 m² to about 100 m², about 90 m², about 80 m², about 70 m², about 60 m², about 50 m², about 45 m², about 40 m², about 35 m², about 30 m², about 25 m², or about 20 m²; about 20 m² to about 100 m², about 90 m², about 80 m², about 70 m², about 60 m², about 50 m², about 45 m², about 40 m², about 35 m², about 30 m², or about 25 m²; about 25 m² to about 100 m², about 90 m², about 80 m², about 70 m², about 60 m², about 50 m², about 45 m², about 40 m², about 35 m², or about 30 m²; about 30 m² to about 50 m², about 45 m², about 40 m², or about 35 m²; about 35 m² to about 100 m², about 90 m², about 80 m², about 70 m², about 60 m², about 50 m², about 45 m², or about 40 m²; about 40 m² to about 100 m², about 90 m², about 80 m², about 70 m², about 60 m², about 50 m² or about 45 m²; about 45 m² to about 100 m², about 90 m², about 80 m², about 70 m², about 60 m², or about 50 m²; about 50 m² to about 100 m², about 90 m², about 80 m², about 70 m², or about 60 m²; about 60 m² to about 100 m², about 90 m², about 80 m², or about 70 m²; about 70 m² to about 100 m², about 90 m², or about 80 m²; about 80 m² to about 100 m², or about 90 m²; or about 90 m² to about 100 m².

In some embodiments, the TFVF unit includes one or more tangential virus filters having a pore size of about 5 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, or about 10 nm; about 10 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, or about 15 nm; about 15 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, about 25 nm, or about 20 nm; about 20 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, about 30 nm, or about 25 nm; about 25 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, about 35 nm, or about 30 nm; about 30 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, about 50 nm, about 45 nm, about 40 nm, or about 35 nm; about 35 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, about 50 nm, about 45 nm, or about 40 nm; about 45 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, about 55 nm, or about 50 nm; about 50 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, about 60 nm, or about 55 nm; about 55 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, about 65 nm, or about 60 nm; about 60 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, about 70 nm, or about 65 nm; about 65 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, about 75 nm, or about 70 nm; about 70 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, about 80 nm, or about 75 nm; about 75 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, about 85 nm, or about 80 nm; about 80 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, about 90 nm, or about 85 nm; about 85 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, about 95 nm, or about 90 nm; about 90 nm to about 220 nm, about 210 nm, about 200 nm, about 190 nm, about 180 nm, about 170 nm, about 160 nm, about 150 nm, about 140 nm, about 130 nm, about 120 nm, about 110 nm, about 100 nm, or about 95 nm; about 95 nm to about 220 nm, about 210 nm, about 200 nm, about 190 nm, about 180 nm, about 170 nm, about 160 nm, about 150 nm, about 140 nm, about 130 nm, about 120 nm, about 110 nm, or about 100 nm; about 100 nm to about 220 nm, about 210 nm, about 200 nm, about 190 nm, about 180 nm, about 170 nm, about 160 nm, about 150 nm, about 140 nm, about 130 nm, about 120 nm, or about 110 nm; about 110 nm to about 220 nm, about 210 nm, about 200 nm, about 190 nm, about 180 nm, about 170 nm, about 160 nm, about 150 nm, about 140 nm, about 130 nm, or about 120 nm; about 120 nm to about 220 nm, about 210 nm, about 200 nm, about 190 nm, about 180 nm, about 170 nm, about 160 nm, about 150 nm, about 140 nm, or about 130 nm; about 130 nm to about 220 nm, about 210 nm, about 200 nm, about 190 nm, about 180 nm, about 170 nm, about 160 nm, about 150 nm, or about 140 nm; about 140 nm to about 220 nm, about 210 nm, about 200 nm, about 190 nm, about 180 nm, about 170 nm, about 160 nm, or about 150 nm; about 150 nm to about 220 nm, about 210 nm, about 200 nm, about 190 nm, about 180 nm, about 170 nm, or about 160 nm; about 160 nm to about 220 nm, about 210 nm, about 200 nm, about 190 nm, about 180 nm, or about 170 nm; about 170 nm to about 220 nm, about 210 nm, about 200 nm, about 190 nm, or about 180 nm; about 180 nm to about 220 nm, about 210 nm, about 200 nm, or about 190 nm; about 190 nm to about 220 nm, about 210 nm, or about 200 nm; about 200 nm to about 220 nm or about 210 nm; or about 210 nm to about 220 nm. A variety of virus filters that can be used in a TFVF unit are known in the art. For example, virus filters that can be used in a TFVF unit are commercially available from Asahi Kasei (Tokyo, Japan). In some embodiments, the virus filter is a Planova™ filter (e.g., a Planova™ 15N, a Planova™ 20N, a Planova™ 35N, or a Planova™ 75N). In some embodiments, the virus filter is a Planova™ BioEX filter. The virus filters that can be used in a TFVF unit can include, e.g., hollow fiber membranes.

The connecting conduit and the conduit in the second circuit system can be simple tubing, e.g., biocompatible tubing. Non-limiting examples of useful tubing include silicone rubber, polycarbonate, polypropylene, polyurethane, polydioxanone (PDO), polyhydroxyalkanoate, polyhydroxybutyrate, poly(glycerol sebacate), polyglycolide, polylactide, polycaprolactone, or polyanhydride, or copolymers or derivatives including these and/or other polymers. Alternatively or in addition, any of the conduits described herein can include polyvinyl chloride. Any of the conduits described herein can be, e.g., weldable transfer tubing.

In some embodiments, the internal diameter of the connecting conduit and/or the conduit in the second circuit system can be about 5 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, about 12 mm, about 10 mm, about 8 mm, or about 6 mm; about 6 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, about 12 mm, about 10 mm, or about 8 mm; about 8 mM to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, about 12 mm, or about 10 mm; about 10 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, about 14 mm, or about 12 mm; about 12 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, about 16 mm, or about 14 mm; about 14 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, about 18 mm, or about 16 mm; about 16 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, about 20 mm, or about 18 mm; about 18 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, about 22 mm, or about 20 mm; about 20 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, about 24 mm, or about 22 mm; about 22 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, about 26 mm, or about 24 mm; about 24 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, about 30 mm, about 28 mm, or about 26 mm; about 26 mm to about 50 mm, about 48 mm, about 46 mm, about 44 mm, about 42 mm, about 40 mm, about 38 mm, about 36 mm, about 34 mm, about 32 mm, about 30 mm, or about 28 mm; about 28 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, about 32 mm, or about 30 mm; about 30 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, about 34 mm, or about 32 mm; about 32 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, about 36 mm, or about 34 mm; about 34 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, about 38 mm, or about 36 mm; about 36 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, about 40 mm, to about 38 mm; about 38 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, about 42 mm, or about 40 mm; about 40 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, about 44 mm, or about 42 mm; about 42 mm to about 100 mm, about 95 mm, about 90 mm, about 85 mm, about 80 mm, about 75 mm, about 70 mm, about 65 mm, about 60 mm, about 55 mm, about 50 mm, about 48 mm, about 46 mm, or about 44 mm; about 44 mm to about 100 mm, about 95 mm, about 90 mm, about 85 mm, about 80 mm, about 75 mm, about 70 mm, about 65 mm, about 60 mm, about 55 mm, about 50 mm, about 48 mm, or about 46 mm; about 46 mm to about 100 mm, about 95 mm, about 90 mm, about 85 mm, about 80 mm, about 75 mm, about 70 mm, about 65 mm, about 60 mm, about 55 mm, about 50 mm, or about 48 mm; about 48 mm to about 100 mm, about 95 mm, about 90 mm, about 85 mm, about 80 mm, about 75 mm, about 70 mm, about 65 mm, about 60 mm, about 55 mm, or about 50 mm; about 50 mm to about 100 mm, about 95 mm, about 90 mm, about 85 mm, about 80 mm, about 75 mm, about 70 mm, about 65 mm, about 60 mm, or about 55 mm; about 55 mm to about 100 mm, about 95 mm, about 90 mm, about 85 mm, about 80 mm, about 75 mm, about 70 mm, or about 65 mm; about 65 mm to about 100 mm, about 95 mm, about 90 mm, about 85 mm, about 80 mm, about 75 mm, or about 70 mm; about 70 mm to about 100 mm, about 95 mm, about 90 mm, about 85 mm, about 80 mm, or about 75 mm; about 75 mm to about 100 mm, about 95 mm, about 90 mm, about 85 mm, or about 80 mm; about 80 mm to about 100 mm, about 95 mm, about 90 mm, or about 85 mm; about 85 mm to about 100 mm, about 95 mm, or about 90 mm; about 90 mm to about 100 mm or about 95 mm; or about 95 mm to about 100 mm.

In some embodiments, the connecting conduit and/or the conduit in the second circuit system has a total length of about 1.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, about 8.0 cm, about 6.0 cm, about 4.0 cm, or about 2.0 cm; about 2.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, about 8.0 cm, about 6.0 cm, or about 4.0 cm; about 4.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, about 8.0 cm, or about 6.0 cm; about 6.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, about 10 cm, or about 8.0 cm; about 8.0 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, about 12 cm, or about 10 cm; about 10 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, about 14 cm, or about 12 cm; about 12 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, about 16 cm, or about 14 cm; about 14 cm to about 75 cm, about 70 cm, about 65 cm, about 60 cm, about 55 cm, about 50 cm, about 45 cm, about 40 cm, about 35 cm, about 30 cm, about 25 cm, about 20 cm, about 18 cm, or about 16 cm; about 16 cm to about 75 cm, about 70 cm, about 65 cm, about 60 cm, about 55 cm, about 50 cm, about 45 cm, about 40 cm, about 35 cm, about 30 cm, about 25 cm, about 20 cm, or about 18 cm; about 18 cm to about 75 cm, about 70 cm, about 65 cm, about 60 cm, about 55 cm, about 50 cm, about 45 cm, about 40 cm, about 35 cm, about 30 cm, about 25 cm, or about 20 cm; about 20 cm to about 75 cm, about 70 cm, about 65 cm, about 60 cm, about 55 cm, about 50 cm, about 45 cm, about 40 cm, about 35 cm, about 30 cm, or about 25 cm; about 25 cm to about 75 cm, about 70 cm, about 65 cm, about 60 cm, about 55 cm, about 50 cm, about 45 cm, about 40 cm, about 35 cm, or about 30 cm; about 30 cm to about 75 cm, about 70 cm, about 65 cm, about 60 cm, about 55 cm, about 50 cm, about 45 cm, about 40 cm, or about 35 cm; about 35 cm to about 75 cm, about 70 cm, about 65 cm, about 60 cm, about 55 cm, about 50 cm, about 45 cm, or about 40 cm; about 40 cm to about 75 cm, about 70 cm, about 65 cm, about 60 cm, about 55 cm, about 50 cm, or about 45 cm; about 45 cm to about 75 cm, about 70 cm, about 65 cm, about 60 cm, about 55 cm, or about 50 cm; about 50 cm to about 75 cm, about 70 cm, about 65 cm, about 60 cm, or about 55 cm; about 55 cm to about 75 cm, about 70 cm, about 65 cm, or about 60 cm; about 60 cm to about 75 cm, about 70 cm, or about 65 cm; about 65 cm to about 75 cm or about 70 cm; or about 70 cm to about 75 cm.

Additional examples of conduits and properties of conduits that can be used in the second circuit system are well-known by those in the art.

In some examples, the second circuit system includes one, two, three, four, or five ports. In some examples, the at least one port in the second circuit system can be a valve. In other examples, the at least one port in the second circuit system can be an injection port or can have a ribbed threading. The at least one port in the second circuit system can be any type of port commonly known in the art.

In some examples, the second circuit system can further include a pump (e.g., a low-turbulence pump, e.g., a peristaltic pump) disposed in the connecting conduit and/or the conduit in second system. In some embodiments, the second circuit system does not include a holding tank. In some embodiments, the connecting conduit is not fluidly connected to a holding tank.

In some examples, step (f) includes continuously flowing (e.g., unidirectionally or bidirectionally flowing) the collected fluid of step (d) into the second system (using the connecting conduit) at a rate of about 0.05 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, about 1.0 mL/minute, about 0.5 mL/minute, or about 0.1 mL/minute; about 0.1 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, about 1.0 mL/minute, or about 0.5 mL/minute; about 0.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, about 1.5 mL/minute, or about 1.0 mL/minute; about 1.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, about 2.0 mL/minute, or about 1.5 mL/minute; about 1.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, about 2.5 mL/minute, or about 2.0 mL/minute; about 2.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, about 3.0 mL/minute, or about 2.5 mL/minute; about 2.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, about 3.5 mL/minute, or about 3.0 mL/minute; about 3.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, about 4.0 mL/minute, or about 3.5 mL/minute; about 3.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, about 4.5 mL/minute, or about 4.0 mL/minute; about 4.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, about 5.0 mL/minute, or about 4.5 mL/minute; about 4.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, about 5.5 mL/minute, or about 5.0 mL/minute; about 5.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, about 6.0 mL/minute, or about 5.5 mL/minute; about 5.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, about 6.5 mL/minute, or about 6.0 mL/minute; about 6.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, about 7.0 mL/minute, or about 6.5 mL/minute; about 6.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, about 7.5 mL/minute, or about 7.0 mL/minute; about 7.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, about 8.0 mL/minute, or about 7.5 mL/minute; about 7.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, about 8.5 mL/minute, or about 8.0 mL/minute; about 8.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, about 9.0 mL/minute, or about 8.5 mL/minute; about 8.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, about 9.5 mL/minute, or about 9.0 mL/minute; about 9.0 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, about 10 mL/minute, or about 9.5 mL/minute; about 9.5 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, about 12 mL/minute, or about 10 mL/minute; about 10 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, about 14 mL/minute, or about 12 mL/minute; about 12 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, about 16 mL/minute, or about 14 mL/minute; about 14 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, about 18 mL/minute, or about 16 mL/minute; about 16 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, about 20 mL/minute, or about 18 mL/minute; about 18 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, about 22 mL/minute, or about 20 mL/minute; about 20 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute, about 24 mL/minute, or about 22 mL/minute; about 22 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, about 25 mL/minute or about 24 mL/minute; about 23 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 50 mL/minute, or about 25 mL/minute; about 25 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, or about 100 mL/minute, or about 50 mL/minute; about 50 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, or about 100 mL/minute; about 100 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, or about 150 mL/minute; about 150 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, or about 200 mL/minute; about 200 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, or about 250 mL/minute; about 250 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, or about 300 mL/minute; about 300 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, or about 350 mL/minute; about 350 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, or about 400 mL/minute; about 400 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, or about 450 mL/minute; about 450 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, or about 500 mL/minute; about 500 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, or about 550 mL/minute; about 550 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, or about 600 mL/minute; about 600 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, or about 650 mL/minute; about 650 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, about 750 mL/minute, or about 700 mL/minute; about 700 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, about 800 mL/minute, or about 750 mL/minute; about 750 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, about 850 mL/minute, or about 800 mL/minute; about 800 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, about 900 mL/minute, or about 850 mL/minute; about 850 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, about 950 mL/minute, or about 900 mL/minute; about 900 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, about 1 L/minute, or about 950 mL/minute; about 950 mL/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, about 5 L/minute, or about 1 L/minute; about 1 L/minute to about 100 L/minute, about 90 L/minute, about 80 L/minute, about 70 L/minute, about 60 L/minute, about 50 L/minute, about 40 L/minute, about 30 L/minute, about 20 L/minute, about 10 L/minute, or about 5 L/minute; about 5 L/minute to about 100 L/minute, about 90 L/minute, about 80 L/minute, about 70 L/minute, about 60 L/minute, about 50 L/minute, about 40 L/minute, about 30 L/minute, about 20 L/minute, or about 10 L/minute; about 10 L/minute to about 100 L/minute, about 90 L/minute, about 80 L/minute, about 70 L/minute, about 60 L/minute, about 50 L/minute, about 40 L/minute, about 30 L/minute, or about 20 L/minute; about 20 L/minute to about 100 L/minute, about 90 L/minute, about 80 L/minute, about 70 L/minute, about 60 L/minute, about 50 L/minute, about 40 L/minute, or about 30 L/minute; about 30 L/minute to about 100 L/minute, about 90 L/minute, about 80 L/minute, about 70 L/minute, about 60 L/minute, about 50 L/minute, or about 40 L/minute; about 40 L/minute to about 100 L/minute, about 90 L/minute, about 80 L/minute, about 70 L/minute, about 60 L/minute, or about 50 L/minute; about 50 L/minute to about 100 L/minute, about 90 L/minute, about 80 L/minute, about 70 L/minute, or about 60 L/minute; about 60 L/minute to about 100 L/minute, about 90 L/minute, about 80 L/minute, or about 70 L/minute; about 70 L/minute to about 100 L/minute, about 90 L/minute, or about 80 L/minute; about 80 L/minute to about 100 L/minute or about 90 L/minute; or about 90 L/minute to about 100 L/minute.

In some examples, the filtrate collected from the TFVF unit in step (f) includes a concentration of recombinant therapeutic protein of about 0.1 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, about 2.0 mg/mL, about 1.5 mg/mL, about 1.0 mg/mL, or about 0.5 mg/mL; about 0.5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, about 2.0 mg/mL, about 1.5 mg/mL, or about 1.0 mg/mL; about 1.0 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, about 2.0 mg/mL, or about 1.5 mg/mL; about 1.5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, about 2.5 mg/mL, or about 2.0 mg/mL; about 2.0 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, about 3 mg/mL, or about 2.5 mg/mL; about 2.5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, about 4 mg/mL, or about 3 mg/mL; about 3 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, about 5 mg/mL, or about 4 mg/mL; about 4 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, about 7 mg/mL, about 6 mg/mL, or about 5 mg/mL; about 5 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, about 8 mg/mL, or about 7 mg/mL; about 7 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, about 9 mg/mL, or about 8 mg/mL; about 8 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, about 10 mg/mL, or about 9 mg/mL; about 9 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, about 12 mg/mL, or about 10 mg/mL; about 10 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, about 14 mg/mL, or about 12 mg/mL; about 12 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, about 16 mg/mL, or about 14 mg/mL; about 14 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, about 18 mg/mL, or about 16 mg/mL; about 16 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, about 20 mg/mL, or about 18 mg/mL; about 18 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, about 22 mg/mL, or about 20 mg/mL; about 20 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, about 24 mg/mL, or about 22 mg/mL; about 22 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, about 26 mg/mL, or about 24 mg/mL; about 24 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, about 28 mg/mL, or about 26 mg/mL; about 26 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, about 30 mg/mL, or about 28 mg/mL; about 28 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, about 32 mg/mL, or about 30 mg/mL; about 30 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, about 34 mg/mL, or about 32 mg/mL; about 32 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, about 36 mg/mL, or about 34 mg/mL; about 34 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, about 38 mg/mL, or about 36 mg/mL; about 36 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, about 40 mg/mL, or about 38 mg/mL; about 38 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, about 44 mg/mL, about 42 mg/mL, or about 40 mg/mL; about 40 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, or about 44 mg/mL, or about 42 mg/mL; about 42 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, about 46 mg/mL, or about 44 mg/mL; about 44 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, about 48 mg/mL, or about 46 mg/mL; about 46 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, about 50 mg/mL, or about 48 mg/mL; about 48 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, about 52 mg/mL, or about 50 mg/mL; about 50 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, about 54 mg/mL, or about 52 mg/mL; about 52 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, about 56 mg/mL, or about 54 mg/mL; about 54 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, about 58 mg/mL, or about 56 mg/mL; about 56 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, about 60 mg/mL, or about 58 mg/mL; about 58 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, about 62 mg/mL, or about 60 mg/mL; about 60 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, about 64 mg/mL, or about 62 mg/mL; about 62 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, about 68 mg/mL, about 66 mg/mL, or about 64 mg/mL; about 64 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, or about 68 mg/mL; about 66 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, about 70 mg/mL, or about 68 mg/mL; about 68 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, about 74 mg/mL, about 72 mg/mL, or about 70 mg/mL; about 70 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, or about 74 mg/mL; about 72 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, about 76 mg/mL, or about 74 mg/mL; about 74 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, about 78 mg/mL, or about 76 mg/mL; about 76 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, about 80 mg/mL, or about 78 mg/mL; about 78 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, about 82 mg/mL, or about 80 mg/mL; about 80 mg/mL to about 100 mg/mL, about 98 mg/mL, 96 mg/mL, about 94 mg/mL, about 92 mg/mL, about 90 mg/mL, about 88 mg/mL, about 86 mg/mL, about 84 mg/mL, or about 82 mg/mL; about 82 mg/mL to about 100 mg/mL, about 98 mg/mL, 96 mg/mL, about 94 mg/mL, about 92 mg/mL, about 90 mg/mL, about 88 mg/mL, about 86 mg/mL, or about 84 mg/mL; about 84 mg/mL to about 100 mg/mL, about 98 mg/mL, 96 mg/mL, about 94 mg/mL, about 92 mg/mL, about 90 mg/mL, about 88 mg/mL, or about 86 mg/mL; about 86 mg/mL to about 100 mg/mL, about 98 mg/mL, 96 mg/mL, about 94 mg/mL, about 92 mg/mL, about 90 mg/mL, or about 88 mg/mL; about 88 mg/mL to about 100 mg/mL, about 98 mg/mL, 96 mg/mL, about 94 mg/mL, about 92 mg/mL, or about 90 mg/mL; about 90 mg/mL to about 100 mg/mL, about 98 mg/mL, 96 mg/mL, about 94 mg/mL, or about 92 mg/mL; about 92 mg/mL to about 100 mg/mL, about 98 mg/mL, 96 mg/mL, or about 94 mg/mL; about 94 mg/mL to about 100 mg/mL, about 98 mg/mL, or 96 mg/mL; about 96 mg/mL to about 100 mg/mL or about 98 mg/mL; or about 98 mg/mL to about 100 mg/mL.

In some examples of these methods, the third period of time can be about 0.1 minute to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, about 5 minutes, about 2 minutes, or about 1 minute; about 1 minute to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, about 5 minutes, or about 2 minutes; about 2 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, about 10 minutes, or about 5 minutes; about 5 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, about 15 minutes, or about 10 minutes; about 10 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, about 20 minutes, or about 15 minutes; about 15 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, about 25 minutes, or about 20 minutes; about 20 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, about 30 minutes, or about 25 minutes; about 25 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, about 35 minutes, or about 30 minutes; about 30 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, about 40 minutes, or about 35 minutes; about 35 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, about 45 minutes, or about 40 minutes; about 40 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, about 50 minutes, or about 45 minutes; about 45 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, about 55 minutes, or about 50 minutes; about 50 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, about 1.0 hour, or about 55 minutes; about 55 minutes to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, about 1.5 hours, or about 1.0 hour; about 1.0 hour to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, about 2.0 hours, or about 1.5 hours; about 1.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, about 2.5 hours, or about 2.0 hours; about 2.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, about 3.0 hours, or about 2.5 hours; about 2.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, about 3.5 hours, or about 3.0 hours; about 3.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, about 4.0 hours, or about 3.5 hours; about 3.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, about 4.5 hours, or about 4.0 hours; about 4.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, about 5.0 hours, or about 4.5 hours; about 4.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, about 5.5 hours, or about 5.0 hours; about 5.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, about 6.0 hours, or about 5.5 hours; about 5.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, about 6.5 hours, or about 6.0 hours; about 6.0 hours to about 12 hours, about 11.5 hours, about 11 hours, about 10.5 hours, about 10 hours, about 9.5 hours, about 9.0 hours, about 8.5 hours, about 8.0 hours, about 7.5 hours, about 7 hours, or about 6.5 hours; about 6.5 hours to about 12 hours, about 11.5 hours, about 11 hours, about 10.5 hours, about 10 hours, about 9.5 hours, about 9.0 hours, about 8.5 hours, about 8.0 hours, about 7.5 hours, or about 7 hours; about 7 hours to about 12 hours, about 11.5 hours, about 11 hours, about 10.5 hours, about 10 hours, about 9.5 hours, about 9.0 hours, about 8.5 hours, about 8.0 hours, or about 7.5 hours; about 7.5 hours to about 12 hours, about 11.5 hours, about 11 hours, about 10.5 hours, about 10 hours, about 9.5 hours, about 9.0 hours, about 8.5 hours, or about 8.0 hours; about 8.0 hours to about 12 hours, about 11.5 hours, about 11 hours, about 10.5 hours, about 10 hours, about 9.5 hours, about 9.0 hours, or about 8.5 hours; about 8.5 hours to about 12 hours, about 11.5 hours, about 11 hours, about 10.5 hours, about 10 hours, about 9.5 hours, or about 9.0 hours; about 9.0 hours to about 12 hours, about 11.5 hours, about 11 hours, about 10.5 hours, about 10 hours, or about 9.5 hours; about 9.5 hours to about 12 hours, about 11.5 hours, about 11 hours, about 10.5 hours, or about 10 hours; about 10 hours to about 12 hours, about 11.5 hours, about 11 hours, or about 10.5 hours; about 10.5 hours to about 12 hours, about 11.5 hours, or about 11 hours; about 11 hours to about 12 hours, or about 11.5 hours.

In some examples of these methods, the third period of time can be, e.g., about 12 hours to about 72 hours, about 12 hours to about 69 hours, about 12 hours to about 66 hours, about 12 hours to about 63 hours, about 12 hours to about 60 hours, about 12 hours to about 57 hours, about 12 hours to about 54 hours, about 12 hours to about 51 hours, about 12 hours to about 48 hours, about 12 hours to about 45 hours, about 12 hours to about 42 hours, about 12 hours to about 39 hours, about 12 hours to about 36 hours, about 12 hours to about 33 hours, about 12 hours to about 30 hours, about 12 hours to about 27 hours, about 12 hours to about 24 hours, about 12 hours to about 21 hours, about 12 hours to about 18 hours, about 12 hours to about 15 hours, about 15 hours to about 72 hours, about 15 hours to about 69 hours, about 15 hours to about 66 hours, about 15 hours to about 63 hours, about 15 hours to about 60 hours, about 15 hours to about 57 hours, about 15 hours to about 54 hours, about 15 hours to about 51 hours, about 15 hours to about 48 hours, about 15 hours to about 45 hours, about 15 hours to about 42 hours, about 15 hours to about 39 hours, about 15 hours to about 36 hours, about 15 hours to about 33 hours, about 15 hours to about 30 hours, about 15 hours to about 27 hours, about 15 hours to about 24 hours, about 15 hours to about 21 hours, about 15 hours to about 18 hours, about 18 hours to about 72 hours, about 18 hours to about 69 hours, about 18 hours to about 66 hours, about 18 hours to about 63 hours, about 18 hours to about 60 hours, about 18 hours to about 57 hours, about 18 hours to about 54 hours, about 18 hours to about 51 hours, about 18 hours to about 48 hours, about 18 hours to about 45 hours, about 18 hours to about 42 hours, about 18 hours to about 39 hours, about 18 hours to about 36 hours, about 18 hours to about 33 hours, about 18 hours to about 30 hours, about 18 hours to about 27 hours, about 18 hours to about 24 hours, about 18 hours to about 21 hours, about 21 hours to about 72 hours, about 21 hours to about 69 hours, about 21 hours to about 66 hours, about 21 hours to about 63 hours, about 21 hours to about 60 hours, about 21 hours to about 57 hours, about 21 hours to about 54 hours, about 21 hours to about 51 hours, about 21 hours to about 48 hours, about 21 hours to about 45 hours, about 21 hours to about 42 hours, about 21 hours to about 39 hours, about 21 hours to about 36 hours, about 21 hours to about 33 hours, about 21 hours to about 30 hours, about 21 hours to about 27 hours, about 21 hours to about 24 hours, about 24 hours to about 72 hours, about 24 hours to about 69 hours, about 24 hours to about 66 hours, about 24 hours to about 63 hours, about 24 hours to about 60 hours, about 24 hours to about 57 hours, about 24 hours to about 54 hours, about 24 hours to about 51 hours, about 24 hours to about 48 hours, about 24 hours to about 45 hours, about 24 hours to about 42 hours, about 24 hours to about 39 hours, about 24 hours to about 36 hours, about 24 hours to about 33 hours, about 24 hours to about 30 hours, about 24 hours to about 27 hours, about 27 hours to about 72 hours, about 27 hours to about 69 hours, about 27 hours to about 66 hours, about 27 hours to about 63 hours, about 27 hours to about 60 hours, about 27 hours to about 57 hours, about 27 hours to about 54 hours, about 27 hours to about 51 hours, about 27 hours to about 48 hours, about 27 hours to about 45 hours, about 27 hours to about 42 hours, about 27 hours to about 39 hours, about 27 hours to about 36 hours, about 27 hours to about 33 hours, about 27 hours to about 30 hours, about 30 hours to about 72 hours, about 30 hours to about 69 hours, about 30 hours to about 66 hours, about 30 hours to about 63 hours, about 30 hours to about 60 hours, about 30 hours to about 57 hours, about 30 hours to about 54 hours, about 30 hours to about 51 hours, about 30 hours to about 48 hours, about 30 hours to about 45 hours, about 30 hours to about 42 hours, about 30 hours to about 39 hours, about 30 hours to about 36 hours, about 30 hours to about 33 hours, about 33 hours to about 72 hours, about 33 hours to about 69 hours, about 33 hours to about 66 hours, about 33 hours to about 63 hours, about 33 hours to about 60 hours, about 33 hours to about 57 hours, about 33 hours to about 54 hours, about 33 hours to about 51 hours, about 33 hours to about 48 hours, about 33 hours to about 45 hours, about 33 hours to about 42 hours, about 33 hours to about 39 hours, about 33 hours to about 36 hours, about 36 hours to about 72 hours, about 36 hours to about 69 hours, about 36 hours to about 66 hours, about 36 hours to about 63 hours, about 36 hours to about 60 hours, about 36 hours to about 57 hours, about 36 hours to about 54 hours, about 36 hours to about 51 hours, about 36 hours to about 48 hours, about 36 hours to about 45 hours, about 36 hours to about 42 hours, about 36 hours to about 39 hours, about 39 hours to about 72 hours, about 39 hours to about 69 hours, about 39 hours to about 66 hours, about 39 hours to about 63 hours, about 39 hours to about 60 hours, about 39 hours to about 57 hours, about 39 hours to about 54 hours, about 39 hours to about 51 hours, about 39 hours to about 48 hours, about 39 hours to about 45 hours, about 39 hours to about 42 hours, about 42 hours to about 72 hours, about 42 hours to about 69 hours, about 42 hours to about 66 hours, about 42 hours to about 63 hours, about 42 hours to about 60 hours, about 42 hours to about 57 hours, about 42 hours to about 54 hours, about 42 hours to about 51 hours, about 42 hours to about 48 hours, about 42 hours to about 45 hours, about 45 hours to about 72 hours, about 45 hours to about 69 hours, about 45 hours to about 66 hours, about 45 hours to about 63 hours, about 45 hours to about 60 hours, about 45 hours to about 57 hours, about 45 hours to about 54 hours, about 45 hours to about 51 hours, about 45 hours to about 48 hours, about 48 hours to about 72 hours, about 48 hours to about 69 hours, about 48 hours to about 66 hours, about 48 hours to about 63 hours, about 48 hours to about 60 hours, about 48 hours to about 57 hours, about 48 hours to about 54 hours, about 48 hours to about 51 hours, about 51 hours to about 72 hours, about 51 hours to about 69 hours, about 51 hours to about 66 hours, about 51 hours to about 63 hours, about 51 hours to about 60 hours, about 51 hours to about 57 hours, about 51 hours to about 54 hours, about 54 hours to about 72 hours, about 54 hours to about 69 hours, about 54 hours to about 66 hours, about 54 hours to about 63 hours, about 54 hours to about 60 hours, about 54 hours to about 57 hours, about 57 hours to about 72 hours, about 57 hours to about 69 hours, about 57 hours to about 66 hours, about 57 hours to about 63 hours, about 57 hours to about 60 hours, about 60 hours to about 72 hours, about 60 hours to about 69 hours, about 60 hours to about 66 hours, about 60 hours to about 63 hours, about 63 hours to about 72 hours, about 63 hours to about 69 hours, about 63 hours to about 66 hours, about 66 hours to about 72 hours, about 66 hours to about 69 hours, or about 69 hours to about 72 hours.

In some embodiments of these methods, the collected fluid of step (d) that is continuously flowed into the second circuit system including the TFVF unit can include a total virus titer of about $10^{-1}$ to about $10^{-20}$, about $10^{-1}$ to about $10^{-19}$, about $10^{-1}$ to about $10^{-18}$, about $10^{-1}$ to about $10^{-17}$, about $10^{-1}$ to about $10^{-16}$, about $10^{-1}$ to about $10^{-15}$, about $10^{-1}$ to about $10^{-14}$, about $10^{-1}$ to about $10^{-13}$, about $10^{-1}$ to about $10^{-12}$, about $10^{-1}$ to about $10^{-11}$, about $10^{-1}$ to about $10^{-10}$, about $10^{-1}$ to about $10^{-9}$, about $10^{-1}$ to about $10^{-8}$, about $10^{-1}$ to about $10^{-7}$, about $10^{-1}$ to about $10^{-6}$, about $10^{-1}$ to about $10^{-5}$, about $10^{-1}$ to about $10^{-4}$, about $10^{-1}$ to about $10^{-3}$, about $10^{-1}$ to about $10^{-2}$, about $10^{-2}$ to about $10^{-20}$, about $10^{-2}$ to about $10^{-19}$, about $10^{-2}$ to about $10^{-18}$, about $10^{-2}$ to about $10^{-17}$, about $10^{-2}$ to about $10^{-16}$, about $10^{-2}$ to about $10^{-15}$, about $10^{-2}$ to about $10^{-14}$, about $10^{-2}$ to about $10^{-13}$, about $10^{-2}$ to about $10^{-12}$, about $10^{-2}$ to about $10^{-11}$, about $10^{-2}$ to about $10^{-10}$, about $10^{-2}$ to about $10^{-9}$, about $10^{-2}$ to about $10^{-8}$, about $10^{-2}$ to about $10^{-7}$, about $10^{-2}$ to about $10^{-2}$, about $10^{-2}$ to about $10^{-5}$, about $10^{-2}$ to about $10^{-4}$, about $10^{-2}$ to about $10^{-3}$, about $10^{-3}$ to about $10^{-20}$, about $10^{-3}$ to about $10^{-19}$, about $10^{-3}$ to about $10^{-18}$, about $10^{-3}$ to about $10^{-17}$, about $10^{-3}$ to about $10^{-16}$, about $10^{-3}$ to about $10^{-15}$, about $10^{-3}$ to about $10^{-14}$, about $10^{-3}$ to about $10^{-13}$, about $10^{-3}$ to about $10^{-12}$, about $10^{-3}$ to about $10^{-11}$, about $10^{-3}$ to about $10^{-10}$, about $10^{-3}$ to about $10^{-9}$, about $10^{-3}$ to about $10^{-8}$, about $10^{-3}$ to about $10^{-7}$, about $10^{-3}$ to about $10^{-6}$, about $10^{-3}$ to about $10^{-5}$, about $10^{-3}$ to about $10^{-4}$, about $10^{-4}$ to about $10^{-20}$, about $10^{-4}$ to about $10^{-19}$, about $10^{-4}$ to about $10^{-18}$, about $10^{-3}$ to about $10^{-17}$, about $10^{-4}$ to about $10^{-16}$, about $10^{-4}$ to about $10^{-15}$, about $10^{-4}$ to about $10^{-14}$, about $10^{-4}$ to about $10^{-13}$, about $10^{-4}$ to about $10^{-12}$, about $10^{-4}$ to about $10^{-11}$, about $10^{-4}$ to about $10^{-10}$, about $10^{-4}$ to about $10^{-9}$, about $10^{-4}$ to about $10^{-8}$, about $10^{-4}$ to about $10^{-7}$, about $10^{-4}$ to about $10^{-6}$, about $10^{-4}$ to about $10^{-5}$, about $10^{-5}$ to about $10^{-20}$, about $10^{-5}$ to about $10^{-19}$, about $10^{-5}$ to about $10^{-18}$, about $10^{-5}$ to about $10^{-17}$, about $10^{-5}$ to about $10^{-16}$, about $10^{-5}$ to about $10^{-15}$, about $10^{-5}$ to about $10^{-14}$, about $10^{-5}$ to about $10^{-13}$, about $10^{-5}$ to about $10^{-12}$, about $10^{-5}$ to about $10^{-11}$, about $10^{-5}$ to about $10^{-10}$, about $10^{-5}$ to about $10^{-9}$, about $10^{-5}$ to about $10^{-8}$, about $10^{-5}$ to about $10^{-7}$, about $10^{-5}$ to about $10^{-6}$, about $10^{-6}$ to about $10^{-20}$, about $10^{-6}$ to about $10^{-19}$, about $10^{-6}$ to about $10^{-18}$, about $10^{-6}$ to about $10^{-17}$, about $10^{-6}$ to about $10^{-16}$, about $10^{-6}$ to about $10^{-15}$, about $10^{-6}$ to about $10^{-14}$, about $10^{-6}$ to about $10^{-13}$, about $10^{-6}$ to about $10^{-12}$, about $10^{-6}$ to about $10^{-11}$, about $10^{-6}$ to about $10^{-10}$, about $10^{-6}$ to about $10^{-9}$, about $10^{-6}$ to about $10^{-8}$, about $10^{-6}$ to about $10^{-7}$, about $10^{-7}$ to about $10^{-20}$, about $10^{-7}$ to about $10^{-19}$, about $10^{-7}$ to about $10^{-18}$, about $10^{-7}$ to about $10^{-17}$, about $10^{-7}$ to about $10^{-16}$, about $10^{-7}$ to about $10^{-15}$, about $10^{-7}$ to about $10^{-14}$, about $10^{-7}$ to about $10^{-13}$, about $10^{-7}$ to about $10^{-12}$, about $10^{-7}$ to about $10^{-11}$, about $10^{-7}$ to about $10^{-10}$, about $10^{-7}$ to about $10^{-9}$, about $10^{-7}$ to about $10^{-8}$, about $10^{-8}$ to about $10^{-20}$, about $10^{-8}$ to about $10^{-19}$, about $10^{-8}$ to about $10^{-18}$, about $10^{-8}$ to about $10^{-17}$, about $10^{-8}$ to about $10^{-16}$, about $10^{-8}$ to about $10^{-15}$, about $10^{-8}$ to about $10^{-14}$, about $10^{-8}$ to about $10^{-13}$, about $10^{-8}$ to about $10^{-12}$, about $10^{-8}$ to about $10^{-11}$, about $10^{-8}$ to about $10^{-10}$, about $10^{-8}$ to about $10^{-9}$, about $10^{-9}$ to about $10^{-20}$, about $10^{-9}$ to about $10^{-19}$, about $10^{-9}$ to about $10^{-18}$, about $10^{-9}$ to about $10^{-17}$, about $10^{-9}$ to about $10^{-16}$, about $10^{-9}$ to about $10^{-15}$, about $10^{-9}$ to about $10^{-14}$, about $10^{-9}$ to about $10^{-13}$, about $10^{-9}$ to about $10^{-12}$, about $10^{-9}$ to about $10^{-11}$, about $10^{-9}$ to about $10^{-10}$, about $10^{-10}$ to about $10^{-20}$, about $10^{-10}$ to about $10^{-19}$, about $10^{-10}$ to about $10^{-18}$, about $10^{-10}$ to about $10^{-17}$, about $10^{-10}$ to about $10^{-16}$, about $10^{-10}$ to about $10^{-15}$, about $10^{-10}$ to about $10^{-14}$, about $10^{-10}$ to about $10^{-13}$, about $10^{-10}$ to about $10^{-12}$, about $10^{-10}$ to about $10^{-11}$, about $10^{-11}$ to about $10^{-20}$, about $10^{-11}$ to about $10^{-19}$, about $10^{-11}$ to about $10^{-18}$, about $10^{-11}$ to about $10^{-17}$, about $10^{-11}$ to about $10^{-16}$, about $10^{-11}$ to about $10^{-15}$, about $10^{-11}$ to about $10^{-14}$, about $10^{-11}$ to about $10^{-13}$, about $10^{-11}$ to about $10^{-12}$, about $10^{-12}$ to about $10^{-20}$, about $10^{-12}$ to about $10^{-19}$, about $10^{-12}$ to about $10^{-18}$, about $10^{-12}$ to about $10^{-17}$, about $10^{-12}$ to about $10^{-16}$, about $10^{-12}$ to about $10^{-15}$, about $10^{-12}$ to about $10^{-14}$, about $10^{-12}$ to about $10^{-13}$, about $10^{-13}$ to about $10^{-20}$, about $10^{-13}$ to about $10^{-19}$, about $10^{-13}$ to about $10^{-18}$, about $10^{-13}$ to about $10^{-17}$, about $10^{-13}$ to about $10^{-16}$, about $10^{-13}$ to about $10^{-15}$, about $10^{-13}$ to about $10^{-14}$, about $10^{-14}$ to about $10^{-20}$, about $10^{-14}$ to about $10^{-19}$, about $10^{-14}$ to about $10^{-18}$, about $10^{-14}$ to about $10^{-17}$, about $10^{-14}$ to about $10^{-16}$, about $10^{-14}$ to about $10^{-15}$, about $10^{-15}$ to about $10^{-20}$, about $10^{-15}$ to about $10^{-19}$, about $10^{-15}$ to about $10^{-18}$, about $10^{-15}$ to about $10^{-17}$, about $10^{-15}$ to about $10^{-16}$, about $10^{-16}$ to about $10^{-20}$, about $10^{-16}$ to about $10^{-19}$, about $10^{-16}$ to about $10^{-18}$, about $10^{-16}$ to about $10^{-17}$, about $10^{-17}$ to about $10^{-20}$, about $10^{-17}$ to about $10^{-19}$, about $10^{-17}$ to about $10^{-18}$, about $10^{-18}$ to about $10^{-20}$, about $10^{-18}$ to about $10^{-19}$, or about $10^{-19}$ to about $10^{-20}$.

In some embodiments, the step of continuously flowing the collected fluid of step (d) into the second circuit system including a TFVF unit can be performed such that the flux across the filter or one or more filters in the TFVF unit is, e.g., about 10 LMH to about 50 LMH, about 10 LMB to about 48 LMH, about 10 LMH to about 46 LMH, about 10 LMH to about 44 LMH, about 10 LMH to about 42 LMH, about 10 LMH to about 40 LMH, about 10 LMH to about 38 LMH, about 10 LMH to about 36 LMH, about 10 LMH to about 34 LMH, about 10 LMH to about 32 LMH, about 10 LMH to about 30 LMH, about 10 LMH to about 28 LMH, about 10 LMH to about 26 LMH, about 10 LMH to about 24 LMH, about 10 LMH to about 22 LMH, about 10 LMH to about 20 LMH, about 10 LMH to about 18 LMH, about 10 LMH to about 16 LMH, about 10 LMH to about 15 LMH, about 15 LMH to about 50 LMH, about 15 LMB to about 48 LMH, about 15 LMH to about 46 LMH, about 15 LMH to about 44 LMH, about 15 LMH to about 42 LMH, about 15 LMH to about 40 LMH, about 15 LMH to about 38 LMH, about 15 LMH to about 36 LMH, about 15 LMH to about 34 LMH, about 15 LMH to about 32 LMH, about 15 LMH to about 30 LMH, about 15 LMH to about 28 LMH, about 15 LMH to about 26 LMH, about 15 LMH to about 24 LMH, about 15 LMH to about 22 LMH, about 15 LMH to about 20 LMH, about 15 LMH to about 18 LMH, about 20 LMH to about 50 LMH, about 20 LMB to about 48 LMH, about 20 LMH to about 46 LMH, about 20 LMH to about 44 LMH, about 20 LMH to about 42 LMH, about 20 LMH to about 40 LMH, about 20 LMH to about 38 LMH, about 20 LMH to about 36 LMH, about 20 LMH to about 34 LMH, about 20 LMH to about 32 LMH, about 20 LMH to about 30 LMH, about 20 LMH to about 28 LMH, about 20 LMH to about 26 LMH, about 20 LMH to about 24 LMH, about 20 LMH to about 22 LMH, about 22 LMH to about 50 LMH, about 22 LMB to about 48 LMH, about 22 LMH to about 46 LMH, about 22 LMH to about 44 LMH, about 22 LMH to about 42 LMH, about 22 LMH to about 40 LMH, about 22 LMH to about 38 LMH, about 22 LMH to about 36 LMH, about 22 LMH to about 34 LMH, about 22 LMH to about 32 LMH, about 22 LMH to about 30 LMH, about 22 LMH to about 28 LMH, about 22 LMH to about 26 LMH, about 22 LMH to about 24 LMH, about 24 LMH to about 50 LMH, about 24 LMB to about 48 LMH, about 24 LMH to about 46 LMH, about 24 LMH to about 44 LMH, about 24 LMH to about 42 LMH, about 24 LMH to about 40 LMH, about 24 LMH to about 38 LMH, about 24 LMH to about 36 LMH, about 24 LMH to about 34 LMH, about 24 LMH to about 32 LMH, about 24 LMH to about 30 LMH, about 24 LMH to about 28 LMH, about 24 LMH to about 26 LMH, about 26 LMH to about 50 LMH, about 26 LMB to about 48 LMH, about 26 LMH to about 46 LMH, about 26 LMH to about 44 LMH, about 26 LMH to about 42 LMH, about 26 LMH to about 40 LMH, about 26 LMH to about 38 LMH, about 26 LMH to about 36 LMH, about 26 LMH to about 34 LMH, about 26 LMH to about 32 LMH, about 26 LMH to about 30 LMH, about 26 LMH to about 28 LMH, about 28 LMH to about 50 LMH, about 28 LMB to about 48 LMH, about 28 LMH to about 46 LMH, about 28 LMH to about 44 LMH, about 28 LMH to about 42 LMH, about 28 LMH to about 40 LMH, about 28 LMH to about 38 LMH, about 28 LMH to about 36 LMH, about 28 LMH to about 34 LMH, about 28 LMH to about 32 LMH, about 28 LMH to about 30 LMH, about 30 LMH to about 50 LMH, about 30 LMB to about 48 LMH, about 30 LMH to about 46 LMH, about 30 LMH to about 44 LMH, about 30 LMH to about 42 LMH, about 30 LMH to about 40 LMH, about 30 LMH to about 38 LMH, about 30 LMH to about 36 LMH, about 30 LMH to about 34 LMH, about 30 LMH to about 32 LMH, about 32 LMH to about 50 LMH, about 32 LMB to about 48 LMH, about 32 LMH to about 46 LMH, about 32 LMH to about 44 LMH, about 32 LMH to about 42 LMH, about 32 LMH to about 40 LMH, about 32 LMH to about 38 LMH, about 32 LMH to about 36 LMH, about 32 LMH to about 34 LMH, about 34 LMH to about 50 LMH, about 34 LMB to about 48 LMH, about 34 LMH to about 46 LMH, about 34 LMH to about 44 LMH, about 34 LMH to about 42 LMH, about 34 LMH to about 40 LMH, about 34 LMH to about 38 LMH, about 34 LMH to about 36 LMH, about 36 LMH to about 50 LMH, about 36 LMB to about 48 LMH, about 36 LMH to about 46 LMH, about 36 LMH to about 44 LMH, about 36 LMH to about 42 LMH, about 36 LMH to about 40 LMH, about 36 LMH to about 38 LMH, about 38 LMH to about 50 LMH, about 38 LMB to about 48 LMH, about 38 LMH to about 46 LMH, about 38 LMH to about 44 LMH, about 38 LMH to about 42 LMH, about 38 LMH to about 40 LMH, about 40 LMH to about 50 LMH, about 40 LMB to about 48 LMH, about 40 LMH to about 46 LMH, about 40 LMH to about 44 LMH, about 40 LMH to about 42 LMH, about 42 LMH to about 50 LMH, about 42 LMB to about 48 LMH, about 42 LMH to about 46 LMH, about 42 LMH to about 44 LMH, about 44 LMH to about 50 LMH, about 44 LMB to about 48 LMH, about 44 LMH to about 46 LMH, about 46 LMH to about 50 LMH, about 46 LMB to about 48 LMH, or about 48 LMH to about 50 LMH.

In some embodiments, the step of continuously flowing the collected fluid from step (d) into the second circuit system including a TFVF unit can be performed such that the pressure across the filter or the one or more filters in the TFVF unit, or the pressure in the second system including the TFVF is, e.g., about 2 psi to about 40 psi, about 2 psi to about 38 psi, about 2 psi to about 36 psi, about 2 psi to about 34 psi, about 2 psi to about 32 psi, about 2 psi to about 30 psi, about 2 psi to about 28 psi, about 2 psi to about 26 psi, about 2 psi to about 24 psi, about 2 psi to about 22 psi, about 2 psi to about 20 psi, about 2 psi to about 18 psi, about 2 psi to about 16 psi, about 2 psi to about 14 psi, about 2 psi to about 12 psi, about 2 psi to about 10 psi, about 2 psi to about 8 psi, about 2 psi to about 6 psi, about 2 psi to about 4 psi, about 4 psi to about 40 psi, about 4 psi to about 38 psi, about 4 psi to about 36 psi, about 4 psi to about 34 psi, about 4 psi to about 32 psi, about 4 psi to about 30 psi, about 4 psi to about 28 psi, about 4 psi to about 26 psi, about 4 psi to about 24 psi, about 4 psi to about 22 psi, about 4 psi to about 20 psi, about 4 psi to about 18 psi, about 4 psi to about 16 psi, about 4 psi to about 14 psi, about 4 psi to about 12 psi, about 4 psi to about 10 psi, about 4 psi to about 8 psi, about 4 psi to about 6 psi, about 6 psi to about 40 psi, about 6 psi to about 38 psi, about 6 psi to about 36 psi, about 6 psi to about 34 psi, about 6 psi to about 32 psi, about 6 psi to about 30 psi, about 6 psi to about 28 psi, about 6 psi to about 26 psi, about 6 psi to about 24 psi, about 6 psi to about 22 psi, about 6 psi to about 20 psi, about 6 psi to about 18 psi, about 6 psi to about 16 psi, about 6 psi to about 14 psi, about 6 psi to about 12 psi, about 6 psi to about 10 psi, about 6 psi to about 8 psi, about 8 psi to about 40 psi, about 8 psi to about 38 psi, about 8 psi to about 36 psi, about 8 psi to about 34 psi, about 8 psi to about 32 psi, about 8 psi to about 30 psi, about 8 psi to about 28 psi, about 8 psi to about 26 psi, about 8 psi to about 24 psi, about 8 psi to about 22 psi, about 8 psi to about 20 psi, about 8 psi to about 18 psi, about 8 psi to about 16 psi, about 8 psi to about 14 psi, about 8 psi to about 12 psi, about 8 psi to about 10 psi, about 10 psi to about 40 psi, about 10 psi to about 38 psi, about 10 psi to about 36 psi, about 10 psi to about 34 psi, about 10 psi to about 32 psi, about 10 psi to about 30 psi, about 10 psi to about 28 psi, about 10 psi to about 26 psi, about 10 psi to about 24 psi, about 10 psi to about 22 psi, about 10 psi to about 20 psi, about 10 psi to about 18 psi, about 10 psi to about 16 psi, about 10 psi to about 14 psi, about 10 psi to about 12 psi, about 12 psi to about 40 psi, about 12 psi to about 38 psi, about 12 psi to about 36 psi, about 12 psi to about 34 psi, about 12 psi to about 32 psi, about 12 psi to about 30 psi, about 12 psi to about 28 psi, about 12 psi to about 26 psi, about 12 psi to about 24 psi, about 12 psi to about 22 psi, about 12 psi to about 20 psi, about 12 psi to about 18 psi, about 12 psi to about 16 psi, about 12 psi to about 14 psi, about 14 psi to about 40 psi, about 14 psi to about 38 psi, about 14 psi to about 36 psi, about 14 psi to about 34 psi, about 14 psi to about 32 psi, about 14 psi to about 30 psi, about 14 psi to about 28 psi, about 14 psi to about 26 psi, about 14 psi to about 24 psi, about 14 psi to about 22 psi, about 14 psi to about 20 psi, about 14 psi to about 18 psi, about 14 psi to about 16 psi, about 16 psi to about 40 psi, about 16 psi to about 38 psi, about 16 psi to about 36 psi, about 16 psi to about 34 psi, about 16 psi to about 32 psi, about 16 psi to about 30 psi, about 16 psi to about 28 psi, about 16 psi to about 26 psi, about 16 psi to about 24 psi, about 16 psi to about 22 psi, about 16 psi to about 20 psi, about 16 psi to about 18 psi, about 18 psi to about 40 psi, about 18 psi to about 38 psi, about 18 psi to about 36 psi, about 18 psi to about 34 psi, about 18 psi to about 32 psi, about 18 psi to about 30 psi, about 18 psi to about 28 psi, about 18 psi to about 26 psi, about 18 psi to about 24 psi, about 18 psi to about 22 psi, about 18 psi to about 20 psi, about 20 psi to about 40 psi, about 20 psi to about 38 psi, about 20 psi to about 36 psi, about 20 psi to about 34 psi, about 20 psi to about 32 psi, about 20 psi to about 30 psi, about 20 psi to about 28 psi, about 20 psi to about 26 psi, about 20 psi to about 24 psi, about 20 psi to about 22 psi, about 22 psi to about 40 psi, about 22 psi to about 38 psi, about 22 psi to about 36 psi, about 22 psi to about 34 psi, about 22 psi to about 32 psi, about 22 psi to about 30 psi, about 22 psi to about 28 psi, about 22 psi to about 26 psi, about 22 psi to about 24 psi, about 24 psi to about 40 psi, about 24 psi to about 38 psi, about 24 psi to about 36 psi, about 24 psi to about 34 psi, about 24 psi to about 32 psi, about 24 psi to about 30 psi, about 24 psi to about 28 psi, about 24 psi to about 26 psi, about 26 psi to about 40 psi, about 26 psi to about 38 psi, about 26 psi to about 36 psi, about 26 psi to about 34 psi, about 26 psi to about 32 psi, about 26 psi to about 30 psi, about 26 psi to about 28 psi, about 28 psi to about 40 psi, about 28 psi to about 38 psi, about 28 psi to about 36 psi, about 28 psi to about 34 psi, about 28 psi to about 32 psi, about 28 psi to about 30 psi, about 30 psi to about 40 psi, about 30 psi to about 38 psi, about 30 psi to about 36 psi, about 30 psi to about 34 psi, about 30 psi to about 32 psi, about 32 psi to about 40 psi, about 32 psi to about 38 psi, about 32 psi to about 36 psi, about 32 psi to about 34 psi, about 34 psi to about 40 psi, about 34 psi to about 38 psi, about 34 psi to about 36 psi, about 36 psi to about 40 psi, about 36 psi to about 38 psi, or about 38 psi to about 40 psi.

Methods of Processing a Fluid Including a Recombinant Therapeutic Protein that Include the Use of a Circuit System Including a TFVF Unit Also provided are methods of processing a fluid including a recombinant therapeutic protein that include: (a) providing a circuit system including (i) a TFVF unit having first and second inlets, and (ii) a conduit in fluid communication between the first and second inlets of the TFVF unit, including at least one port for flowing fluid into or out of, or both, of the system, where the system is configured such that fluid can be flowed through the conduit and the TFVF unit, and filtrate including the recombinant therapeutic protein can be collected from the TFVF unit; (b) continuously flowing a fluid including a recombinant therapeutic protein into the circuit system through one of the at least one port, and collecting filtrate including the recombinant therapeutic protein from the TFVF unit for a period of time. As can be appreciated by those skilled in the art, some embodiments of these methods can further include recirculating any fluid including the recombinant therapeutic protein in the conduit of the circuit system including a TFVF unit that did not pass through the one or more tangential virus filters in the TFVF unit (e.g., acts as a buffer when a new volume of a fluid including the recombinant therapeutic protein is flowed into the conduit of the circuit system including a TFVF unit).

In some embodiments, the TFVF unit includes one, two, three, four, five, six, seven, eight, nine, ten, eleven, or twelve tangential virus filters. In some examples of these methods, the TFVF unit can include one or more tangential virus filter(s) having a surface area of about 0.05 cm$^2$ to about 100 m$^2$ (or any of the subranges of this range described herein).

In some embodiments, the TFVF unit includes one or more tangential virus filters having a pore size of about 5 nm to about 220 nm (or any of the subranges of this range described herein). A variety of virus filters that can be used in a TFVF unit are known in the art. For example, virus filters that can be used in a TFVF unit are commercially available from Asahi Kasei (Tokyo, Japan). In some embodiments, the virus filter is a Planova™ filter (e.g, a Planova™ 15N, a Planova™ 20N, a Planova™ 35N, a Planova™ 75N). In some embodiments, the virus filter is a Planova™ BioEX filter. The virus filters that can be used in a TFVF unit can include, e.g., hollow fiber membranes.

The conduit can be simple tubing, e.g., biocompatible tubing. Non-limiting examples of useful tubing include silicone rubber, polyurethane, polydioxanone (PDO), polyhydroxyalkanoate, polyhydroxybutyrate, poly(glycerol sebacate), polyglycolide, polylactide, polycaprolactone, or polyanhydride, or copolymers or derivatives including these and/or other polymers. Alternatively or in addition, the conduit can include polyvinyl chloride. The conduit can be, e.g., weldable transfer tubing.

In some embodiments, the internal diameter of the conduit in the circuit system can be about 5 mm to about 50 mm (e.g., or any of the subranges thereof described herein). In some embodiments, the conduit in the circuit system has a total length of about 1.0 cm to about 75 cm (or any of the subranges of this range described herein). Additional examples of conduits and properties of conduits that can be used in the second circuit system are well-known by those in the art.

In some examples, the circuit system includes one, two, three, four, or five ports. In some examples, the at least one port in the circuit system can be a valve. In other examples, the at least one port in the circuit system can be an injection port or can have a ribbed threading. The at least one port in the circuit system can be any type of port commonly known in the art. In some examples, the circuit system can further include a pump (e.g., a low-turbulence pump, e.g., a peristaltic pump) disposed in the conduit. In some embodiments, the circuit system does not include a holding tank.

In some examples, step (b) includes continuously flowing (e.g., unidirectionally or bidirectionally flowing) a fluid including a recombinant therapeutic protein into the circuit system at a rate of between about 0.05 mL/minute to about 25 mL/minute (or any of the subranges of this range described herein). In some examples, the filtrate collected from the TFVF unit in step (b) includes a concentration of recombinant therapeutic protein of about 0.1 mg/mL to about 100 mg/mL (or any of the subranges of this range described herein). In some examples of these methods, the period of time can be about 5 minutes to about 12 hours (or any of the subranges of this range described herein).

In some examples of these methods, the period of time can be, e.g., about 12 hours to about 72 hours (or any of the subranges of this range described herein).

In some embodiments, the fluid that is continuously flowed into the circuit system including the TFVF unit through one of the at least one port can include a total virus titer of about $10^{-1}$ to about $10^{-20}$ (or any of the subranges of this range described herein).

In some embodiments, the step of continuously flowing the fluid through the circuit system including a TFVF unit can be performed such that the flux across the filter or one or more filters in the TFVF unit is, e.g., about 10 LMH to about 50 LMH (or any of the subranges of this range described herein).

In some embodiments, the step of continuously flowing the fluid through the circuit system including a TFVF unit can be performed such that the pressure across the filter or the one or more filters in the TFVF unit, or the pressure in the system including the TFVF is, e.g., about 2 psi to about 40 psi (or any of the subranges of this range described herein).

In some embodiments, the method can further include performing one or more unit operations on a fluid including the recombinant protein. Non-limiting examples of these unit operations include: capturing a recombinant therapeutic protein, purifying a recombinant therapeutic protein, polishing a recombinant therapeutic protein, viral inactivation, viral filtration, adjusting the ionic concentration and/or pH of a fluid containing the recombinant therapeutic protein, filtration of a fluid containing the recombinant therapeutic protein, precipitation and flocculation, aqueous two-phase extraction, lyophilization, and crystallization. Non-limiting aspects of each of these exemplary unit operations are described herein.

Figure 2:
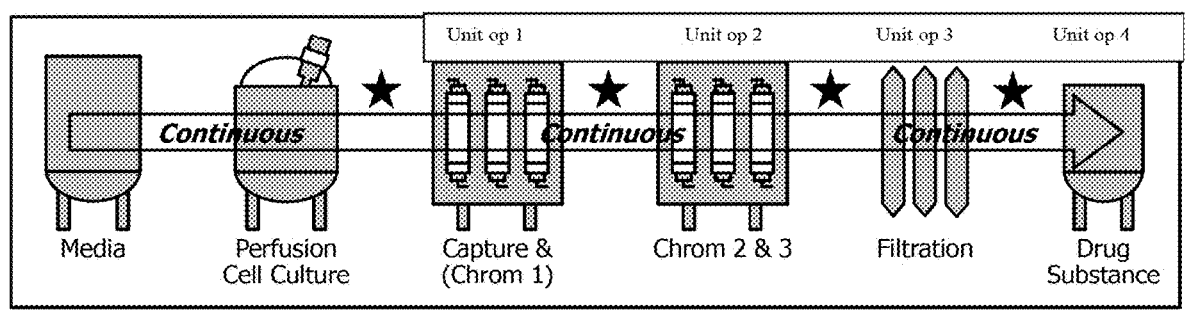
FIG. 2 is a schematic showing a manufacturing system connected with a perfusion culture bioreactor that results in the continuous manufacture of a therapeutic protein drug substance. The asterisks indicate exemplary positions where one or both of a circuit system including a TFF unit (e.g., any of the circuit systems including a TFF unit described herein) and a circuit system including a tangential flow virus filtration (TFVF) unit (e.g., any of the circuit systems including a TFVF unit described herein) can be positions in this exemplary manufacturing system.

Integrated and Continuous Processes for Manufacturing a Therapeutic Protein Drug Substance Provided herein are integrated and continuous processes for manufacturing a therapeutic protein drug substance. These processes include providing a liquid culture medium containing a recombinant therapeutic protein that is substantially free of cells, where the liquid culture medium is fed into a first multi-column chromatography system (MCCS1); capturing the recombinant therapeutic protein in the liquid culture medium using the MCCS1, where the eluate of the MCCS1 containing the recombinant therapeutic protein is continuously fed into a second multi-column chromatography system (MCCS2); purifying and polishing the recombinant therapeutic protein using the MCCS2, where the eluate from the MCCS2 is a fluid including the recombinant therapeutic protein; processing the fluid including the recombinant therapeutic protein using any of the methods described herein, where the process is integrated and runs continuously from the liquid culture medium to the collected fluid or filtrate including the recombinant therapeutic protein, where the collected fluid or filtrate is the therapeutic protein drug substance. Examples of systems that can be used to perform these processes are shown in FIGS. 1 and 2 (where asterisks indicate where one or both of a circuit system including tangential flow filtration unit and a tangential flow virus filtration unit can optionally be introduced into the system). For example, one or both of a circuit system including tangential flow filtration unit and a tangential flow viral filtration unit can be used before the performance of a first unit operation, between the performance of a first and second unit operation, between the performance of a second and a third unit operation, between the performance of a third and a fourth unit operation, between the performance of a fourth and a fifth unit operation, between the performance of a fifth and a sixth unit operation, between the performance of a sixth and a seventh unit operation, between the performance of a seventh and an eighth unit operation, and/or between an eighth and a ninth unit operation.

The processes described herein provide continuous and time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the second MCCS can be, e.g., between about 4 hours and about 48 hours, inclusive, e.g., between about 4 hours and about 40 hours, between about 4 hours and about 35 hours, between about 4 hours and about 30 hours, between about 4 hours and about 28 hours, between about 4 hours and about 26 hours, between about 4 hours and about 24 hours, between about 4 hours and about 22 hours, between about 4 hours and about 20 hours, between about 4 hours and about 18 hours, between about 4 hours and about 16 hours, between about 4 hours and about 14 hours, between about 4 hours and about 12 hours, between about 6 hours and about 12 hours, between about 8 hours and about 12 hours, between about 6 hours and about 20 hours, between about 6 hours and about 18 hours, between about 6 hours and about 14 hours, between about 8 hours and about 16 hours, between about 8 hours and about 14 hours, between about 8 hours and about 12 hours, between about 10 hours and 20 hours, between about 10 hours and 18 hours, between about 10 hours and 16 hours, between about 10 hours and 14 hours, between about 12 hours and about 14 hours, between about 10 hours and about 40 hours, between about 10 hours and about 35 hours, between about 10 hours and about 30 hours, between about 10 hours and about 25 hours, between about 15 hours and about 40 hours, between about 15 hours and about 35 hours, between about 15 hours and about 30 hours, between about 20 hours and about 40 hours, between about 20 hours and about 35 hours, or between about 20 hours and about 30 hours, inclusive. In other examples, the elapsed time between feeding the fluid (e.g., a liquid culture medium) containing a therapeutic protein into the MCCS1 and eluting a therapeutic protein drug substance (containing the therapeutic protein) from the MCCS2 is, e.g., greater than about 4 hours and less than about 40 hours, inclusive, e.g., greater than about 4 hours and less than about 39 hours, about 38 hours, about 37 hours, about 36 hours, about 35 hours, about 34 hours, about 33 hours, about 32 hours, about 31 hours, about 30 hours, about 29 hours, about 28 hours, about 27 hours, about 26 hours, about 25 hours, about 24 hours, about 23 hours, about 22 hours, about 21 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, or about 4.5 hours, inclusive.

Some exemplary processes do not utilize a holding step (e.g., do not use a reservoir (e.g., break tank) in the entire process). Others may use a maximum of 1, 2, 3, 4, or 5 reservoir(s) (e.g., break tank(s)) in the entire process. Any of the processes described herein can utilize a maximum of 1, 2, 3, 4, or 5 reservoir(s) (e.g., break tank(s)) in the entire process, where each break tank only holds a therapeutic protein for a total time period of, e.g., between about 5 minutes and less than about 6 hours, inclusive, e.g., between about 5 minutes and about 5 hours, about 4 hours, about 3 hours, about 2 hours, about 1 hour, or about 30 minutes, inclusive. Any of the reservoir(s) (e.g., break tank(s)) used in the processes described herein can have a capacity that is, e.g., between 1 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL (inclusive); between about 5 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL (inclusive); between about 10 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, or about 20 mL (inclusive); between about 20 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, or about 40 mL (inclusive); between about 40 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, or about 60 mL (inclusive); between about 60 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, or about 80 mL (inclusive); between about 80 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, about 120 mL, or about 100 mL (inclusive); between about 100 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, about 140 mL, or about 120 mL (inclusive); between about 120 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, about 160 mL, or about 140 mL (inclusive); between about 140 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, about 180 mL, or about 160 mL (inclusive); between about 160 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, about 200 mL, or about 180 mL (inclusive); between about 180 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, about 220 mL, or about 200 mL (inclusive); between about 200 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, about 240 mL, or about 220 mL (inclusive); between about 220 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, about 260 mL, or about 240 mL (inclusive); between about 240 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 280 mL, or about 260 mL (inclusive); between about 260 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, or about 280 mL (inclusive); between about 280 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, or about 300 mL (inclusive); between about 300 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, about 400 mL, or about 350 mL (inclusive); between about 350 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, about 450 mL, or about 400 mL (inclusive); between about 400 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, about 500 mL, or about 450 mL (inclusive); between about 450 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, about 550 mL, or about 500 mL (inclusive); between about 500 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, about 600 mL, or about 550 mL (inclusive); between about 550 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, about 650 mL, or about 600 mL (inclusive); between about 600 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, about 700 mL, or about 650 mL (inclusive); between about 650 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, about 750 mL, or about 700 mL (inclusive); between about 700 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, about 800 mL, or about 750 mL (inclusive); between about 750 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, about 850 mL, or about 800 mL (inclusive); between about 800 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, about 900 mL, or about 850 mL (inclusive); between about 850 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, about 950 mL, or about 900 mL (inclusive); between about 900 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, about 1,000 L, or about 950 mL (inclusive); between about 950 mL and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, about 1,500 L, or about 1,000 L (inclusive); between about 1,000 L and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, about 2,000 L, or about 1,500 L (inclusive); between about 1,500 L and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, about 2,500 L, or about 2,000 L (inclusive); between about 2,000 L and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, about 3,000 L, or about 2,500 L (inclusive); between about 2,500 L and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, about 3,500 L, or about 3,000 L (inclusive); between about 3,000 L and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, about 4,000 L, or about 3,500 L (inclusive); between about 3,500 L and about 10,000 L, about 9,500 L, about 9,000 L, about 8,500 L, about 8,000 L, about 7,500 L, about 7,000 L, about 6,500 L, about 6,000 L, about 5,500 L, about 5,000 L, about 4,500 L, or about 4,000 L (inclusive); between about 4,000 L and about 10,000 L, about 9,500 L, about 9,000 L, about 8,500 L, about 8,000 L, about 7,500 L, about 7,000 L, about 6,500 L, about 6,000 L, about 5,500 L, about 5,000 L, or about 4,500 L (inclusive); between about 4,500 L and about 10,000 L, about 9,500 L, about 9,000 L, about 8,500 L, about 8,000 L, about 7,500 L, about 7,000 L, about 6,500 L, about 6,000 L, about 5,500 L, or about 5,000 L (inclusive); between about 5,000 L and about 10,000 L, about 9,500 L, about 9,000 L, about 8,500 L, about 8,000 L, about 7,500 L, about 7,000 L, about 6,500 L, about 6,000 L, or about 5,500 L (inclusive); between about 5,500 L and about 10,000 L, about 9,500 L, about 9,000 L, about 8,500 L, about 8,000 L, about 7,500 L, about 7,000 L, about 6,500 L, or about 6,000 L (inclusive); between about 6,000 L and about 10,000 L, about 9,500 L, about 9,000 L, about 8,500 L, about 8,000 L, about 7,500 L, about 7,000 L, or about 6,500 L (inclusive); between about 6,500 L and about 10,000 L, about 9,500 L, about 9,000 L, about 8,500 L, about 8,000 L, about 7,500 L, or about 7,000 L (inclusive); between about 7,000 L and about 10,000 L, about 9,500 L, about 9,000 L, about 8,500 L, about 8,000 L, or about 7,500 L (inclusive); between about 7,500 L and about 10,000 L, about 9,500 L, about 9,000 L, about 8,500 L, or about 8,000 L (inclusive); between about 8,000 L and about 10,000 L, about 9,500 L, about 9,000 L, or about 8,500 L (inclusive); between about 8,500 L and about 10,000 L, about 9,500 L, or about 9,000 L (inclusive); between about 9,000 L and about 10,000 L or about 9,500 L (inclusive); or between about 9,500 L and about 10,000 L (inclusive).

Any reservoir(s) (e.g., break tank(s)) used (in any of the processes described herein) to hold fluid before it enters into the first MCCS can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the first MCCS. Any of the reservoir(s) (e.g., break tanks(s)) used (in any of the processes described herein) to hold fluid before it enters into the second MCCS (and after the fluid leaves the first MCCS) can have a capacity that is, e.g., between 1 mL and about 100%, inclusive, e.g., between 1 mL and about 90%, about 80%, about 70%, about 60%, about 50%, about 40%, about 30%, about 20%, about 10%, or about 5%, inclusive, of the loading volume of the first column of the second MCCS.

Various additional aspects of these processes are described in detail below and can be used in any combination in the processes provided herein without limitation. Exemplary aspects of the provided processes are described below; however, one skilled in the art will appreciate that additional steps (e.g., the performance of additional unit operations) can be added to the processes described herein and other materials can be used to perform any of the steps of the processes described herein.

Liquid Culture Medium

Liquid culture medium that contains a recombinant therapeutic protein that is substantially free of cells can be derived from any source. For example, the liquid culture medium can be obtained from a recombinant cell culture (e.g., a recombinant bacterial, yeast, or mammalian cell culture). The liquid culture medium can be obtained from a fed-batch cell (e.g., mammalian cell) culture (e.g., a fed-batch bioreactor containing a culture of mammalian cells that secrete the recombinant therapeutic protein) or a perfusion cell (e.g., mammalian cell) culture (e.g., a perfusion bioreactor containing a culture of mammalian cells that secrete the recombinant therapeutic protein). The liquid culture medium can also be a clarified liquid culture medium from a culture of bacterial or yeast cells that secrete the recombinant therapeutic protein.

Liquid culture medium obtained from a recombinant cell culture can be filtered or clarified to obtain a liquid culture medium that is substantially free of cells and/or viruses. Methods for filtering or clarifying a liquid culture medium in order to remove cells are known in the art (e.g., 0.2-μm filtration and filtration using an Alternating Tangential Flow (ATF™) system).

Additional exemplary methods for filtering or clarifying a liquid culture medium include, e.g., immobilized cell separation (e.g., hollow fiber membranes, flat plate membranes, gel encapsulation, ceramic matrices, and fluidized beds, e.g., as described in Kühtreiber et al., *Springer Science & Business Media*, 2013; Meuwly et al., *Biotechnol. Adv.* 25(1): 45-56, 2007; Jen et al., *Biotechnol. Bioeng.* 50(4):357-364, 1996; Piret et al., *Biotechnol. Adv.* 8(4):763-783, 1990; and Tyo et al., *Enzyme Microb. Technol.* 9(9):514-520, 1987); density-based cell separation (e.g., gravitational settling (e.g., gravitational settling performed using conical sedimentation columns (e.g., as described in Kitano et al., *Appl. Microbiol. Biotechnol.* 24(4):282-286, 1986; Shintani et al., *Cytotechnology* 6(3):197-208, 1991), intra-reactor settling zone (e.g., as described in Takazawa et al., *Appl. Microbiol. Biotechnol.* 32(3):280-284, 1989), a Dortmund settler (e.g., as described in Hülscher et al., *Biotechnol. Bioeng.* 39(4): 442-446, 1992), and inclined settlers (e.g., as described in Boycott et al., *Nature* 104:532, 1920; Acrivos et al., *J. Fluid Mechanics* 92(3):435-457, 1979; Searles et al., *Biotechnol. Prog.* 10(2):198-206, 1994; Kohara et al., *J. Chem. Eng. Japan* 28(6):703-707, 1995; Shen et al., *Biotechnol. Prog.* 27(5):1282-1296, 2011; Wang et al., *Biotechnol. Prog.* 26(5):1361-1366, 2010; Pohlscheidt et al., *Biotechnol. Prog.* 29(1):222-229, 2013; Hecht et al., *Biotechnol. Prog.* 30(3): 607-615, 2014)); centrifugation (e.g., continuous centrifugation (e.g., as described in Hamamoto et al., *J. Ferment. Bioeng.* 67(3):190-194, 1989; Tokashiki et al., *Cytotechnology* 3(3):239-244, 1990; and Takamatsu et al., *Appl. Microbiol. Biotechnol.* 45(4):454-457, 1996), Centritech centrifugation (commercially available from Pneumatic Scale Angelus and as described in, e.g., Johnson et al., *Biotechnol. Prog.* 12(6):855-864, 1996; Kim et al., *Biotechnol. Prog.* 23 (5):1186-1197, 2007; Kim et al., *Biotechnol. Prog.* 24(1): 166-174, 2008; Hecht et al., *Biotechnol. Prog.* 30 (3):607-615, 2014; Chotteau et al., Perfusion Processes, In: Al-Rubeai M (Ed.), *Animal Cell Culture*, Springer, Cham, Switzerland, 2015), and centrifuges that utilize continuous counterflow (e.g., as described in Pattasseril et al., *BioProcess Int.* 11(3):38-47, 2013)); acoustic settling (e.g., using an acoustic settler, e.g., the acoustic settlers described in Kilburn et al., *Biotechnol Bioeng.* 34(4):559-562, 1989; Shirgaonkar et al., *Biotechnol. Adv.* 22(6):433-444, 2004; Doblhoff-Dier et al., *Biotechnol. Prog.* 10(4):428-432, 1994; Gaida et al., *Biotechnol. Prog.* 12(1):73-76, 1996; Bierau et al., *J. Biotechnol.* 62 (3):195-207, 1998; Crowley et al., *BioProcess Int.* 2(3):46-50, 2004; Gorenflo et al., *Biotechnol. Prog.* 19(1):30-36, 2003; Pui et al., *Biotechnol. Prog.* 11(2):146-152, 1995; Gorenflo et al, *Biotechnol. Bioeng.* 80 (4):438-444, 2002; Dalm et al., *Biotechnol. Bioeng.* 88(5): 547-557, 2004; Gorenflo et al., *Biotechnol. Prog.* 19(1):30-36, 2005); and hydrocyclone separation (e.g., using the hydroclone separators described in Elsayed et al., *Int. J. Biotechnol. Wellness Indust.* 2(4):153, 2013; Castilho et al., Continuous animal cell perfusion processes: the first step toward integrated continuous biomanufacturing, in Subramanian G. (Ed.), Continuous Processing in Pharmaceutical Manufacturing, Wiley-VCH, Weinheim, Germany, 2014; Jockwer et al., The use of hydroclones for mammalian cell retention in perfusion bioreactors, in Animal Cell Technology: From Target to Market, Springer, pp. 301-306, 2001; Pinto et al., *Cytotechnology* 56(1):57-67, 2008; Elsayed et al., *Eng. Life Sci.* 6(4):347-354, 2006; Elsayed et al., *BMC Proceedings* 5(Supp. 8): p 65, 2001; Castilho et al., Animal cell separation, in Castilho et al. (Ed.), Animal Cell Technology: From Biopharmaceuticals to Gene Therapy, Taylor & Francis, New York, NY, pp. 273-294, 2008).

Additional exemplary methods for filtering or clarifying a liquid culture medium include, e.g., size-based cell separation, e.g., performed using spin filtration (e.g., spin filtration as described in Himmelfarb et al., *Science* 164(3879):555-557, 1969; Tolbert et al., *In Vitro* 17(10):885-890, 1981; Reuveny et al., *J. Immunol. Methods* 86(1):61-69, 1986; Avgerinos et al., *Nat. Biotechnol.* 8 (1):54-58, 1990; Kim et al., *Biotechnol. Prog.* 24(1):166-174, 2008; Bierau et al., *J. Biotechnol.* 62 (3):195-207, 1998; Castilho et al., *Biotechnol. Prog.* 18(4):776-781, 2002; Deo et al., *Biotechnol. Prog.* 12(1):57-64, 1996; Emery et al., *Appl. Microbiol. Biotechnol.* 43(6):1028-1033, 1995; Hecht et al., *Biotechnol. Prog.* 30(3):607-615, 2014; Vallez-Chetreaunu et al., *J. Biotechnol.* 130(3):265-273, 2007; Yabannavar et al., *Biotechnol. Bioeng.* 40 (8):925-933, 1992; Yabannavar et al., *Biotechnol. Bioeng.* 40 (8):925-933, 1994; Deo et al., *Biotechnol. Prog.* 12 (1):57-64 1996; and Castilho et al., *Biotechnol. Prog.* 18(4):776-781, 2002); hollow-fiber filtration (e.g., placement of hollow-fiber cartridges placed directly within a bioreactor (e.g., as described in Seamans et al., *J. Ferment. Bioeng.* 70(4):241-245, 1990, and Kyung et al., *Cytotechnology* 14(3):183-190, 1994), tangential-flow-filtration (TFF) (e.g., as described in Brennan et al., *Biotechnol. Tech.* 1(3):169-174, 1987; Velez et al., *Biotechnol. Bioeng.* 33(7):938-940, 1989; de la Broise et al., *Biotechnol. Bioeng.* 38(7):781-787, 1991; Greenfield et al., *Bioprocess Eng.* 6(5):213-219, 1991; Kawahara et al., *Cytotechnology* 14(1):61-66, 1994; Karst et al., *Biochem. Eng. J.* 110:17-26, 2016; Martin et al., *BMC Proceedings* 9: p 1, 2015; Clincke et al., *Biotechnol. Prog.* 29 (3):754-767, 2013); alternating tangential flow (ATF) filtration (e.g., as described in Kelly et al., *Biotechnol. Prog.* 30 (6):1291-1300, 2014; Karst et al., *Biochem. Eng. J.* 110:17-26, 2016; Kim et al., *Cytotechnology* pp. 1-10, 2015; Xu et al., *J. Biotechnol.* 231:149-159, 2016; Warikoo et al., *Biotechnol. Bioeng.* 109(12):3018-3029, 2012; Clincke et al., *Biotechnol. Prog.* 29(3):754-767, 2013; Wright et al., *Bioprocess International*, Volume 13, Mar. 10, 2015; Yang et al., *Biotechnol. Prog.* 30(3):616-625, 2014; and Padawer et al., *Biotechnol. Prog.* 29(3):829-832, 2013); use of a disposable floating filter (e.g., Tao et al., *Biotechnol. Prog.* 27(3):824-829, 2011); vortex flow filtration (VFF) (e.g., as described in Mercille et al., *Biotechnol. Bioeng.* 43 (9):833-846, 1994; Mercille et al., *Biotechnol. Bioeng.* 67 (4):435-450, 2000; and Roth et al., *Pharmaceutical Technology* 21(10), 1997); and continuous depth filtration (as described in Vogel et al., *Biotechnol. Bioeng.* 109 (12):3049-3058, 2012, and Klutz et al., *Chemical Engineering Processing: Process Intensification* 102:88-101, 2015).

Recombinant cells can also be removed from liquid culture medium using centrifugation and removing the supernatant that is liquid culture medium that is substantially free of cells, or by allowing the cells to settle to the gravitational bottom of a container (e.g., bioreactor) containing the liquid culture medium, and removing the liquid culture medium (the liquid culture medium that is substantially free of cells) that is distant from the settled recombinant cells.

The liquid culture medium can be obtained from a culture of recombinant cells (e.g., recombinant bacteria, yeast, or mammalian cells) producing any of the recombinant therapeutic proteins described herein. Some examples of any of the processes described herein can further include a step of culturing recombinant cells (e.g., recombinant bacteria, yeast, or mammalian cells) that produce the recombinant therapeutic protein.

The liquid culture medium can be any of the types of liquid culture medium described herein or known in the art. For example, the liquid culture medium can be selected from the group of: animal-derived component free liquid culture medium, serum-free liquid culture medium, serum-containing liquid culture medium, chemically-defined liquid culture medium, and protein-free liquid culture medium. In any of the processes described herein, a liquid culture medium obtained from a culture can be diluted by addition of a second fluid (e.g., a buffer) before it is fed into the first MCCS (e.g., first PCCS).

The liquid culture medium containing a recombinant therapeutic protein that is substantially free of cells can be stored (e.g., at a temperature below about 15° C. (e.g., below about 10° C., below about 4° C., below about 0° C., below about −20° C., below about −50° C., below about −70 C.°, or below about −80° C.) for at least 1 day (e.g., at least about 2 days, at least about 5 days, at least about 10 days, at least about 15 days, at least about 20 days, or at least about 30 days) prior to feeding the liquid culture medium into the first MCCS (e.g., first PCCS). Alternatively, in some examples the liquid culture medium is fed into the first MCCS (e.g., first PCCS) directly from a bioreactor (e.g., fed into the first MCCS (e.g., first PCCS) directly from the bioreactor after a filtering or clarification step).

Recombinant Therapeutic Proteins

Non-limiting examples of recombinant therapeutic proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). The recombinant therapeutic protein can be an engineered antigen-binding polypeptide that contains at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant therapeutic proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab. Additional examples of recombinant therapeutic antibodies that can be produced by the methods described herein are known in the art. Additional non-limiting examples of recombinant therapeutic proteins that can be produced by the present methods include: alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-1a, imiglucerase, dornase alfa, epoetin alfa, insulin or insulin analogs, mecasermin, factov VIII, factor VIIa, anti-thrombin III, protein C, human albumin, erythropoietin, granulocute colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha (e.g., Thyrogen®) and alteplase. Additional examples of recombinant proteins that can be produced by the present methods include acid α-glucosidase, alglucosidase alpha (e.g., Myozyme® and Lumizyme®), α-L-iduronidase (e.g., Aldurazyme®), iduronate sulfatase, heparan N-sulfatase, galactose-6-sulfatase, acid β-galactosidase, β-glucoronidase, N-acetylglucosamine-1-phosphotransferase, α-N-acetylgalactosaminidase, acid lipase, lysosomal acid ceramidase, acid sphingomyelinase, β-glucosidase (e.g., Cerezyme® and Ceredase®), galactosylceramidase, α-galactosidase-A (e.g., Fabrazyme®), acid β-galactosidase, β-galactosidase, neuraminidase, hexosaminidase A, and hexosaminidase B.

A secreted, soluble recombinant therapeutic protein can be recovered from the liquid culture medium (e.g., a first and/or second liquid culture medium) by removing or otherwise physically separating the liquid culture medium from the cells (e.g., mammalian cells). A variety of different methods for removing liquid culture medium from cells (e.g., mammalian cells) are known in the art, including, for example, centrifugation, filtration, pipetting, and/or aspiration. The secreted recombinant therapeutic protein can then be recovered and further purified from the liquid culture medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

Multi-Column Chromatography Systems

The processes described herein include the use of two or more (e.g., two, three, four, five, or six) multi-column chromatography systems (MCCSs). A MCCS can include two or more chromatography columns, two or more chromatographic membranes, or a combination of at least one chromatography column and at least one chromatographic membrane. In non-limiting examples, a MCCS (e.g., the first and/or second MCCS described in any of the processes herein) can include four chromatographic columns, three chromatographic columns and a chromatographic membrane, three chromatographic columns, two chromatographic columns, two chromatographic membranes, and two chromatographic columns and one chromatographic membrane. Additional examples of combinations of chromatography columns and/or chromatographic membranes can be envisioned for use in an MCCS (e.g., a first and/or second MCCS) by one skilled in the art without limitation. The individual chromatography columns and/or chromatographic membranes present in a MCCS can be identical (e.g., have the same shape, volume, resin, capture mechanism, and unit operation), or can be different (e.g., have one or more of a different shape, volume, resin, capture mechanism, and unit operation). The individual chromatography column(s) and/or chromatographic membrane(s) present in a MCCS (e.g., the first and/or second MCCS) can perform the same unit operation (e.g., the unit operation of capturing, purifying, or polishing) or different unit operations (e.g., different unit operations selected from, e.g., the group of capturing, purifying, polishing, inactivating viruses, adjusting the ionic concentration and/or pH of a fluid containing the recombinant therapeutic protein, and filtering).

The one or more chromatography column(s) that can be present in an MCCS (e.g., present in the first and/or second MCCS) can have a resin volume of, e.g., at least about 2 mL, at least about 5 mL, at least about 10 mL, at least about 15 mL, at least about 20 mL, at least about 25 mL, at least about 30 mL, at least about 35 mL, at least about 40 mL, at least about 45 mL, at least about 50 mL, at least about 55 mL, at least about 60 mL, at least about 65 mL, at least about 70 mL, at least about 75 mL, at least about 80 mL, at least about 85 mL, at least about 90 mL, at least about 95 mL, at least about 100 mL, at least about 110 mL, at least about 120 mL, at least about 130 mL, at least about 140 mL, at least about 150 mL, at least about 160 mL, at least about 170 mL, at least about 180 mL, at least about 190 mL, at least about 200 mL, at least about 250 mL, at least about 300 mL, at least about 350 mL, at least about 400 mL, at least about 450 mL, at least about 500 mL, at least about 550 mL, at least about 600 mL, at least about 650 mL, at least about 700 mL, at least about 750 mL, at least about 800 mL, at least about 850 mL, at least about 900 mL, at least about 950 mL, at least about 1 L, at least about 10 L, at least about 20 L, at least about 30 L, at least about 40 L, at least about 50 L, at least about 60 L, at least about 70 L, at least about 80 L, at least about 90 L, at least about 100 L, at least about 110 L, at least about 120 L, at least about 130 L, at least about 140 L, at least about 150 L, at least about 160 L, at least about 170 L, at least about 180 L, at least about 190 L, or at least about 200 L.

The one or more chromatography column(s) that can be present in an MCCS (e.g., present in the first and/or second MCCS) can have a resin volume of between about 2 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, about 40 mL, about 35 mL, about 30 mL, about 25 mL, about 20 mL, about 15 mL, about 10 mL, or about 5 mL; between about 5 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, about 40 mL, about 35 mL, about 30 mL, about 25 mL, about 20 mL, about 15 mL, or about 10 mL; between about 10 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, about 40 mL, about 35 mL, about 30 mL, about 25 mL, about 20 mL, or about 15 mL; between about 15 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, about 40 mL, about 35 mL, about 30 mL, about 25 mL, or about 20 mL; between about 20 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, about 40 mL, about 35 mL, about 30 mL, or about 25 mL; between about 25 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, about 40 mL, about 35 mL, or about 30 mL; between about 30 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, about 40 mL, or about 35 mL; between about 35 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, about 45 mL, or about 40 mL; between about 40 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, about 50 mL, or about 45 mL; between about 45 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, about 60 mL, or about 50 mL; between about 50 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, about 70 mL, or about 60 mL; between about 60 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, about 80 mL, or about 70 mL; between about 70 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, about 90 mL, or about 80 mL; between about 80 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, about 100 mL, or about 90 mL; between about 90 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, about 200 mL, or about 100 mL; between about 100 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, about 300 mL, or about 200 mL; between about 200 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, about 400 mL, or about 300 mL; about 300 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, about 500 mL, or about 400 mL; between about 400 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, about 600 mL, or about 500 mL; between about 500 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, about 700 mL, or about 600 mL; between about 600 mL and about 200 L, about 180 L, about 160 L, about 140 L, about 120 L, about 100 L, about 80 L, about 60 L, about 40 L, about 20 L, about 10 L, about 5 L, about 1 L, about 900 mL, about 800 mL, or about 700 mL; between about 700 mL and about 200 L, about 180 L, about 160 L, about 140 L, about 120 L, about 100 L, about 80 L, about 60 L, about 40 L, about 20 L, about 10 L, about 5 L, about 1 L, about 900 mL, or about 800 mL; between about 800 mL and about 200 L, about 180 L, about 160 L, about 140 L, about 120 L, about 100 L, about 80 L, about 60 L, about 40 L, about 20 L, about 10 L, about 5 L, about 1 L, or about 900 mL; between about 900 mL and about 200 L, about 180 L, about 160 L, about 140 L, about 120 L, about 100 L, about 80 L, about 60 L, about 40 L, about 20 L, about 10 L, about 5 L, or about 1 L; between about 1 L and about 200 L, about 180 L, about 160 L, about 140 L, about 120 L, about 100 L, about 80 L, about 60 L, about 40 L, about 20 L, about 10 L, or about 5 L; between about 5 L and about 200 L, about 180 L, about 160 L, about 140 L, about 120 L, about 100 L, about 80 L, about 60 L, about 40 L, about 20 L, or about 10 L; between 10 L and about 200 L, about 180 L, about 160 L, about 140 L, about 120 L, about 100 L, about 80 L, about 60 L, about 40 L, or about 20 L; between 20 L and about 200 L, about 180 L, about 160 L, about 140 L, about 120 L, about 100 L, about 80 L, about 60 L, or about 40 L; between about 40 L and about 200 L, about 180 L, about 160 L, about 140 L, about 120 L, about 100 L, about 80 L, or about 60 L; between about 60 L and about 200 L, about 180 L, about 160 L, about 140 L, about 120 L, about 100 L, or about 80 L; between about 80 L and about 200 L, about 180 L, about 160 L, about 140 L, about 120 L, or about 100 L; between about 100 L and about 200 L, about 180 L, about 160 L, about 140 L, or about 120 L; between about 120 L and about 200 L, about 180 L, about 160 L, or about 140 L; between about 140 L and about 200 L, about 180 L, or about 160 L; between about 160 L and about 200 L or about 180 L; or about 180 L to about 200 L.

The one or more chromatography column(s) in an MCCS (e.g., the first and/or second MCCS) used in any of the processes described herein can have the substantially the same resin volume or can have different resin volumes. The flow rate used for the one or more chromatography column(s) in an MCCS (e.g., the first and/or second MCCS) can be, e.g., between about 0.2 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, about 30 mL/minute, about 25 mL/minute, about 20 mL/minute, about 15 mL/minute, about 10 mL/minute, about 5 mL/minute, about 2 mL/minute, or about 1 mL/minute; between about 1 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, about 30 mL/minute, about 25 mL/minute, about 20 mL/minute, about 15 mL/minute, about 10 mL/minute, about 5 mL/minute, or about 2 mL/minute; between about 2 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, about 30 mL/minute, about 25 mL/minute, about 20 mL/minute, about 15 mL/minute, about 10 mL/minute, or about 5 mL/minute; between about 5 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, about 30 mL/minute, about 25 mL/minute, about 20 mL/minute, about 15 mL/minute, or about 10 mL/minute; between about 10 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, about 30 mL/minute, about 25 mL/minute, about 20 mL/minute, or about 15 mL/minute; between about 15 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, about 30 mL/minute, about 25 mL/minute, or about 20 mL/minute; between about 20 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, about 30 mL/minute, or about 25 mL/minute; between about 25 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, about 40 mL/minute, or about 30 mL/minute; between about 30 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, about 50 mL/minute, or about 40 mL/minute; between about 40 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, about 60 mL/minute, or about 50 mL/minute; between about 50 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, about 70 mL/minute, or about 60 mL/minute; between about 60 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, about 80 mL/minute, or about 70 mL/minute; between about 70 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 90 mL/minute, or about 80 mL/minute; between about 80 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, or about 90 mL/minute; between about 90 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, about 150 mL/minute, or about 100 mL/minute; between about 100 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, about 200 mL/minute, or about 150 mL/minute; between about 150 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, about 250 mL/minute, or about 200 mL/minute; between about 200 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, about 300 mL/minute, or about 250 mL/minute; between about 250 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, about 350 mL/minute, or about 300 mL/minute; between about 300 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, about 400 mL/minute, or about 350 mL/minute; between about 350 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, about 450 mL/minute, or about 400 mL/minute; between about 400 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, about 500 mL/minute, or about 450 mL/minute; between about 450 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, about 600 mL/minute, or about 500 mL/minute; between about 500 mL/minute to about 100 L/minute, about 80 L/minute, about 60 L/minute, about 40 L/minute, about 20 L/minute, about 10 L/minute, about 5 L/minute, about 1 L/minute, about 900 mL/minute, about 800 mL/minute, about 700 mL/minute, or about 600 mL/minute; between about 600 mL/minute to about 100 L/minute, about 80 L/minute, about 60 L/minute, about 40

L/minute, about 20 L/minute, about 10 L/minute, about 5 L/minute, about 1 L/minute, about 900 mL/minute, about 800 mL/minute, or about 700 mL/minute; between about 700 mL/minute to about 100 L/minute, about 80 L/minute, about 60 L/minute, about 40 L/minute, about 20 L/minute, about 10 L/minute, about 5 L/minute, about 1 L/minute, about 900 mL/minute, or about 800 mL/minute; between about 800 mL/minute to about 100 L/minute, about 80 L/minute, about 60 L/minute, about 40 L/minute, about 20 L/minute, about 10 L/minute, about 5 L/minute, about 1 L/minute, or about 900 mL/minute; between about 900 mL/minute to about 100 L/minute, about 80 L/minute, about 60 L/minute, about 40 L/minute, about 20 L/minute, about 10 L/minute, about 5 L/minute, or about 1 L/minute; between about 1 L/minute to about 100 L/minute, about 80 L/minute, about 60 L/minute, about 40 L/minute, about 20 L/minute, about 10 L/minute, or about 5 L/minute; about 5 L/minute to about 100 L/minute, about 80 L/minute, about 60 L/minute, about 40 L/minute, about 20 L/minute, or about 10 L/minute; between about 10 L/minute to about 100 L/minute, about 80 L/minute, about 60 L/minute, about 40 L/minute, or about 20 L/minute; between about 20 L/minute to about 100 L/minute, about 80 L/minute, about 60 L/minute, or about 40 L/minute; between about 40 L/minute to about 100 L/minute, about 80 L/minute, or about 60 L/minute; between about 60 L/minute to about 100 L/minute or about 80 L/minute; or about 80 L/minute to about 100 L/minute.

The one or more chromatography column (s) in an MCCS (e.g., the first and/or second MCCS) can have substantially the same shape or can have substantially different shapes. For example, the one or more chromatography column(s) in an MCCS (e.g., in the first and/or second MCCS) can have substantially the shape of a circular cylinder or can have substantially the same shape of an oval cylinder.

The one or more chromatographic membrane(s) that can be present in an MCCS (e.g., present in the first and/or second MCCS) can have a bed volume of, e.g., between about 1 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, about 15 mL, about 10 mL, or about 5 mL (inclusive); between about 2 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, about 15 mL, about 10 mL, or about 5 mL (inclusive); between about 5 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, about 15 mL, or about 10 mL (inclusive); between about 10 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, or about 15 mL (inclusive); between about 15 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, or about 20 mL (inclusive); between about 20 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, or about 25 mL (inclusive); between about 25 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, or about 30 mL (inclusive); between about 30 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, or about 35 mL (inclusive); between about 35 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, about 45 mL, or about 40 mL (inclusive); between about 40 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, about 50 mL, or about 45 mL (inclusive); between about 45 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, about 55 mL, or about 50 mL (inclusive); between about 50 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, about 60 mL, or about 55 mL (inclusive); between about 55 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, about 65 mL, or about 60 mL (inclusive); between about 60 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, about 70 mL, or about 65 mL (inclusive); between about 65 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, about 75 mL, or about 70 mL (inclusive); between about 70 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, about 80 mL, or about 75 mL (inclusive); between about 75 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, about 85 mL, or about 80 mL (inclusive); between about 80 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, about 90 mL, or about 85 mL (inclusive); between about 85 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, about 95 mL, or about 90 mL (inclusive); between about 90 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, about 100 mL, or about 95 mL (inclusive); between about 95 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, about 125 mL, or about 100 mL; between about 100 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, about 150 mL, or about 125 mL (inclusive); between about 125 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, about 175 mL, or about 150 mL (inclusive); between about 150 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, about 200 mL, or about 175 mL (inclusive); between about 175 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, about 225 mL, or about 200 mL (inclusive); between about 200 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, about 250 mL, or about 225 mL (inclusive); between about 225 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, about 275 mL, or about 250 mL (inclusive); between about 250 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, about 300 mL, or about 275 mL (inclusive); between about 275 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, about 325 mL, or about 300 mL (inclusive); between about 300 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, about 350 mL, or about 325 mL (inclusive); between about 325 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, about 375 mL, or about 350 mL (inclusive); between about 350 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, about 400 mL, or about 375 mL (inclusive); between about 375 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, about 425 mL, or about 400 mL (inclusive); between about 400 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, about 450 mL, or about 425 mL (inclusive); between about 425 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, about 475 mL, or about 450 mL (inclusive); between about 450 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, about 500 mL, or about 475 mL (inclusive); between about 475 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, about 550 mL, or about 500 mL (inclusive); between about 500 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, about 600 mL, or about 550 mL (inclusive); between about 550 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, about 650 mL, or about 600 mL (inclusive); between about 600 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, about 700 mL, or about 650 mL (inclusive); between about 650 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, about 750 mL, or about 700 mL (inclusive); between about 700 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, about 800 mL, or about 750 mL (inclusive); between about 750 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, about 850 mL, or about 800 mL (inclusive); between about 800 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, about 900 mL, or about 850 mL (inclusive); between about 850 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, about 950 mL, or about 900 mL (inclusive); between about 900 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, about 1 L, or about 950 mL (inclusive); between about 950 mL and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, about 1.5 L, or about 1 L (inclusive); between about 1 L and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, about 2 L, or about 1.5 L (inclusive); between about 1.5 L and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, about 2.5 L, or about 2 L (inclusive); between about 2 L and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, about 3 L, or about 2.5 L (inclusive); between about 2.5 L and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, about 3.5 L, or about 3 L (inclusive); between about 3.0 L and about 10 L, about 9.5 L, about 9 L, about 8.5 L, about 8 L, about 7.5 L, about 7 L, about 6.5 L, about 6 L, about 5.5 L, about 5 L, about 4.5 L, about 4 L, or about 3.5 L (inclusive); between about 3.5 L and about 9.5 L, about 9 L, about 8.5 L, about 8 L, about 7.5 L, about 7 L, about 6.5 L, about 6 L, about 5.5 L, about 5 L, about 4.5 L, or about 4 L (inclusive); between about 4 L and about 10 L, about 9.5 L, about 9 L, about 8.5 L, about 8 L, about 7.5 L, about 7 L, about 6.5 L, about 6 L, about 5.5 L, about 5 L, or about 4.5 L (inclusive); between about 4.5 L and about 10 L, about 9.5 L, about 9 L, about 8.5 L, about 8 L, about 7.5 L, about 7 L, about 6.5 L, about 6 L, about 5.5 L, or about 5 L (inclusive); between about 5 L and about 10 L, about 9.5 L, about 9 L, about 8.5 L, about 8 L, about 7.5 L, about 7 L, about 6.5 L, about 6 L, or about 5.5 L (inclusive); between about 5.5 L and about 10 L, about 9.5 L, about 9 L, about 8.5 L, about 8 L, about 7.5 L, about 7 L, about 6.5 L, or about 6 L (inclusive); between about 6 L and about 10 L, about 9.5 L, about 9 L, about 8.5 L, about 8 L, about 7.5 L, about 7 L, or about 6.5 L (inclusive); between about 6.5 L and about 10 L, about 9.5 L, about 9 L, about 8.5 L, about 8 L, about 7.5 L, or about 7 L (inclusive); between about 7 L and about 10 L, about 9.5 L, about 9 L, about 8.5 L, about 8 L, or about 7.5 L (inclusive); between about 7.5 L and about 10 L, about 9.5 L, about 9 L, about 8.5 L, or about 8 L (inclusive); between about 8 L and about 10 L, about 9.5 L, about 9 L, or about 8.5 L (inclusive); between about 8.5 L and about 10 L, about 9.5 L, or about 9 L (inclusive); between about 9 L and about 10 L or about 9.5 L (inclusive); or between about 9.5 L and about 10 L.

One or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of buffer can be employed during the use of the two or more MCCSs in any of the processes described herein. As is known in the art, the one or more types of buffer used in the two or more MCCSs used in the processes described herein will depend on the resin present in the chromatography column(s) and/or the chromatographic membrane(s) of the two or more MCCSs (e.g., the first and second MCCSs), the recombinant therapeutic protein, and unit operation (e.g., any of the exemplary unit operations described herein) performed by the specific chromatography column(s) and/or chromatography membranes of the two or more MCCSs. The volume and type of buffer employed during the use of the two or more MCCSs in any of the processes described herein can also be determined by one skilled in the art (e.g., discussed in more detail below). For example, the volume and type(s) of buffer employed during the use of the two or more MCCSs in any of the processes described herein can be chosen in order to optimize one or more of the following in the recombinant protein drug product: the overall yield of recombinant therapeutic protein, the activity of the recombinant therapeutic protein, the level of purity of the recombinant therapeutic protein, and the removal of biological contaminants from a fluid containing the recombinant therapeutic protein (e.g., absence of active viruses, mycobacteria, yeast, bacteria, or mammalian cells).

Figure 3:
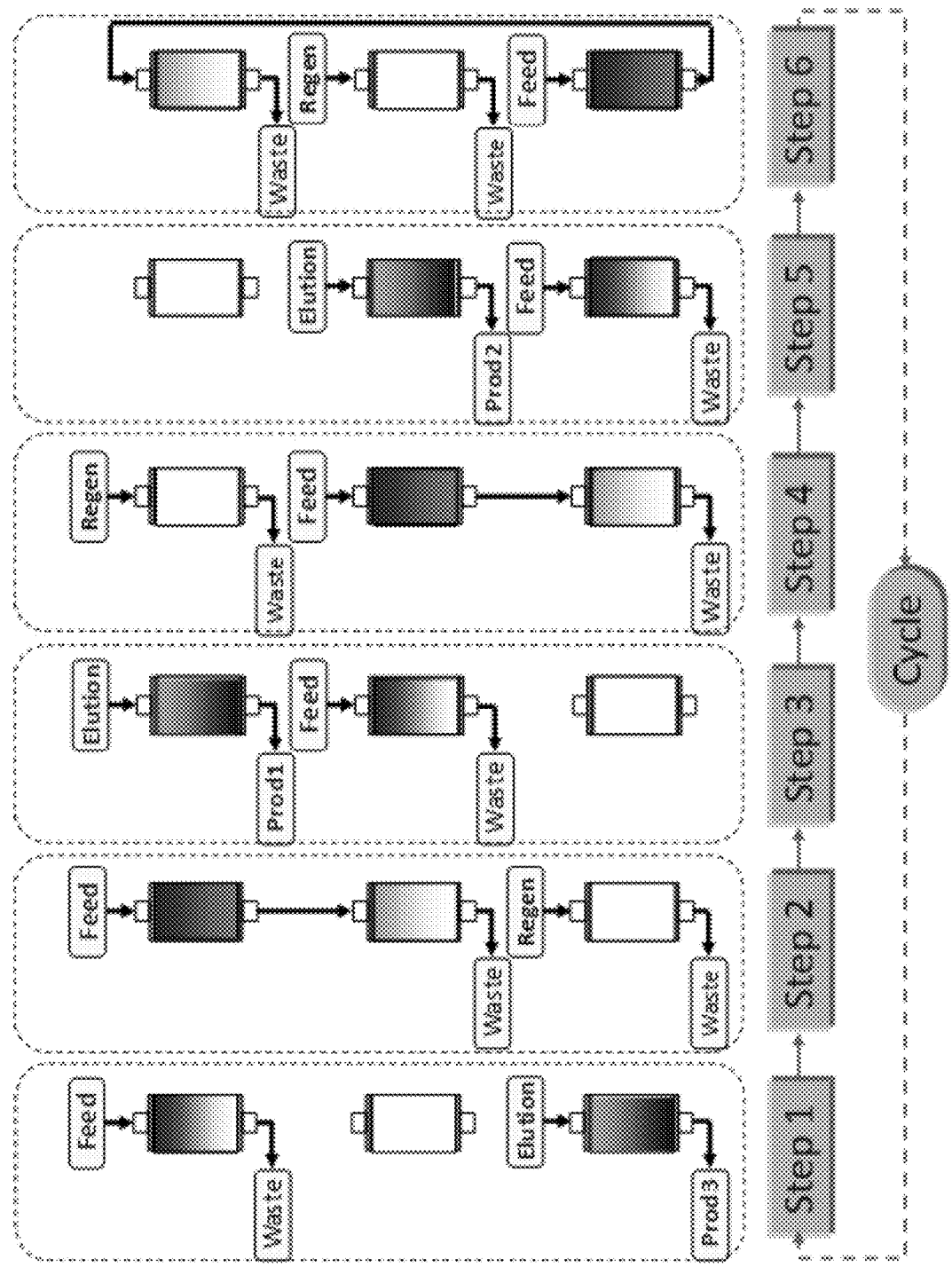
FIG. 3 is a diagram of a PCC system cycle containing three chromatography columns. At the beginning of a cycle, the feed solution is loaded onto column 1, and the flow through goes to waste until product breakthrough occurs (step 1). At this point, the flow through from column 1 is directed to column 2 to capture the unbound recombinant therapeutic protein from column 1 (step 2). Once column 1 is fully loaded, the feed is now directed loaded onto column 2, while column 1 is washed, eluted, regenerated, and re-equilibrated for the next cycle (steps 3 and 4). Column 2 now goes through steps 3-5, which are identical to steps 1-3 for column 1. Finally, column 3 goes through steps 5-6, the same as columns 1 and 2. Once all three columns have completed these steps, the cycle restarts with column 1.

The first and/or second MCCS can be a periodic counter current chromatography system (PCCS). A PCCS can, e.g., include two or more chromatography columns (e.g., three columns or four columns) that are switched in order to allow for the continuous elution of recombinant therapeutic protein from the two or more chromatography columns. A PCCS can include two or more chromatography columns, two or more chromatographic membranes, or at least one chromatographic column and at least one chromatographic membrane. A column operation generally consists of the load, wash, eluate, and regeneration steps. In PCCSs, multiple columns are used to run the same steps discretely and continuously in a cyclic fashion. Since the columns are operated in series, the flow through and wash from one column is captured by another column. This unique feature of PCCSs allows for loading of the resin close to its static binding capacity instead of to the dynamic binding capacity, as is typical during batch mode chromatography. An example of the three column-switching technique used in a PCCS containing three columns is shown in FIG. 3. A cycle is defined as three complete column operations resulting in an elution pool from each of the three columns used in the column-switching technique. Once all the steps in the cycle are completed, the cycle is re-started. As a result of the continuous cycling and elutation, fluid entering a PCCS is processed continuously, and the eluate containing recombinant therapeutic protein is continuously produced.

To advance from one step to another in a PCCS cycle, such as the exemplary cycle shown in FIG. 3, a column-switching strategy is employed. The column switching method employs two automated switching operations per column in the three-columns in the exemplary PCCS system shown in FIG. 3, the first of which is related to the initial product breakthrough, while the second coincides with column saturation. The determination of when the column switching operations should take place is determined by monitoring the recombinant therapeutic protein concentration (e.g., monitoring performed by UV monitoring) in the eluate from each chromatography column present in a PCCS. For example, column switching can be determined by any PAT tool capable of in-line measurement of product concentration with feedback control. The PAT tool is capable of real-time in-line measurement of product concentration with feedback control.

Figure 4:
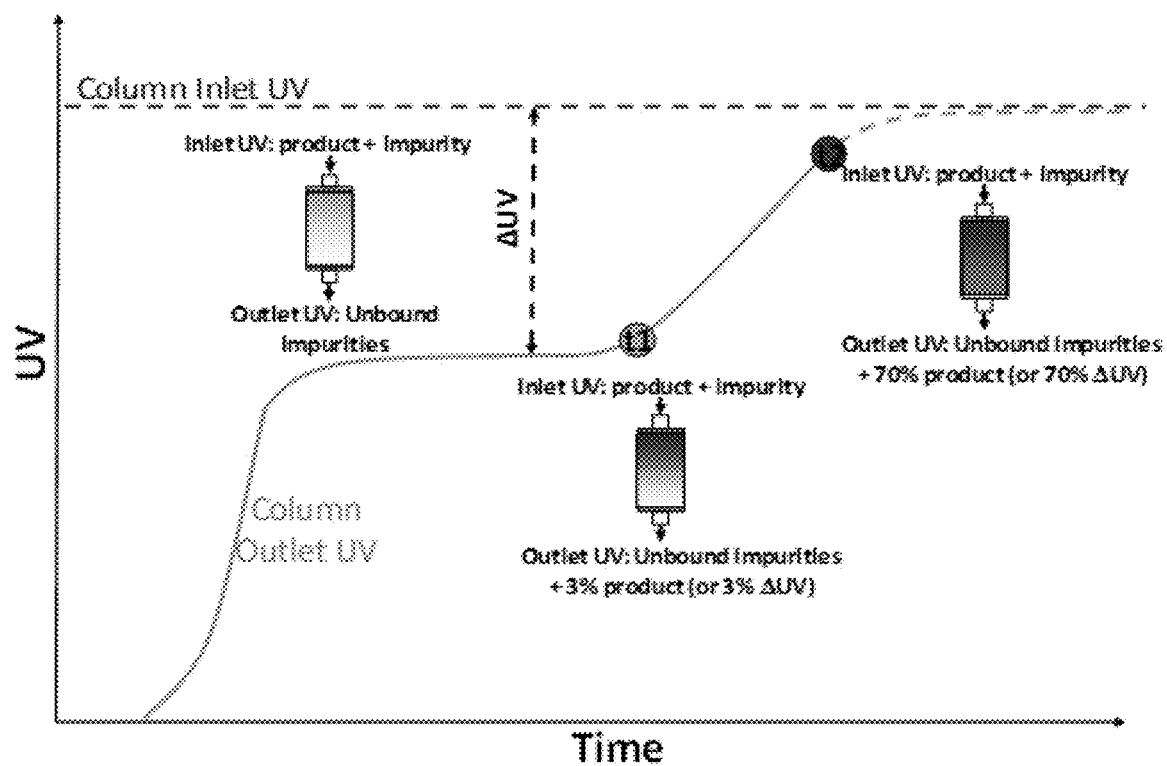
FIG. 4 is a schematic diagram demonstrating the principle of column switching based on ΔUV. T1 designates the time when the ΔUV has reached a pre-determined threshold level. Once this threshold level is reached, the flow through from column 1 is directed onto column 2 rather than to the waste. T2 designates the time when the column has been saturated with product. The ΔUV value for both T1 and T2 are process specific.

FIG. 4 depicts an example of column switching in an exemplary PCCS based on the UV absorbance difference (ΔUV) between the feed inlet and column outlet. For example, during column loading (Step 1; FIG. 3), the PCC control system determines the impurity baseline level when the absorbance stabilizes. As the product breaks through (Step 2; FIG. 3), there is an increase in the outlet UV signal above the impurity baseline. At the point when ΔUV has reached a pre-determined threshold (e.g., 3% breakthrough of the product), the flow-through from column 1 is directed onto column 2 instead of to the waste (t1; FIG. 4). When column 1 is nearly saturated with product and the ΔUV has reached a pre-determined value (t2; FIG. 4), the feed is switched to column 2. The column-switching strategy used in PCCSs allows for the uniform loading of the columns irrespective of the feed product concentration and the capacity. Similar switches of the columns based on the level of recombinant protein detected in the eluate from each column can be designed. As in known in the art, column switches can also be designed based on time or the amount of fluid (e.g., buffer) passed through the one or more chromatography column(s) and/or chromatographic membranes in the first or second MCCS.

In PCCSs, the residence time (RT) of the recombinant therapeutic protein on the each chromatography column and/or chromatographic membrane present in the PCCS can be decreased without increasing the column/membrane size because the breakthrough from the first column/membrane can be captured on another column/membrane in the PCCS. A continuous process system can be designed to process liquid culture medium at any perfusion rate (D) by varying the column/membrane volume (V) and RT using the equation of: V=D*RT.

The one or more unit operations that can be performed by the at least two MCCSs (e.g., the first and/or second MCCSs) used in the presently described processes include, for example, capturing the recombinant therapeutic protein, inactivating viruses present in a fluid containing the recombinant therapeutic protein, purifying the recombinant therapeutic protein, polishing the recombinant therapeutic protein, holding a fluid containing the recombinant therapeutic protein (e.g., using any of the exemplary break tank(s) described herein), filtering or removing particulate material and/or cells from a fluid containing the recombinant therapeutic protein, and adjusting the ionic concentration and/or pH of a fluid containing the recombinant therapeutic protein.

The unit operation of capturing can be performed using one or more MCCSs (e.g., a first and/or second MCCS) that includes at least one chromatography column and/or chromatography resin, e.g., that utilizes a capture mechanism. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Capturing can also be performed using a resin that can be used to perform cation exchange or anion exchange chromatography, or molecular sieve chromatography. Non-limiting resins that can be used to capture a recombinant therapeutic protein are described herein. Additional examples of resins that can be used to capture a recombinant therapeutic protein are known in the art.

The unit operation of inactivating viruses present in a fluid containing the recombinant therapeutic protein can be performed using one or more MCCSs (e.g., a first and/or second MCCS) that include(s), e.g., a chromatography column, a chromatography membrane, or a holding tank that is capable of incubating a fluid containing the recombinant therapeutic protein at a pH of between about 3.0 to 5.0 (e.g., between about 3.5 to about 4.5, between about 3.5 to about 4.25, between about 3.5 to about 4.0, between about 3.5 to about 3.8, or about 3.75) for a period of at least 30 minutes (e.g., a period of between about 30 minutes to 1.5 hours, a period of between about 30 minutes to 1.25 hours, a period of between about 0.75 hours to 1.25 hours, or a period of about 1 hour).

The unit operation of purifying a recombinant protein can be performed using one or more MCCSs (e.g., a first and/or second MCCS) that include(s), e.g., a chromatography column or chromatographic membrane that contains a resin, e.g., that utilizes a capture system. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Purifying can also be performed using a resin that can be used to perform cation exchange or anion exchange chromatography, or molecular sieve chromatography. Non-limiting resins that can be used to purify a recombinant therapeutic protein are described herein. Additional examples of resins that can be used to purify a recombinant therapeutic protein are known in the art.

The unit operation of polishing a recombinant protein can be performed using one or more MCCSs (e.g., a first and/or second MCCS) that include(s), e.g., a chromatography column or chromatographic membrane that contains a resin, e.g., that can be used to perform cation exchange, anion exchange, or molecular sieve chromatography. Non-limiting resins that can be used to polish a recombinant therapeutic protein are described herein. Additional examples of resins that can be used to polish a recombinant therapeutic protein are known in the art.

The unit operation of holding a fluid containing the recombinant therapeutic protein can be performed using an MCCS (e.g., a first and/or second MCCS) that includes at least one reservoir (e.g., a break tank) or a maximum of 1, 2, 3, 4, or 5 reservoir(s) (e.g., break tank(s)) in the first and second MCCS combined. For example, the reservoir(s) (e.g., break tank(s)) that can be used to achieve this unit operation can each have a volume of, e.g., between about 1 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL (inclusive); between about 5 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, about 20 mL, or about 10 mL (inclusive); between about 10 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, about 40 mL, or about 20 mL (inclusive); between about 20 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, about 60 mL, or about 40 mL (inclusive); between about 40 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600

L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, about 80 mL, or about 60 mL (inclusive); between about 60 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, about 120 mL, about 100 mL, or about 80 mL (inclusive); between about 80 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, about 120 mL, or about 100 mL (inclusive); between about 100 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, about 140 mL, or about 120 mL (inclusive); between about 120 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, about 160 mL, or about 140 mL (inclusive); between about 140 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, about 180 mL, or about 160 mL (inclusive); between about 160 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, about 200 mL, or about 180 mL (inclusive); between about 180 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, about 220 mL, or about 200 mL (inclusive); between about 200 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, about 240 mL, or about 220 mL (inclusive); between about 220 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, about 260 mL, or about 240 mL (inclusive); between about 240 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, about 280 mL, or about 260 mL (inclusive); about 260 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, about 300 mL, or about 280 mL (inclusive); about 280 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, about 350 mL, or about 300 mL (inclusive); between about 300 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, about 400 mL, or about 350 mL (inclusive); between about 350 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, about 500 mL, or about 400 mL (inclusive); between about 400 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, about 600 mL, or about 500 mL (inclusive); between about 500 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, about 800 mL, or about 600 mL (inclusive); between about 600 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, about 900 mL, or about 800 mL (inclusive); between about 800 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, about 1 L, or about 900 mL (inclusive); between about 900 mL to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, about 5 L, or about 1 L (inclusive); between about 1 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, about 10 L, or about 5 L (inclusive); between about 5 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, about 20 L, or about 10 L (inclusive); between about 10 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, about 40 L, or about 20 L (inclusive); between about 20 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, about 60 L, or about 40 L (inclusive); between about 40 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, about 80 L, or about 60 L (inclusive); between about 60 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, about 100 L, or about 80 L (inclusive); between about 80 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, about 200 L, or about 100 L (inclusive); between about 100 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, about 300 L, or about 200 L (inclusive); between about 200 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, about 400 L, or about 300 L (inclusive); between about 300 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, about 500 L, or about 400 L (inclusive); between about 400 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, about 600 L, or about 500 L (inclusive); between about 500 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, about 700 L, or about 600 L (inclusive); between about 600 L to about 10,000 L, about 9,000 L, about 8,000 L, about 7,000 L, about 6,000 L, about 5,000 L, about 4,000 L, about 3,000 L, about 2,000 L, about 1,000 L, about 900 L, about 800 L, or about 700 L (inclusive); between about 700 L to about 10,000 L, about 9,000 L, about 8,000 L, about 7,000 L, about 6,000 L, about 5,000 L, about 4,000 L, about 3,000 L, about 2,000 L, about 1,000 L, about 900 L, or about 800 L (inclusive); between about 800 L to about 10,000 L, about 9,000 L, about 8,000 L, about 7,000 L, about 6,000 L, about 5,000 L, about 4,000 L, about 3,000 L, about 2,000 L, about 1,000 L, or about 900 L (inclusive); between about 900 L to about 10,000 L, about 9,000 L, about 8,000 L, about 7,000 L, about 6,000 L, about 5,000 L, about 4,000 L, about 3,000 L, about 2,000 L, or about 1,000 L (inclusive); between about 1,000 L to about 10,000 L, about 9,000 L, about 8,000 L, about 7,000 L, about 6,000 L, about 5,000 L, about 4,000 L, about 3,000 L, or about 2,000 L (inclusive); between about 2,000 L to about 10,000 L, about 9,000 L, about 8,000 L, about 7,000 L, about 6,000 L, about 5,000 L, about 4,000 L, or about 3,000 L (inclusive); between about 3,000 L to about 10,000 L, about 9,000 L, about 8,000 L, about 7,000 L, about 6,000 L, about 5,000 L, or about 4,000 L (inclusive); between about 4,000 L to about 10,000 L, about 9,000 L, about 8,000 L, about 7,000 L, about 6,000 L, or about 5,000 L (inclusive); between about 5,000 L to about 10,000 L, about 9,000 L, about 8,000 L, about 7,000 L, or about 6,000 L (inclusive); between about 6,000 L to about 10,000

L, about 9,000 L, about 8,000 L, or about 7,000 L (inclusive); between about 7,000 L to about 10,000 L, about 9,000 L, or about 8,000 L (inclusive); between about 8,000 L to about 10,000 L or about 9,000 L (inclusive); or between about 9,000 L to about 10,000 L (inclusive).

The reservoir(s) (e.g., break tank(s)) used in the processes described herein can have a capacity that is, e.g., between about 1 mL to about 10,000 L, inclusive (or any of the subranges of this range of volumes described herein). Any of the reservoir(s) (e.g., break tank(s)) used (in any of the processes described herein) to hold fluid before it enters into the first MCCS can have a capacity that is, e.g., between 1 mL and about 100%, inclusive, between about 1 mL and about 90%, about 80%, about 70%, about 60%, about 50%, about 40%, about 30%, about 20%, about 10%, or about 5%, inclusive, of the loading volume of the first column of the first MCCS. Any of the reservoir(s) (e.g., break tanks(s)) used to hold a fluid before it enters the second MCCS (and after the fluid leaves the first MCCS) can have a capacity that is, e.g., between 1 mL and about 100%, inclusive, e.g., between about 1 mL and about 90%, about 80%, about 70%, about 60%, about 50%, about 40%, about 30%, about 20%, about 10%, or about 5%, inclusive, of the loading volume of the first column of the second MCCS.

The reservoir(s) (e.g., break tank(s)) can each hold the fluid containing the recombinant therapeutic protein for at least 10 minutes (e.g., at least 20 minutes, at least 30 minutes, at least 1 hour, at least 2 hours, at least 4 hours, at least 6 hours, at least 8 hours, at least 10 hours, at least 12 hours, at least 14 hours, at least 16 hours, at least 18 hours, at least 20 hours, at least 22 hours, at least 24 hours, at least 26 hours, at least 28 hours, at least 30 hours, at least 32 hours, at least 34 hours, at least 36 hours, at least 38 hours, at least 40 hours, at least 42 hours, at least 44 hours, at least 46 hours, or at least 48 hours). In other examples, the reservoir(s) (e.g., break tank(s)) only holds a therapeutic protein for a total time period of, e.g., between about 5 minutes and less than about 48 hours, inclusive, e.g., between about 5 minutes and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4 hours, about 3 hours, about 2 hours, about 1 hour, or about 30 minutes, inclusive; between about 30 minutes and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4 hours, about 3 hours, about 2 hours, or about 1 hour, inclusive; between about 1 hour and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4 hours, about 3 hours, or about 2 hours, inclusive; between about 2 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, or about 4 hours, inclusive; between about 3 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, or about 4 hours, inclusive; between about 4 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, about 7 hours, about 6 hours, or about 5 hours, inclusive; between about 5 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, about 7 hours, or about 6 hours, inclusive; between about 6 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, about 8 hours, or about 7 hours, inclusive; between about 7 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, about 9 hours, or about 8 hours, inclusive; between about 8 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, about 10 hours, or about 9 hours, inclusive; between about 9 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, about 12 hours, or about 10 hours, inclusive; between about 10 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, about 14 hours, or about 12 hours, inclusive; between about 12 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, about 16 hours, or about 14 hours, inclusive; between about 14 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, about 18 hours, or about 16 hours, inclusive; between about 16 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, about 20 hours, or about 18 hours, inclusive; between about 18 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, about 22 hours, or about 20 hours, inclusive; between about 20 hours and about 48 hours, about 46 hours, about 44 hours, about 42 hours, about 40 hours, about 38 hours, about 36 hours, about 34 hours, about 32 hours, about 30 hours, about 28 hours, about 26 hours, about 24 hours, or about 22 hours, inclusive; between about 22 hours and about 48 hours, about 46 hours, about 44 hours, about 42 hours, about 40 hours, about 38 hours, about 36 hours, about 34 hours, about 32 hours, about 30 hours, about 28 hours, about 26 hours, or about 24 hours, inclusive; between about 24 hours and about 48 hours, about 46 hours, about 44 hours, about 42 hours, about 40 hours, about 38 hours, about 36 hours, about 34 hours, about 32 hours, about 30 hours, about 28 hours, or about 26 hours, inclusive; between about 26 hours and about 48 hours, about 46 hours, about 44 hours, about 42 hours, about 40 hours, about 38 hours, about 36 hours, about 34 hours, about 32 hours, about 30 hours, or about 28 hours, inclusive; between about 28 hours and about 48 hours, about 46 hours, about 44 hours, about 42 hours, about 40 hours, about 38 hours, about 36 hours, about 34 hours, about 32 hours, or about 30 hours, inclusive; between about 30 hours and about 48 hours, about 46 hours, about 44 hours, about 42 hours, about 40 hours, about 38 hours, about 36 hours, about 34 hours, or about 32 hours, inclusive; between about 32 hours and about 48 hours, about 46 hours, about 44 hours, about 42 hours, about 40 hours, about 38 hours, about 36 hours, or about 34 hours, inclusive; between about 34 hours and about 48 hours, about 46 hours, about 44 hours, about 42 hours, about 40 hours, about 38 hours, or about 36 hours, inclusive; between about 36 hours and about 48 hours, about 46 hours, about 44 hours, about 42 hours, about 40 hours, or about 38 hours, inclusive; between about 38 hours and about 48 hours, about 46 hours, about 44 hours, about 42 hours, or about 40 hours, inclusive; between about 40 hours and about 48 hours, about 46 hours, about 44 hours, or about 42 hours, inclusive; between about 42 hours and about 48 hours, about 46 hours, or about 44 hours, inclusive; between about 44 hours and about 48 hours or about 46 hours, inclusive; between about 46 hours and about 48 hours, inclusive.

The reservoir(s) (e.g., break tank(s)) can be used to both hold and refrigerate (e.g., at a temperature of less than 25° C., less than 15° C., or less than 10° C.) the fluid containing the recombinant therapeutic protein. The reservoir can have any shape, including a circular cylinder, an oval cylinder, or an approximately rectangular sealed and nonpermeable bag.

The unit operations of filtering a fluid containing the recombinant therapeutic protein can be performed using an MCCS (e.g., the first and/or second MCCS) that includes, e.g., a filter, or a chromatography column or chromatographic membrane that contains a molecule sieve resin. As is known in the art, a wide variety of submicron filters (e.g., a filter with a pore size of less than 1 µm, less than 0.5 µm, less than 0.3 µm, about 0.2 µm, less than 0.2 µm, less than 100 nm, less than 80 nm, less than 60 nm, less than 40 nm, less than 20 nm, or less than 10 nm) are available in the art that are capable of removing any precipitated material and/or cells (e.g., precipitated, unfolded protein; precipitated, unwanted host cell proteins; precipitated lipids; bacteria; yeast cells; fungal cells; mycobacteria; and/or mammalian cells). Filters having a pore size of about 0.2 µm or less than 0.2 µm are known to effectively remove bacteria from the fluid containing the recombinant therapeutic protein. As is known in the art, a chromatography column or a chromatographic membrane containing a molecular sieve resin can also be used in an MCCS (e.g., the first and/or second MCCS) to perform the unit operation of filtering a fluid containing a recombinant therapeutic protein.

The unit operations of adjusting the ionic concentration and/or pH of a fluid containing the recombinant therapeutic protein can be performed using a MCCS (e.g., the first and/or second MCCS) that includes and utilizes a buffer adjustment reservoir (e.g., an in-line buffer adjustment reservoir) that adds a new buffer solution into a fluid that contains the recombinant therapeutic protein (e.g., between columns within a single MCCS, or after the last column in a penultimate MCCS (e.g., the first MCCS) and before the fluid containing the recombinant therapeutic protein is fed into the first column of the next MCCS (e.g., the second MCCS). As can be appreciated in the art, the in-line buffer adjustment reservoir can be any size (e.g., greater than 100 mL) and can contain any buffered solution (e.g., a buffered solution that has one or more of: an increased or decreased pH as compared to the fluid containing the recombinant therapeutic protein, a an increased or decreased ionic (e.g., salt) concentration compared to the fluid containing the recombinant therapeutic protein, and/or an increased or decreased concentration of an agent that competes with the recombinant therapeutic protein for binding to resin present in at least one chromatographic column or at least one chromatographic membrane in an MCCS (e.g., the first or the second MCCS)). In other examples, the unit operations of adjusting the ionic concentration and/or pH of a fluid can be performed using size exclusion chromatography and counter-current dialysis (see, e.g., Kurnik et al., *Biotechnol. Bioeng.* 45(2):149-157, 1995; and Klutz et al., *J. Biotechnol.* 213:120-130, 2015).

The first and/or second MCCS can perform two or more unit operations. For example, the first and/or second MCCS can each perform at least the following unit operations: capturing the recombinant therapeutic protein and inactivating viruses present in the fluid containing the recombinant therapeutic protein; capturing the recombinant therapeutic protein, inactivating viruses present in the fluid containing the recombinant therapeutic protein, and adjusting the ionic concentration and/or pH of a liquid containing the recombinant therapeutic protein; purifying the recombinant therapeutic protein and polishing the recombinant therapeutic protein; purifying the recombinant therapeutic protein, polishing the recombinant therapeutic protein, and filtering a fluid containing the recombinant therapeutic protein or removing precipitates and/or particular matter from a fluid containing the recombinant therapeutic protein; and purifying the recombinant therapeutic protein, polishing the recombinant therapeutic protein, filtering a fluid containing the recombinant therapeutic protein or removing precipitates and/or particular matter from a fluid containing the recombinant therapeutic protein, and adjusting the ionic concentration and/or pH of a liquid containing the recombinant therapeutic protein.

Capturing the Recombinant Therapeutic Protein

The present processes include a step of capturing the recombinant therapeutic protein using a first MCCS. As can be appreciated in the art, the liquid culture medium containing the recombinant therapeutic protein can be continuously fed onto the first MCCS using a variety of different means. For example, the liquid culture medium can be actively pumped into the first MCCS or the liquid culture medium can be fed into the first MCCS using gravitational force. The liquid culture medium can be stored in a reservoir (e.g., a holding tank) before it is fed into the first MCCS or the liquid culture medium can be actively pumped from a bioreactor containing a culture of cells (e.g., mammalian cells that secrete the recombinant therapeutic protein into the culture medium) into the first MCCS.

The liquid culture medium can be fed (loaded) into the first MCCS at a flow rate of, e.g., between about 0.2 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, about 25 mL/minute, about 20 mL/minute, about 15 mL/minute, about 10 mL/minute, about 5 mL/minute, or about 2 mL/minute (inclusive); between about 0.5 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, about 25 mL/minute, about 20 mL/minute, about 15 mL/minute, about 10 mL/minute, about 5 mL/minute, or about 2 mL/minute (inclusive); between about 1 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, about 25 mL/minute, about 20 mL/minute, about 15 mL/minute, about 10 mL/minute, about 5 mL/minute, or about 2 mL/minute (inclusive); between about 2 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, about 25 mL/minute, about 20 mL/minute, about 15 mL/minute, about 10 mL/minute, or about 5 mL/minute (inclusive); between about 5 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, about 25 mL/minute, about 20 mL/minute, about 15 mL/minute, or about 10 mL/minute (inclusive); between 10 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, about 25 mL/minute, about 20 mL/minute, or about 15 mL/minute (inclusive); between about 15 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, about 25 mL/minute, or about 20 mL/minute (inclusive); between about 20 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, about 30 mL/minute, or about 25 mL/minute (inclusive); between about 25 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, about 35 mL/minute, or about 30 mL/minute (inclusive); between about 30 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, about 40 mL/minute, or about 35 mL/minute (inclusive); between about 35 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, about 45 mL/minute, or about 40 mL/minute (inclusive); between about 40 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, about 50 mL/minute, or about 45 mL/minute (inclusive); between about 45 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, about 55 mL/minute, or about 50 mL/minute (inclusive); between about 50 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, about 60 mL/minute, or about 55 mL/minute (inclusive); between about 55 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, about 65 mL/minute, or about 60 mL/minute (inclusive); between about 60 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, about 70 mL/minute, or about 65 mL/minute (inclusive); between about 65 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, about 75 mL/minute, or about 70 mL/minute (inclusive); between about 70 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, about 80 mL/minute, or about 75 mL/minute (inclusive); between about 75 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, about 85 mL/minute, or about 80 mL/minute (inclusive); between about 80 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, about 90 mL/minute, or about 85 mL/minute (inclusive); between about 85 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, about 95 mL/minute, or about 90 mL/minute (inclusive); between about 90 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, about 100 mL/minute, or about 95 mL/minute (inclusive); between about 95 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, about 150 mL/minute, or about 100 mL/minute (inclusive); between about 100 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, about 200 mL/minute, or about 150 mL/minute (inclusive); between about 150 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, about 250 mL/minute, or about 200 mL/minute (inclusive); between about 200 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, about 300 mL/minute, or about 250 mL/minute (inclusive); between about 250 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, about 350 mL/minute, or about 300 mL/minute (inclusive); about 300 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, about 400 mL/minute, or about 350 mL/minute (inclusive); between about 350 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, about 450 mL/minute, or about 400 mL/minute (inclusive); about 400 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, about 500 mL/minute, or about 450 mL/minute (inclusive); between about 450 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, about 550 mL/minute, or about 500 mL/minute (inclusive); between about 500 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, about 600 mL/minute, or about 550 mL/minute (inclusive); between about 550 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, about 650 mL/minute, or about 600 mL/minute (inclusive); between about 600 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, about 700 mL/minute, or about 650 mL/minute (inclusive); between about 650 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, about 750 mL/minute, or about 700 mL/minute (inclusive); between about 700 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, about 800 mL/minute, or about 750 mL/minute (inclusive); between about 750 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, about 850 mL/minute, or about 800 mL/minute (inclusive); between about 800 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, about 900 mL/minute, or about 850 mL/minute (inclusive); between about 850 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, about 950 mL/minute, or about 900 mL/minute (inclusive); between about 900 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, about 1 L/minute, or about 950 mL/minute (inclusive); between about 950 mL/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, about 5 L/minute, or about 1 L/minute (inclusive); between about 1 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, about 10 L/minute, or about 5 L/minute (inclusive); between about 5 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, about 15 L/minute, or about 10 L/minute (inclusive); between about 10 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, about 20 L/minute, or about 15 L/minute (inclusive); between about 15 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, about 25 L/minute, or about 20 L/minute (inclusive); between about 20 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, about 30 L/minute, or about 25 L/minute (inclusive); between about 25 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, about 35 L/minute, or about 30 L/minute (inclusive); between about 30 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, about 40 L/minute, or about 35 L/minute (inclusive); between about 35 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, about 45 L/minute, or about 40 L/minute (inclusive); between about 40 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, about 50 L/minute, or about 45 L/minute (inclusive); between about 45 L/minute to about 100 L/minute, about 95 L/minute, about 90 L/minute, about 85 L/minute, about 80 L/minute, about 75 L/minute, about 70 L/minute, about 65 L/minute, about 60 L/minute, about 55 L/minute, or about 50 L/minute (inclusive); between about 50 L/minute to about 100 L/minute, about 95 L/minute, about 90 L/minute, about 85 L/minute, about 80 L/minute, about 75 L/minute, about 70 L/minute, about 65 L/minute, about 60 L/minute, or about 55 L/minute (inclusive); between about 55 L/minute to about 100 L/minute, about 95 L/minute, about 90 L/minute, about 85 L/minute, about 80 L/minute, about 75 L/minute, about 70 L/minute, about 65 L/minute, or about 60 L/minute (inclusive); between about 60 L/minute to about 100 L/minute, about 95 L/minute, about 90 L/minute, about 85 L/minute, about 80 L/minute, about 75 L/minute, about 70 L/minute, or about 65 L/minute (inclusive); between about 65 L/minute to about 100 L/minute, about 95 L/minute, about 90 L/minute, about 85 L/minute, about 80 L/minute, about 75 L/minute, or about 70 L/minute (inclusive); between about 70 L/minute to about 100 L/minute, about 95 L/minute, about 90 L/minute, about 85 L/minute, about 80 L/minute, or about 75 L/minute (inclusive); between about 75 L/minute to about 100 L/minute, about 95 L/minute, about 90 L/minute, about 85 L/minute, or about 80 L/minute (inclusive); between about 80 L/minute to about 100 L/minute, about 95 L/minute, about 90 L/minute, or about 85 L/minute (inclusive); between about 85 L/minute to about 100 L/minute, about 95 L/minute, or about 90 L/minute (inclusive); between about 90 L/minute to about 100 L/minute or about 95 L/minute (inclusive); or about 95 L/minute to about 100 L/minute (inclusive). The liquid culture medium containing the recombinant therapeutic protein can be derived from any of the exemplary sources described herein or known in the art.

Some examples further include the optional step of filtering the liquid culture medium before it is fed onto the first MCCS. Any of the exemplary means of filtering a liquid culture medium or a fluid containing the recombinant therapeutic protein described herein, or any filtration means known in the art, can be used to filter the liquid culture medium containing the recombinant therapeutic protein before it is fed into the first MCCS.

In the methods described herein, the capturing of the recombinant therapeutic protein from the liquid culture medium is performed using a first MCCS. As can be appreciated in the art, in order to achieve the capture of the recombinant therapeutic protein, at least one chromatographic column or at least one chromatographic membrane in the first MCCS must contain a resin that utilizes a capturing mechanism (e.g., any of the exemplary capturing mechanisms described herein), or contains a resin capable of performing cation exchange, anion exchange, or molecule sieve chromatography. For example, if the recombinant therapeutic protein is an antibody or an antibody fragment, the capturing system can be a protein A-binding capturing mechanism or an antigen-binding capturing mechanism (where the capturing antigen is specifically recognized by the recombinant therapeutic antibody or antibody fragment). If the recombinant therapeutic protein is an enzyme, the capturing mechanism can use an antibody or antibody fragment that specifically binds to the enzyme to capture the recombinant therapeutic enzyme, a substrate of the enzyme to capture the recombinant therapeutic enzyme, a cofactor of the enzyme to capture the recombinant therapeutic enzyme, or, if the recombinant therapeutic enzyme contains a tag, a protein, metal chelate, or antibody (or antibody fragment) that specifically binds to the tag present in the recombinant therapeutic enzyme. Non-limiting resins that can be used to capture a recombinant therapeutic protein are described herein and additional resins that can be used to capture a recombinant therapeutic protein are known in the art. One non-limiting example of resin that utilizes a protein A-binding capture mechanism is MabSelect SuRe resin (GE Healthcare, Piscataway, NJ).

Exemplary non-limiting sizes and shapes of the chromatography column(s) or chromatographic membrane(s) present in the first MCCS that can be used to capture the recombinant therapeutic protein are described herein. The liquid culture medium fed (loaded) into the first MCCS can contain, e.g., between about 0.05 mg/mL to about 100 mg/mL recombinant therapeutic protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between about 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant therapeutic protein). The mean time required for the recombinant therapeutic protein to bind to the resin used to perform the unit operation of capturing can be, e.g., between about 1 second to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, about 4 minutes, about 3 minutes, about 2 minutes, about 1 minute, about 30 seconds, about 20 seconds, about 10 seconds, or about 5 seconds (inclusive); between about 5 seconds to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, about 4 minutes, about 3 minutes, about 2 minutes, about 1 minute, about 30 seconds, about 20 seconds, or about 10 seconds (inclusive); between about 10 seconds to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, about 4 minutes, about 3 minutes, about 2 minutes, about 1 minute, about 30 seconds, or about 20 seconds (inclusive); between about 20 seconds to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, about 4 minutes, about 3 minutes, about 2 minutes, about 1 minute, or about 30 seconds (inclusive); between about 30 seconds to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, about 4 minutes, about 3 minutes, about 2 minutes, or about 1 minute (inclusive); between about 1 minute to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, about 4 minutes, about 3 minutes, or about 2 minutes (inclusive); between about 2 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, about 4 minutes, or about 3 minutes (inclusive); between about 3 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, about 5 minutes, or about 4 minutes (inclusive); between about 4 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, about 6 minutes, or about 5 minutes (inclusive); between about 5 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, about 8 minutes, or about 6 minutes (inclusive); between about 6 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, about 10 minutes, or about 8 minutes (inclusive); between about 8 minutes to about 60 minutes, about 55 minutes, about 50 minutes, about 45 minutes, about 40 minutes, about 35 minutes, about 30 minutes, about 25 minutes, about 20 minutes, about 18 minutes, about 16 minutes, about 14 minutes, about 12 minutes, or about 10 minutes (inclusive); between about 10 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, about 14 minutes, or about 12 minutes (inclusive); between about 12 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, about 16 minutes, or about 14 minutes (inclusive); between about 14 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, about 20 minutes, about 18 minutes, or about 16 minutes (inclusive); between about 16 minutes to about 60 minutes, about 55 minutes, about 50 minutes, about 45 minutes, about 40 minutes, about 35 minutes, about 30 minutes, about 25 minutes, about 20 minutes, or about 18 minutes (inclusive); between about 18 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, about 25 minutes, or about 20 minutes (inclusive); between about 20 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, about 30 minutes, or about 25 minutes (inclusive); between about 25 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, about 35 minutes, or about 30 minutes (inclusive); between about 30 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, about 40 minutes, or about 35 minutes (inclusive); between about 35 minutes to about 24 hours, about 20 hours, about 16 hours, about 12 hours, about 8 hours, about 4 hours, about 3 hours, about 2 hours, about 1 hour, about 55 minutes, about 50 minutes, about 45 minutes, or about 40 minutes (inclusive); between about 40 minutes to about 24 hours, about 20 hours, about 16 hours, about 12 hours, about 8 hours, about 4 hours, about 3 hours, about 2 hours, about 1 hour, about 55 minutes, about 50 minutes, or about 45 minutes (inclusive); between about 45 minutes to about 24 hours, about 20 hours, about 16 hours, about 12 hours, about 8 hours, about 4 hours, about 3 hours, about 2 hours, about 1 hour, about 55 minutes, or about 50 minutes (inclusive); between about 50 minutes to about 24 hours, about 20 hours, about 16 hours, about 12 hours, about 8 hours, about 4 hours, about 3 hours, about 2 hours, about 1 hour, or about 55 minutes (inclusive); about 55 minutes to about 24 hours, about 20 hours, about 16 hours, about 12 hours, about 8 hours, about 4 hours, about 3 hours, about 2 hours, about 1 hour, or about 60 minutes (inclusive); between about 60 minutes to about 24 hours, about 20 hours, about 16 hours, about 12 hours, about 8 hours, about 4 hours, about 3 hours, about 2 hours, or about 1 hour (inclusive); between about 1 hour to about 24 hours, about 20 hours, about 16 hours, about 12 hours, about 8 hours, about 4 hours, about 3 hours, or about 2 hours (inclusive); between about 2 hours to about 24 hours, about 20 hours, about 16 hours, about 12 hours, about 8 hours, about 4 hours, or about 3 hours (inclusive); between about 3 hours to about 24 hours, about 20 hours, about 16 hours, about 12 hours, about 8 hours, or about 4 hours (inclusive); between about 4 hours to about 24 hours, about 20 hours, about 16 hours, about 12 hours, or about 8 hours (inclusive); between about 8 hours to about 24 hours, about 20 hours, about 16 hours, or about 12 hours (inclusive); between about 12 hours to about 24 hours, about 20 hours, or about 16 hours (inclusive); between about 16 hours to about 24 hours or about 20 hours (inclusive); or between about 20 hours to about 24 hours (inclusive).

As can be appreciated in the art, in order to capture the recombinant therapeutic protein using the chromatography column(s) or chromatographic membrane(s) present in the first MCCS, one must perform the sequential chromatographic steps of loading, washing, eluting, and regenerating the chromatography column(s) or chromatography membrane(s) present in the first MCCS. Any of the exemplary flow rates, buffer volumes, and/or lengths of time allotted for each sequential chromatographic step described herein can be used in the one or more of these different sequential chromatographic steps (e.g., one or more of the sequential chromatographic steps of loading, washing, eluting, and regenerating the chromatography column(s) or chromatography membrane(s) present in the first MCCS that are used for capturing the recombinant therapeutic protein). Non-limiting flow rates, buffer volumes, and/or lengths of time allotted for each sequential chromatographic step that can be used for capturing chromatographic column(s) and/or chromatographic membrane(s) in the first MCCS (e.g., a first PCC system) are provided below. In addition, exemplary buffers elution buffers that can be used in the first MCCS are described below.

The first MCCS containing at least one chromatographic column and/or chromatographic membrane containing a resin that can perform the unit operation of capturing (e.g., any of exemplary resins that can be used for capturing described herein) can be loaded with the liquid culture medium containing a recombinant therapeutic protein using any of loading flow rates (fed rates) described above. In some examples, a single chromatographic column or single chromatographic membrane containing a resin that is capable of performing the unit operation of capturing is loaded in, e.g., between about 10 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, about 80 minutes, about 70 minutes, about 60 minutes, about 50 minutes, about 40 minutes, about 30 minutes, about 20 minutes, or about 15 minutes (inclusive); between about 15 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, about 80 minutes, about 70 minutes, about 60 minutes, about 50 minutes, about 40 minutes, about 30 minutes, or about 20 minutes (inclusive); between about 20 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, about 80 minutes, about 70 minutes, about 60 minutes, about 50 minutes, about 40 minutes, or about 30 minutes (inclusive); between about 30 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, about 80 minutes, about 70 minutes, about 60 minutes, about 50 minutes, or about 40 minutes (inclusive); between about 40 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, about 80 minutes, about 70 minutes, about 60 minutes, or about 50 minutes (inclusive); between about 50 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, about 80 minutes, about 70 minutes, or about 60 minutes (inclusive); between about 60 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, about 80 minutes, or about 70 minutes (inclusive); between about 70 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, about 90 minutes, or about 80 minutes (inclusive); between about 80 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, about 100 minutes, or about 90 minutes (inclusive); between about 90 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, about 110 minutes, or about 100 minutes (inclusive); between about 100 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, about 2 hours, or about 110 minutes (inclusive); between about 110 minutes to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, about 3 hours, or about 2 hours (inclusive); between about 2 hours to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, about 4 hours, or about 3 hours (inclusive); between about 3 hours to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, about 5 hours, or about 4 hours (inclusive); between about 4 hours to about 48 hours, about 44 hours, about 40 hours, about 36 hours, about 32 hours, about 28 hours, about 24 hours, about 20 hours, about 16 hours, about 12 hours, about 8 hours, about 7 hours, about 6 hours, or about 5 hours (inclusive); between about 5 hours to about 48 hours, about 44 hours, about 40 hours, about 36 hours, about 32 hours, about 28 hours, about 24 hours, about 20 hours, about 16 hours, about 12 hours, about 8 hours, about 7 hours, or about 6 hours (inclusive); between about 6 hours to about 48 hours, about 44 hours, about 40 hours, about 36 hours, about 32 hours, about 28 hours, about 24 hours, about 20 hours, about 16 hours, about 12 hours, about 8 hours, or about 7 hours (inclusive); between about 7 hours to about 48 hours, about 44 hours, about 40 hours, about 36 hours, about 32 hours, about 28 hours, about 24 hours, about 20 hours, about 16 hours, about 12 hours, or about 8 hours (inclusive); between about 8 hours to about 48 hours, about 44 hours, about 40 hours, about 36 hours, about 32 hours, about 28 hours, about 24 hours, about 20 hours, about 16 hours, or about 12 hours (inclusive); between about 12 hours to about 48 hours, about 44 hours, about 40 hours, about 36 hours, about 32 hours, about 28 hours, about 24 hours, about 20 hours, or about 16 hours (inclusive); between about 16 hours to about 48 hours, about 44 hours, about 40 hours, about 36 hours, about 32 hours, about 28 hours, about 24 hours, or about 20 hours (inclusive); between about 20 hours to about 48 hours, about 44 hours, about 40 hours, about 36 hours, about 32 hours, about 28 hours, or about 24 hours (inclusive); between about 24 hours to about 48 hours, about 44 hours, about 40 hours, about 36 hours, about 32 hours, or about 28 hours (inclusive); between about 28 hours to about 48 hours, about 44 hours, about 40 hours, about 36 hours, or about 32 hours (inclusive); between about 32 hours to about 48 hours, about 44 hours, about 40 hours, or about 36 hours (inclusive); between about 36 hours to about 48 hours, about 44 hours, or about 40 hours (inclusive); between about 40 hours to about 48 hours or about 44 hours (inclusive), or about 44 hours to about 48 hours (inclusive). In some examples, wherein the first MCCS includes at least two chromatographic columns that contain a resin that is capable of performing the unit operation of capturing in series, the time required to load two of the chromatographic columns in series is, e.g., between about 50 minutes to about 180 minutes (e.g., between about 60 minutes and about 180 minutes, between about 70 minutes and about 180 minutes, between about 80 minutes and about 180 minutes, between about 90 minutes and about 180 minutes, between about 100 minutes and about 180 minutes, between about 110 minutes and 150 minutes, and between about 125 minutes and about 145 minutes).

Following the loading of the recombinant therapeutic protein onto the at least one chromatographic column or chromatographic membrane in the first MCCS that contains a resin that is capable of performing the unit operation of capturing, the at least one chromatographic column or chromatographic membrane is washed with at least one washing buffer. As can be appreciated in the art, the at least one (e.g., two, three, or four) washing buffer is meant to elute all proteins that are not the recombinant therapeutic protein from the at least one chromatography column or chromatographic membrane, while not disturbing the interaction of the recombinant therapeutic protein with the resin.

The wash buffer can be passed through the at least one chromatography column or chromatographic membrane at a flow rate of, e.g., between about 0.2 mL/minute to about 100 L/minute (inclusive) (e.g., any of the subranges of this flow rate range described herein). The volume of wash buffer used (e.g., combined total volume of wash buffer used when more than one wash buffer is used) can be, e.g., between about 1× column volume (CV) to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, about 4×CV, or about 3×CV (inclusive); between about 2×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, or about 4×CV (inclusive); between about 3×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 5×CV (inclusive); between about 4×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 6×CV (inclusive); between about 5×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, or about 7×CV (inclusive); between about 6×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, or about 8×CV (inclusive); between about 7×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, or about 9×CV (inclusive); between about 8×CV to about 30×CV, about 28×CV, about 26×CV, about 24×CV, about 22×CV, about 20×CV, about 18×CV, about 16×CV, about 14×CV, about 13×CV, about 12×CV, about 11×CV, or about 10×CV (inclusive); between about 9 CV to about 30×CV, about 28×CV, about 26×CV, about 24×CV, about 22×CV, about 20×CV, about 18×CV, about 16×CV, about 14×CV, about 13×CV, about 12×CV, or about 11×CV (inclusive); between about 10×CV to about 30×CV, about 28×CV, about 26×CV, about 24×CV, about 22×CV, about 20×CV, about 18×CV, about 16×CV, about 14×CV, about 13×CV, or about 12×CV (inclusive); between about 11×CV to about 30×CV, about 28×CV, about 26×CV, about 24×CV, about 22×CV, about 20×CV, about 18×CV, about 16×CV, about 14×CV, or about 13×CV (inclusive); between about 12×CV to about 30×CV, about 28×CV, about 26×CV, about 24×CV, about 22×CV, about 20×CV, about 18×CV, about 16×CV, or about 14×CV (inclusive); between about 14×CV to about 30×CV, about 28×CV, about 26×CV, about 24×CV, about 22×CV, about 20×CV, about 18×CV, or about 16×CV (inclusive); between about 16×CV to about 30×CV, about 28×CV, about 26×CV, about 24×CV, about 22×CV, about 20×CV, or about 18×CV (inclusive); between about 18×CV to about 30×CV, about 28×CV, about 26×CV, about 24×CV, about 22×CV, or about 20×CV (inclusive); between about 20×CV to about 30×CV, about 28×CV, about 26×CV, about 24×CV, or about 22×CV (inclusive); between about 22×CV to about 30×CV, about 28×CV, about 26×CV, or about 24×CV (inclusive); between about 24×CV to about 30×CV, about 28×CV, or about 26×CV (inclusive); between about 26×CV to about 30×CV or about 28×CV (inclusive); or between about 28×CV to about 30×CV (inclusive).

The total time of the washing can be, e.g., between about 2 minutes to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, about 1.5 hours, about 1 hour, about 50 minutes, about 40 minutes, about 30 minutes, about 20 minutes, about 10 minutes, or about 5 minutes (inclusive); between about 5 minutes to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, about 1.5 hours, about 1 hour, about 50 minutes, about 40 minutes, about 30 minutes, about 20 minutes, or about 10 minutes (inclusive); about 10 minutes to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, about 1.5 hours, about 1 hour, about 50 minutes, about 40 minutes, about 30 minutes, or about 20 minutes (inclusive); between about 20 minutes to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, about 1.5 hours, about 1 hour, about 50 minutes, about 40 minutes, or about 30 minutes (inclusive); between about 30 minutes to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, about 1.5 hours, about 1 hour, about 50 minutes, or about 40 minutes (inclusive); between about 40 minutes to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, about 1.5 hours, about 1 hour, or about 50 minutes (inclusive); between about 50 minutes to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, about 1.5 hours, or about 1 hour (inclusive); between about 1 hour to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, about 2 hours, or about 1.5 hours (inclusive); between about 1.5 hours to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, about 2.5 hours, or about 2 hours (inclusive); between about 2 hours to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, about 3 hours, or about 2.5 hours (inclusive); between about 2.5 hours to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, about 3.5 hours, or about 3 hours (inclusive); between about 3 hours to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, about 4 hours, or about 3.5 hours (inclusive); between about 3.5 hours to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, about 4.5 hours, or about 4 hours (inclusive); between about 4 hours to about 24 hours, about 22 hours, about 20 hours, about 18 hours, about 16 hours, about 14 hours, about 12 hours, about 10 hours, about 9 hours, about 8 hours, about 7 hours, about 6 hours, about 5 hours, or about 4.5 hours (inclusive); between about 4.5 hours to about 24 hours, about 22 hours, about 20 hours, about 18 hours, about 16 hours, about 14 hours, about 12 hours, about 10 hours, about 9 hours, about 8 hours, about 7 hours, about 6 hours, or about 5 hours (inclusive); between about 5 hours to about 24 hours, about 22 hours, about 20 hours, about 18 hours, about 16 hours, about 14 hours, about 12 hours, about 10 hours, about 9 hours, about 8 hours, about 7 hours, or about 6 hours (inclusive); between about 6 hours to about 24 hours, about 22 hours, about 20 hours, about 18 hours, about 16 hours, about 14 hours, about 12 hours, about 10 hours, about 9 hours, about 8 hours, or about 7 hours (inclusive); between about 7 hours to about 24 hours, about 22 hours, about 20 hours, about 18 hours, about 16 hours, about 14 hours, about 12 hours, about 10 hours, about 9 hours, or about 8 hours (inclusive); between about 8 hours to about 24 hours, about 22 hours, about 20 hours, about 18 hours, about 16 hours, about 14 hours, about 12 hours, about 10 hours, or about 9 hours (inclusive); between about 9 hours to about 24 hours, about 22 hours, about 20 hours, about 18 hours, about 16 hours, about 14 hours, about 12 hours, or about 10 hours (inclusive); between about 10 hours to about 24 hours, about 22 hours, about 20 hours, about 18 hours, about 16 hours, about 14 hours, or about 12 hours (inclusive); between about 12 hours to about 24 hours, about 22 hours, about 20 hours, about 18 hours, about 16 hours, or about 14 hours (inclusive); between about 14 hours to about 24 hours, about 22 hours, about 20 hours, about 18 hours, or about 16 hours (inclusive); between about 16 hours to about 24 hours, about 22 hours, about 20 hours, or about 18 hours (inclusive); between about 18 hours to about 24 hours, about 22 hours, or about 20 hours (inclusive); between about 20 hours to about 24 hours or about 22 hours (inclusive); or between about 22 hours to about 24 hours (inclusive).

Following the washing of the at least one chromatographic column or chromatographic membrane in the first MCCS that contains a resin that is capable of performing the unit operation of capturing, the recombinant therapeutic protein is eluted from the at least one chromatographic column or chromatographic membrane by passing an elution buffer through the at least one chromatographic column or chromatographic membrane in the first MCCS that contains a resin that is capable of performing the unit operation of capturing. The elution buffer can be passed through the at least one chromatography column or chromatographic membrane that contains a resin that is capable of performing the unit operation of capturing at a flow rate of between about 0.2 mL/minute to about 100 L/minute (inclusive) (e.g., any of the subranges of this flow rate range described herein). The volume of elution buffer used to elute the recombinant therapeutic protein from each of the at least one chromatographic column or chromatographic membrane containing a resin that is capable of performing the unit operation of purifying can be, e.g., between about 1× column volume (CV) to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, or about 4×CV (inclusive); between about 3×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, or about 5×CV (inclusive); between about 4×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 6×CV (inclusive); between about 5×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, or about 7×CV (inclusive); between about 6×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, or about 8×CV (inclusive); between about 7×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, or about 9×CV (inclusive); between about 8×CV to about 30×CV, about 28×CV, about 26×CV, about 24×CV, about 22×CV, about 20×CV, about 18×CV, about 16×CV, about 14×CV, about 13×CV, about 12×CV, about 11×CV, or about 10×CV (inclusive); between about 9 CV to about 30×CV, about 28×CV, about 26×CV, about 24×CV, about 22×CV, about 20×CV, about 18×CV, about 16×CV, about 14×CV, about 13×CV, about 12×CV, or about 11×CV (inclusive); between about 10×CV to about 30×CV, about 28×CV, about 26×CV, about 24×CV, about 22×CV, about 20×CV, about 18×CV, about 16×CV, about 14×CV, about 13×CV, or about 12×CV (inclusive); between about 11×CV to about 30×CV, about 28×CV, about 26×CV, about 24×CV, about 22×CV, about 20×CV, about 18×CV, about 16×CV, about 14×CV, or about 13×CV (inclusive); between about 12×CV to about 30×CV, about 28×CV, about 26×CV, about 24×CV, about 22×CV, about 20×CV, about 18×CV, about 16×CV, or about 14×CV (inclusive); between about 14×CV to about 30×CV, about 28×CV, about 26×CV, about 24×CV, about 22×CV, about 20×CV, about 18×CV, or about 16×CV (inclusive); between about 16×CV to about 30×CV, about 28×CV, about 26×CV, about 24×CV, about 22×CV, about 20×CV, or about 18×CV (inclusive); between about 18×CV to about 30×CV, about 28×CV, about 26×CV, about 24×CV, about 22×CV, or about 20×CV (inclusive); between about 20×CV to about 30×CV, about 28×CV, about 26×CV, about 24×CV, or about 22×CV (inclusive); between about 22×CV to about 30×CV, about 28×CV, about 26×CV, or about 24×CV (inclusive); between about 24×CV to about 30×CV, about 28×CV, or about 26×CV (inclusive); between about 26×CV to about 30×CV or about 28×CV (inclusive); or between about 28×CV to about 30×CV (inclusive).

The total time of the eluting can be, e.g., between about 2 minutes to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, about 1.5 hours, about 1.25 hours, about 1 hour, about 40 minutes, about 30 minutes, about 20 minutes, about 10 minutes, or about 5 minutes, inclusive; between about 5 minutes to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, about 1.5 hours, about 1.25 hours, about 1 hour, about 40 minutes, about 30 minutes, about 20 minutes, or about 10 minutes, inclusive; between about 10 minutes to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, about 1.5 hours, about 1.25 hours, about 1 hour, about 40 minutes, about 30 minutes, or about 20 minutes, inclusive; between about 20 minutes to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, about 1.5 hours, about 1.25 hours, about 1 hour, about 40 minutes, or about 30 minutes, inclusive; between about 30 minutes to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, about 1.5 hours, about 1.25 hours, about 1 hour, or about 40 minutes, inclusive; between about 40 minutes to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, about 1.5 hours, about 1.25 hours, or about 1 hour, inclusive; between about 1 hour to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, about 1.5 hours, or about 1.25 hours, inclusive; between about 1.25 hours to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, about 1.5 hours, or about 1.5 hours, inclusive; between about 1.5 hour to about 24 hours, about 22 hours, about 20 hours, about 18 hours, about 16 hours, about 14 hours, about 12 hours, about 10 hours, about 7.5 hours, about 5 hours, about 2.5 hours, about 2.0 hours, or about 1.5 hours, inclusive; between about 1.5 hours to about 24 hours, about 22 hours, about 20 hours, about 18 hours, about 16 hours, about 14 hours, about 12 hours, about 10 hours, about 7.5 hours, about 5 hours, about 2.5 hours, or about 2.0 hours, inclusive; between about 2.0 hours to about 24 hours, about 22 hours, about 20 hours, about 18 hours, about 16 hours, about 14 hours, about 12 hours, about 10 hours, about 7.5 hours, about 5 hours, or about 2.5 hours, inclusive; between about 2.5 hours to about 24 hours, about 22 hours, about 20 hours, about 18 hours, about 16 hours, about 14 hours, about 12 hours, about 10 hours, about 7.5 hours, or about 5 hours, inclusive; between about 5 hours to about 24 hours, about 22 hours, about 20 hours, about 18 hours, about 16 hours, about 14 hours, about 12 hours, about 10 hours, or about 7.5 hours, inclusive; between about 7.5 hours to about 24 hours, about 22 hours, about 20 hours, about 18 hours, about 16 hours, about 14 hours, about 12 hours, or about 10 hours, inclusive; between about 10 hours to about 24 hours, about 22 hours, about 20 hours, about 18 hours, about 16 hours, about 14 hours, or about 12 hours, inclusive; between about 12 hours to about 24 hours, about 22 hours, about 20 hours, about 18 hours, about 16 hours, or about 14 hours, inclusive; between about 14 hours to about 24 hours, about 22 hours, about 20 hours, about 18 hours, or about 16 hours, inclusive; between about 16 hours to about 24 hours, about 22 hours, about 20 hours, or about 18 hours, inclusive; between about 18 hours to about 24 hours, about 22 hours, or about 20 hours, inclusive; between about 20 hours to about 24 hours or about 22 hours, inclusive; or between about 22 hours to about 24 hours, inclusive. Non-limiting examples of elution buffers that can be used in these methods will depend on the capture mechanism and/or the therapeutic protein. For example, an elution buffer can contain a different concentration of salt (e.g., increased salt concentration), a different pH (e.g., an increased or decreased salt concentration), or a molecule that will compete with the recombinant therapeutic protein for binding to the resin that is capable of performing the unit operation of capturing. Examples of such elution buffers for each exemplary capture mechanism described herein are well known in the art.

Following the elution of the recombinant therapeutic protein from the at least one chromatographic column or chromatographic membrane in the first MCCS that contains a resin that is capable of performing the unit operation of capturing, and before the next volume of liquid culture medium can be loaded onto the at least one chromatographic column or chromatographic membrane, the at least one chromatography column or chromatographic membrane must be equilibrated using an regeneration buffer. The regeneration buffer can be passed through the at least one chromatography column or chromatographic membrane that contains a resin that is capable of performing the unit operation of capturing at a flow rate of, e.g., between about 0.2 mL/minute to about 100 L/minute (inclusive) (e.g., any of the subranges of this flow rate range described herein). The volume of regeneration buffer used to equilibrate the at least one chromatography column or chromatographic membrane that contains a resin that is capable of performing the unit operation of capturing can be, e.g., between about 1× column volume (CV) to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, about 4×CV, or about 3×CV (inclusive); between about 2×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, or about 4×CV (inclusive); between about 3×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 5×CV (inclusive); between about 4×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 6×CV (inclusive); between about 5×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, or about 7×CV (inclusive); between about 6×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, or about 8×CV (inclusive); between about 7×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, or about 9×CV (inclusive); between about 8×CV to about 30×CV, about 28×CV, about 26×CV, about 24×CV, about 22×CV, about 20×CV, about 18×CV, about 16×CV, about 14×CV, about 13×CV, about 12×CV, about 11×CV, or about 10×CV (inclusive); between about 9 CV to about 30×CV, about 28×CV, about 26×CV, about 24×CV, about 22×CV, about 20×CV, about 18×CV, about 16×CV, about 14×CV, about 13×CV, about 12×CV, or about 11×CV (inclusive); between about 10×CV to about 30×CV, about 28×CV, about 26×CV, about 24×CV, about 22×CV, about 20×CV, about 18×CV, about 16×CV, about 14×CV, about 13×CV, or about 12×CV (inclusive); between about 11×CV to about 30×CV, about 28×CV, about 26×CV, about 24×CV, about 22×CV, about 20×CV, about 18×CV, about 16×CV, about 14×CV, or about 13×CV (inclusive); between about 12×CV to about 30×CV, about 28×CV, about 26×CV, about 24×CV, about 22×CV, about 20×CV, about 18×CV, about 16×CV, or about 14×CV (inclusive); between about 14×CV to about 30×CV, about 28×CV, about 26×CV, about 24×CV, about 22×CV, about 20×CV, about 18×CV, or about 16×CV (inclusive); between about 16×CV to about 30×CV, about 28×CV, about 26×CV, about 24×CV, about 22×CV, about 20×CV, or about 18×CV (inclusive); between about 18×CV to about 30×CV, about 28×CV, about 26×CV, about 24×CV, about 22×CV, or about 20×CV (inclusive); between about 20×CV to about 30×CV, about 28×CV, about 26×CV, about 24×CV, or about 22×CV (inclusive); between about 22×CV to about 30×CV, about 28×CV, about 26×CV, or about 24×CV (inclusive); between about 24×CV to about 30×CV, about 28×CV, or about 26×CV (inclusive); between about 26×CV to about 30×CV or about 28×CV (inclusive); or between about 28×CV to about 30×CV (inclusive).

In some of the processes described herein, the first MCCS includes a reservoir that holds a fluid containing the recombinant therapeutic protein at low pH (e.g., a pH below 4.6, below 4.4, below 4.2, below 4.0, below 3.8, below 3.6, below 3.4, below 3.2, or below 3.0) for, e.g., about 1 minute to 3.0 hours (e.g., about 1 hour), and inactivates the viruses present in a fluid containing the recombinant therapeutic protein. An example of a reservoir that can be used to perform the unit operation of inactivating viruses is a stir flask (e.g., 500-mL stir flask, e.g., a 500-mL stir flask with a programmed stir plate) that is capable of holding a fluid containing a recombinant therapeutic protein for, e.g., about 1 minute to 1.5 hours, before the fluid containing the recombinant therapeutic protein is fed into the second MCCS. The reservoir that is used to perform the unit operation of inactivation of viruses can be a 500-mL stir flask with a programmed stir plate (e.g., a stir plate programmed to mix (e.g., periodically mix) the fluid within the reservoir, e.g., every 4 hours). Another example of a reservoir that can be used to perform the unit operation of inactivation of viruses is a plastic bag (e.g., 500-mL plastic bag) that is capable of holding a fluid containing a recombinant therapeutic protein for, e.g., about 1 minute to 1.5 hours, before the fluid containing the recombinant therapeutic protein is fed into the second MCCS. In some examples, the fluid containing the recombinant therapeutic protein can already have a low pH (e.g., a pH below 4.6, below 4.4, below 4.2, below 4.0, below 3.8, below 3.6, below 3.4, below 3.2, or below 3.0) when it is fed into the reservoir that is used to perform the unit operation of viral inactivation. Viral inactivation can also be performed using a tubular reactor (e.g., as described in Klutz et al., *Chemical Engineering Processing: Process Intensification* 102:88-101, 2016b; Klutz et al., *Chemical Engineering Research Design* 95:22-33, 2015) or a coiled flow inverter (see, e.g., Klutz et al., *Chemical Engineering Research Design* 95:22-33, 2015; and Klutz et al., *Chemical Engineering Processing: Process Intensification* 102:88-101, 2016b). As can be appreciated by those skilled in the art, a variety of other means can be used to perform the unit operation of inactivating viruses.

For example, UV irradiation (e.g., using UV-C light) of a fluid containing recombinant therapeutic protein can also be used to perform the unit operation of inactivating viruses (see, e.g., Lorenz et al., *Biotechnol. Prog.* 25(2):476-482, 2009; Caillet-Fauquet et al., *J. Virol. Methods* 118(2):131-139, 2004; Gunn et al., U.S. Pat. No. 6,586,172, 2003; Kaiser et al., U.S. Pat. No. 7,695,675, 2002; Bae et al., *Kor. J. Microbiol. Biotechnol.* 4:377-382, 2009; Li et al., *Biologicals* 33(2):101-110, 2005; and Wang et al., *Vox Sang.* 86(4):230-238, 2004). Non-limiting examples of reservoirs that can be used to perform the unit operation of inactivation of viruses present in a fluid containing the recombinant therapeutic protein are described herein.

The first MCCS can include a PCCS containing four chromatography columns, where at least three of the four chromatography columns perform the unit operation of capturing the recombinant therapeutic protein from the liquid culture medium (e.g., using a first MCCS that includes any of the at least one chromatography columns that contain a resin that is capable of performing the unit operation of capturing (e.g., any of those described herein)). In these examples, the fourth-column of the PCC can perform the unit operation of inactivating viruses in a fluid that contains the recombinant therapeutic protein (e.g., any of the exemplary columns described herein that can be used to achieve viral inactivation of a fluid containing the recombinant therapeutic protein).

A fluid containing the recombinant therapeutic protein is continuously eluted from the first MCCS (e.g., the first PCC system), and is continuously fed into the second MCCS. The percent of the recombinant therapeutic protein recovered in the eluate of the first MCCS (e.g., the first PCC system) can be, e.g., at least 70%, at least 72%, at least 74%, at least 76%, at least 78%, at least 80%, at least 82%, at least 84%, at least 86%, at least 88%, at least 90%, at least 92%, at least 94%, at least 96%, or at least 98%). The eluate from the first MCCS (e.g., the first PCC system) can be fed into the second MCCS (e.g., second PCC system) using a variety of means known in the art (e.g., tubing). The eluate of the first MCCS (e.g., first PCC system) can be fed into the second MCCS (e.g., second PCC system) at a flow rate of, e.g., between about 0.2 mL/minute to about 100 L/minute (inclusive) (e.g., any of the subranges of this flow rate range described herein).

Some processes described herein can further include a step of adjusting the ionic concentration and/or pH of the eluate from the first MCCS (e.g., first PCC system) before it is fed into the second MCCS (e.g., second PCC system). As described herein, the ionic concentration and/or pH of the eluate from the first MCCS (e.g., first PCC system) can be adjusted (before it is fed into the second MCCS) by adding a buffer to the eluate (e.g., through the use of an in-line buffer adjustment reservoir). The buffer can be added to the eluate from the first MCCS at a flow rate of, e.g., between about 0.2 mL/minute to about 100 L/minute (inclusive) (e.g., any of the subranges of this flow rate range described herein).

The processes described herein can further include a step of holding or storing (and optionally also refrigerating) the eluate from the first MCCS prior to feeding the eluate from the first MCCS into the second MCCS. As described herein, this holding or storing step can be performed using any of the reservoirs (e.g., back-up tanks) described herein.

The processes described herein can also include a step of filtering the eluate from the first MCCS before the eluate is fed into the second MCCS. Any of the exemplary filters or methods for filtration described herein can be used to filter the eluate from the first MCCS before the eluate is fed into the second MCCS.

Polishing and Purifying the Recombinant Therapeutic Protein

The processes described herein include a step of purifying and polishing the recombinant therapeutic protein using a second MCCS, where the eluate from the MCC2 is a therapeutic protein drug substance. The second MCCS can include at least one (e.g., two, three, or four) chromatography column or chromatographic membrane that can be used to perform the unit operation of purifying a recombinant therapeutic protein, and at least one (e.g., two, three, or four) chromatography column or chromatographic membrane that can be used to perform the unit operation of polishing the recombinant therapeutic protein.

The at least one chromatography column or chromatographic membrane that can be used to perform the unit operation of purifying the recombinant therapeutic protein can contain a resin that utilizes a capture mechanism (e.g., any of the capture mechanisms described herein or known in the art), or a resin that can be used to perform anion exchange, cation exchange, or molecular sieve chromatography. The at least one chromatography column or chromatographic membrane that can be used to perform the unit of operation of polishing the recombinant therapeutic protein can contain a resin can be used to perform anion exchange, cation exchange, or molecular sieve chromatography (e.g., any of the exemplary resins for performing anion exchange, cation exchange, or molecular sieve chromatography described herein or known in the art).

The size, shape, and volume of the at least one chromatography column or chromatography membrane that can be used to perform the unit of operation of purifying the recombinant therapeutic protein, and/or the size and shape of the at least one chromatographic membrane that can be used to perform the unit of operation of polishing the recombinant membrane can any of combination of the exemplary sizes, shapes, and volumes of chromatography columns or chromatographic membranes described herein. As can be appreciated by one skilled in the art, the step of purifying or polishing a recombinant therapeutic protein can, e.g., include the steps of loading, washing, eluting, and equilibrating the at least one chromatography column or chromatographic membrane used to perform the unit of operation of purifying or polishing the recombinant therapeutic protein. Typically, the elution buffer coming out of a chromatography column or chromatographic membrane used to perform the unit operation of purifying contains the recombinant therapeutic protein. Typically, the loading and/or wash buffer coming out of a chromatography column or chromatographic membrane used to perform the unit operation of polishing contains the recombinant therapeutic protein.

For example, the size of the at least one chromatography column or chromatographic membrane that can be used to perform unit operation of purifying the recombinant therapeutic protein can have a volume of, e.g., between about 2.0 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, about 15 mL, about 10 mL, or about 5.0 mL (inclusive); between about 5.0 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, about 15 mL, or about 10 mL (inclusive); between about 10 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, or about 15 mL (inclusive); between about 15 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, about 25 mL, or about 20 mL (inclusive); between about 20 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, about 30 mL, or about 25 mL (inclusive);

between about 25 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, about 35 mL, or about 30 mL (inclusive); between about 30 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, about 40 mL, or about 35 mL (inclusive); between about 35 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, about 45 mL, or about 40 mL (inclusive); between about 40 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, about 50 mL, or about 45 mL (inclusive); between about 45 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, about 55 mL, or about 50 mL (inclusive); between about 50 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, about 60 mL, or about 55 mL (inclusive); between about 55 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, about 65 mL, or about 60 mL (inclusive); between about 60 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, about 70 mL, or about 65 mL (inclusive); between about 65 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, about 75 mL, or about 70 mL (inclusive); between about 70 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, about 80 mL, or about 75 mL (inclusive);

between about 75 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, about 85 mL, or about 80 mL (inclusive); between about 80 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, about 90 mL, or about 85 mL (inclusive); between about 85 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, about 95 mL, or about 90 mL (inclusive); between about 90 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, about 100 mL, or about 95 mL (inclusive); between about 95 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, about 120 mL, or about 100 mL (inclusive); between about 100 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, about 140 mL, or about 120 mL (inclusive); between about 120 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, about 160 mL, or about 140 mL (inclusive); between about 140 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, about 180 mL, or about 160 mL (inclusive); between about 160 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, about 200 mL, or about 180 mL (inclusive); between about 180 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, about 250 mL, or about 200 mL (inclusive); between about 200 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, about 300 mL, or about 250 mL (inclusive); between about 250 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, about 350 mL, or about 300 mL (inclusive); between about 300 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35

L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, about 400 mL, or about 350 mL (inclusive); between about 350 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, about 450 mL, or about 400 mL (inclusive); between about 400 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, about 500 mL, or about 450 mL (inclusive); between about 450 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, about 550 mL, or about 500 mL (inclusive); between about 500 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, about 600 mL, or about 550 mL (inclusive); between about 550 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, about 650 mL, or about 600 mL (inclusive); between about 600 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, about 700 mL, or about 650 mL; between about 650 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, about 750 mL, or about 700 mL (inclusive); between about 700 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, about 800 mL, or about 750 mL (inclusive); between about 750 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, about 850 mL, or about 800 mL (inclusive); between about 800 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, about 900 mL, or about 850 mL (inclusive); between about 850 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, about 950 mL, or about 900 mL (inclusive); between about 900 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, about 1 L, or about 950 mL (inclusive); between about 950 mL to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, about 5 L, or about 1 L (inclusive); between about 1 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, about 10 L, or about 5 L (inclusive); between about 5 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, about 15 L, or about 10 L (inclusive); between about 10 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, about 20 L, or about 15 L (inclusive); between about 15 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, about 25 L, or about 20 L (inclusive); between about 20 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, about 30 L, or about 25 L (inclusive); between about 25 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, about 40 L, about 35 L, or about 30 L (inclusive); between about 30 L to 200 L, about 180 L, about 160 L, about 140

L, about 120 L, about 100 L, about 95 L, about 90 L, about 85 L, about 80 L, about 75 L, about 70 L, about 65 L, about 60 L, about 55 L, about 50 L, about 45 L, about 40 L, or about 35 L (inclusive); between about 35 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, about 45 L, or about 40 L (inclusive); between about 40 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, about 50 L, or about 45 L (inclusive); between about 45 L to 200 L, about 180 L, about 160 L, about 140 L, about 120 L, about 100 L, about 95 L, about 90 L, about 85 L, about 80 L, about 75 L, about 70 L, about 65 L, about 60 L, about 55 L, or about 50 L (inclusive); between about 50 L to 200 L, about 180 L, about 160 L, about 140 L, about 120 L, about 100 L, about 95 L, about 90 L, about 85 L, about 80 L, about 75 L, about 70 L, about 65 L, about 60 L, or about 55 L (inclusive); between about 55 L to 200 L, about 180 L, about 160 L, about 140 L, about 120 L, about 100 L, about 95 L, about 90 L, about 85 L, about 80 L, about 75 L, about 70 L, about 65 L, or about 60 L (inclusive); between about 60 L to 200 L, about 180 L, about 160 L, about 140 L, about 120 L, about 100 L, about 95 L, about 90 L, about 85 L, about 80 L, about 75 L, about 70 L, or about 65 L (inclusive); between about 65 L to 200 L, about 180 L, about 160 L, about 140 L, about 120 L, about 100 L, about 95 L, about 90 L, about 85 L, about 80 L, about 75 L, or about 70 L (inclusive); between about 70 L to 200 L, about 180 L, about 160 L, about 140 L, about 120 L, about 100 L, about 95 L, about 90 L, about 85 L, about 80 L, or about 75 L (inclusive); between about 75 L to 200 L, about 180 L, about 160 L, about 140 L, about 120 L, about 100 L, about 95 L, about 90 L, about 85 L, or about 80 L (inclusive); between about 80 L to 200 L, about 180 L, about 160 L, about 140 L, about 120 L, about 100 L, about 95 L, about 90 L, or about 85 L (inclusive); between about 85 L to 200 L, about 180 L, about 160 L, about 140 L, about 120 L, about 100 L, about 95 L, or about 90 L (inclusive); between about 90 L to 200 L, about 180 L, about 160 L, about 140 L, about 120 L, about 100 L, or about 95 L (inclusive); between about 95 L to 200 L, about 180 L, about 160 L, about 140 L, about 120 L, or about 100 L (inclusive); between about 100 L to 200 L, about 180 L, about 160 L, about 140 L, or about 120 L (inclusive); between about 120 L to 200 L, about 180 L, about 160 L, or about 140 L (inclusive); between about 140 L to 200 L, about 180 L, or about 160 L (inclusive); between about 160 L to about 200 L or about 180 L (inclusive); or between about 180 L to about 200 L (inclusive).

The flow rate of the fluid containing the recombinant therapeutic protein as it is loaded onto the at least one chromatography column or at least one chromatographic that can be used to perform the unit operation of purifying the recombinant therapeutic protein can be, e.g., between about 0.1 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, about 10.0 mL/minute, about 8.0 mL/minute, about 6 mL/minute, about 4 mL/minute, about 3 mL/minute, about 2 mL/minute, about 1 mL/minute, or about 0.5 mL/minute (inclusive); between about 0.5 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, about 8.0 mL/minute, about 10.0 mL/minute, about 8.0 mL/minute, about 6 mL/minute, about 4 mL/minute, about 3 mL/minute, about 2 mL/minute, or about 1 mL/minute (inclusive); between about 1 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, about 10.0 mL/minute, about 8.0 mL/minute, about 6 mL/minute, about 4 mL/minute, about 3 mL/minute, or about 2 mL/minute (inclusive); between about 2 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, about 10.0 mL/minute, about 8.0 mL/minute, about 6 mL/minute, about 4 mL/minute, or about 3 mL/minute (inclusive); between about 3 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, about 10.0 mL/minute, about 8.0 mL/minute, about 6 mL/minute, or about 4 mL/minute (inclusive); between about 4 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, about 10.0 mL/minute, about 8.0 mL/minute, or about 6 mL/minute (inclusive); between about 6 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, about 10.0 mL/minute, or about 8.0 mL/minute (inclusive); between about 8 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, about 12.5 mL/minute, or about 10.0 mL/minute (inclusive); between about 10 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 25 mL/minute, or about 12.5 mL/minute (inclusive); between about 12.5 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, or about 25 mL/minute (inclusive); between about 25 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, or about 100 mL/minute (inclusive); between about 100 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, or about 200 mL/minute (inclusive); between about 200 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, or about 400 mL/minute (inclusive); between about 400 mL/minute to about 100 L/minute, about 80 L/minute, about 60 L/minute, about 40 L/minute, about 20 L/minute, about 10 L/minute, about 5 L/minute, about 1 L/minute, about 800 mL/minute, or about 600 mL/minute (inclusive); between about 600 mL/minute to about 100 L/minute, about 80 L/minute, about 60 L/minute, about 40 L/minute, about 20 L/minute, about 10 L/minute, about 5 L/minute, about 1 L/minute, or about 800 mL/minute (inclusive); between about 800 mL/minute to about 100 L/minute, about 80 L/minute, about 60 L/minute, about 40 L/minute, about 20 L/minute, about 10 L/minute, about 5 L/minute, or about 1 L/minute (inclusive); between about 1 L/minute to about 100 L/minute, about 80 L/minute, about 60 L/minute, about 40 L/minute, about 20 L/minute, about 10 L/minute, or about 5 L/minute (inclusive); between about 5 L/minute to about 100 L/minute, about 80 L/minute, about 60 L/minute, about 40 L/minute, about 20 L/minute, or about 10 L/minute (inclusive); between about 10 L/minute to about 100 L/minute, about 80 L/minute, about 60 L/minute, about 40 L/minute, or about 20 L/minute (inclusive); between about 20 L/minute to about 100 L/minute, about 80 L/minute, about 60 L/minute, or about 40 L/minute (inclusive); between about 40 L/minute to about 100 L/minute, about 80 L/minute, or about 60 L/minute (inclusive); between about 60 L/minute to 100 L/minute or about 80 L/minute (inclusive); or between about 80 L/minute to about 100 L/minute (inclusive)

The concentration of the recombinant therapeutic protein in the fluid loaded onto the at least one chromatography column or chromatographic membrane that can be used to perform the unit operation of purifying the recombinant therapeutic protein can be, e.g., between about 0.05 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, or between about 0.5 mg/mL to about 10 mg/mL recombinant therapeutic protein). The resin in the at least one chromatography column or chromatographic membrane used to perform unit operation of purifying can be a resin that can be used to perform anion exchange or cation exchange chromatography. The resin in the at least one chromatography column or chromatographic membrane that is used to perform the unit operation of purifying can be a cationic exchange resin (e.g., Capto-S resin, GE Healthcare Life Sciences, Piscataway, NJ).

Following the loading of the recombinant therapeutic protein onto the at least one chromatographic column or chromatographic membrane in the second MCCS that can be used to perform the unit operation of purifying the recombinant therapeutic protein, the at least one chromatographic column or chromatographic membrane is washed with at least one washing buffer. As can be appreciated in the art, the at least one (e.g., two, three, or four) washing buffer is meant to elute all proteins that are not the recombinant therapeutic protein from the at least one chromatography column or chromatographic membrane, while not disturbing the interaction of the recombinant therapeutic protein with the resin or otherwise eluting the recombinant therapeutic protein.

The wash buffer can be passed through the at least one chromatography column or chromatographic membrane at a flow rate of, e.g., between about 0.2 mL/minute to about 100 L/minute (inclusive) (e.g., any of the subranges of this flow rate range described herein). The volume of wash buffer used (e.g., combined total volume of wash buffer used when more than one wash buffer is used) can be, e.g., between about 1× column volume (CV) to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, about 4×CV, or about 3×CV (inclusive); between about 2×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, or about 4×CV (inclusive); between about 3×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 5×CV (inclusive); between about 4×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 6×CV (inclusive); between about 5×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, or about 7×CV (inclusive); between about 6×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, or about 8×CV (inclusive); between about 7×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, or about 9×CV (inclusive); between about 8×CV to about 30×CV, about 28×CV, about 26×CV, about 24×CV, about 22×CV, about 20×CV, about 18×CV, about 16×CV, about 14×CV, about 13×CV, about 12×CV, about 11×CV, or about 10×CV (inclusive); between about 9 CV to about 30×CV, about 28×CV, about 26×CV, about 24×CV, about 22×CV, about 20×CV, about 18×CV, about 16×CV, about 14×CV, about 13×CV, about 12×CV, or about 11×CV (inclusive); between about 10×CV to about 30×CV, about 28×CV, about 26×CV, about 24×CV, about 22×CV, about 20×CV, about 18×CV, about 16×CV, about 14×CV, about 13×CV, or about 12×CV (inclusive); between about 11×CV to about 30×CV, about 28×CV, about 26×CV, about 24×CV, about 22×CV, about 20×CV, about 18×CV, about 16×CV, about 14×CV, or about 13×CV (inclusive); between about 12×CV to about 30×CV, about 28×CV, about 26×CV, about 24×CV, about 22×CV, about 20×CV, about 18×CV, about 16×CV, or about 14×CV (inclusive); between about 14×CV to about 30×CV, about 28×CV, about 26×CV, about 24×CV, about 22×CV, about 20×CV, about 18×CV, or about 16×CV (inclusive); between about 16×CV to about 30×CV, about 28×CV, about 26×CV, about 24×CV, about 22×CV, about 20×CV, or about 18×CV (inclusive); between about 18×CV to about 30×CV, about 28×CV, about 26×CV, about 24×CV, about 22×CV, or about 20×CV (inclusive); between about 20×CV to about 30×CV, about 28×CV, about 26×CV, about 24×CV, or about 22×CV (inclusive); between about 22×CV to about 30×CV, about 28×CV, about 26×CV, or about 24×CV (inclusive); between about 24×CV to about 30×CV, about 28×CV, or about 26×CV (inclusive); between about 26×CV to about 30×CV or about 28×CV (inclusive); or between about 28×CV to about 30×CV (inclusive). The total time of the washing can be, e.g., between about 2 minutes to about 48 hours, about 40 hours, about 36 hours, about 32 hours, about 28 hours, about 24 hours, about 20 hours, about 16 hours, about 12 hours, about 8 hours, about 4 hours, about 2.5 hours, about 2.0 hours, about 1.5 hours, about 1.25 hours, about 1 hour, about 30 minutes, about 20 minutes, about 10 minutes, or about 5 minutes (inclusive); between about 5 minutes to about 48 hours, about 40 hours, about 36 hours, about 32 hours, about 28 hours, about 24 hours, about 20 hours, about 16 hours, about 12 hours, about 8 hours, about 4 hours, about 2.5 hours, about 2.0 hours, about 1.5 hours, about 1.25 hours, about 1 hour, about 30 minutes, about 20 minutes, or about 10 minutes (inclusive); between about 10 minutes to about 48 hours, about 40 hours, about 36 hours, about 32 hours, about 28 hours, about 24 hours, about 20 hours, about 16 hours, about 12 hours, about 8 hours, about 4 hours, about 2.5 hours, about 2.0 hours, about 1.5 hours, about 1.25 hours, about 1 hour, about 30 minutes, or about 20 minutes (inclusive); between about 20 minutes to about 48 hours, about 40 hours, about 36 hours, about 32 hours, about 28 hours, about 24 hours, about 20 hours, about 16 hours, about 12 hours, about 8 hours, about 4 hours, about 2.5 hours, about 2.0 hours, about 1.5 hours, about 1.25 hours, about 1 hour, or about 30 minutes (inclusive); between about 30 minutes to about 48 hours, about 40 hours, about 36 hours, about 32 hours, about 28 hours, about 24 hours, about 20 hours, about 16 hours, about 12 hours, about 8 hours, about 4 hours, about 2.5 hours, about 2.0 hours, about 1.5 hours, about 1.25 hours, or about 1 hour (inclusive); between about 1 hour to about 48 hours, about 40 hours, about 36 hours, about 32 hours, about 28 hours, about 24 hours, about 20 hours, about 16 hours, about 12 hours, about 8 hours, about 4 hours, about 2.5 hours, about 2.0 hours, about 1.5 hours, or about 1.25 hours (inclusive); between about 1.25 hours to about 48 hours, about 40 hours, about 36 hours, about 32 hours, about 28 hours, about 24 hours, about 20 hours, about 16 hours, about 12 hours, about 8 hours, about 4 hours, about 2.5 hours, about 2.0 hours, or about 1.5 hours (inclusive); between about 1.5 hours to about 48 hours, about 40 hours, about 36 hours, about 32 hours, about 28 hours, about 24 hours, about 20 hours, about 16 hours, about 12 hours, about 8 hours, about 4 hours, about 2.5 hours, or about 2.0 hours (inclusive); between about 2.0 hours to about 48 hours, about 40 hours, about 36 hours, about 32 hours, about 28 hours, about 24 hours, about 20 hours, about 16 hours, about 12 hours, about 8 hours, about 4 hours, or about 2.5 hours (inclusive); between about 2.5 hours to about 48 hours, about 40 hours, about 36 hours, about 32 hours, about 28 hours, about 24 hours, about 20 hours, about 16 hours, about 12 hours, about 8 hours, or about 4 hours (inclusive); between about 4 hours to about 48 hours, about 40 hours, about 36 hours, about 32 hours, about 28 hours, about 24 hours, about 20 hours, about 16 hours, about 12 hours, or about 8 hours (inclusive); between about 8 hours to about 48 hours, about 40 hours, about 36 hours, about 32 hours, about 28 hours, about 24 hours, about 20 hours, about 16 hours, or about 12 hours (inclusive); between about 12 hours to about 48 hours, about 40 hours, about 36 hours, about 32 hours, about 28 hours, about 24 hours, about 20 hours, or about 16 hours (inclusive); between about 16 hours to about 48 hours, about 40 hours, about 36 hours, about 32 hours, about 28 hours, about 24 hours, or about 20 hours (inclusive); between about 20 hours to about 48 hours, about 40 hours, about 36 hours, about 32 hours, about 28 hours, or about 24 hours (inclusive); between about 24 hours to about 48 hours, about 40 hours, about 36 hours, about 32 hours, or about 28 hours (inclusive); between about 28 hours to about 48 hours, about 40 hours, about 36 hours, or about 32 hours (inclusive); between about 32 hours to about 48 hours, about 40 hours, or about 36 hours (inclusive); between about 36 hours to about 48 hours or about 40 hours (inclusive); or between about 40 hours to about 48 hours (inclusive).

Following the washing of the at least one chromatographic column or chromatographic membrane in the second MCCS that can be used to perform the unit operation of purifying the recombinant therapeutic protein, the recombinant therapeutic protein is eluted from the at least one chromatographic column or chromatographic membrane by passing an elution buffer through the at least one chromatographic column or chromatographic membrane in the second MCCS that can be used to perform the unit operation of purifying the recombinant therapeutic protein. The elution buffer can be passed through the at least one chromatography column or chromatographic membrane that can be used to perform the unit operation of purifying the recombinant therapeutic protein at a flow rate of, e.g., between about 0.2 mL/minute to about 100 L/minute (inclusive) (e.g., any of the subranges of this flow rate range described herein). The volume of elution buffer used to elute the recombinant therapeutic protein from each the at least one chromatographic column or chromatographic membrane that can be used to perform the unit operation of purifying the recombinant therapeutic protein can be, e.g., between about 1× column volume (CV) to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, about 4×CV, or about 3×CV (inclusive); between about 2×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, or about 4×CV (inclusive); between about 3×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 5×CV (inclusive); between about 4×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 6×CV (inclusive); between about 5×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, or about 7×CV (inclusive); between about 6×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, or about 8×CV (inclusive); between about 7×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, or about 9×CV (inclusive); between about 8×CV to about 30×CV, about 28×CV, about 26×CV, about 24×CV, about 22×CV, about 20×CV, about 18×CV, about 16×CV, about 14×CV, about 13×CV, about 12×CV, about 11×CV, or about 10×CV (inclusive); between about 9 CV to about 30×CV, about 28×CV, about 26×CV, about 24×CV, about 22×CV, about 20×CV, about 18×CV, about 16×CV, about 14×CV, about 13×CV, about 12×CV, or about 11×CV (inclusive); between about 10×CV to about 30×CV, about 28×CV, about 26×CV, about 24×CV, about 22×CV, about 20×CV, about 18×CV, about 16×CV, about 14×CV, about 13×CV, or about 12×CV (inclusive); between about 11×CV to about 30×CV, about 28×CV, about 26×CV, about 24×CV, about 22×CV, about 20×CV, about 18×CV, about 16×CV, about 14×CV, or about 13×CV (inclusive); between about 12×CV to about 30×CV, about 28×CV, about 26×CV, about 24×CV, about 22×CV, about 20×CV, about 18×CV, about 16×CV, or about 14×CV (inclusive); between about 14×CV to about 30×CV, about 28×CV, about 26×CV, about 24×CV, about 22×CV, about 20×CV, about 18×CV, or about 16×CV (inclusive); between about 16×CV to about 30×CV, about 28×CV, about 26×CV, about 24×CV, about 22×CV, about 20×CV, or about 18×CV (inclusive); between about 18×CV to about 30×CV, about 28×CV, about 26×CV, about 24×CV, about 22×CV, or about 20×CV (inclusive); between about 20×CV to about 30×CV, about 28×CV, about 26×CV, about 24×CV, or about 22×CV (inclusive); between about 22×CV to about 30×CV, about 28×CV, about 26×CV, or about 24×CV (inclusive); between about 24×CV to about 30×CV, about 28×CV, or about 26×CV (inclusive); between about 26×CV to about 30×CV or about 28×CV (inclusive); or between about 28×CV to about 30×CV (inclusive). The total time of the eluting can be, e.g., between about 2 minutes to about 3 hours (e.g., between about 2 minutes to about 2.5 hours, between about 2 minutes to about 2.0 hours, between about 2 minutes to about 1.5 hours, between about 2 minutes to about 1.5 hours, between about 2 minutes to about 1.25 hours, between about 2 minutes to about 1.25 hours, between about 2 minutes to about 1 hour, between about 2 minutes and about 40 minutes, between about 10 minutes and about 40 minutes, between about 20 minutes and about 40 minutes, or between about 30 minutes and 1.0 hour). Non-limiting examples of elution buffers that can be used in these methods will depend on the resin and/or the therapeutic protein. For example, an elution buffer can contain a different concentration of salt (e.g., increased salt concentration), a different pH (e.g., an increased or decreased salt concentration), or a molecule that will compete with the recombinant therapeutic protein for binding to the resin. Examples of such elution buffers for each of the exemplary capture mechanisms described herein are well known in the art.

Following the elution of the recombinant therapeutic protein from the at least one chromatographic column or chromatographic membrane in the second MCCS that can be used to perform the unit operation of purifying the recombinant therapeutic protein, and before the next volume of fluid containing a recombinant therapeutic protein can be loaded onto the at least one chromatographic column or chromatographic membrane, the at least one chromatography column or chromatographic membrane must be equilibrated using an regeneration buffer. The regeneration buffer can be passed through the at least one chromatography column or chromatographic membrane that can be used to perform the unit operation of purifying the recombinant therapeutic protein at a flow rate of, e.g., between about 0.2 mL/minute to about 100 L/minute (inclusive) (e.g., any of the subranges of this flow rate range described herein). The volume of regeneration buffer used to equilibrate the at least one chromatography column or chromatographic membrane that contains a resin that can be used to perform the unit operation of purifying the recombinant therapeutic protein can be, e.g., between about 1× column volume (CV) to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, about 4×CV, or about 3×CV (inclusive); between about 2×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, about 6×CV, about 5×CV, or about 4×CV (inclusive); between about 3×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 5×CV (inclusive); between about 4×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, about 7×CV, or about 6×CV (inclusive); between about 5×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, about 8×CV, or about 7×CV (inclusive); between about 6×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, about 9×CV, or about 8×CV (inclusive); between about 7×CV to about 30×CV, about 28×CV, about 26×CV, about 24×CV, about 22×CV, about 20×CV, about 18×CV, about 16×CV, about 14×CV, about 13×CV, about 12×CV, about 11×CV, about 10×CV, or about 9×CV (inclusive); between about 8×CV to about 30×CV, about 28×CV, about 26×CV, about 24×CV, about 22×CV, about 20×CV, about 18×CV, about 16×CV, about 14×CV, about 13×CV, about 12×CV, about 11×CV, or about 10×CV (inclusive); between about 9 CV to about 30×CV, about 28×CV, about 26×CV, about 24×CV, about 22×CV, about 20×CV, about 18×CV, about 16×CV, about 14×CV, about 13×CV, about 12×CV, or about 11×CV (inclusive); between about 10×CV to about 30×CV, about 28×CV, about 26×CV, about 24×CV, about 22×CV, about 20×CV, about 18×CV, about 16×CV, about 14×CV, about 13×CV, or about 12×CV (inclusive); between about 11×CV to about 30×CV, about 28×CV, about 26×CV, about 24×CV, about 22×CV, about 20×CV, about 18×CV, about 16×CV, about 14×CV, or about 13×CV (inclusive); between about 12×CV to about 30×CV, about 28×CV, about 26×CV, about 24×CV, about 22×CV, about 20×CV, about 18×CV, about 16×CV, or about 14×CV (inclusive); between about 14×CV to about 30×CV, about 28×CV, about 26×CV, about 24×CV, about 22×CV, about 20×CV, about 18×CV, or about 16×CV (inclusive); between about 16×CV to about 30×CV, about 28×CV, about 26×CV, about 24×CV, about 22×CV, about 20×CV, or about 18×CV (inclusive); between about 18×CV to about 30×CV, about 28×CV, about 26×CV, about 24×CV, about 22×CV, or about 20×CV (inclusive); between about 20×CV to about 30×CV, about 28×CV, about 26×CV, about 24×CV, or about 22×CV (inclusive); between about 22×CV to about 30×CV, about 28×CV, about 26×CV, or about 24×CV (inclusive); between about 24×CV to about 30×CV, about 28×CV, or about 26×CV (inclusive); between about 26×CV to about 30×CV or about 28×CV (inclusive); or between about 28×CV to about 30×CV (inclusive). The concentration of recombinant therapeutic protein in the eluate of the at least one chromatography column or chromatographic membrane that can be used to perform the unit operation of purifying the recombinant therapeutic protein can be, e.g., between about 0.05 mg/mL to about 100 mg/mL recombinant therapeutic protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 2.5 mg/mL and about 7.5 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, between about 0.5 mg/mL to about 10 mg/mL, between about 10 mg/mL to about 200 mg/mL, between about 10 mg/mL to about 150 mg/mL, between about 10 mg/mL to about 100 mg/mL, between about 10 mg/mL to about 50 mg/mL, between about 50 mg/mL to about 200 mg/mL, between about 50 mg/mL to about 150 mg/mL, between about 50 mg/mL to about 100 mg/mL, between about 100 mg/mL to about 200 mg/mL, between about 100 mg/mL to about 150 mg/mL, or about 150 mg/mL to about 200 mg/mL recombinant therapeutic protein).

The at least one chromatography column or chromatographic membrane that can be used to perform the unit operation of polishing the recombinant therapeutic protein can contain a resin that can be used to perform cation exchange, anion exchange, or molecular sieve chromatography. As can be appreciated in the art, polishing a recombinant therapeutic protein using the at least one chromatography column or chromatography membrane that can be used to perform the unit operation of polishing the recombinant therapeutic protein in the second MCCS can include, e.g., the steps of loading, chasing, and regenerating the at least one chromatography column or chromatographic membrane that can be used to perform the unit operation of polishing the recombinant therapeutic protein. For example, when the steps of loading, chasing, and regenerating are used to perform the polishing, the recombinant therapeutic protein does not bind the resin in the at least one chromatography column or chromatography membrane in the second MCCS that is used to perform the unit operation of polishing the recombinant therapeutic protein, and the recombinant therapeutic protein is eluted from the at least one chromatography column or chromatographic membrane in the loading and chasing steps, and the regenerating step is used to remove any impurities from the at least one chromatography column or chromatographic membrane before additional fluid containing the recombinant therapeutic protein can be loaded onto the at least one chromatography column or chromatographic membrane. Exemplary flow rates and buffer volumes to be used in each of the loading, chasing, and regenerating steps are described below.

The size, shape, and volume of the at least one chromatography column or chromatography membrane that can be used to perform the unit operation of polishing the recombinant therapeutic protein, and/or the size and shape of the at least one chromatographic membrane that can be used to perform the unit operation of polishing the recombinant therapeutic protein can any of combination of the exemplary sizes, shapes, and volumes of chromatography columns or chromatographic membranes described herein. For example, the size of the at least one chromatography column or chromatographic membrane that can be used to perform the unit operation of polishing the recombinant therapeutic protein can have a volume of, e.g., between about 0.5 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, about 80 mL, about 60 mL, about 40 mL, about 30 mL, about 20 mL, about 10 mL, about 5 mL, or about 2.5 mL (inclusive); between about 2.5 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, about 80 mL, about 60 mL, about 40 mL, about 30 mL, about 20 mL, about 10 mL, or about 5 mL (inclusive); between about 5 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, about 80 mL, about 60 mL, about 40 mL, about 30 mL, about 20 mL, or about 10 mL (inclusive); between about 10 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, about 80 mL, about 60 mL, about 40 mL, or about 20 mL (inclusive); between about 20 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, about 80 mL, about 60 mL, about 40 mL, or about 30 mL (inclusive); between about 30 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, about 80 mL, about 60 mL, or about 40 mL (inclusive); between about 40 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, about 80 mL, about 60 mL, or about 60 mL (inclusive); between about 60 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, about 100 mL, or about 80 mL (inclusive); between about 80 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, about 140 mL, about 120 mL, or about 100 mL (inclusive); between about 100 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, about 160 mL, or about 140 mL (inclusive); between about 140 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, about 180 mL, or about 160 mL (inclusive); between about 160 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, about 200 mL, or about 180 mL (inclusive); between about 180 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, about 400 mL, or about 200 mL (inclusive); between about 200 mL to about 200 L, about 180 L, about 160 L, about 140 L, about 120 L, about 100 L, about 80 L, about 60 L, about 40 L, about 20 L, about 10 L, about 1 L, about 800 mL, about 600 mL, or about 400 mL (inclusive); between about 400 mL to about 200 L, about 180 L, about 160 L, about 140 L, about 120 L, about 100 L, about 80 L, about 60 L, about 40 L, about 20 L, about 10 L, about 1 L, about 800 mL, or about 600 mL (inclusive); between about 600 mL to about 200 L, about 180 L, about 160 L, about 140 L, about 120 L, about 100 L, about 80 L, about 60 L, about 40 L, about 20 L, about 10 L, about 1 L, or about 800 mL (inclusive); between about 800 mL to about 200 L, about 180 L, about 160 L, about 140 L, about 120 L, about 100 L, about 80 L, about 60 L, about 40 L, about 20 L, about 10 L, or about 1 L (inclusive); between about 1 L to about 200 L, about 180 L, about 160 L, about 140 L, about 120 L, about 100 L, about 80 L, about 60 L, about 40 L, about 20 L, or about 10 L (inclusive); between about 10 L to about 200 L, about 180 L, about 160 L, about 140 L, about 120 L, about 100 L, about 80 L, about 60 L, about 40 L, or about 20 L (inclusive); between about 20 L to about 200 L, about 180 L, about 160 L, about 140 L, about 120 L, about 100 L, about 80 L, about 60 L, or about 40 L (inclusive); between about 40 L to about 200 L, about 180 L, about 160 L, about 140 L, about 120 L, about 100 L, about 80 L, or about 60 L (inclusive); between about 60 L to about 200 L, about 180 L, about 160 L, about 140 L, about 120 L, about 100 L, or about 80 L (inclusive); between about 80 L to about 200 L, about 180 L, about 160 L, about 140 L, about 120 L, or about 100 L (inclusive); between about 100 L to about 200 L, about 180 L, about 160 L, about 140 L, or about 120 L (inclusive); between about 120 L to about 200 L, about 180 L, about 160 L, or about 140 L (inclusive); between about 140 L to about 200 L, about 180 L, or about 160 L (inclusive); between about 160 L to about 200 L or about 180 L (inclusive); or between about 180 L to about 200 L (inclusive). The flow rate of the fluid containing the recombinant therapeutic protein as it is loaded onto the at least one chromatography column or chromatographic membrane that can be used to perform the unit operation of polishing the recombinant therapeutic protein can be, e.g., between about 0.1 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, about 10.0 mL/minute, about 8.0 mL/minute, about 6 mL/minute, about 4 mL/minute, about 3 mL/minute, about 2 mL/minute, about 1 mL/minute, about 0.5 mL/minute, or about 0.2 mL/minute (inclusive); between about 0.2 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, about 10.0 mL/minute, about 8.0 mL/minute, about 6 mL/minute, about 4 mL/minute, about 3 mL/minute, about 2 mL/minute, or about 1 mL/minute (inclusive); between about 1 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, about 10.0 mL/minute, about 8.0 mL/minute, about 6 mL/minute, about 4 mL/minute, about 3 mL/minute, or about 2 mL/minute (inclusive); between about 2 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, about 10.0 mL/minute, about 8.0 mL/minute, about 6 mL/minute, about 4 mL/minute, or about 3 mL/minute (inclusive); between about 3 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, about 10.0 mL/minute, about 8.0 mL/minute, about 6 mL/minute, or about 4 mL/minute (inclusive); between about 4 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, about 10.0 mL/minute, about 8.0 mL/minute, or about 6 mL/minute (inclusive); between about 6 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, about 10.0 mL/minute, or about 8.0 mL/minute (inclusive); between about 8 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, about 12.5 mL/minute, or about 10.0 mL/minute (inclusive); between about 10 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, about 25 mL/minute, or about 12.5 mL/minute (inclusive); between about 12.5 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, about 50 mL/minute, or about 25 mL/minute (inclusive); between about 25 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, about 100 mL/minute, or about 50 mL/minute (inclusive); between about 50 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, about 200 mL/minute, or about 100 mL/minute (inclusive); between about 100 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, about 400 mL/minute, or about 200 mL/minute (inclusive); between about 200 mL/minute to about 100 L/minute, about 80 L/minute, about 60 L/minute, about 40 L/minute, about 20 L/minute, about 10 L/minute, about 5 L/minute, about 1 L/minute, about 800 mL/minute, about 600 mL/minute, or about 400 mL/minute (inclusive); between about 400 mL/minute to about 100 L/minute, about 80 L/minute, about 60 L/minute, about 40 L/minute, about 20 L/minute, about 10 L/minute, about 5 L/minute, about 1 L/minute, about 800 mL/minute, or about 600 mL/minute (inclusive); between about 600 mL/minute to about 100 L/minute, about 80 L/minute, about 60 L/minute, about 40 L/minute, about 20 L/minute, about 10 L/minute, about 5 L/minute, about 1 L/minute, or about 800 mL/minute (inclusive); between about 800 mL/minute to about 100 L/minute, about 80 L/minute, about 60 L/minute, about 40 L/minute, about 20 L/minute, about 10 L/minute, about 5 L/minute, or about 1 L/minute (inclusive); between about 1 L/minute to about 100 L/minute, about 80 L/minute, about 60 L/minute, about 40 L/minute, about 20 L/minute, about 10 L/minute, or about 5 L/minute (inclusive); between about 5 L/minute to about 100 L/minute, about 80 L/minute, about 60 L/minute, about 40 L/minute, about 20 L/minute, or about 10 L/minute (inclusive); between about 10 L/minute to about 100 L/minute, about 80 L/minute, about 60 L/minute, about 40 L/minute, or about 20 L/minute (inclusive); between about 20 L/minute to about 100 L/minute, about 80 L/minute, about 60 L/minute, or about 40 L/minute (inclusive); between about 40 L/minute to about 100 L/minute, about 80 L/minute, or about 60 L/minute (inclusive); between about 60 L/minute to about 100 L/minute or about 80 L/minute (inclusive); or between about 80 L/minute to about 100 L/minute (inclusive). The total volume of fluid containing a recombinant therapeutic protein loaded onto the at least one chromatography column or chromatographic membrane that can be used to perform the unit operation of polishing the recombinant therapeutic protein can be, e.g., between about 1.0 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, about 150 mL, about 125 mL, about 100 mL, about 75 mL, about 50 mL, about 25 mL, about 10 mL, or about 5 mL (inclusive); between about 5 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, about 150 mL, about 125 mL, about 100 mL, about 75 mL, about 50 mL, about 25 mL, or about 10 mL (inclusive); between about 10 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, about 150 mL, about 125 mL, about 100 mL, about 75 mL, about 50 mL, or about 25 mL (inclusive); between about 25 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, about 150 mL, about 125 mL, about 100 mL, about 75 mL, or about 50 mL (inclusive); between about 50 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, about 150 mL, about 125 mL, about 100 mL, or about 75 mL (inclusive); between about 75 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, about 150 mL, about 125 mL, or about 100 mL (inclusive); between about 100 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, about 150 mL, or about 125 mL (inclusive); between about 125 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, about 175 mL, or about 150 mL (inclusive); between about 150 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, about 200 mL, or about 175 mL (inclusive); between about 175 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, about 225 mL, or about 200 mL (inclusive); between about 200 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, about 250 mL, or about 225 mL (inclusive);

between about 225 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, about 400 mL, or about 250 mL (inclusive); between about 250 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, about 600 mL, or about 400 mL (inclusive); between about 400 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, about 800 mL, or about 600 mL (inclusive); between about 600 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, about 1 L, or about 800 mL (inclusive); between about 800 mL to about 1,000 L, about 900 L, about 800 L, about 700 L, about 600 L, about 500 L, about 400 L, about 300 L, about 200 L, about 100 L, about 50 L, about 25 L, about 10 L, about 5 L, or about 1 L (inclusive); between about 1 L to about 1,000 L, about 900 L, about 800 L, about 700 L, about 600 L, about 500 L, about 400 L, about 300 L, about 200 L, about 100 L, about 50 L, about 25 L, about 10 L, or about 5 L (inclusive); between about 5 L to about 1,000 L, about 900 L, about 800 L, about 700 L, about 600 L, about 500 L, about 400 L, about 300 L, about 200 L, about 100 L, about 50 L, about 25 L, or about 10 L (inclusive); between about 10 L to about 1,000 L, about 900 L, about 800 L, about 700 L, about 600 L, about 500 L, about 400 L, about 300 L, about 200 L, about 100 L, about 50 L, or about 25 L (inclusive); between about 25 L to about 1,000 L, about 900 L, about 800 L, about 700 L, about 600 L, about 500 L, about 400 L, about 300 L, about 200 L, about 100 L, or about 50 L (inclusive); between about 50 L to about 1,000 L, about 900 L, about 800 L, about 700 L, about 600 L, about 500 L, about 400 L, about 300 L, about 200 L, or about 100 L (inclusive); between about 100 L to about 1,000 L, about 900 L, about 800 L, about 700 L, about 600 L, about 500 L, about 400 L, about 300 L, or about 200 L (inclusive); between about 200 L to about 1,000 L, about 900 L, about 800 L, about 700 L, about 600 L, about 500 L, or about 400 L (inclusive); between about 400 L to about 1,000 L, about 900 L, about 800 L, about 700 L, about 600 L, or about 500 L (inclusive); between about 500 L to about 1,000 L, about 900 L, about 800 L, about 700 L, or about 600 L (inclusive); between about 600 L to about 1,000 L, about 900 L, about 800 L, or about 700 L (inclusive); between about 700 L to about 1,000 L, about 900 L, or about 800 L (inclusive); between about 800 L to about 1,000 L or about 900 L (inclusive); or about 900 L to about 1,000 L (inclusive). The resin in the at least one chromatography column or chromatographic membrane used to perform the polishing can be an anion exchange or cation exchange resin. The resin in the at least one chromatography column or chromatographic membrane that is used to perform the unit operation of polishing can be a cationic exchange resin (e.g., Sartobind® Q resin, Sartorius, Goettingen, Germany).

Following the loading step, the at least one chromatographic column or chromatographic membrane in the second MCCS that can be used to perform the unit operation of polishing the recombinant therapeutic protein, a chasing step is performed (e.g., a chase buffer is passed through the at least one chromatography membrane or chromatographic membrane to collect the recombinant therapeutic protein which does not substantially bind to the at least one chromatography column or chromatographic membrane). In these examples, the chase buffer can be passed through the at least one chromatography column or chromatographic membrane at a flow rate of, e.g., between about 0.2 mL/minute to about 100 L/minute (inclusive) (e.g., any of the subranges of this flow rate range described herein). The volume of chase buffer used can be, e.g., between about 1× column volume (CV) to about 100×CV (e.g., between about 1× CV to about 90×CV, between about 1× CV to about 80×CV, between about 1×CV to about 70×CV, between about 1× CV to about 60×CV, between about 1× to about 50×CV, between about 1× CV to about 40×CV, between about 1×CV to about 30×CV, between about 1× CV to about 20×CV, between about 1×CV to about 15×CV, between about 5×CV to about 20×CV, between about 5×CV to about 30×CV, between about 1× CV to about 14×CV, about 1×CV to about 13×CV, about 1×CV to about 12×CV, about 1× CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV). The total time of the chasing can be, e.g., between about 1 minute to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, about 1.5 hours, about 1.25 hours, about 1 hour, about 30 minutes, about 20 minutes, about 10 minutes, about 5 minutes, or about 2 minutes (inclusive); between about 2 minutes to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, about 1.5 hours, about 1.25 hours, about 1 hour, about 30 minutes, about 20 minutes, about 10 minutes, or about 5 minutes (inclusive); between about 5 minutes to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, about 1.5 hours, about 1.25 hours, about 1 hour, about 30 minutes, about 20 minutes, or about 10 minutes (inclusive); between about 10 minutes to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, about 1.5 hours, about 1.25 hours, about 1 hour, about 30 minutes, or about 20 minutes (inclusive); between about 20 minutes to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, about 1.5 hours, about 1.25 hours, about 1 hour, or about 30 minutes (inclusive); between about 30 minutes to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, about 1.5 hours, about 1.25 hours, or about 1 hour (inclusive); between about 1 hour to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, about 1.5 hours, or about 1.25 hours (inclusive); between about 1.25 hours to about 24 hours, about 22 hours, about 20 hours, about 18 hours, about 16 hours, about 14 hours, about 12 hours, about 10 hours, about 8 hours, about 6 hours, about 4 hours, about 3 hours, about 2 hours, or about 1.5 hours (inclusive); between about 1.5 hours to about 24 hours, about 22 hours, about 20 hours, about 18 hours, about 16 hours, about 14 hours, about 12 hours, about 10 hours, about 8 hours, about 6 hours, about 4 hours, about 3 hours, or about 2 hours (inclusive); between about 2 hours to about 24 hours, about 22 hours, about 20 hours, about 18 hours, about 16 hours, about 14 hours, about 12 hours, about 10 hours, about 8 hours, about 6 hours, about 4 hours, or about 3 hours (inclusive); between about 3 hours to about 24 hours, about 22 hours, about 20 hours, about 18 hours, about 16 hours, about 14 hours, about 12 hours, about 10 hours, about 8 hours, about 6 hours, or about 4 hours (inclusive); between about 4 hours to about 24 hours, about 22 hours, about 20 hours, about 18 hours, about 16 hours, about 14 hours, about 12 hours, about 10 hours, about 8 hours, or about 6 hours (inclusive); between about 6 hours to about 24 hours, about 22 hours, about 20 hours, about 18 hours, about 16 hours, about 14 hours, about 12 hours, about 10 hours, or about 8 hours (inclusive); between about 8 hours to about 24 hours, about 22 hours, about 20 hours, about 18 hours, about 16 hours, about 14 hours, about 12 hours, or about 10 hours (inclusive); between about 10 hours to about 24 hours, about 22 hours, about 20 hours, about 18 hours, about 16 hours, about 14 hours, or about 12 hours (inclusive); between about 12 hours to about 24 hours, about 22 hours, about 20 hours, about 18 hours, about 16 hours, or about 14 hours (inclusive); between about 14 hours to about 24 hours, about 22 hours, about 20 hours, about 18 hours, or about 16 hours (inclusive); between about 16 hours to about 24 hours, about 22 hours, about 20 hours, or about 18 hours (inclusive); between about 18 hours to about 24 hours, about 22 hours, or about 20 hours (inclusive); between about 20 hours to about 24 hours to about 22 hours (inclusive); or between about 22 hours to about 24 hours (inclusive). The combined concentration of therapeutic recombinant protein present in the eluate coming through the column in the loading step and the chasing step can be, e.g., between about 0.1 mg/mL to about 100 mg/mL recombinant protein (e.g., between about 0.1 mg/mL to about 90 mg/mL, between about 0.1 mg/mL to about 80 mg/mL, between about 0.1 mg/mL to about 70 mg/mL, between about 0.1 mg/mL to about 60 mg/mL, between about 0.1 mg/mL to about 50 mg/mL, between about 0.1 mg/mL to about 40 mg/mL, between about 2.5 mg/mL and about 7.5 mg/mL, between about 0.1 mg/mL to about 30 mg/mL, between about 0.1 mg/mL to about 20 mg/mL, between 0.5 mg/mL to about 20 mg/mL, between about 0.1 mg/mL to about 15 mg/mL, between about 0.5 mg/mL to about 15 mg/mL, between about 0.1 mg/mL to about 10 mg/mL, between about 0.5 mg/mL to about 10 mg/mL, or between about 1 mg/mL and about 5 mg/mL recombinant therapeutic protein).

Following the chasing step and before the next volume fluid containing a recombinant therapeutic protein can be loaded onto the at least one chromatographic column or chromatographic membrane that can be used to perform the unit operation of polishing, the at least one chromatography column or chromatographic membrane must be regenerated using a regeneration buffer. The regeneration buffer can be passed through the at least one chromatography column or chromatographic membrane that can be used to perform the unit operation of polishing the recombinant therapeutic protein at a flow rate of, e.g., between about 0.2 mL/minute to about 100 L/minute (inclusive) (e.g., any of the subranges of this flow rate range described herein). The volume of regeneration buffer used to regenerate the at least one chromatography column or chromatographic membrane that can be used to perform the unit operation of polishing can be, e.g., between about 1× column volume (CV) to about 500×CV (e.g., between about 1× CV to about 450×CV, between about 1×CV to about 400×CV, between about 1× CV to about 350×CV, between about 1×CV to about 300× CV, between about 1× CV to about 250×CV, between about 1×CV to about 200×CV, between about 1× CV to about 150×CV, between about 1×CV to about 100×CV, between about 1× CV to about 90×CV, between about 1×CV to about 80×CV, between about 1×CV to about 70×CV, between about 1× CV to about 60×CV, between about 1× to about 50×CV, between about 1× CV to about 40×CV, between about 1×CV to about 30×CV, between about 1× CV to about 20×CV, between about 1×CV to about 15×CV, between about 5×CV to about 20×CV, between about 5×CV to about 30×CV, between about 1× CV to about 14×CV, about 1×CV to about 13×CV, about 1×CV to about 12×CV, about 1× CV to about 11×CV, about 2×CV to about 11×CV, about 3×CV to about 11×CV, about 4×CV to about 11×CV, about 2.5×CV to about 5.0×CV, about 5×CV to about 11×CV, or about 5×CV to about 10×CV).

In other examples, the one or more chromatography column(s) and/or chromatographic membranes used to perform the unit operation of polishing contain a resin that selectively binds or retains the impurities present in a fluid containing the recombinant therapeutic protein, and instead of regenerating the one or more column(s) and/or membrane(s), the one or more column(s) and/or membrane(s) are replaced (e.g., replaced with a substantially similar column(s) and/or membrane(s)) once the binding capacity of the resin in the one or more column(s) and/or membrane(s) has been reached or is substantially close to being reached.

In some examples of these processes, the second MCCS includes a PCCS containing three chromatography columns and one chromatographic membrane, e.g., where the three chromatography columns in the PCCS perform the unit operation of purifying the recombinant therapeutic protein (e.g., using at least one chromatography column(s) that can be used to perform the unit of operation of purifying the protein) and the chromatographic membrane in the PCCS performs the unit operation of polishing the recombinant therapeutic protein. In these examples, the chromatographic membrane in the PCCS that can be used to perform the unit operation of polishing the recombinant therapeutic protein can be any of the exemplary chromatographic membranes described herein that can be used to perform the unit operation of polishing the recombinant therapeutic protein. Any of the column switching methods described herein can be used to determine when the first three chromatography columns and the chromatographic membrane in the PCCS in this example can be switched.

Some embodiments of this example can further include a step of adjusting the ionic concentration and/or pH of the eluate from the three chromatographic columns in the PCCS before the eluate is fed into the chromatographic membrane in the PCCS. As described herein, the ionic concentration and/or pH of the eluate from the three chromatography columns in PCCS can be adjusted (before it is fed into the chromatographic membrane in the PCCS in this example)) by adding a buffer to the eluate of the three chromatography columns in the PCCS (e.g., through the use of an in-line buffer adjustment reservoir). The buffer can be added to the eluate at a flow rate of, e.g., between about 0.2 mL/minute to about 100 L/minute (inclusive) (e.g., any of the subranges of this flow rate range described herein).

These examples can further include a step of holding or storing the eluate from the three chromatography columns in the PCCS in this example prior to feeding the eluate into the chromatographic membrane (chromatographic membrane that can be used to perform the unit operation of polishing the recombinant therapeutic protein). As described herein, this holding or storing step can be performed using any of the reservoirs (e.g., back-up tanks) described herein.

These examples can also include a step of filtering the eluate from the chromatographic membrane in the exemplary PCCS system (eluate of the chromatographic membrane that can be used to perform the unit operation of polishing the recombinant therapeutic protein). Any of the exemplary filters or methods for filtration described herein can be used to filter the eluate from the chromatographic membrane in this exemplary PCCS (eluate of the chromatographic membrane that can be used to perform the unit operation of polishing the recombinant therapeutic protein).

As can be appreciated by those in the art, the therapeutic protein drug substance can be periodically eluted from the second MCCS using any of the processes described herein. For example, any of the processes described herein can elute the therapeutic protein drug substance for a duration of, e.g., between about 30 seconds and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, about 2 hours, about 1.5 hours, about 1 hour, about 30 minutes, about 20 minutes, about 10 minutes, about 5 minutes, or about 1 minute (inclusive); between about 1 minute and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, about 2 hours, about 1.5 hours, about 1 hour, about 30 minutes, about 20 minutes, about 10 minutes, and about 5 minutes (inclusive); between about 5 minutes and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, about 2 hours, about 1.5 hours, about 1 hour, about 30 minutes, about 20 minutes, or about 10 minutes (inclusive); between about 10 minutes and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, about 2 hours, about 1.5 hours, about 1 hour, about 30 minutes, or about 20 minutes (inclusive); between about 20 minutes and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, about 2 hours, about 1.5 hours, about 1 hour, or about 30 minutes (inclusive); between about 30 minutes and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, about 2 hours, about 1.5 hours, or about 1 hour (inclusive); between about 1 hour and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, about 2 hours, or about 1.5 hours (inclusive); between about 1.5 hours and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, about 3 hours, or about 2 hours (inclusive); between about 2 hours and about 48 hours, about 44 hours, about 40 hours, about 36 hours, about 32 hours, about 28 hours, about 24 hours, about 20 hours, about 16 hours, about 12 hours, about 8 hours, about 5 hours, about 4 hours, or about 3 hours (inclusive); between about 3 hours and about 48 hours, about 44 hours, about 40 hours, about 36 hours, about 32 hours, about 28 hours, about 24 hours, about 20 hours, about 16 hours, about 12 hours, about 8 hours, about 5 hours, or about 4 hours (inclusive); between about 4 hours and about 48 hours, about 44 hours, about 40 hours, about 36 hours, about 32 hours, about 28 hours, about 24 hours, about 20 hours, about 16 hours, about 12 hours, about 8 hours, or about 5 hours (inclusive); between about 5 hours and about 48 hours, about 44 hours, about 40 hours, about 36 hours, about 32 hours, about 28 hours, about 24 hours, about 20 hours, about 16 hours, about 12 hours, or about 8 hours (inclusive); between about 8 hours and about 48 hours, about 44 hours, about 40 hours, about 36 hours, about 32 hours, about 28 hours, about 24 hours, about 20 hours, about 16 hours, or about 12 hours (inclusive); between about 12 hours and about 48 hours, about 44 hours, about 40 hours, about 36 hours, about 32 hours, about 28 hours, about 24 hours, about 20 hours, or about 16 hours (inclusive); between about 16 hours and about 48 hours, about 44 hours, about 40 hours, about 36 hours, about 32 hours, about 28 hours, about 24 hours, or about 20 hours (inclusive); between about 20 hours and about 48 hours, about 44 hours, about 40 hours, about 36 hours, about 32 hours, about 28 hours, or about 24 hours (inclusive); between about 24 hours and about 48 hours, about 44 hours, about 40 hours, about 36 hours, about 32 hours, or about 28 hours (inclusive); between about 28 hours and about 48 hours, about 44 hours, about 40 hours, about 36 hours, or about 32 hours (inclusive); between about 32 hours and about 48 hours, about 44 hours, about 40 hours, or about 36 hours (inclusive); between about 36 hours and about 48 hours, about 44 hours, or about 40 hours (inclusive); between about 40 hours and about 48 hours or about 44 hours (inclusive); or between about 44 hours and about 48 hours (inclusive), depending on, e.g., the chromatography column(s) and/or chromatographic membrane(s) used in the first and second MCCS.

Culturing Methods

Some of the processes described herein further include a step of culturing cells (e.g., recombinant mammalian cells) that secrete a recombinant therapeutic protein in a bioreactor (e.g., a perfusion or fed-batch bioreactor) that contains a liquid culture medium, wherein a volume of the liquid culture medium that is substantially free of cells (e.g., mammalian cells) is continuously or periodically removed from the perfusion bioreactor and fed into the first multicolumn chromatography system (MCC1). The bioreactor can have a volume of, e.g., between about 1 L to about 10,000 L (e.g., between about 1 L to about 50 L, between about 50 L to about 500 L, between about 500 L to about 1000 L, between 500 L to about 5000 L, between about 500 L to about 10,000 L, between about 5000 L to about 10,000 L, between about 1 L and about 10,000 L, between about 1 L and about 8,000 L, between about 1 L and about 6,000 L, between about 1 L and about 5,000 L, between about 100 L and about 5,000 L, between about 10 L and about 100 L, between about 10 L and about 4,000 L, between about 10 L and about 3,000 L, between about 10 L and about 2,000 L, or between about 10 L and about 1,000 L). The amount of liquid culture medium present in a bioreactor can be, e.g., between about between about 0.5 L to about 5,000 L (e.g., between about 0.5 L to about 25 L, between about 25 L to about 250 L, between about 250 L to about 500 L, between 250 L to about 2500 L, between about 250 L to about 5,000 L, between about 2500 L to about 5,000 L, between about 0.5 L and about 5,000 L, between about 0.5 L and about 4,000 L, between about 0.5 L and about 3,000 L, between about 0.5 L and about 2,500 L, between about 50 L and about 2,500 L, between about 5 L and about 50 L, between about 5 L and about 2,000 L, between about 5 L and about 1,500 L, between about 5 L and about 1,000 L, or between about 5 L and about 500 L). Culturing cells can be performed, e.g., using a fed-batch bioreactor or a perfusion bioreactor. Non-limiting examples and different aspects of culturing cells (e.g., culturing mammalian cells) are described below and can be used in any combination.

Cells

The cells that are cultured in some of the processes described herein can be bacteria (e.g., gram negative bacteria), yeast (e.g., *Saccharomyces cerevisiae, Pichia pastoris, Hansenula polymorpha, Kluyveromyces lactis, Schizosaccharomyces pombe, Yarrowia lipolytica*, or *Arxula adeninivorans*), or mammalian cells. The mammalian cell can be a cell that grows in suspension or an adherent cell. Non-limiting examples of mammalian cells that can be cultured in any of the processes described herein include: Chinese hamster ovary (CHO) cells (e.g., CHO DG44 cells or CHO-Kls cells), Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, and Madin-Darby Canine (Cocker Spaniel) kidney epithelial cells (MDCK) cells. In some examples where an adherent cell is cultured, the culture can also contain a plurality of microcarriers (e.g., microcarriers that contain one or more pores). Additional mammalian cells that can be cultured in any of the processes described herein are known in the art.

The mammalian cell can contain a recombinant nucleic acid (e.g., a nucleic acid stably integrated in the mammalian cell's genome) that encodes a recombinant therapeutic protein. Non-limiting examples of recombinant nucleic acids that encode exemplary recombinant therapeutic proteins are described below, as are recombinant therapeutic proteins that can be produced using the methods described herein. In some instances, the mammalian cell that is cultured in a bioreactor (e.g., any of the bioreactors described herein) was derived from a larger culture.

A nucleic acid encoding a recombinant therapeutic protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant therapeutic protein is not stably integrated into a chromosome of the mammalian cell (transient transfection), while in others the nucleic acid is integrated. Alternatively or in addition, the nucleic acid encoding a recombinant therapeutic protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the recombinant therapeutic protein is a secreted protein and is released by the mammalian cell into the extracellular medium (e.g., the first and/or second liquid culture medium). For example, a nucleic acid sequence encoding a soluble recombinant therapeutic protein can contain a sequence that encodes a secretion signal peptide at the N- or C-terminus of the recombinant therapeutic protein, which is cleaved by an enzyme present in the mammalian cell, and subsequently released into the extracellular medium (e.g., the first and/or second liquid culture medium).

Culture Media

Liquid culture media are known in the art. The liquid culture media (e.g., a first and/or second tissue culture medium) can be supplemented with a mammalian serum (e.g., fetal calf serum and bovine serum), and/or a growth hormone or growth factor (e.g., insulin, transferrin, and epidermal growth factor). Alternatively or in addition, the liquid culture media (e.g., a first and/or second liquid culture medium) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid culture medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells (e.g., mammalian cells) in any of the methods described herein are known in the art. Medium components that also may be useful in the present processes include, but are not limited to, chemically-defined (CD) hydrolysates, e.g., CD peptone, CD polypeptides (two or more amino acids), and CD growth factors. Additional examples of liquid tissue culture medium and medium components are known in the art.

Skilled practitioners will appreciate that the first liquid culture medium and the second liquid culture medium described herein can be the same type of media or different media.

Additional Features of Exemplary Bioreactors

The interior surface of any of the bioreactors described herein may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an ATF system).

Temperature

The step of culturing of mammalian cells can be performed at a temperature of about 31° C. to about 40° C. Skilled practitioners will appreciate that the temperature can be changed at specific time point(s) in during the culturing step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the bioreactor with the cell (e.g., mammalian cell). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20 degrees C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

$CO_2$

The culturing step described herein can further include exposing the liquid culture medium in the bioreactor to an atmosphere containing at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$).

Perfusion Bioreactor

The culturing step described herein can be performed using a perfusion bioreactor. Culturing a cell (e.g., a mammalian cell) in a perfusion bioreactor includes the removal from the bioreactor of a first volume of a first liquid culture medium (e.g., containing any concentration of mammalian cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume.

Skilled practitioners will appreciate that the first liquid culture medium and the second liquid culture medium can be the same type of media. In other instances, the first liquid culture medium and the second liquid culture medium can be different.

The first volume of the first liquid culture medium can be removed, e.g., by a mechanical system that can remove the first volume of the first liquid culture medium from the bioreactor (e.g., the first volume of the first liquid culture medium that is substantially free of cells from the bioreactor). Alternatively or in addition, the first volume of the first liquid culture medium can be removed by seeping or gravity flow of the first volume of the first liquid culture medium through a sterile membrane with a molecular weight cut-off that excludes the cell (e.g., mammalian cell).

The second volume of the second liquid culture medium can be added to the first liquid culture medium in an automated fashion, e.g., by perfusion pump.

In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell.

Fed-Batch Bioreactor

The culturing step described herein can be performed using a fed-batch bioreactor. Culturing a cell in a fed-batch bioreactor includes, over the majority of the culturing period, the addition (e.g., periodic or continuous addition) to the first liquid culture medium of a second volume of a second liquid culture medium. The adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the second volume of the second liquid culture medium is added (volume/unit of time) can be varied over the entire or part of the culturing period. For example, the volume of the second liquid culture medium added can change (e.g., gradually increase) over each 24-hour period (or alternatively, an incremental time period of between 1 hour and about 24 hours or an incremental time period of greater than 24 hours) during the culturing period. For example the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume. The rate at which the second volume of the second liquid culture medium is added (volume/unit of time) can be about the same over the entire or part of the culturing period.

Skilled practitioners will appreciate that the first liquid culture medium and the second liquid culture medium can be the same type of media. In other instances, the first liquid culture medium and the second liquid culture medium can be different. The volume of the second liquid culture medium can be added to the first liquid culture medium in an automated fashion, e.g., by perfusion pump.

In some instances, adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell. The cell culture medium in fed-batch cultures is typically harvested at the end of culture period and used in any of the processes described herein, however, the cell culture medium in fed-batch cultures can also be harvested at one or more time points during the culturing period and used in any of the processes described herein.

Skilled practitioners will appreciate that any of the various culture parameters (e.g., containers, volumes, rates or frequencies of replacing culture volumes, agitation frequencies, temperatures, media, and $CO_2$ concentrations) can be used in any combination in to perform these methods. Further, any of the mammalian cells described herein or known in the art can be used to produce a recombinant protein.

Additional Examples of Unit Operations

Some examples of the methods of processing a fluid including a recombinant therapeutic protein can further include performing one or more additional unit operations (e.g., one or more of capturing a recombinant therapeutic protein, purifying a recombinant therapeutic protein, polishing a recombinant therapeutic protein, viral inactivation, viral filtration, adjusting the ionic concentration and/or pH of a fluid containing the recombinant therapeutic protein, filtration of a fluid containing the recombinant therapeutic protein, precipitation and flocculation, aqueous two-phase extraction, lyophilization, and crystallization). Some examples of the integrated and continuous processes for manufacturing a therapeutic protein drug substance can further include one or more additional unit operations, e.g., one or more of precipitation and flocculation, aqueous two-phase extraction, lyophilization, and crystallization.

Precipitation and Flocculation

In some examples, the processes and methods described herein further include performing the unit operation(s) of precipitation and/or flocculation. Methods for performing precipitation are described in, e.g., McNerney et al., PDAD-MAC Flocculation of Chinese Hamster Ovary Cells: Enabling a Centrifuge-*Less Harvest* Process for Monoclonal Antibodies, in MAbs, vol. 2, Taylor & Francis, pp. 413-427, 2015, Roush et al., *Biotechnol. Prog.* 24(3):488-495, 2008; Liu et al., Recovery and Purification Process Development for Monoclonal Antibody Production, in *MAbs*, vol. 5, Taylor & Francis, pp. 480-499, 2010; Tscheliessnig et al., *J. Biotechnol.* 188:17-28, 2014; Sommer et al., *Process Biochem.* 49 (11):2001-2009, 2014; Brodsky et al., *Biotechnol. Bioeng.* 109 (10):2589-2598, 2012; Lydersen et al., *Ann. NY Acad. Sci.* 745(1):222-231, 1994; and Ito et al., *J. Chromatogr. B* 878(2):154-164, 2010. Precipitation methods can be achieved by altering factors like pH and/or conductivity (salting-in or salting-out) of solution, or through addition of precipitants, e.g., ethanol, ammonium sulfate, polyethylene glycol (PEG), caprylic acid, and divalent ions. Methods for performing flocculation are described in, e.g., Riske et al., *J. Biotechnol.* 128(4):813-823, 2007; Kang et al., *Biotechnol. Bioeng.* 110(11):2928-2937, 2013; Singh et al., *Biotechnol. Bioeng.* 113(4):698-716, 2015; Gagnon et al., *J. Chromatogr. A* 1221:57-70, 2012; Buchacher et al., *Biotechnol. J.* 1(2):148-163, 2006; Watt et al., *Vox Sang.* 18(1):42-61, 1970; Bell et al., The formation of protein precipitates and their centrifugal recovery, in Downstream Processing, Springer, pp. 1-72, 1983; Chang et al., *Biotechnol. Bioeng.* 31(8):841-846, 1988; Ito et al., *J. Chromatogr. B* 878(2):154-164, 2010; Hammerschmidt et al., *Biotechnol. J.* 10(8):1196-1205, 2015; Hammerschmidt et al., *Process Biochem.* 51(2):325-332, 2016; Hammerschmidt et al., *Biotechnol. J.* 9(6):766-775, 2014; and Warikoo et al., *Biotechnol. J.* 10(8):1101-1102, 2015). Flocculation relies on flocculating agents, e.g., polyelectrolytes, which cause adhesion of dispersed particulates into larger-size clusters, resulting in an increase in the average particle size distribution. The floccules can then be collected by filtration, sedimentation, or centrifugation.

Continuous Aqueous Two-Phase Extraction

In some examples, the processes and methods described herein further include performing the unit operation(s) of aqueous two-phase extraction, e.g., as described in Azevedo et al., *Sep. Purif. Technol.* 65(1):14-21, 2009; Gomes et al., *Sep. Purif. Technol.* 65(1):22-30, 2009; Kumar et al., *Biotechnol. Bioeng.* 75(5):570-580, 2001; Mashayekhi et al., *Biotechnol. Bioeng.* 102(6):1613-1623, 2009; Rosa et al., *J. Chromatogr. A* 1217(16):2296-2305, 2010; Haraguchi et al., *Fluid Phase Equilibria* 215(1):1-15, 2004; Hart et al., *Nat. Biotechnol.* 12(11):1113-1117, 1994; and Azevedo et al., *Trends Biotechnol.* 27(4):240-247, 2009b).

Aqueous two-phase extraction relies on formation of two immiscible aqueous phases such that the recombinant therapeutic protein partitions into one phase while impurities partition into the other. Organic solvent mixtures are not suitable as proteins can denature in organic phase. Hence, aqueous two-phase extraction for recombinant therapeutic proteins is usually carried out with either polymer-polymer or a polymer-salt dissolved in water above critical concentration (Azevedo et al., *Trends Biotechnol.* 27(4):240-247, 2009). Polymers, such as PEG, polyvinyl alcohol, dextran, and starch, and buffering salts, such as phosphates, sulfates, and citrates, have been used to create the two phases. To improve the specificity of the recombinant therapeutic protein to a particular phase, functionalization of the phase-forming component is also possible (Ruiz-Ruiz et al., *J. Chromatogr. A* 1244:1-13, 2012).

The mechanism of phase extraction in aqueous two phase systems and in conventional organic-aqueous systems is similar; hence most of the standard extraction equipment used in chemical industry can be applied for aqueous two-phase extraction (Kula and Selber, Encyclopedia of Bioprocess Technology, 2002, and Vazquez-Villegas et al., *Sep. Purif. Technol.* 141:263-268, 2015). Aqueous two-phase extraction can be performed using appropriate column contactors, spray columns, rotating disk contactors, or mixer-settler units (Rosa et al., *J. Chromatogr. B* 880:148-156, 2012; Muendges et al., *Biotechnol. Prog.* 31 (4):925-936, 2015; and Espitia-Saloma et al., *Food Bioprod. Process* 92(2):101-112, 2014). Use of multi-stage aqueous two-phase extraction devices such as multi-plate column contactors and mixer-settler configurations can overcome the limitations of single stage extraction through improved recovery and/or purity (Espitia-Saloma et al., *Biotechnol. J.* 11(5):708-716, 2016, and Rosa et al., *J. Biotechnol.* 139(4): 306-313, 2009). Multi-stage aqueous two-phase extraction has been successfully evaluated for the purification of mAbs (Muendges et al., *Biotechnol. Prog.* 31(4):925-936, 2015; Rosa et al., *Biotechnol. J.* 8(3):352-362, 2013; Rosa et al., *J. Biotechnol.* 139(4):306-313, 2009; Eggersgluess et al., *Chemical Engineering & Technology* 37(4):675-682, 2014). Continuous ATPE devices provide a promising non-chromatographic alternative for use in downstream processing of monoclonal antibodies; allowing simultaneously clarification, concentration and partial purification in one unit. One of the concerns on the application of ATPE at industrial scale is related to the high consumption of polymers and salt needed in the process and, consequently, to their impact on water treatment (Espitia-Saloma et al., *Biotechnol. J.* 11(5): 708-716, 2016).

Lyophilization

In some examples, the processes and methods described herein further include performing the unit operation of lyophilization (e.g., continuous lyophilization). Methods for performing continuous lyophilization is described in De Meyer et al., *Int. J. Pharm.* 496(1):75-85, 2015; Weisselberg, U.S. Pat. No. 8,528,225, 2013; and Rey et al., Glimpses into the Realm of Freeze-Drying: Classical Issues and New Ventures, in Freeze Drying/Lyophilization of Pharmaceutical and Biological Products, Informa Healthcare, London, UK, pp. 1-28, 2010.

Crystallization

In some examples, the processes and methods described herein further include performing the unit operation of crystallization (e.g., continuous crystallization). Methods for performing crystallization are described in, e.g., Peters et al., *Protein Expression Purif.* 39(1):43-53, 2005; Schmidt et al., *Eng. Life Sci.* 5(3):273-276, 2005; Hekmat, *Bioprocess Biosystems Eng.* 38(7):1209-1231, 2015; Basu et al., *Expert Opin. Biol. Ther.* 4(3):301-317, 2004; Hekmat, *Bioprocess Biosystems Eng.* 38(7):1209-1231, 2015; Power et al., *Chem. Eng. Sci.* 133:125-139, 2015; Lawton et al., *Organic Process Research Development* 13(6):1357-1363, 2009; Wong et al., *Crystal Growth Design* 12(11):5701-5707, 2012; Li et al., *Organic Process Research Development* 20(2):510-516, 2015; Poechlauer et al., *Organic Process Research Development* 16(10):1586-1590, 2012; Mascia et al., *Angewandte Chemie International Edition* 52(47): 12359-12363, 2013; Furuta et al., *Chem. Eng. Process* 102:210-218, 2016; Power et al., *Chem. Eng. Sci.* 133:125-139, 2015; and Neugebauer et al., *Crystal Growth Design* 15(3):1089-1095, 2015). Continuous crystallization can be performed using mixed-suspension mixed-product removal reactors (MSMPR), plug flow reactors (PFRs), and continuous oscillatory baffled crystallizers (COBCs) (see, e.g., Su et al., *Chemical Engineering Processing: Process Intensification* 89:41-53, 2015).

Exemplary Types of Chromatography

Exemplary types of chromatography that can be used in the present methods and processes (e.g., in the unit operations performed in the methods and processes described herein) include continuous cross-current chromatography (e.g., continuous annular chromatography and continuous radial flow chromatography), continuous counter-current chromatography (e.g., simulated moving bed chromatography, periodic counter-current chromatography, continuous counter-current tangential chromatography, and multicolumn counter-current solvent gradient purification), and flow-through chromatography (e.g., expanded bed chromatography).

In cross-current chromatography, the resin bed moves perpendicular to the direction of the liquid flow within the bed. In continuous cross-current systems, a steady-state separation occurs in the axial and circumferential direction, which is in contrast to conventional batch systems where separation occurs only in axial direction (Bridges and Barker, Continuous Cross-Current Chromatographic Refiners, in Ganetsos et al. (Eds.), Preparative and Production Scale Chromatography, Vol. 61, Marcel Dekker, Inc., New York, NY, pp. 113-126, 1992). Non-limiting examples of cross-current chromatography are continuous annular chromatography and continuous radial flow chromatography.

Continuous annular chromatography allows for the continuous separation of multicomponent mixtures using a rotating annular bed of chromatography matrix. Methods for performing continuous annular chromatography are described in, e.g., Martin, Discussions of the Faraday Society 7:332-336, 1949; Giddings, *Anal. Chem.* 34 (3):314-319, 1962; Fox et al., *J. Chromatogr. A* 43:48-54, 1969; Fox, *J. Chromatogr. A* 43:55-60, 1969; and Nicholas and Fox, *J. Chromatogr. A* 43:61-65, 1969; Giovannini and Freitag, *Biotechnol. Bioeng.* 73 (6):522-529, 2001; Bloomingburg and Carta, *Chem. Eng. J.* 55(1-2):B19-B27, 1994; Takahashi and Goto, *Separation Sci. Technol.* 26(1):1-13, 1991; and Vogel et al., *Biotechnol. Bioeng.* 80(5):559-568, 2002. Continuous annular chromatography typically uses a bed of conventional adsorbent which is packed between two concentric cylinders that forms the annulus. The annular bed slowly rotates about its vertical axis. The feed mixture to be separated is introduced continuously through a stationary nozzle on top of the moving adsorbent bed. In the simplest case of isocratic chromatography, the rotating annulus is flooded with elution buffer which is flowing in the direction of feed (cross-current flow). As time progresses, different components of the feed separate in axial direction and develop helical bands from the fixed inlet point to the bottom of the annular bed. Several fixed outlets are kept at the bottom of the bed where the separated components are continuously recovered. The angular displacement of each component band from the feed point, i.e. slope of the helical bands is dependent upon the flow rate, rotational speed of the annulus, and the component affinity for the stationary phase.

Continuous radial flow chromatography operates similarly to continuous annular chromatography except feed and all necessary buffers flow in the radial direction (inwards from periphery or outwards from center in horizontal direction) instead of axial direction (along the axis). Effective bed height of a radial flow column is the distance between the inner and outer cylinders while cross sectional area is associated with the surface area of the tube. Short bed depth and large column cross-sectional area enables separations at high flow rates while maintaining low pressure drops (Besselink et al., *J. Chromatogr. A* 1271(1):105-114, 2013). Additional aspects of continuous radial flow chromatography are described in, e.g., Cabanne et al., *J. Chromatogr. B* 845 (2):191-199, 2007; Kinna et al., *Biotechnol. Bioeng.* 113 (1):130-140, 2016; Weaver et al., *BioPharm* 3(7):25-28, 1990; Sun et al., *Biomed. Chromatogr.* 14(7):478-482, 2000; Tharakan and Belizaire, *J. Chromatogr. A* 702(1):191-196, 1995; Gu et al., *Chem. Eng. Sci.* 46(5):1279-1288, 1991; Huang et al., *Chem. Eng. J.* 38(3):179-186, 1988; Kinna et al., *Biotechnol. Bioeng.* 113(1):130-140, 2016; and Lay et al., *Food Bioprod. Process.* 84(1):78-83, 2006.

Non-limiting examples of continuous counter-current chromatography include simulating moving bed chromatography, periodic counter-current chromatography, continuous counter-current tangential chromatography, and multicolumn counter-current solvent gradient purification.

Counter-current chromatography allows stationary phase to be used more efficiently improving productivity and decreasing solvent/buffer consumption as compared to batch chromatography. The liquid-solid counter-current movement could be obtained by rotating the solid phase adsorbent (chromatography resin) in the opposite direction to the liquid phase flow. This can be achieved by physically rotating the solid adsorbent/columns in the opposite direction to the liquid flow (true moving bed) or by simulating the continuous movement of solid phase using an elaborate column and valve movement in a periodic or semi-continuous manner (simulated moving bed).

Simulating moving bed chromatography utilizes a flow scheme that takes advantages of continuous and countercurrent movement of liquid and solid phase without actual movement of the adsorbent. Instead of a large packed bed used in traditional batch chromatography; SMB chromatography systems are characterized by the connection of multiple smaller packed beds. The simulated counter-current flow is carried out through a complex valve system located between the columns, such that inlet and outlet positions are periodically switched from column to column in the direction of liquid flow. Methods of using simulated moving bed chromatography are described in, e.g., Jungbauer et al., *Trends Biotechnol.* 31(8):479-492, 2013; Low et al., *J. Chromatogr. B* 848(1):48-63, 2007; Xie et al., *Biotechnol. Bioprocess Eng.* 6(6):363-375, 2001; Imamoglu, Simulated Moving Bed Chromatography (SMB) for Application in Bioseparation, in Modern Advances in Chromatography, Springer, pp. 211-231, 2002; Mun et al., *Ind. Eng. Chem. Res.* 42 (9):1977-1993, 2003; Rajendran et al., *J. Chromatogr. A* 1216 (4):709-738, 2009; Gottschlich and Kashe, *J. Chromatogr. A* 765(2):201-206, 1997; Kepler et al., *J. Chromatogr. A* 1176 (1):69-78, 2007; Kröber et al., *J. Chromatogr. A* 1307:99-110, 2013; Rodrigues, Simulated Moving Bed Technology: Principles, Design, and Process Applications, Butterworth-*Heinemann,* 2015; and Aniceto et al., *Separation Purification Reviews* 44(1):41-73, 2015.

Another example of counter-current chromatography is periodic counter-current chromatography. Exemplary methods for performing counter-current chromatography are described herein. Additional methods for performing counter-current chromatography are described in, e.g., Mahajan et al., *J. Chromatogr. A* 1227:154-162, 2012; Warikoo et al., *Biotechnol. Bioeng.* 109(12):3018-3029, 2012; and Godawat et al., *Biotechnol. J.* 7(12):1496-1508, 2012.

Continuous counter-current tangential chromatography is a type of counter-current chromatography whereby, instead of packing the resin particles in a fixed bed column, the resin (in the form of a slurry) flows through a series of static mixers and hollow fiber membrane modules. The microporous hollow fiber membranes retain the large resin particles while letting all dissolved species (protein and buffer components) pass through the membrane and into the permeate. The buffers used in the binding, washing, elution, stripping, and equilibration steps flow countercurrent to the resin slurry in a multi-stage configuration. Methods of performing continuous counter-current tangential chromatography are described in, e.g., Dutta et al., *Biotechnol. Prog.* 32(2):430-439, 2016; Shinkazh et al., U.S. Pat. No. 7,988,859, 2011; Napadensky et al., *Separation Science Technology* 48(9): 1289-1297, 2013; and Dutta et al., *J. Biotechnol.* 213:54-64, 2015.

Multicolumn counter-current solvent gradient purification is a multicolumn chromatographic process that is capable of using linear gradients for high-resolution separation of three component fractions. Methods for performing multicolumn counter-current solvent gradient purification are described in Aumann and Morbidelli, *Biotechnol. Bioeng.* 98 (5):1043-1055, 2007; Müller-Spath et al., *Biotechnol. Bioeng.* 100 (6):1166-1177, 2008; and Aumann and Morbidelli, *Biotechnol. Bioeng.* 99 (3):728-733, 2008.

An example of flow-through chromatography is expanded bed chromatography. Expanded-bed chromatography (EBC) utilizes a fluidized chromatographic adsorbent bed, which allows desired proteins to be purified directly from crude (e.g., particulate containing) feedstock (Chase, *Trends Biotechnol.* 12(8):296-303, 1994; Thömmes, Fluidized Bed Absorption as a Primary Recovery Step in Protein Purification, in New Enzymes for Organic Synthesis, Springer, pp. 185-230, 1997; Anspach et al., *J. Chromatogr. A* 865 (1): 129-144, 1999; and Gagnon, *J. Chromatogr. A* 1221:57-70, 2012). The primary difference in setup of expanded bed chromatography compared to traditional chromatography columns is that the top flow adapter is appropriately positioned such that the bed is allowed to expand upward in the direction of liquid flow. Methods for performing expanded bed chromatography are described in, e.g., Kinna et al., *Biotechnol. Bioeng.* 113(1):130-140, 2016; Farid, *J. Chromatogr. B* 848(1):8-18, 2007; Chhatre et al., *Bioprocess Biosystems Eng.* 30(1):1-11, 2007; Lin et al., *J. Chromatogr. A* 1304:78-84, 2013; Zhao et al., *Chinese J. Chem. Eng.* 17(4):678-687, 2009; Smith et al., *J. Chromatogr. A* 968 (1):121-128, 2002; Feuser et al., *Process Biochem.* 34(2): 159-165, 1999; Ozyurt et al., *J. Chromatogr. A* 944(1):203-210, 2002; Anspach et al., *J. Chromatogr. A* 865(1):129-144, 1999; Owen and Chase, *J. Chromatogr. A* 757 (1):41-49, 1997; and Owen and Chase, Chem. Eng. Sci. 54(17):3765-3781, 1999.

Exemplary Advantages

The processes described herein can result in a substantial increase in the volumetric productivity of the recombinant therapeutic protein present in the therapeutic protein drug substance. For example, the processes described herein can result at least a 2-fold, 3-fold, 4-fold, 5-fold, 6-fold, 7-fold, 8-fold, 9-fold, and 10-fold increase in the volumetric productivity of the recombinant therapeutic protein present in the therapeutic protein drug substance. The biological activity of a recombinant therapeutic protein can be assessed using a variety of methods known in the art, and will depend on the activity of the specific recombinant therapeutic protein. For example, the biological activity of a recombinant therapeutic protein that is an immunoglobulin (e.g., an antibody or an antibody fragment) can be determined by measuring the affinity of the recombinant therapeutic antibody to bind to its specific epitope (e.g., using Biocore or competitive enzyme-linked immunosorbent assays). The recombinant therapeutic protein may be an enzyme (e.g., a recombinant galactosidase, e.g., a recombinant alpha-galactosidase) and the biological activity may be determined by measuring the recombinant therapeutic enzyme's activity (e.g., determining the catalytic rate constant of the recombinant therapeutic enzyme by measuring a decrease in the concentration of a detectable substrate or an increase in the concentration of a detectable product (e.g., using spectrophotometry or light emission). For example, the biological activity of a recombinant therapeutic galactosidase can be detected by measuring a decrease in the level of globotriasylceramide (GL-3) or galabiosylceramide, or an increase in the level of ceramide dihexoside or galactose.

The processes described herein can result in an increased percentage of recovery of the recombinant therapeutic protein (e.g., increased percentage of yield of the recombinant therapeutic protein present in the liquid culture medium in the therapeutic protein drug substance). For example, the present processes can result in a percentage yield of recombinant therapeutic protein of greater than about 70%, greater than about 80%, greater than about 82%, greater than about 84%, greater than about 86%, greater than about 88%, greater than about 90%, greater than about 92%, greater than about 94%, greater than about 96%, or greater than about 98%. The present processes can result in a percentage yield of between about 80% to about 90%, between about 82% to about 90%, between about 84% to about 90%, between about 84% to about 88%, between about 84% to about 94%, between about 82% to about 92%, or between about 85% to about 95%. The concentration of recombinant therapeutic protein present in the therapeutic protein drug substance can be greater than about 1.0 mg/mL, greater than about 1.5 mg/mL, greater than about 2.0 mg/mL, greater than about 2.5 mg/mL, greater than about 3.0 mg/mL, greater than about 3.5 mg/mL, greater than about 4.0 mg/mL, greater than about 4.5 mg/mL, greater than about 5.0 mg/mL, greater than about 5.5 mg/mL, greater than about 6.0 mg/mL, greater than about 6.5 mg/mL, greater than about 7.0 mg/mL, greater than about 7.5 mg/mL, greater than about 8.0 mg/mL, greater than about 8.5 mg/mL, greater than about 9.0 mg/mL, greater than about 10.0 mg/mL, greater than about 12.5 mg/mL, or greater than about 15.0 mg/mL.

The processes described herein can result in a net yield of recombinant therapeutic protein in the therapeutic protein drug substance of at least about 5 g/day, at least about 6 g/day, at least about 7 g/day, at least about 8 g/day, at least about 9 g/day, at least about 10 g/day, at least about 11 g/day, at least about 12 g/day, at least about 13 g/day, at least about 14 g/day, at least about 15 g/day, at least about 16 g/day, at least about 17 g/day, at least about 18 g/day, at least about 19 g/day, at least about 20 g/day, at least about 25 g/day, at least about 30 g/day, at least about 35 g/day, or at least about 40 g/day over a continuous period of at least about 5 days, at least about 10 days, at least about 15 days, at least about 20 days, at least about 25 days, at least about 30 days, at least about 35 days, at least about 40 days, at least about 45 days, at least about 50 days, at least about 55 days, at least about 60 days, at least about 65 days, at least about 70 days, at least about 75 days, at least about 80 days, at least about 85 days, at least about 90 days, at least about 95 days, at least about 100 days, at least about 110 days, at least about 120 days, at least about 130 days, at least about 140 days, at least about 150 days, at least about 160 days, at least about 170 days, at least about 180 days, at least about 190 days, at least about 200 days, at least about 210 days, at least about 220 days, at least about 230 days, at least about 240 days, at least about 250 days, at least about 260 days, at least about 270 days, at least about 280 days, at least about 290 days, at least about 300 days, at least about 310 days, at least about 320 days, at least about 330 days, at least about 340 days, at least about 350 days, or at least about 365 days.

The processes provided herein can result in a significantly improved specific productivity rate. For example, the specific productivity rate achieved in the recombinant protein drug substance is at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold greater than the specific productivity rate achieved using a different process (e.g., a batch purification process or a process that is not integrated and/or continuous). The productivity in the recombinant protein drug substance achieved by the present processes can be at least 10,000 units/L, at least 15,000 units/L, at least about 20,000 units/L, at least about 25,000 units/L, at least about 30,000 units/L, at least about 35,000 units/L, or at least about 40,000 units/L (in the first and/or second liquid culture medium). The productivity in the recombinant protein drug substance achieved by the present methods can be at least 1 g/L, at least 1.5 g/L, at least 2.0 g/L, at least 2.5 g/L, at least 3.0 g/L, at least 4.0 g/L, at least 4.5 g/L, or at least 5.0 g/L.

The processes described herein also provide for time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the outlet of the second MCCS is, e.g., between about 4 hours and about 48 hours, inclusive, e.g., between about 4 hours and about 40 hours, between about 4 hours and about 35 hours, between about 4 hours and about 30 hours, between about 4 hours and about 28 hours, between about 4 hours and about 26 hours, between about 4 hours and about 24 hours, between about 4 hours and about 22 hours, between about 4 hours and about 20 hours, between about 4 hours and about 18 hours, between about 4 hours and about 16 hours, between about 4 hours and about 14 hours, between about 4 hours and about 12 hours, between about 6 hours and about 12 hours, between about 8 hours and about 12 hours, between about 6 hours and about 20 hours, between about 6 hours and about 18 hours, between about 6 hours and about 14 hours, between about 8 hours and about 16 hours, between about 8 hours and about 14 hours, between about 8 hours and about 12 hours, between about 10 hours and 20 hours, between about 10 hours and 18 hours, between about 10 hours and 16 hours, between about 10 hours and 14 hours, between about 12 hours and about 14 hours, between about 10 hours and about 40 hours, between about 10 hours and about 35 hours, between about 10 hours and about 30 hours, between about 10 hours and about 25 hours, between about 15 hours and about 40 hours, between about 15 hours and about 35 hours, between about 15 hours and about 30 hours, between about 20 hours and about 40 hours, between about 20 hours and about 35 hours, or between about 20 hours and about 30 hours, inclusive. In other examples, the elapsed time between feeding the fluid (e.g., a liquid culture medium) containing a therapeutic protein into the first MCCS and eluting a therapeutic protein drug substance (containing the therapeutic protein) from the outlet of the second MCCS is, e.g., greater than about 4 hours and is less than about 40 hours, inclusive, e.g., greater than 4 hours and less than about 39 hours, about 38 hours, about 37 hours, about 36 hours, about 35 hours, about 34 hours, about 33 hours, about 32 hours, about 31 hours, about 30 hours, about 29 hours, about 28 hours, about 27 hours, about 26 hours, about 25 hours, about 24 hours, about 23 hours, about 22 hours, about 21 hours, about 20 hours, about 19 hours, about 18 hours, about 17 hours, about 16 hours, about 15 hours, about 14 hours, about 13 hours, about 12 hours, about 11 hours, about 10 hours, about 9 hours, about 8 hours, about 7 hours, about 6 hours, about 5 hours, or about 4.5 hours, inclusive.

The invention is further described in the following examples, which do not limit the scope of the invention described in the claims.

EXAMPLES

Example 1. Performance of Ultrafiltration/Diafiltration Using a Circuit System An ultrafiltration/diafiltration circuit system was created to continuously concentrate and buffer exchange a fluid including a recombinant bispecific antibody. The recombinant bispecific antibody was first purified over a Protein A column and the eluate, at a concentration of 24 g/L, was then used in the ultrafiltration/diafiltration circuit system. The circuit system included a tangential flow filtration (TFF) unit having first and second inlets, and a conduit in fluid communication between the first and second inlets, including a port for flowing fluid into or out of, or both, of the system. The fluid containing the recombinant bispecific antibody was continuously flowed through circuit system and filtrate not including the recombinant bispecific antibody (see "permeate" in FIG. 5) was discarded for a first period of time. A constant volume of fluid was maintained within the conduit during the first period of time.

Figure 5:
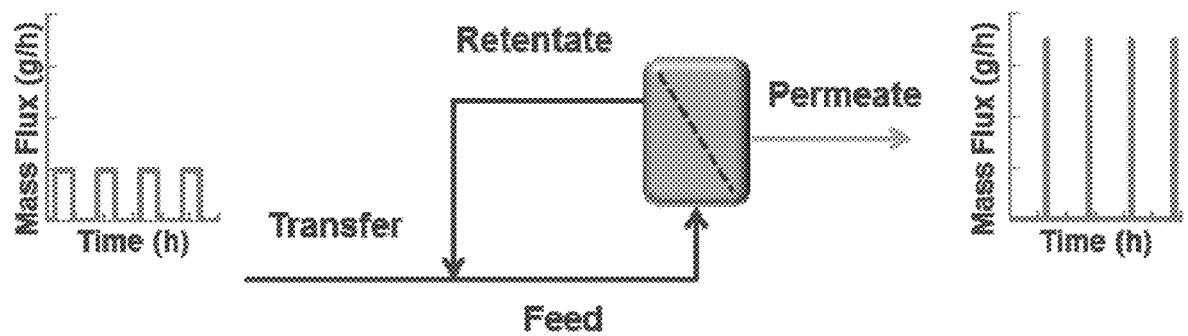
FIG. 5 is a schematic of the circuit system including a tangential flow filtration unit during a first period of time, when a fluid including a recombinant therapeutic protein is continuously flowed through into the system ("transfer") and a filtrate not including the recombinant therapeutic protein is discarded ("permeate") (left panel) and a graph showing the mass flux (g/h) over time (h) during the first period of time (right panel). The recombinant therapeutic protein is retained within the circuit system and is recirculated through the circuit system ("retentate") during the first period of time.
Figure 6:
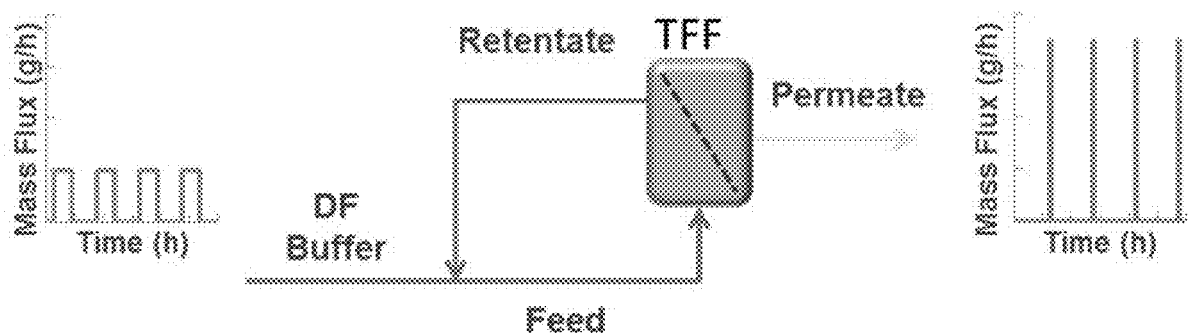
FIG. 6 is a schematic of the circuit system including a tangential flow filtration unit during a second period of time, when a diafiltration medium is continuously flowed through into the system ("DF buffer") and a filtrate not including the recombinant therapeutic protein is discarded ("permeate") (left panel) and a graph showing the mass flux (g/h) over time (h) during the second period of time (right panel). The recombinant therapeutic protein is retained within the circuit system and is recirculated through the circuit system ("retentate") during the second period of time.

Following this step, a diafiltration medium was continuously flowed into the circuit system through the at least one port and filtrate not including the recombinant bispecific antibody was discarded for a second period of time (FIG. 6). A constant volume of fluid was maintained within the conduit during the first period of time. The mass flow of this circuit system in this process is depicted in FIG. 5 and FIG. 6.

Figure 7:
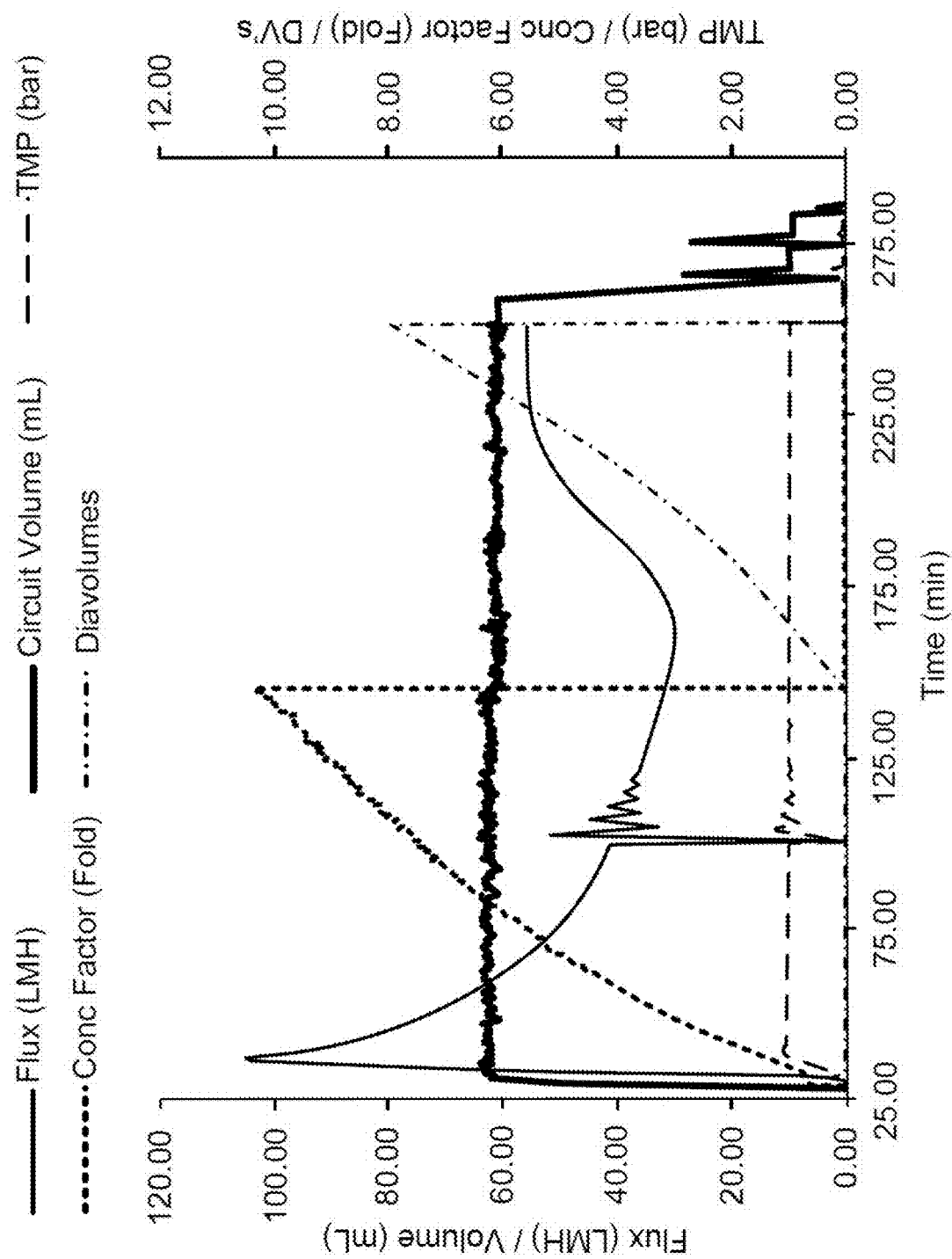
FIG. 7 is a graph illustrating the results of the use of an exemplary circuit system including a tangential flow filtration unit to perform ultrafiltration/diafiltration of a fluid including a recombinant therapeutic protein. The flux (LMH), the fold-concentration of the recombinant therapeutic protein (Fold), the volume of fluid in the circuit system, the diavolumes, and transmembrane pressure (TMP) of the circuit system including a tangential flow filtration unit over time are shown.
Figure 8:
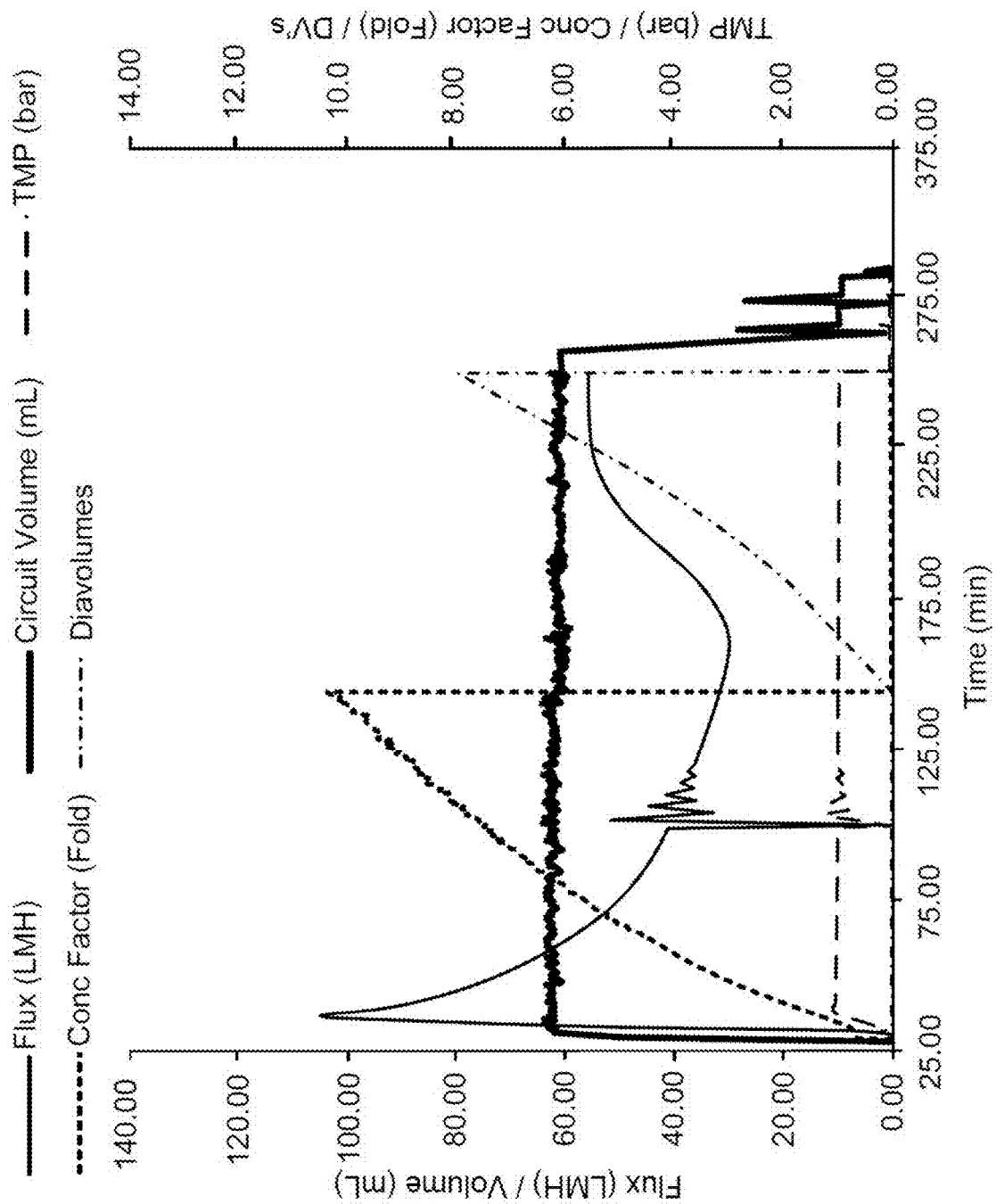
FIG. 8 is a graph illustrating the results of the use of an exemplary circuit system including a tangential flow filtration unit to perform ultrafiltration/diafiltration of a fluid including a recombinant therapeutic protein. The flux (LMH), the fold-concentration of the recombinant therapeutic protein (Fold), the volume of fluid in the circuit system, the diavolumes, and transmembrane pressure (TMP) of the circuit system including a tangential flow filtration unit over time are shown.
Figure 9:
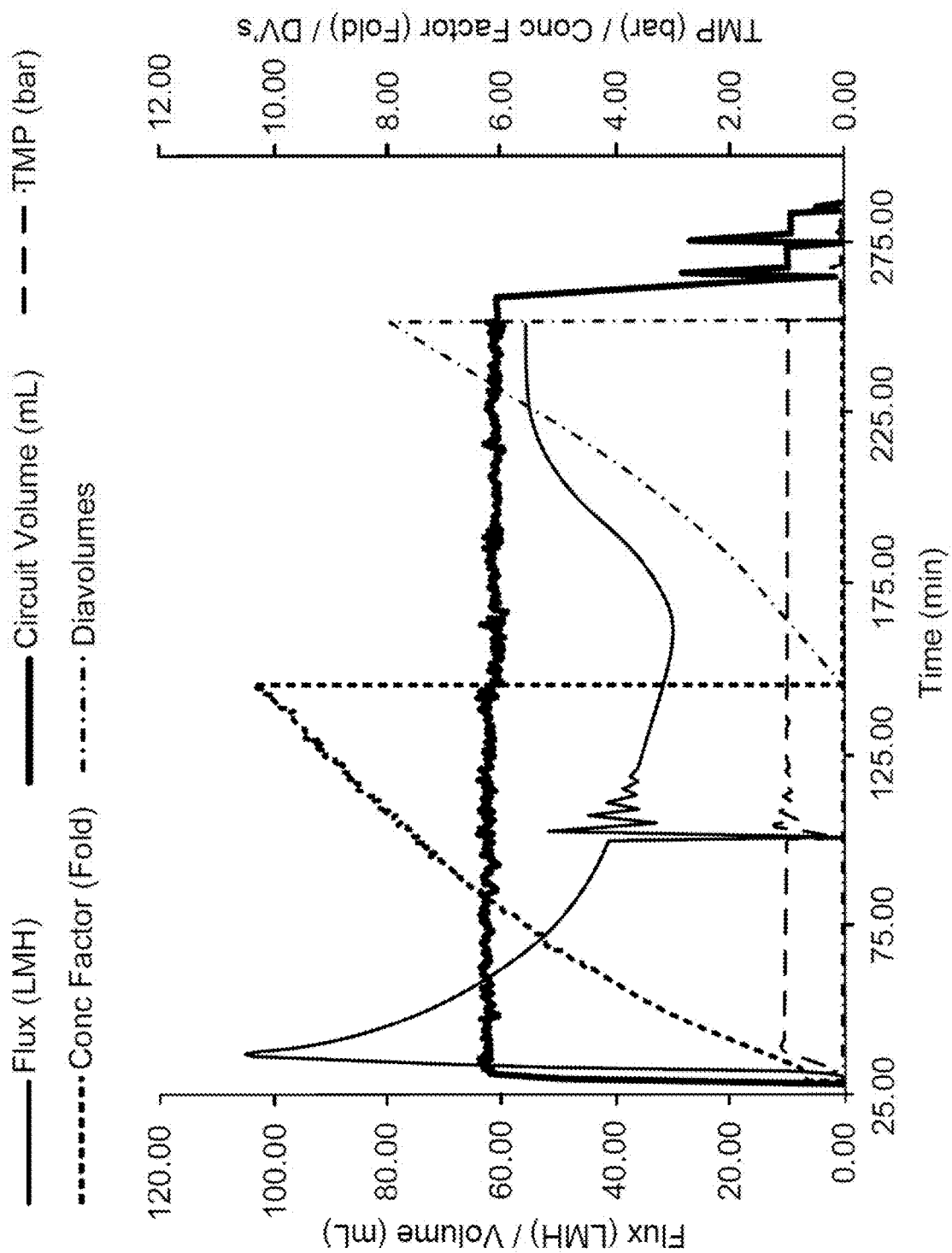
FIG. 9 is a graph illustrating the results of the use of an exemplary circuit system including a tangential flow filtration unit to perform ultrafiltration/diafiltration of a fluid including a recombinant therapeutic protein. The flux (LMH), the fold-concentration of the recombinant therapeutic protein (Fold), the volume of fluid in the circuit system, the diavolumes, and transmembrane pressure (TMP) of the circuit system including a tangential flow filtration unit over time are shown.

The fluid including the recombinant bispecific protein in the circuit system at the end of the second period of time is then collected from the circuit system. This process resulted in a 96% recovery of the recombinant bispecific antibody. Data from experiments using an exemplary circuit system including a tangential flow filtration unit is shown in FIGS. 7-9.

Example 2. Performance of Viral Filtration Using a Circuit System

A circuit system including a tangential flow virus filtration unit was then created to provide for continuous removal of viruses from fluid including a recombinant bispecific antibody recovered from the circuit system including a tangential flow filtration unit described in Example 1. The pore size of the filter in the tangential flow virus filtration unit was about 20 nm in order to provide for parvovirus removal.

Figure 10:
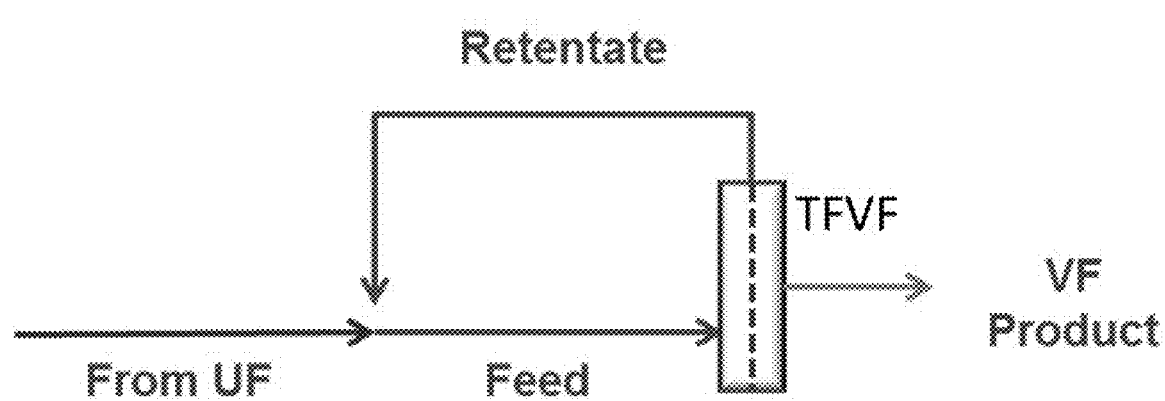
FIG. 10 is a schematic of the circuit system including a tangential flow virus filtration unit, when a fluid including a recombinant therapeutic protein is continuously flowed into the system ("from UF") and a filtrate including the recombinant therapeutic protein is continuously collected ("VF product").
Figure 11:
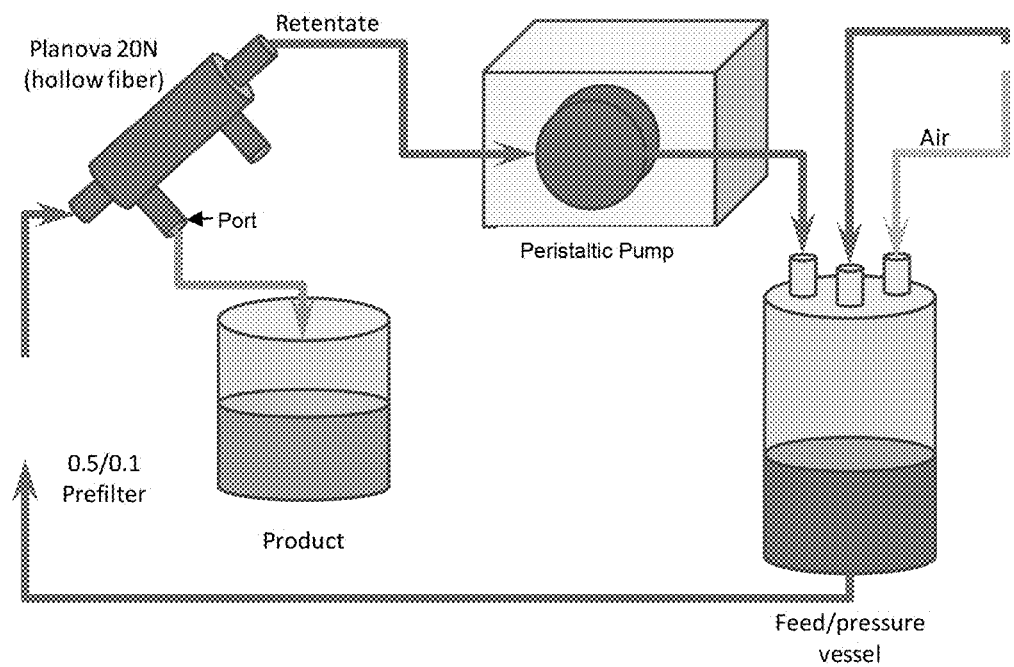
FIG. 11 is a schematic showing an exemplary circuit system including a tangential flow virus filtration unit.
Figure 12:
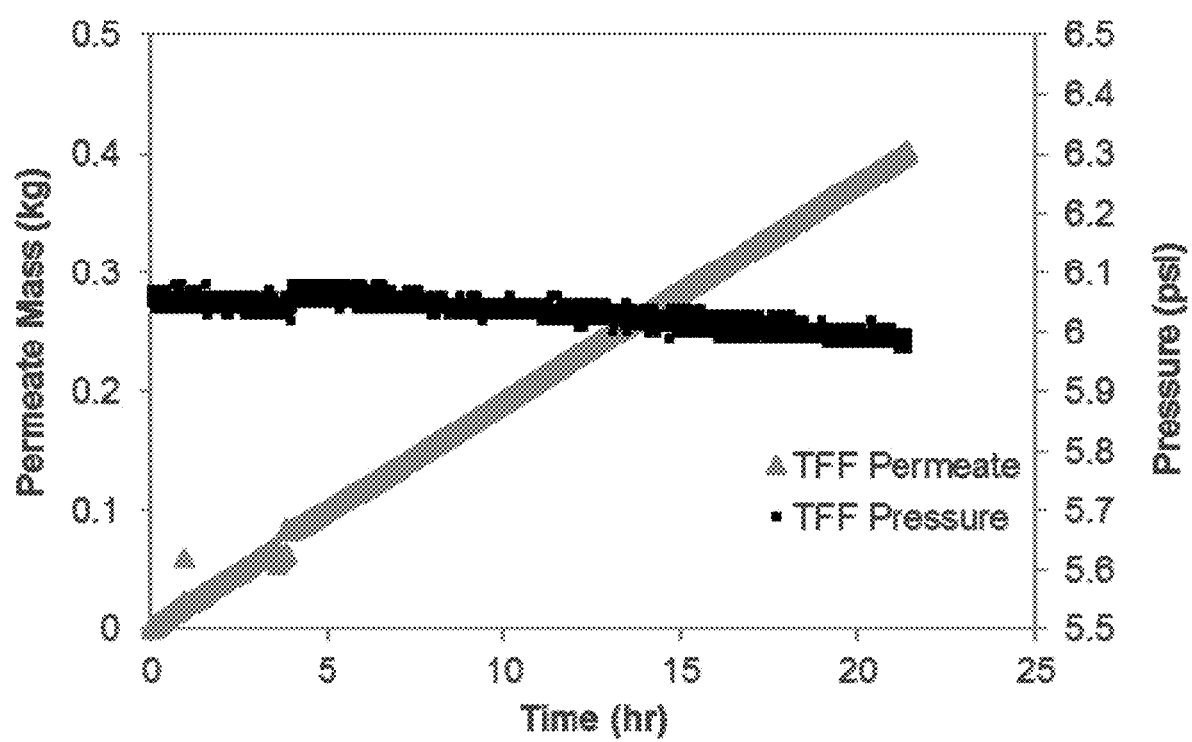
FIG. 12 is a graph showing the data obtained from the use of a circuit system including a tangential flow virus filtration unit to perform virus filtration. The black line represents the pressure (psi) and the gray line represents the mass of the permeate (kg) over time.

The concentrated and buffer exchanged fluid including the recombinant bispecific antibody removed from the circuit system described in Example 1 was fed into a second circuit system including a tangential flow virus filtration unit as indicated in FIG. 10. (Another example of a circuit system including a tangential flow virus filtration unit is shown in FIG. 11.) The fluid was continuously flowed through the second circuit system and the fluid including the recombinant bispecific antibody was recovered from the tangential flow virus filtration unit (see "virus-free" VF product in FIG. 10). Any viral particles present in the fluid flowed into the circuit system are retained within the circuit system and the fluid including the recombinant bispecific antibody was collected from the tangential flow virus filtration unit. This circuit system was operated for about 24 hours and no flux decay or pressure increases were observed over this period of time (see FIG. 12).

Example 3. Performance of Viral Clearance Using a Circuit System Including a TFVF Unit The viral clearance capabilities for a circuit system including a TFVF unit were tested in several experiments using Murine Minute Virus (MMV). Filtration was performed using a test fluid included 5 mg/mL of a recombinant human antibody that was spiked with 0.5% viral material to yield a final MMV titer of approximately 6 logs, unless otherwise noted below. The tested TFVF units included either a 3 cm² Planova™ BioEX filter or a 10 cm² Planova™ 20N or Planova™ BioEX filter.

Figure 13:
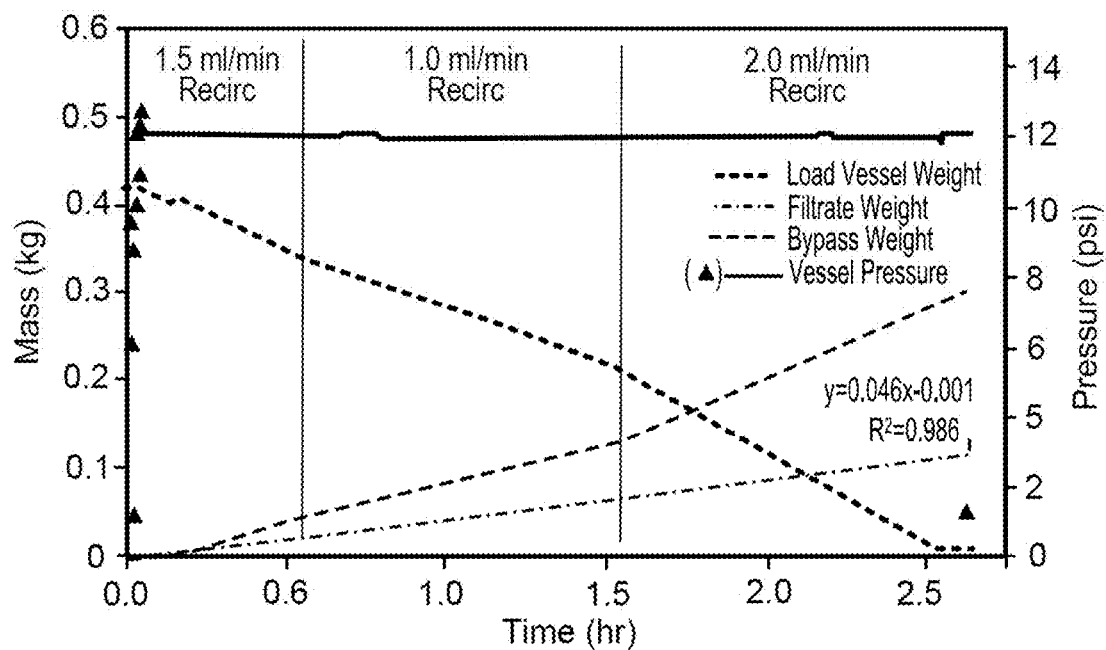
FIG. 13 is a graph illustrating the results of the use of an exemplary circuit system including a TFVF unit to perform viral filtration of Murine Minute Virus (MMV) from a recombinant human antibody (mAb) using a Planova™ 20N filter operated at 12 psi with a varying recirculation rate from 1-2 mL/min. The mass and pressure profiles of the circuit system including a TFVF unit over 2.5 hours are shown.

An experiment was designed to test the amount of MMV virus retained by the TFVF unit in the tested systems when the test fluid was flowed once through the TFVF unit. For this experiment, the retentate was collected in a separate pressure vessel rather than flowed back into the main feed vessel, in order to allow for a determination of the viral titer in the retentate. The system with a TFVF unit including a 10 cm² Planova™ 20N filter was operated at 12 psi with a flow rate varying between 1 and 2 mL/min. As indicated in FIG. 13 by the linear fit to the filtrate weight, the flow rate had no impact on the filter flux rate of 45.6 LMH, meaning the flow rate can be adjusted independently to maximize membrane life. At the conclusion of the experiment, the filtrate was found to represent 28% of volume of the test fluid, while 72% of the volume of the test fluid was collected in the retentate collection vessel. The viral titer of the filtrate was below the limit of detection, while the retentate titer was higher than the titer in the starting test fluid. A mass balance for the virus indicates that when the system is operated, a significant fraction of the virus is not captured by the filter in the TFVF unit, but flows through to concentrate in the retentate.

Figure 14:
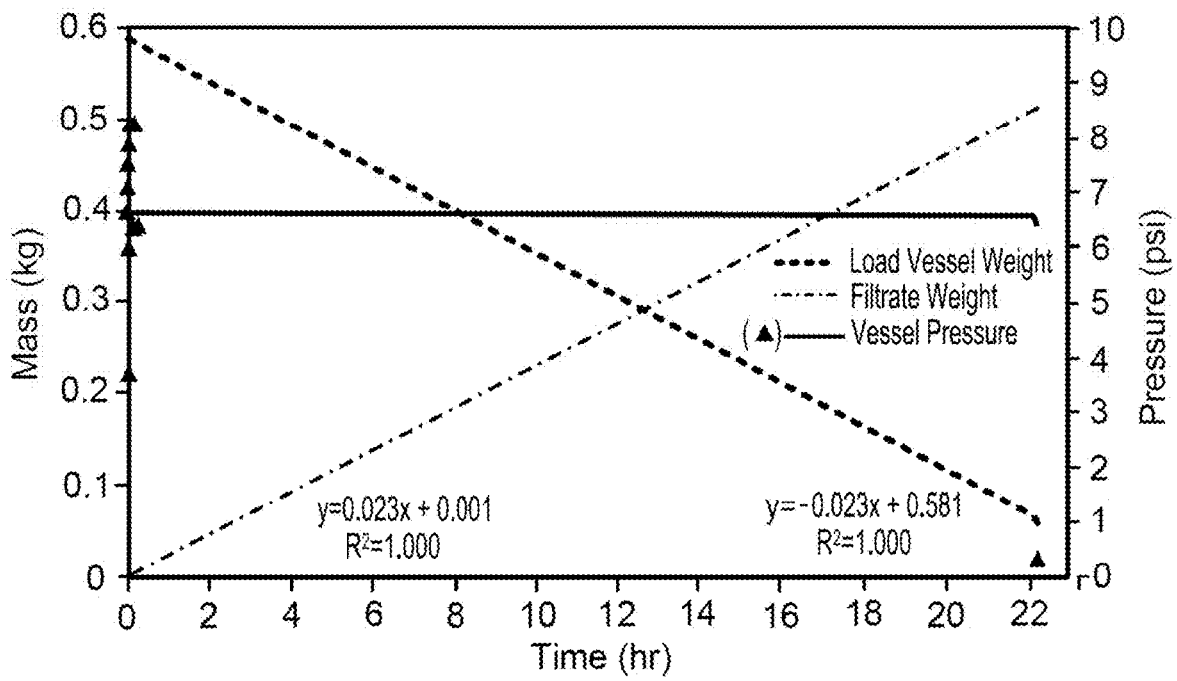
FIG. 14 is a graph illustrating the results of the use of an exemplary circuit system including a TFVF unit to perform continuous viral filtration of Murine Minute Virus (MMV) from a recombinant human antibody (mAb) using a Planova™ 20N filter operated at 6.6 psi with a varying recirculation rate of 2 mL/min. The mass and pressure profiles of the TFVF unit over 22 hours are shown.

The viral clearance for a circuit system including a TFVF unit including a 10 cm$^2$ Planova™ 20N filter was tested for a 22-hour period, while operated at 6.6 psi with a recirculation rate of 2 mL/min (FIG. 14). The system was charged with an initial load of 579 mL of test fluid and following operation (5.95 log titer), produced 510 mL of filtrate before the system was stopped to collect samples. The loading of 510 L/m$^2$ was achieved without any flux decay, with the flux across the filter remaining a constant 23.0 LMH. The 69 mL remaining in the retentate vessel was found to be visibly cloudy at the completion of the experiment, though no filter flux decay was found at any point during the run. The viral titer of the filtrate was below the limit of detection (<0.83 log), while the retentate titer was 6.48 log, 0.53 log higher than the titer in the test fluid. This result represents a 3.4× concentration of the virus in the load/retentate vessel. About half of the total virus load was not captured by the filter, but instead continued to recirculate, reducing the capture burden for the filter and preventing flux decay.

Figure 15:
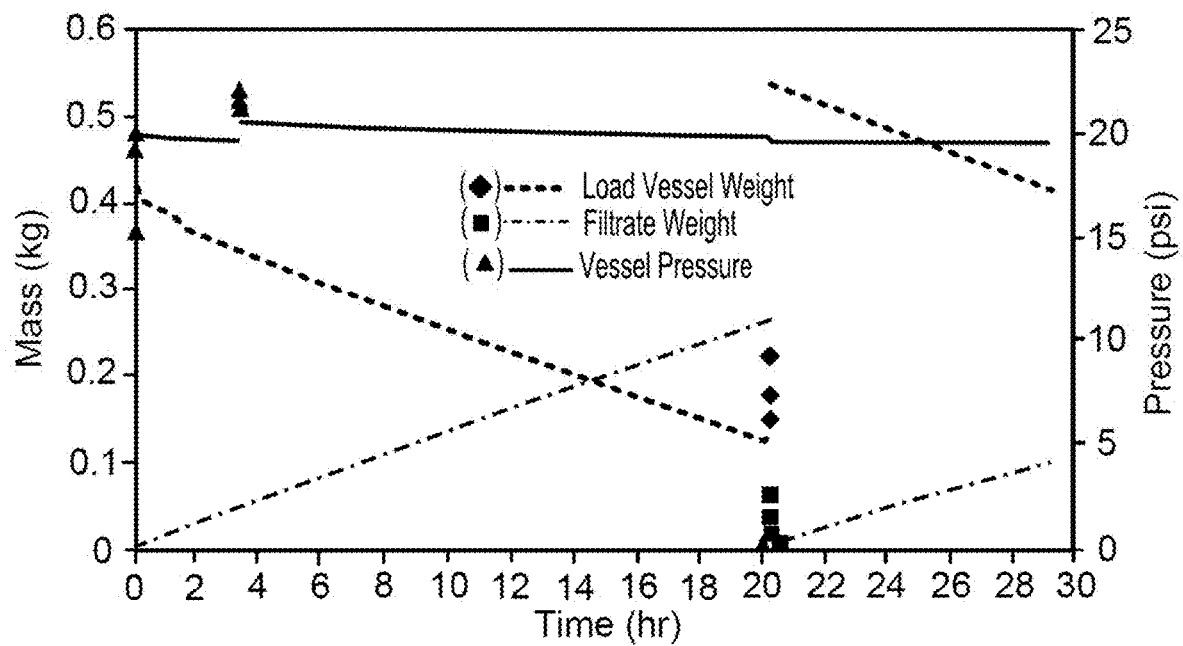
FIG. 15 is a graph illustrating the results of the use of an exemplary circuit system including a TFVF unit to perform continuous viral filtration of Murine MinuteVirus (MMV) from a recombinant human antibody (mAb) with refeed using a Planova™ BioEx (3 $cm^2$ area) operated at 19.8 psi with a varying recirculation rate of 1 mL/min. The mass and pressure profiles of the TFVF unit over 29 hours are shown.
Figure 16:
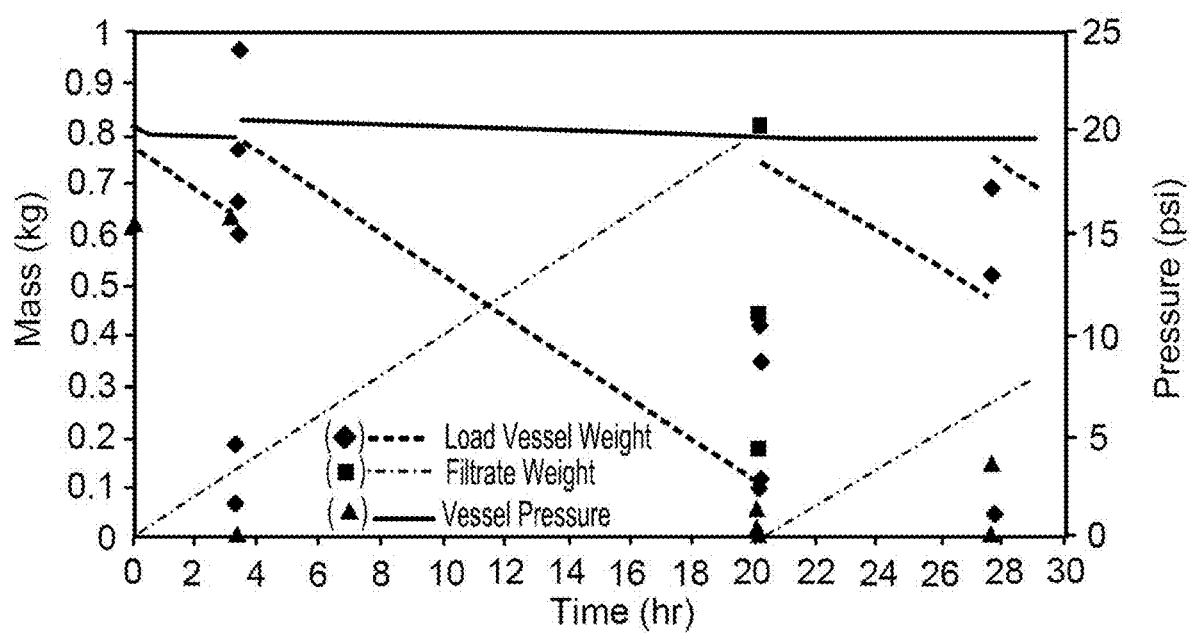
FIG. 16 is a graph illustrating the results of the use of an exemplary circuit system including a TFVF unit to perform continuous viral filtration of Murine Minute Virus (MMV) from a recombinant human antibody (mAb) with refeed using a Planova™ BioEx (10 $cm^2$ area) operated at 19.8 psi with a varying recirculation rate of 3 mL/min. The mass and pressure profiles of the TFVF unit over 29 hours are shown.

The viral clearance for a circuit system including a TFVF unit including 3 cm$^2$ or 10 cm$^2$ Planova™ BioEX filters when run for 29 hours at 20 psi with a recirculation rate of 1 mL/min or 3 mL/min, respectively, with periodic refeed of fresh fluid (FIGS. 15 and 16, respectively). The experiment performed using a TFVF unit with the 3 cm$^2$ filter was designed to replicate a scenario where a large bolus of virus at high titer is introduced to the system (e.g., through external contamination) and subsequently diluted out with virus-free material. This system was charged with an initial bolus of ~400 mL of test fluid spiked with 6.13 logs of virus and filtered for 20 hours. The viral titer in the filtrate from the first 20 hours of filtration was below the limit of detection (<1.09 logs). After ~20 hours of filtration, a fresh bolus of ~400 mL virus-free antibody solution was added. This material was filtered for an additional 9 hours and the virus titer in the filtrate was below the limit of detection. FIG. 15 shows the pressure and mass profiles using the circuit system including a TFVF including the 3 cm$^2$ Planova™ BioEX filter. The flux remained constant at 42.8 LMH through the first 20 hours but dropped to a new constant rate of 36.4 LMH after the refeed. The total throughput for the filter was 1190 L/m$^2$.

The experiment performed using the circuit system including a TFVF unit including the 10 cm$^2$ Planova™ BioEX filters was designed to replicate a scenario where a low titer stream of virus is continuously introduced into the system (e.g., from a contaminated buffer). The initial virus spike material (a MMV titer of 6.13 logs) was diluted 1:30 into a fresh recombinant antibody solution to create a diluted feedstock. The viral titer of the diluted feedstock was 4.66 logs. This diluted feedstock was filtered through the system for 29 hours, with fresh diluted feedstock added periodically to maintain the working volume above a minimum threshold. The virus titer of the filtrate was determined for the first 20 hours and for the next 9 hours, and was below the limit of detection (<0.83 logs) for both samples. FIG. 16 shows the pressure and mass profiles for the experiment. The flux remained constant at 39.4 LMH through the first 20 hours but dropped to a new rate of 34.5 LMH after the feed. The total throughput for the filter was 1120 L/m$^2$.

These results indicate that operating viral filtration with a continuous recirculation prolongs the useful life of the membrane by reducing plugging by captured virus. The ability to adjust the permeate rate (via system pressure) and recirculation rate (via pump speed) independently allow for process optimization to extend the operation of a single filter to multiple days.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of processing a fluid comprising a recombinant therapeutic protein, the method comprising:
   (a) providing a circuit system comprising (i) a tangential flow virus filtration (TFVF) unit having first and second inlets, and (ii) a conduit in fluid communication between the first and second inlets of the TFVF unit, comprising at least one port for flowing fluid into or out of, or both, of the circuit system,
   wherein the circuit system is configured such that fluid can be flowed through the conduit and the TFVF unit, and filtrate comprising the recombinant therapeutic protein can be collected from the TFVF unit;
   (b) flowing a fluid including a recombinant therapeutic protein into the circuit system through one of the at least one port, recirculating retentate in the circuit system, and collecting filtrate comprising the recombinant therapeutic protein from the TFVF unit for a period of time;
   wherein rate of recirculating the retentate in the circuit system and rate of flowing the fluid into the circuit system are independently controlled.

2. The method of claim 1, wherein step (b) comprises flowing the fluid into the circuit system at a rate of about 0.1 mL/minute to about 100 L/minute.

3. The method of claim 2, wherein step (b) comprises flowing the fluid into the circuit system at a rate of about 0.5 mL/minute to about 200 mL/minute.

4. The method of claim 1, wherein the flowing of the fluid into the circuit system in step (b) occurs unidirectionally.

5. The method of claim 1, wherein the TFVF unit comprises one or more tangential virus filter(s) having a surface area of about 0.1 cm$^2$ to about 100 m$^2$.

6. The method of claim 1, wherein circuit system further comprises a pump disposed in the conduit.

7. The method of claim 6, wherein the pump disposed in the conduit is a peristaltic pump.

8. The method of claim 1, wherein the circuit system further comprises a pump disposed between the first and second inlets of the TFVF unit.

9. The method of claim 8, wherein the pump disposed between the first and second inlets of the TFVF unit is a peristaltic pump.

10. An integrated and continuous process for manufacturing a therapeutic protein drug substance, the process comprising:
(a) providing a liquid culture medium comprising the recombinant therapeutic protein that is substantially free of cells, wherein the liquid culture medium is fed into a first multi-column chromatography system (MCCS1);
(b) capturing the recombinant therapeutic protein in the liquid culture medium using the MCCS1, wherein the eluate of the MCCS1 containing the recombinant therapeutic protein is continuously fed into a second multi-column chromatography system (MCCS2);
(c) purifying and polishing the recombinant therapeutic protein using the MCCS2, wherein the eluate from the MCCS2 is a fluid comprising the recombinant therapeutic protein;
(d) processing the fluid comprising the recombinant therapeutic protein using a method of claim 1 to produce the filtrate comprising the recombinant therapeutic protein, wherein the process is integrated and runs continuously from the liquid culture medium of step (a) to the filtrate comprising the recombinant therapeutic protein, wherein the filtrate comprising the recombinant therapeutic protein is the therapeutic protein drug substance.

11. The process of claim 10, wherein the MCCS1 performs at least two different unit operations.

12. The process of claim 11, wherein the MCCS1 performs the unit operations of capturing the recombinant therapeutic protein and inactivating viruses.

13. The process of claim 11, wherein the use of the MCCS1 or the MCCS2, or both, involves column switching.

14. The process of claim 10, wherein the MCCS1 is a first periodic counter current chromatography system (PCCS1).

15. The process of claim 14, wherein the PCCS1 comprises a four-column PCCS.

16. The process of claim 15, wherein three of the four columns in the four-column PCCS perform the unit operation of capturing the recombinant therapeutic protein from the liquid culture medium.

17. The process of claim 16, wherein the fourth column of the four-column PCCS performs the unit operation of inactivating viruses by holding the eluate containing recombinant therapeutic protein at a low pH for viral inactivation.

18. The process of claim 17, wherein the MCCS2 is a second periodic counter current chromatography system (PCCS2).

19. The process of claim 10, wherein the method further comprises formulating the therapeutic protein drug substance into a pharmaceutical composition.

20. The process of claim 10, wherein the recombinant therapeutic protein is an antibody or antibody fragment, an enzyme, an engineered protein, or an immunogenic protein or protein fragment.

* * * * *